United States Patent
Heimann et al.

(10) Patent No.: US 12,043,625 B2
(45) Date of Patent: Jul. 23, 2024

(54) PYRIDINE DERIVATIVES WITH C-LINKED CYCLIC SUBSTITUENTS AS cGAS INHIBITORS

(71) Applicant: BOEHRINGER INGELHEIM INTERNATIONAL GMBH, Ingelheim am Rhein (DE)

(72) Inventors: Annekatrin Charlotte Heimann, Biberach an der Riss (DE); Sandra Ruth Handschuh, Biberach an der Riss (DE); Christoph Hoenke, Biberach an der Riss (DE); Christian Gnamm, Biberach an der Riss (DE); Cédrickx Godbout, Attenweiler (DE); Patrick Gross, Biberach (DE); Joerg Kley, Mittelbiberach (DE); Christian Andreas Kuttruff, Schemmerhofen (DE); Dirk Reinert, Bad Duerkheim (DE); Raphael Stuber, Schwendi (DE); Marc Grundl, Biberach an der Riss (DE); Theodor Theis, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 17/741,050

(22) Filed: May 10, 2022

(65) Prior Publication Data

US 2023/0002401 A1 Jan. 5, 2023

(30) Foreign Application Priority Data

May 12, 2021 (EP) ..................... 21173693
Aug. 20, 2021 (EP) ..................... 21192434

(51) Int. Cl.
| | | |
|---|---|---|
| C07D 491/048 | (2006.01) | |
| A61P 1/00 | (2006.01) | |
| A61P 9/00 | (2006.01) | |
| A61P 11/00 | (2006.01) | |
| A61P 21/00 | (2006.01) | |
| A61P 25/00 | (2006.01) | |
| A61P 27/00 | (2006.01) | |
| A61P 29/00 | (2006.01) | |
| A61P 35/00 | (2006.01) | |
| C07D 401/04 | (2006.01) | |
| C07D 405/04 | (2006.01) | |
| C07D 409/04 | (2006.01) | |
| C07D 495/10 | (2006.01) | |
| C07D 498/04 | (2006.01) | |

(52) U.S. Cl.
CPC ............... C07D 491/048 (2013.01)

(58) Field of Classification Search
CPC ......... C07D 491/048; C07D 405/04; C07D 409/04; C07D 495/10; C07D 498/04; C07D 401/04; A61P 1/00; A61P 9/00; A61P 11/00; A61P 21/00; A61P 25/16; A61P 27/02; A61P 29/00; A61P 35/00; A61P 1/16; A61P 37/00; A61K 31/4418; A61K 31/496; A61K 31/519; A61K 45/06; A61K 2300/00
See application file for complete search history.

(56) References Cited

FOREIGN PATENT DOCUMENTS

| WO | 2011143129 A1 | 11/2011 |
|---|---|---|
| WO | 2011143366 A1 | 11/2011 |
| WO | 2011143495 A1 | 11/2011 |

(Continued)

OTHER PUBLICATIONS

ACS Chemical Abstracts Service Registry Nos. 1352719-62-0 (2012), 1227176-92-2 (2020) 161610-12-4 (1995); 1.p.*

(Continued)

Primary Examiner — John M Mauro
(74) Attorney, Agent, or Firm — Shelley A. Jones

(57) ABSTRACT

The invention relates to new proline derivatives of formula (I) as cGAS inhibitors,

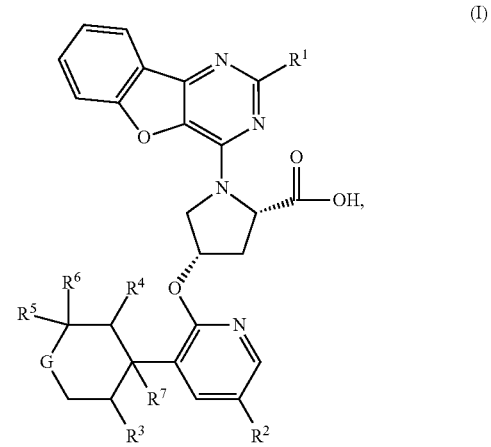

wherein
$R^1$, $R^2$, $R^3$, $R^4$, $R^5$, $R^6$, $R^7$, $R^8$, $R^9$, $R^{10}$ and G are defined as in claim 1,
and prodrugs or pharmaceutically acceptable salts of these compounds
for the treatment of diseases such as systemic lupus erythematosus, systemic sclerosis (SSc), non-alcoholic steatotic hepatitis (NASH), interstitial lung disease (ILD) and idiopathic pulmonary fibrosis (IPF).

55 Claims, No Drawings

(56) References Cited

FOREIGN PATENT DOCUMENTS

| WO | 2020142729 A1 | 7/2020 |
| WO | WO-2022174012 A1 * | 8/2022 |

OTHER PUBLICATIONS

ACS Chemical Abstracts Service Registry Nos. 2228596-77-6 (2018), 1260826-93-4 (2011) and 1260895-56-4 ( 2011); 1p.*

Ablasser et al., cGAS produces a 2'-5'-linked cyclic dinucleotide second messenger that activates STING, Nature, 2013, vol. 498, No. 7454, pp. 380-384.

Ahn et al., "STING manifests self DNA-dependent inflammatory disease", Proceedings of the National Academy of Sciences, 2012, vol. 109, No. 47, pp. 19386-19391.

Barbalat et al., "Nucleic Acid Recognition by the Innate Immune System", Annual Review of Immunology, 2011, vol. 29, No. 1, pp. 185-214.

Chen et al., "cGAS suppresses genomic instability as a decelerator of replication forks", Science Advances, 2020, No. 6, pp. 1-10.

Cho et al., "Lipotoxicity induces hepatic protein inclusions through TANK binding kinase 1-mediated p62/sequestosome 1 phosphorylation", Hepatology, 2018, vol. 68, No. 4, pp. 1331-1346.

Crow et al., "Mutations in the gene encoding the 3 ?- 5? DNA exonuclease TREX1 cause Aicardi-Goutières syndrome at the AGS1 locus", Nature Genetics, 2006, vol. 38, No. 8, pp. 917-920.

Gao et al., "Activation of cyclic GMP-AMP synthase by self-DNA causes autoimmune diseases", Proceedings of the National Academy of Sciences, 2015, vol. 112, No. 42, pp. E5699-E5705.

Gao et al., "Cyclic GMP-AMP Synthase Is an Innate Immune Sensor of HIV and Other Retroviruses", Science, 2013, vol. 341, pp. 903-907.

Glück et al., "Innate immune sensing of cytosolic chromatin fragments through cGAS promotes senescence", Nature Cell Biology, 2017, vol. 19, No. 9, pp. 1061-1070.

Gratia et al., "Bloom syndrome protein restrains innate immune sensing of micronuclei by cGAS", The Journal of Experimental Medicine, 2019, vol. 216, No. 5, pp. 1199-1213.

Gray et al., "Cutting Edge: cGAS Is Required for Lethal Autoimmune Disease in the Trex1-Deficient Mouse Model of Aicardi-Goutières Syndrome", The Journal of Immunology, 2015, vol. 195, No. 5, pp. 1939-1943.

Hansen et al., "Listeria monocytogenes induces IFN? expression through an IFI16?, cGAS? and STING?dependent pathway", The EMBO Journal, 2014, vol. 33, No. 15, pp. 1654-1666.

Harding et al., "Mitotic progression following DNA damage enables pattern recognition within micronuclei", Nature, 2017, vol. 548, No. 7668, pp. 466-470.

Hoong et al., "cGAS-STING pathway in oncogenesis and cancer therapeutics", Oncotarget, 2020, vol. 11, No. 30, pp. 2930-2955.

Hu et al., "Cytosolic DNA sensor cGAS plays an essential pathogenetic role in pressure overload-induced heart failure", American Journal of Physiology—Heart and Circulatory Physiology, 2020, vol. 318, No. 6, pp. H1525-H1537.

Hu et al., "Discovery of Phosphodiesterade 10A (PDE10A) Pet Tracer AMG 580 to Support Clinical Studies", ACS Medicinal Chemistry Letters, 2016, vol. 7, No. 7, pp. 719-723.

Kerur et al., "cGAS drives non-canonical inflammasome activation in age-related macular degeneration", Nature Medicine, 2018, vol. 24, No. 1, pp. 50-61.

Ma et al., "Gasdermin D in macrophages restrains colitis by controlling cGAS-mediated inflammation", Science Advances, 2020, vol. 6, No. 21, pp. eaaz6717.

Ma et al., "Modulation of the cGAS-STING DNA sensing pathway by gammaherpesviruses", Proceedings of the National Academy of Sciences, 2015, vol. 112, No. 31, pp. E4306-E4315.

Mackenzie et al., "cGAS surveillance of micronuclei links genome instability to innate immunity", Nature, 2017, vol. 548, No. 7668, pp. 461-465.

Moseley et al., "Investigation of an Alternative Route to ZD3638 and Cost-Benefit Analysis Comparison of Raw Materials with the Previous Route", Organic Process Research & Development, 2001, vol. 5, No. 5, pp. 491-497.

Nascimento et al., "Self-DNA release and STING-dependent sensing drives inflammation to cigarette smoke in mice", Scientific Reports, 2019, vol. 9, No. 1, pp. 14848.

Papinska et al., "Activation of Stimulator of Interferon Genes (STING) and Sjögren Syndrome", Journal of Dental Research, 2018, vol. 97, No. 8, pp. 893-900.

Ryu et al., "Bioactive Plasma Mitochondrial DNA Is Associated With Disease Progression in Scleroderma?Associated Interstitial Lung Disease", Arthritis & Rheumatology, 2020, vol. 72, No. 11, pp. 1905-1915.

Schuliga et al., "Self DNA perpetuates IPF lung fibroblast senescence in a cGAS-dependent manner", Clinical Science, 2020, vol. 134, No. 7, pp. 889-905.

Sliter et al., "Parkin and PINK1 mitigate STING-induced inflammation", Nature, 2018, vol. 561, No. 7722, pp. 258-262.

Sun et al., "Cyclic GMP-AMP Synthase Is a Cytosolic DNA Sensor That Activates the Type I Interferon Pathway", Science, 2013, vol. 339, No. 6121, pp. 786-791.

Wu et al., "Cyclic GMP-AMP Is an Endogenous Second Messenger in Innate Immune Signaling by Cytosolic DNA", Science, 2013, vol. 339, pp. 826-831.

Yang et al., "cGAS is essential for cellular senescence", Proceedings of the National Academy of Sciences, 2017, vol. 114, No. 23, pp. E4612-E4620.

* cited by examiner

PYRIDINE DERIVATIVES WITH C-LINKED CYCLIC SUBSTITUENTS AS cGAS INHIBITORS

1 BACKGROUND OF THE INVENTION

1.1 cGAS Inhibitors

Innate immunity is considered a first line cellular stress response defending the host cell against invading pathogens and initiating signaling to the adaptive immune system. These processes are triggered by conserved pathogen-associated molecular patterns (PAMPs) through sensing by diverse pattern recognition receptors (PRRs) and subsequent activation of cytokine and type I interferon gene expression. The major antigen-presenting cells, such as monocytes, macrophages, and dendritic cells produce type I interferons and are critical for eliciting adaptive T- and B-cell immune system responses. The major PRRs detect aberrant, i.e. mislocalized, immature or unmodified nucleic acids on either the cell surface, the inside of lysosomal membranes or within other cellular compartments (Barbalat et al., Annu. Rev. Immunol. 29, 185-214 (2011)).

"Cyclic GMP-AMP Synthase" (cGAS, UniProtKB—Q8N884)) is the predominant sensor for aberrant double-stranded DNA (dsDNA) originating from pathogens or mislocalization or misprocessing of nuclear or mitochondrial cellular dsDNA (Sun et al., Science 339, 786-791 (2013); Wu et al., Science 339, 826-830 (2013); Ablasser et al., Nature 498, 380-384 (2013)). Binding of dsDNA to cGAS activates the reaction of GTP and ATP to form the cyclic dinucleotide GMP-AMP (referred to as cGAMP). cGAMP then travels to and activates the endoplasmatic reticulum membrane-anchored adaptor protein, "Stimulator of Interferon Genes" (STING). Activated STING recruits and activates TANK-binding kinase 1 (TBK1) which in turn phosporylates the transcription factor family of interferon regulatory factors (IRFs) inducing cytokine and type I interferon mRNA expression.

The critical role of cGAS in dsDNA sensing has been established in different pathogenic bacteria (Hansen et al., EMBOJ. 33, 1654 (2014)), viruses (Ma et al., PNAS 112, E4306 (2015)) and retroviruses (Gao et al., Science 341, 903-906 (2013)). Additionally, cGAS is essential in various other biological processes such as cellular senescence (Yang et al., PNAS 114, E4612 (2017), Gluck et al., Nat. Cell Biol. 19, 1061-1070 (2017)) and recognition of ruptured micronuclei in the surveillance of potential cancer cells (Mackenzie et al., Nature 548, 461-465 (2017); Harding et al., Nature 548, 466-470 (2017)).

While the cGAS pathway is important for host defense against invading pathogens, cellular stress and genetic factors may also cause production of aberrant cellular dsDNA, e.g. by nuclear or mitochondrial leakage, and thereby trigger autoinflammatory responses. Aicardi-Goutieres syndrome (AGS; Crow et al., Nat. Genet. 38, 917-920 (2006))—a lupus-like severe autoinflammatory immune-mediated disorder—arises from loss-of-function mutations in TREX1, a primary DNA exonuclease responsible for degrading aberrant DNA in cytosol. Knock-out of cGAS in TREX1-deficient mice prevented otherwise lethal autoimmune responses, supporting cGAS as driver of interferonopathies (Gray et al., J. Immunol. 195, 1939-1943 (2015); Gao et al., PNAS 112, E5699-E5705 (2015)). Likewise, embryonic lethality caused by deficiency of DNAse2, an endonuclease responsible for degradation of excessive DNA in lysosomes during endocytosis, was completely rescued by additional knock-out of cGAS (Gao et. al, PNAS 112, E5699-E5705 (2015)) or STING (Ahn et al., PNAS 109, 19386-19391 (2012)). These observations support cGAS as a drug target and inhibition of cGAS may provide a therapeutic strategy for preventing autoinflammation and treating diseases such as systemic lupus erythematosus (SLE) with involvement of anti-dsDNA antibodies (Pisetsky et al., Nat. Rev. Rheumatol. 12, 102-110 (2016)).

1.2 Prior Art

Due to the observation that inhibition of the cGAS-pathway may provide a therapeutic strategy for preventing autoinflammation and for treating e.g. autoimmune diseases many efforts to develop cGAS inhibitors have been undertaken.

In WO 2019/241787 for example, methyl 4-amino-6-(phenylamino)-1,3,5-triazine-2-carboxylates such as CU-32 and CU-76 have been disclosed as cGAS-inhibitors with "in vitro hcGAS IC50-values" slightly below 1 µM (IC50(CU-32)=0.66 µM and IC50(CU-76)=0.27 µM).

In Hall et al., PLoS ONE 12(9); e0184843 (2017), compound PF-06928215 has been published as an inhibitor of cGAS with an "in vitro hcGAS IC50-value" of 0.049 µM as measured by a fluorescence polarization assay. However, compound PF-06928215 showed no acceptable cellular activity as a cGAS inhibitor.

In WO 2020/142729, (benzofuro[3,2-d]pyrimidin-4-yl) pyrrolidine-2-carboxylic acid derivatives have been disclosed as cGAS inhibitors for the therapy of autoimmune disorders such as Aicardi-Goutieres Syndrome (AGS), lupus erythematosus, scleroderma, inflammatory bowel disease and non-alcoholic steatotic hepatitis (NASH). However, the compounds of this invention differ from the (benzofuro[3,2-d]pyrimidin-4-yl)pyrrolidine-2-carboxylic acid derivatives of WO 2020/142729 in their completely different substitution pattern in the 4-position of the pyrrolidine ring.

Recently provided cGAS inhibitors, such as the ones in WO 2020/142729, usually show an insufficient cellular cGAS inhibitory potency (with IC50-values regarding inhibition of the cGAS/STING pathway as measured in cellular assays of usually larger than 1 µM, often of larger than 5 µM). However, it is crucial to provide therapeutic cGAS inhibitors that do not only show a satisfying biochemical (in vitro) inhibitory potency ("hcGAS IC50"), but also a satisfying cellular inhibitory potency (for example by showing inhibition of IFN induction in virus-stimulated THP-1 cells (THP1$_{(vir)}$ IC50)) in order to ensure that the compound is able to show a therapeutic effect in a patient. Other important properties that may be predictive for successful development of a cGAS inhibitor as a therapeutic agent are satisfying cGAS-selectivity (versus off-target activity) and acceptable inhibitory potency in human whole blood.

Surprisingly it has now been found that the compounds of formulas (I), (I'), (I''), (II') and (II'') show at the same time the following three properties:
  a satisfying "biochemical (in vitro) IC50-value regarding cGAS inhibition" (with a hcGAS IC50 of ≤100 nM, preferably of ≤50 nM, in particular of ≤10 nM),
  a satisfying "inhibition of IFN induction in virus-stimulated THP-1 cells (with a THP1 IC50$_{(vir)}$ of ≤1 µM, preferably of 500 nM, more preferably of ≤100 nM, in particular of 50 nM) and
  a satisfying selectivity for cGAS-inhibition
  (with a ratio THP1 IC50$_{(cGAMP)}$/THP1 IC50$_{(vir)}$ of ≥10, more preferably ≥50, more preferably ≥500, in particular ≥1000).

Additionally the compounds of formulas (I), (I'), (I"), (II') and (II") also show acceptable IC50-values with regard to inhibition of IFN induction in dsDNA-stimulated human whole blood assays, preferably with human whole blood IC50-values with regard to cGAS inhibition (hWB IC50) of ≤5000 nM, more preferably of ≤1000 nM, in particular of ≤100 nM.

The cGAS inhibitors of the invention with this particular pharmacological profile which combines an excellent in vitro inhibitory potency and an excellent cellular inhibitory potency with a high selectivity for cGAS inhibition have a high probability to also exhibit a good therapeutic effect in the patient. Due to their high cellular inhibitory potency compounds with this particular pharmacological profile should be able to pass the cell membrane barrier and therefore reach their intracellular target location and due to their selectivity to exclusively inhibit cGAS activity, these compounds should not show unwanted off target effects, for example side effects somewhere within the signaling pathway downstream of cGAS or cytotoxic effects.

2 DESCRIPTION OF THE INVENTION

The invention concerns compounds of formula (I),

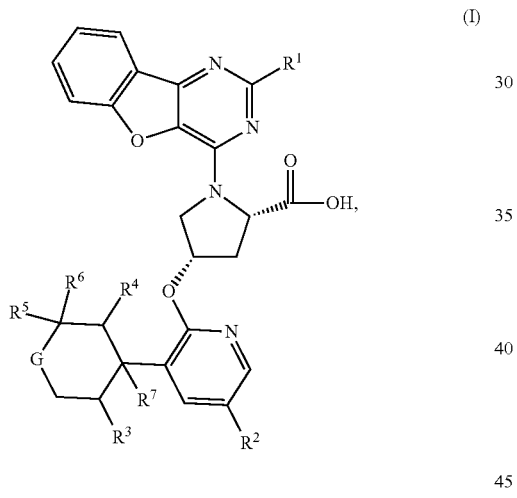

(I)

wherein
$R^1$ is selected from methyl, ethyl, halomethyl and halogen,
wherein
G is selected from $SO_2$, S, O, N, and $NR^8$;
wherein
$R^2$ is selected from H, halogen, cyclopropyl, $C_{1-3}$-alkyl, $C_{2-5}$-alkynyl and CN,
or wherein $R^2$ is a cyclic group, wherein this cyclic group is selected from the group consisting of a phenyl and a five- to six-membered heteroaryl comprising 1, 2, 3 or 4 heteroatoms each independently selected from N, S and O, and wherein this cyclic group is substituted by one or two, identical or different substituents $R^{10}$,
wherein
$R^3$ is selected from H, methyl and $—CF_3$,
$R^4$ is selected from H, methyl and $—CF_3$,
$R^5$ is selected from H, methyl, —CN, -methylene-OH and $—CF_3$,
or $R^5$ may be absent,
$R^6$ is selected from H, methyl, —CN, -methylene-OH and $—CF_3$, $R^7$ is selected from hydrogen, halogen, methyl, —O-methyl and —OH;
$R^8$ is selected from CN, H, methyl, $—CO—NH_2$, $—CO—(C_{1-3}$-alkyl), cycloalkyl and oxetane,
wherein each $R^{10}$ is independently selected from the group consisting of hydrogen, halogen, haloalkyl, -methyl, -ethyl, —NH—CO-methyl, $—N(CH_3)_2$, $—CH_2—OH$, $—NH(CH_3)$, $—O—CH_3$ and —CN,
or wherein $R^5$ and $R^6$ together with the C-atoms in between form a ring selected from oxetane, tetrahydrofurane, cyclopropane and cyclobutane,
or in the case that G is $NR^8$, then—while $R^5$ is absent—$R^8$ and $R^6$ and the C-atoms in between form an annulated five-membered aromatic or non-aromatic heterocycle comprising two heteroatoms each independently selected from N and O, wherein this five-membered annulated heterocycle may optionally be substituted by an oxo-group,
or $R^7$ and $R^3$ together with the C-atoms in between form an annulated cyclopropane ring,
or prodrugs or pharmaceutically acceptable salts thereof.

A preferred embodiment of the invention relates to the aforementioned compounds which falls into the scope of formula (I')

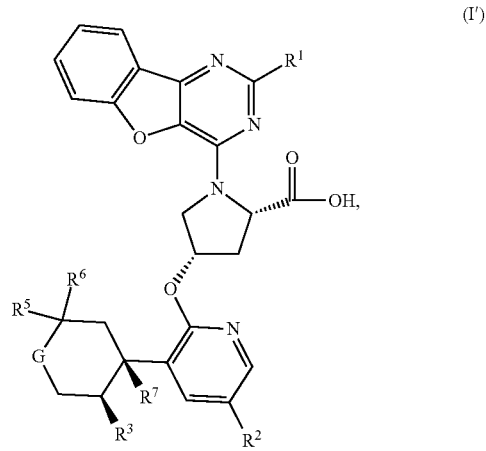

(I')

or of formula (I")

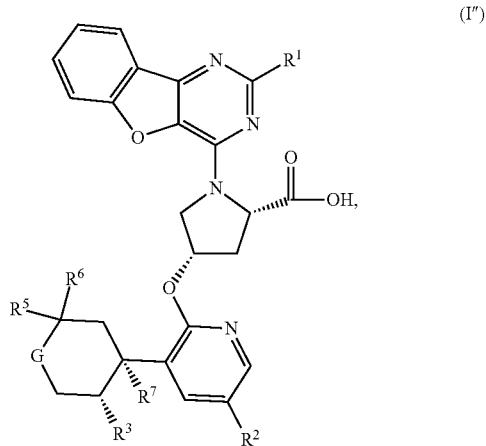

(I")

wherein $R^1$, $R^2$, $R^3$, $R^5$, $R^6$, $R^7$, $R^8$, $R^9$, $R^{10}$ and G are defined as mentioned above, and prodrugs or pharmaceutically acceptable salts thereof.

Another preferred embodiment of the invention refers to the abovementioned compounds which fall into the scope of formula (II')

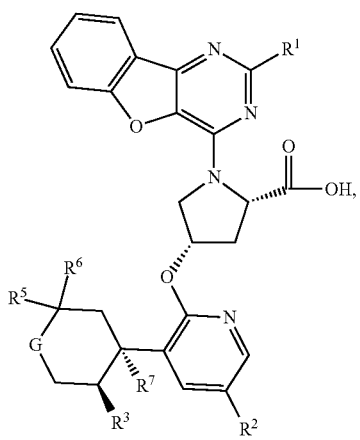

(II')

or of formula (II")

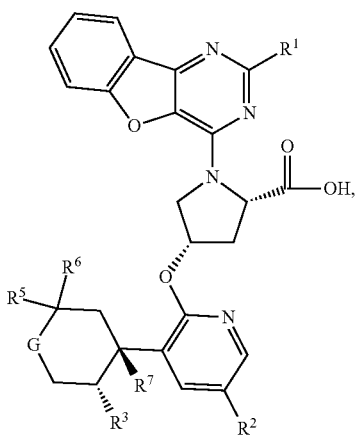

(II")

wherein $R^1$, $R^2$, $R^3$, $R^5$, $R^6$, $R^7$, $R^8$, $R^9$, $R^{10}$ and G are defined as mentioned above, and prodrugs or pharmaceutically acceptable salts thereof.

In a further preferred embodiment the invention relates to the aforementioned compounds of one or more of formulas (I), (I'), (I"), (II') or (II"),
wherein
G is selected from $SO_2$, O and NRs;
and wherein
$R^8$ is selected from CN, H, methyl, —CO—$NH_2$, —CO-methyl and oxetane,
and wherein
$R^2$ is selected from H, halogen, 1-propynyl and ethynyl,
or wherein $R^2$ is a cyclic group selected from the group consisting of a five- to six-membered heteroaryl comprising 1 or 2 heteroatoms each independently selected from N, S and O, wherein this cyclic group is selected from the group consisting of pyridinyl and pyrazolyl, and
wherein this cyclic group is substituted by one or two, identical or different substituents $R^{10}$ selected from the group consisting of halogen, methyl and —NH($CH_3$),
or prodrugs or pharmaceutically acceptable salts thereof.

In another preferred embodiment the invention refers to the above-mentioned compounds of at least one of formulas (I), (I'), (I"), (II') or (II"),
wherein $R^1$ is halomethyl,
or prodrugs or pharmaceutically acceptable salts thereof.

In a further preferred embodiment the invention relates to the above-mentioned compounds of at least one of formulas (I), (I'), (I"), (II') or (II"),
wherein $R^1$ is a fluoromethyl selected from the group consisting of —$CF_3$, —$CHF_2$ and —$CH_2F$, or prodrugs or pharmaceutically acceptable salts thereof.

In another preferred embodiment the invention refers to the above-mentioned compounds of at least one of formulas (I), (I'), (I"), (II') or (II"),
wherein $R^3$ is methyl and $R^4$ is hydrogen,
or prodrugs or pharmaceutically acceptable salts thereof.

In a further preferred embodiment the invention relates to the above-mentioned compounds of at least one of formulas (I), (I'), (I"), (II') or (II"),
wherein $R^7$ is halogen,
or prodrugs or pharmaceutically acceptable salts thereof.

In another preferred embodiment the invention refers to the above-mentioned compounds of at least one of formulas (I), (I'), (I"), (II') or (II"),
wherein $R^7$ is F,
or prodrugs or pharmaceutically acceptable salts thereof.

In a further preferred embodiment the invention relates to the above-mentioned compounds of at least one of formulas (I), (I'), (I"), (II') or (II"),
wherein G is selected from the group consisting of O and $SO_2$,
and wherein $R^7$ is F,
or prodrugs or pharmaceutically acceptable salts thereof.

In another preferred embodiment the invention refers to the above-mentioned compounds of at least one of formulas (I), (I'), (I"), (II') or (II"),
wherein G is selected from the group consisting of O and $SO_2$,
wherein $R^7$ is F,
and wherein $R^2$ is selected from ethynyl and halogen,
or prodrugs or pharmaceutically acceptable salts thereof.

In a further preferred embodiment the invention relates to the above-mentioned compounds of at least one of formulas (I), (I'), (I"), (II') or (II"),
wherein G is selected from the group consisting of 0 and $SO_2$,
wherein $R^7$ is F,
wherein $R^2$ is selected from ethynyl, 1-propynyl and halogen,
and wherein $R^3$ is methyl and $R^4$ is hydrogen,
or prodrugs or pharmaceutically acceptable salts thereof.

In another preferred embodiment the invention refers to the above-mentioned compounds of at least one of formulas (I), (I'), (I"), (II') or (II"), wherein
$R^1$ is fluoromethyl;
G is $SO_2$;
$R^7$ is F;
and wherein $R^5$ and $R^6$ are either both methyl or both hydrogen
or wherein $R^5$ and $R^6$ form together with the C-atoms in between a ring selected from the group consisting of oxetane, cyclopropane and cyclobutane,
or prodrugs or pharmaceutically acceptable salts thereof.

In a further preferred embodiment the invention relates to the above-mentioned compounds of at least one of formulas (I), (I'), (I''), (II') or (II''), wherein
R¹ is fluoromethyl;
G is SO₂;
R⁷ is F;
wherein R⁵ and R⁶ are either both methyl or both hydrogen
or wherein R⁵ and R⁶ form together with the C-atoms in between a ring selected from the group consisting of oxetane, cyclopropane and cyclobutane,
and wherein R³ is methyl and R⁴ is hydrogen,
or prodrugs or pharmaceutically acceptable salts thereof.

In another preferred embodiment the invention refers to the above-mentioned compounds of at least one of formulas (I), (I'), (I''), (II') or (II''), wherein
R¹ is fluoromethyl;
G is SO₂;
R⁷ is F;
and wherein R⁵ and R⁶ are either both methyl,
or wherein R⁵ and R⁶ form together with the C-atoms in between a ring selected from the group consisting of oxetane, cyclopropane and cyclobutane,
or prodrugs or pharmaceutically acceptable salts thereof.

In a further preferred embodiment the invention relates to the above-mentioned compounds of at least one of formulas (I), (I'), (I''), (II') or (II''), wherein
G is O
R¹ is fluoromethyl,
R⁷ is selected from F, —O-methyl and —OH
R⁵ and R⁶ are both hydrogen,
or prodrugs or pharmaceutically acceptable salts thereof.

In another preferred embodiment the invention refers to the above-mentioned compounds of at least one of formulas (I), (I'), (I''), (II') or (II''), wherein
G is O
R¹ is fluoromethyl,
R⁷ is selected from F, —O-methyl and —OH
R⁵ and R⁶ are both hydrogen,
and wherein R³ is methyl and R⁴ is hydrogen,
or prodrugs or pharmaceutically acceptable salts thereof.

In a further preferred embodiment the invention relates to the above-mentioned compounds of at least one of formulas (I), (I'), (I''), (II') or (II''),
wherein R² is selected from the group consisting of H, ethynyl, 1-propynyl and halogen,
or prodrugs or pharmaceutically acceptable salts thereof.

In another preferred embodiment the invention refers to the above-mentioned compounds of at least one of formulas (I), (I'), (I''), (II') or (II''),
wherein R³ is methyl and R⁴ is hydrogen,
wherein R⁷ is F;
wherein R⁵ and R⁶ are both hydrogen
and wherein R² is a cyclic group selected from the group consisting of a five- to six-membered heteroaryl with 1 or 2 heteroatoms each independently selected from N, S and O, wherein this cyclic group is selected from the group consisting of pyridine and pyrazole, and wherein this cyclic group is substituted by one or two, identical or different substituents R¹⁰ selected from the group consisting of halogen, methyl and —NH(CH₃),
or prodrugs or pharmaceutically acceptable salts thereof.

In a further preferred embodiment the invention relates to the above-mentioned compounds of at least one of formulas (I), (I'), (I''), (II') or (II''),
which is selected from the group consisting of

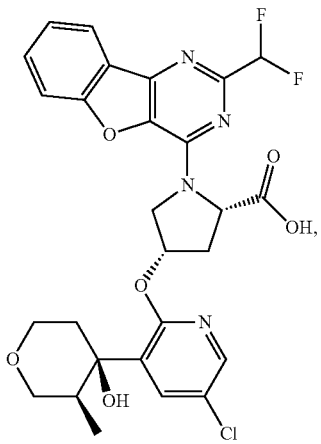

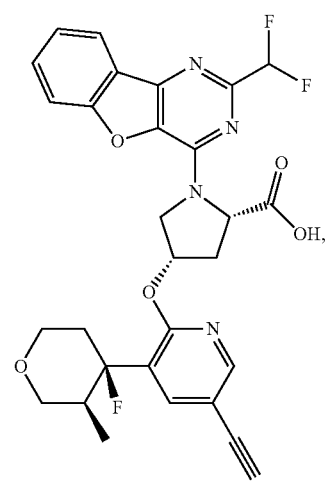

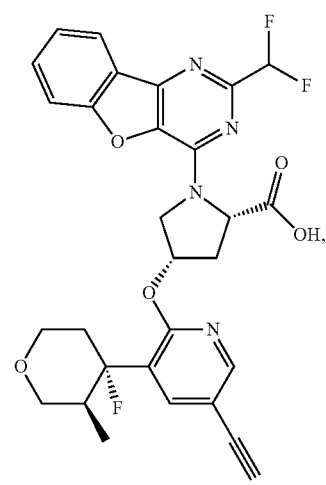

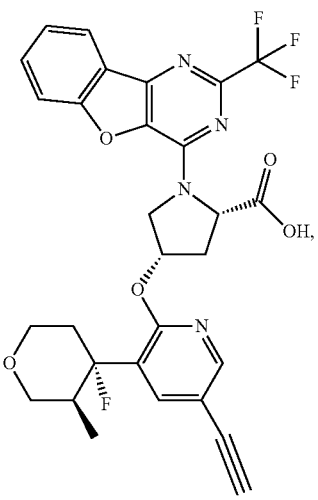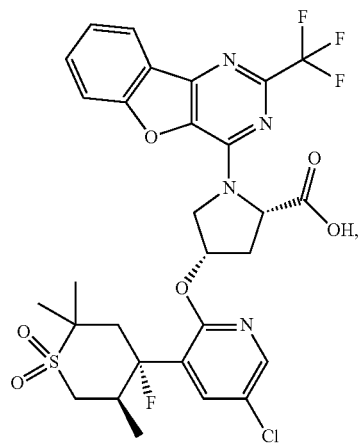

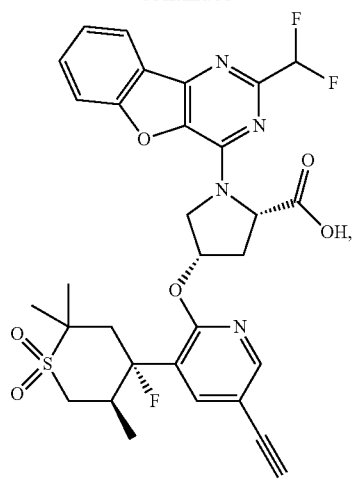
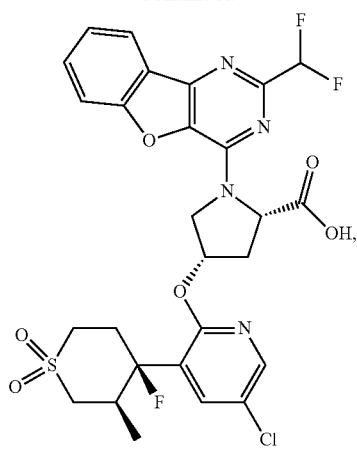
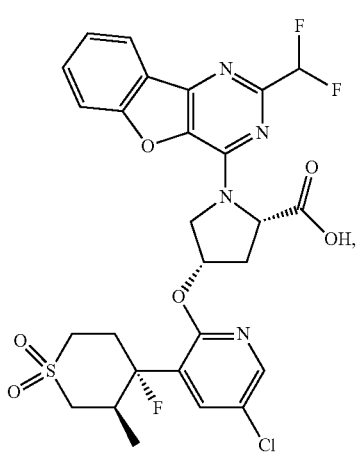
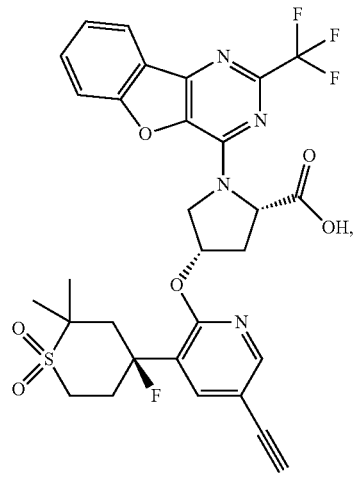
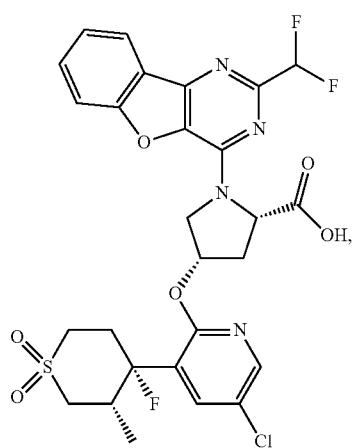
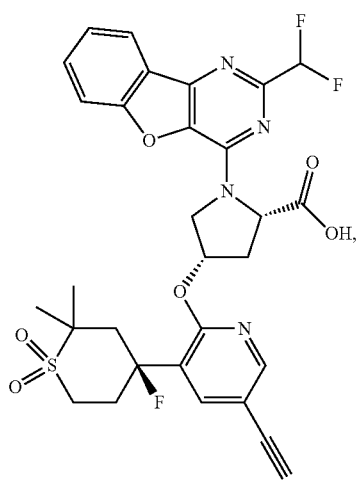

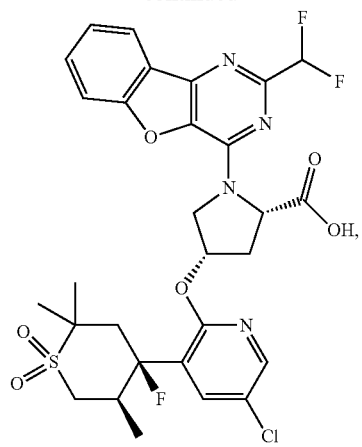
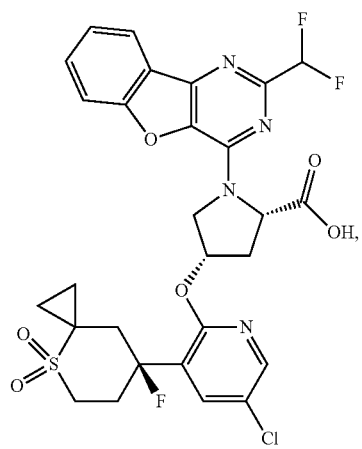
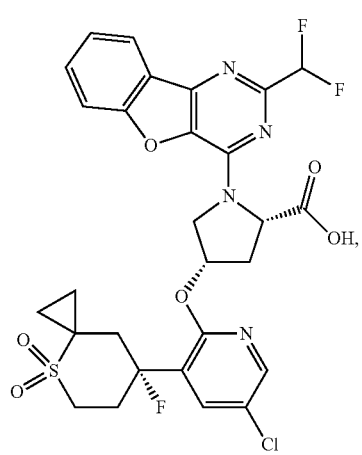
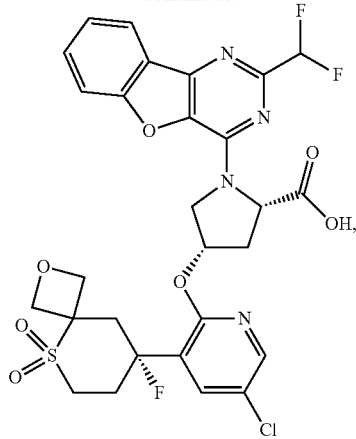
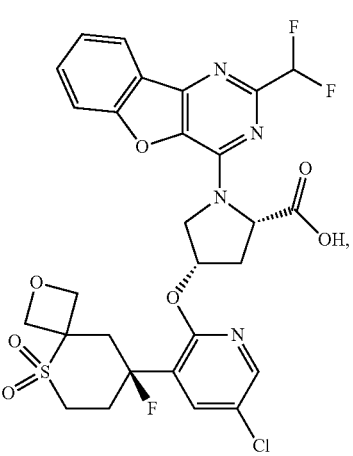
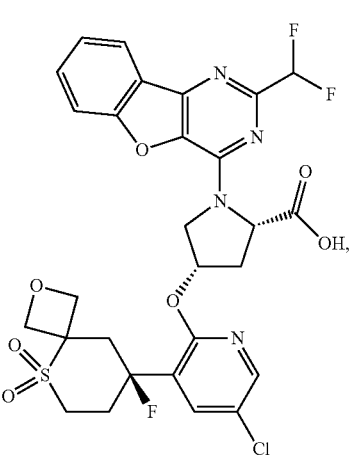

15
-continued
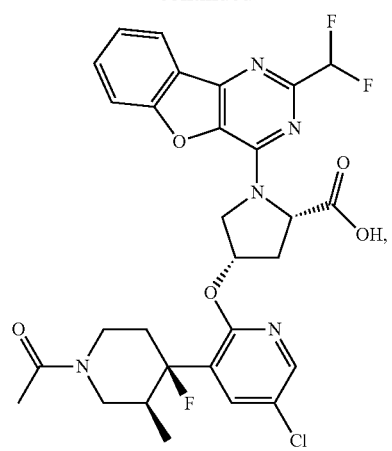
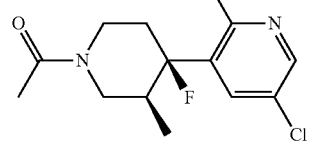
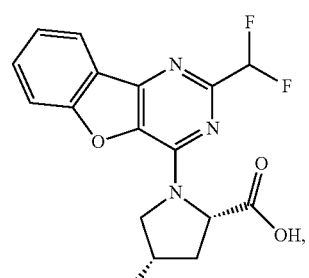
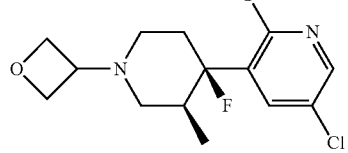
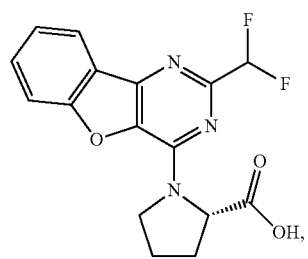
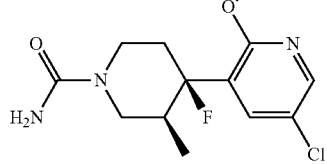
16
-continued
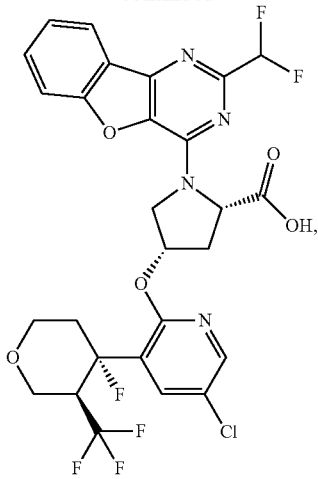
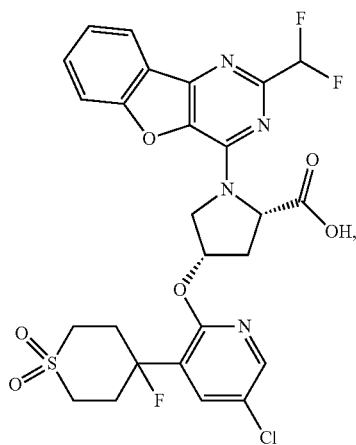
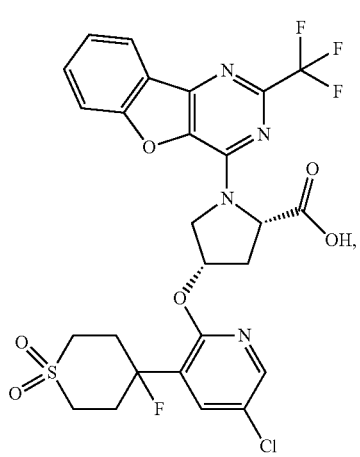

17
-continued
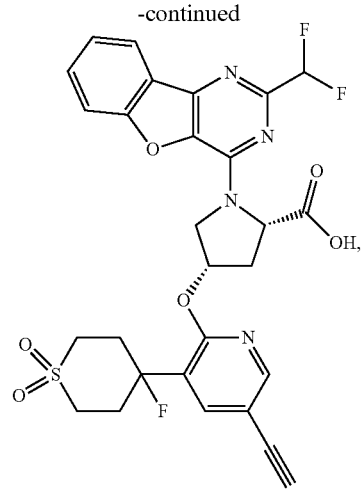
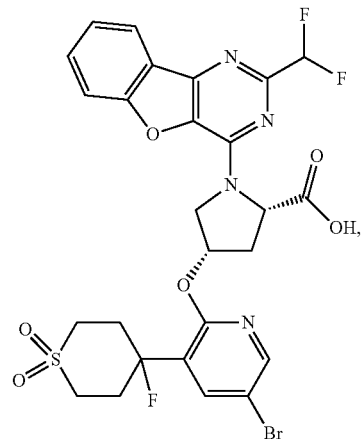
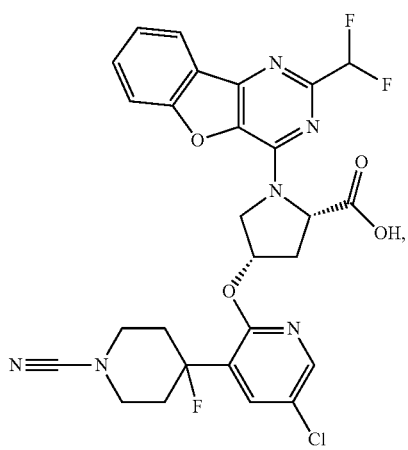
18
-continued
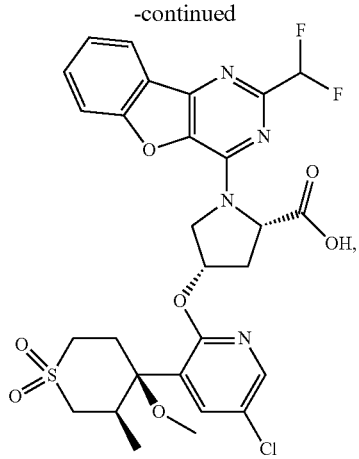
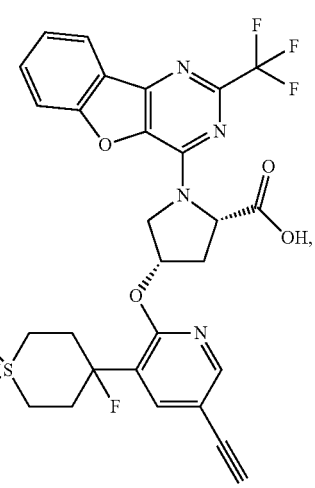
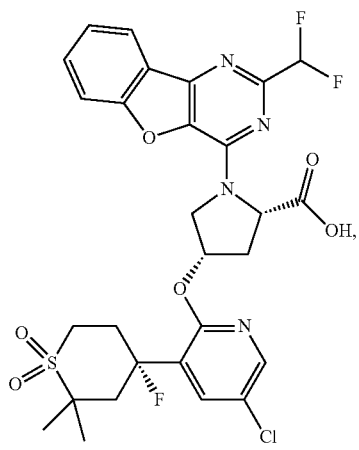

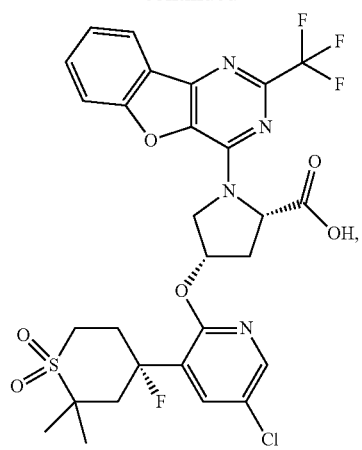
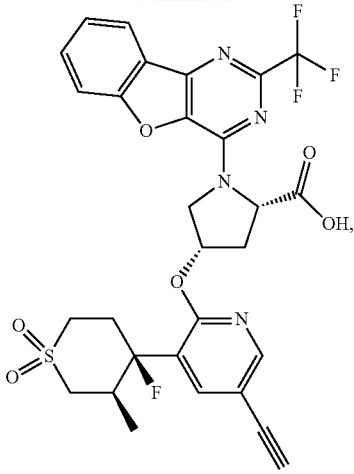
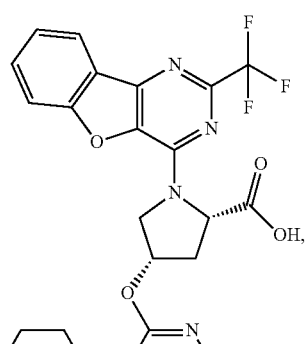
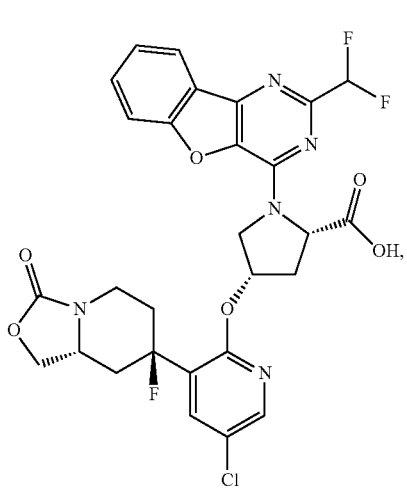
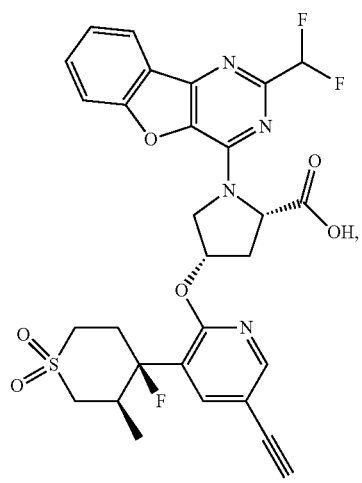
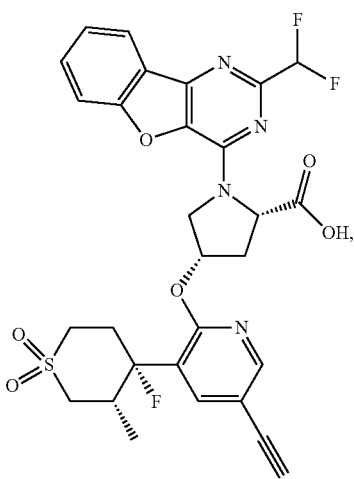

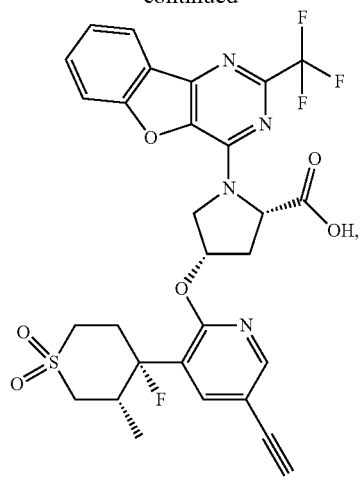
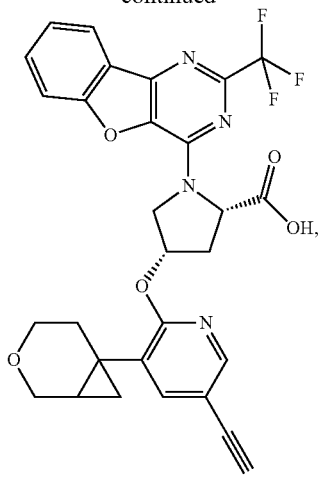
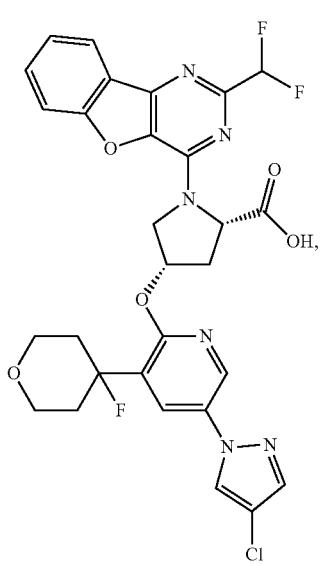
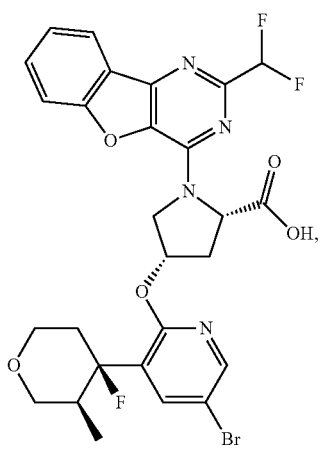

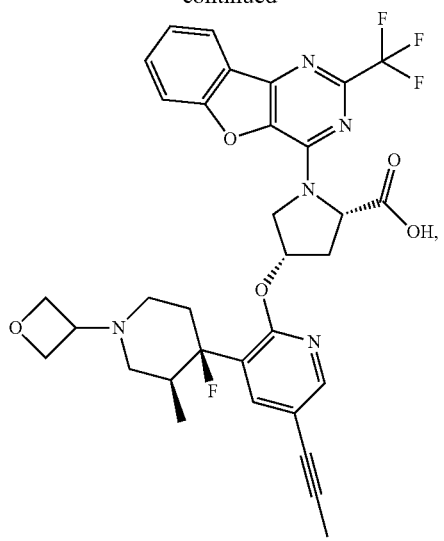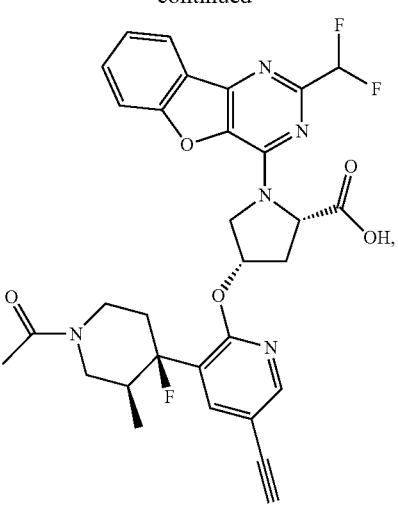

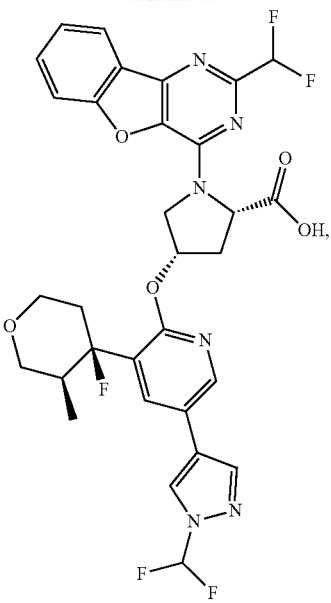

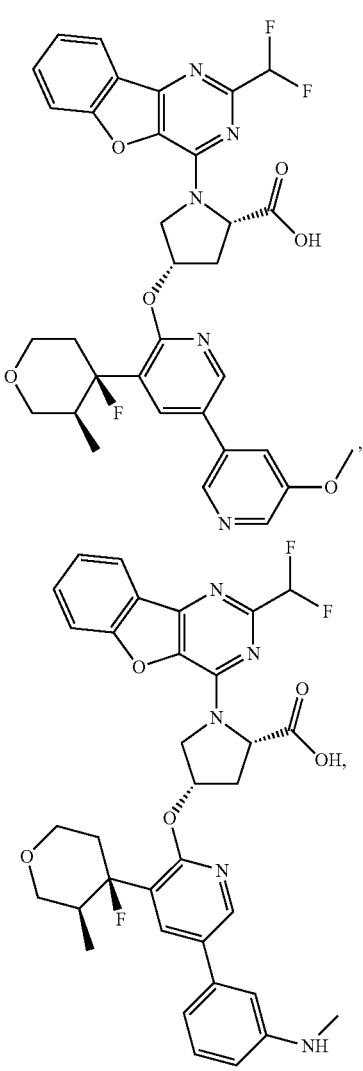

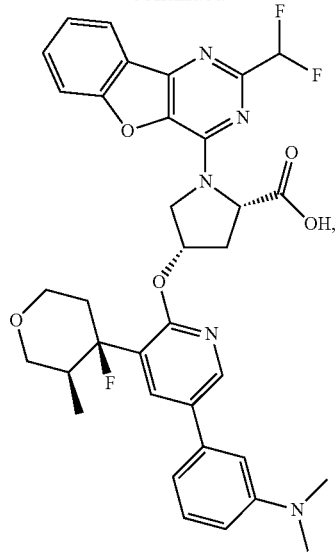 [SMILES: C[C@H]1COCC[C@]1(F)c1cc(-c2cccc(N(C)C)c2)cnc1O[C@H]1C[C@@H](C(=O)O)N(c2nc(C(F)F)nc3c2oc2ccccc23)C1]

and prodrugs or pharmaceutically acceptable salts thereof.

A further preferred embodiment of the invention refers to an intermediate of formula (IV)

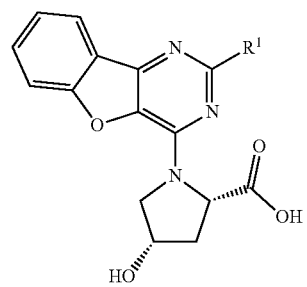

(IV)

as defined in Scheme 1,
or of formula (V)

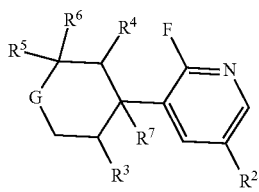

(V)

as defined in Scheme 1,
wherein $R^1$, $R^2$, $R^3$, $R^4$, $R^5$, $R^6$, $R^7$ and G are defined as mentioned above.

Another preferred embodiment of the invention relates to a prodrug of any of the aforementioned compounds which fall into the scope of formula (A), (A)

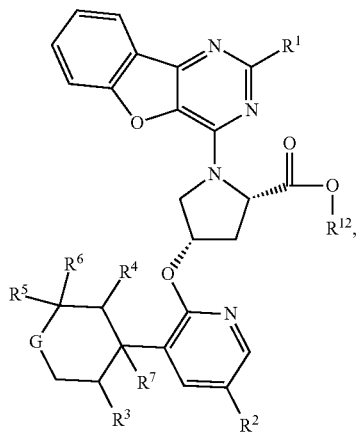

wherein R¹, R², R³, R⁴, R⁵, R⁶, R⁷ and G are defined as mentioned above and wherein R¹² is $C_{1-4}$-alkyl, aryl, —CH₂-aryl or NH—SO₂—$C_{1-3}$-alkyl.

Particularly preferred are the above-mentioned prodrugs of formula (A), wherein R¹² is methyl.

A further preferred embodiment of the invention refers to the aforementioned compounds of at least one of formulas (I), (I'), (I''), (II') or (II'') for use in the treatment of a disease that can be treated by the inhibition of cGAS.

In a further preferred embodiment the invention relates to the aforementioned compounds of at least one of formulas (I), (I'), (I''), (II') or (II'') for use in the treatment of a disease selected from the group consisting of systemic lupus erythematosus (SLE), interferonopathies, Aicardi-Goutières syndrome, age-related macular degeneration (AMD), amyotrophic lateral sclerosis (ALS), inflammatory bowel disease (IBD), chronic obstructive pulmonary disease (COPD), Bloom's syndrome, Sjogren's syndrome, Parkinsons disease, heart failure and cancer, systemic sclerosis (SSc), non-alcoholic steatotic hepatitis (NASH), interstitial lung disease (ILD), preferably progressive fibrosing interstitial lung disease (PF-ILD), in particular idiopathic pulmonary fibrosis (IPF).

In a further preferred embodiment the invention relates to the aforementioned compounds of at least one of formulas (I), (I'), (I''), (II') or (II'') for use in the treatment of a disease selected from the group consisting of systemic lupus erythematosus (SLE), interferonopathies, Aicardi-Goutières syndrome, age-related macular degeneration (AMD), amyotrophic lateral sclerosis (ALS), inflammatory bowel disease (IBD), chronic obstructive pulmonary disease (COPD), Bloom's syndrome, Sjogren's syndrome and Parkinsons disease.

In another preferred embodiment the invention refers to the aforementioned compounds of at least one of formulas (I), (I'), (I''), (II') or (II'') for use in the treatment of a fibrosing disease selected from the group consisting of systemic sclerosis (SSc), interferonopathies, non-alcoholic steatotic hepatitis (NASH), interstitial lung disease (ILD), preferably progressive fibrosing interstitial lung disease (PF-ILD), in particular idiopathic pulmonary fibrosis (IPF).

In a further preferred embodiment the invention relates to the aforementioned compounds of at least one of formulas (I), (I'), (I''), (II') or (II'') for use in the treatment of a disease selected from the group consisting of age-related macular degeneration (AMD), heart failure, COVID-19/SARS-CoV-2 infection, renal inflammation, renal fibrosis, dysmetabolism, vascular diseases, cardiovascular diseases and cancer.

In a further preferred embodiment the invention relates to a pharmaceutical composition comprising an above-mentioned compound of at least one of formulas (I), (I'), (I''), (II') or (II'') and optionally one or more pharmaceutically acceptable carriers and/or excipients.

In a another preferred embodiment the invention refers to a pharmaceutical composition comprising an aforementioned compound of at least one of formulas (I), (I'), (I''), (II') or (II'') in combination with one or more active agents selected from the group consisting of anti-inflammatory agents, anti-fibrotic agents, anti-allergic agents/anti-histamines, bronchodilators, beta 2 agonists/betamimetics, adrenergic agonists, anticholinergic agents, methotrexate, mycophenolate mofetil, leukotriene modulators, JAK inhibitors, anti-interleukin antibodies, non-specific immunotherapeutics such as interferons or other cytokines/chemokines, cytokine/chemokine receptor modulators, toll-like receptor agonists, immune checkpoint regulators, an anti-TNF antibody such as Adalimumab (Humira™), and an anti-BAFF antibody such as Belimumab or Etanercept.

In a further preferred embodiment the invention relates to a pharmaceutical composition, wherein an above-mentioned compound of at least one of formulas (I), (I'), (I''), (II') or (II'') is combined with one or more anti-fibrotic agents selected from the group consisting of Pirfenidon and Nintedanib.

In a further preferred embodiment the invention relates to a pharmaceutical composition, wherein an above-mentioned compound of at least one of formulas (I), (I'), (I''), (II') or (II'') is combined with one or more anti-inflammatory agents selected from the group consisting of NSAIDs and corticosteroids.

In another preferred embodiment the invention refers to a pharmaceutical composition, wherein an above-mentioned compound of at least one of formulas (I), (I'), (I''), (II') or (II'') is combined with one or more active agents selected from the group of bronchodilators, beta 2 agonists/betamimetics, adrenergic agonists and anticholinergic agents.

In a further preferred embodiment the invention refers to a pharmaceutical composition, wherein the aforementioned compound of at least one of formulas (I), (I'), (I''), (II') or (II'') is combined with one or more anti-interleukin antibodies selected from the group consisting of anti-IL-23 antibodies such as Risankizumab, anti-IL-17 antibodies, anti-IL-1 antibodies, anti-IL-4 antibodies, anti-IL-13 antibodies, anti-IL-5 antibodies, anti-IL-6 antibodies such as Tocilizumab (Actemra™), anti-IL-12 antibodies and anti-IL-15 antibodies.

In another preferred embodiment the invention concerns a pharmaceutical composition comprising a compound of at least one of formulas (I), (I'), (I''), (II') or (II'') combined with any of the above-mentioned active agents.

3 TERMS AND DEFINITIONS USED

Unless stated otherwise, all the substituents are independent of one another. If for example a number of $C_{1-6}$-alkyl groups are possible substituents at a group, in the case of three substituents, for example, $C_{1-6}$-alkyl could represent, independently of one another, a methyl, a n-propyl and a tert-butyl.

By the term "$C_{1-6}$-alkyl" (including those which are part of other groups) are meant branched and unbranched alkyl groups with 1 to 6 carbon atoms and by the term "$C_{1-3}$- alkyl" are meant branched and unbranched alkyl groups with 1 to 3 carbon atoms. "$C_{1-4}$-alkyl" accordingly denotes branched and unbranched alkyl groups with 1 to 4 carbon atoms. Alkyl groups with 1 to 4 carbon atoms are preferred. Examples of these include methyl, ethyl, n-propyl, iso-propyl, n-butyl, iso-butyl, sec-butyl, tert-butyl, n-pentyl, iso-pentyl, neo-pentyl and hexyl. The abbreviations Me, Et, n-Pr, i-Pr, n-Bu, i-Bu, t-Bu, etc., may also optionally be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples of these include methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene and hexylene. Unless stated otherwise, the definitions propylene, butylene, pentylene and hexylene include all the possible isomeric forms of the groups in question with the same number of carbons. Thus, for example, propyl includes also 1-methylethylene and butylene includes 1-methylpropylene, 1,1-dimethylethylene, 1,2-dimethylethylene etc.

If the carbon chain is substituted by a group which together with one or two carbon atoms of the alkylene chain forms a carbocyclic ring with 3, 4, 5 or 6 carbon atoms, this includes, inter alia, the following examples of the rings:

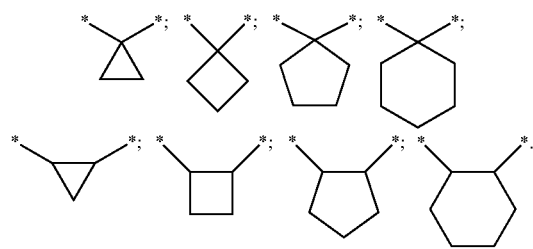

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-5}$-alkynyl" (including those which are part of other groups) are meant branched and unbranched alkynyl groups with 2 to 5 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples of these include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene and hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

By the term "aryl" (including those which are part of other groups) are meant aromatic ring systems with 6 or 10 carbon atoms. Examples include phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "aryl-$C_{1-6}$-alkylene" (including those which are part of other groups) are meant branched and unbranched alkylene groups with 1 to 6 carbon atoms, which are substituted by an aromatic ring system with 6 or 10 carbon atoms. Examples include benzyl, 1- or 2-phenylethyl and 1- or 2-naphthylethyl. Unless otherwise stated, the aromatic groups may be substituted by one or more groups selected from among methyl, ethyl, iso-propyl, tert-butyl, hydroxy, fluorine, chlorine, bromine and iodine.

By the term "heteroaryl-$C_{1-6}$-alkylene" (including those which are part of other groups) are meant—even though they are already included under "aryl-$C_{1-6}$-alkylene"—branched and unbranched alkylene groups with 1 to 6 carbon atoms, which are substituted by a heteroaryl.

If not specifically defined otherwise, a heteroaryl of this kind includes five- or six-membered heterocyclic aromatic groups or 5-10-membered, bicyclic heteroaryl rings which may contain one, two, three or four heteroatoms selected from among oxygen, sulfur and nitrogen, and contain so many conjugated double bonds that an aromatic system is formed. The following are examples of five- or six-membered heterocyclic aromatic groups and bicyclic heteroaryl rings:

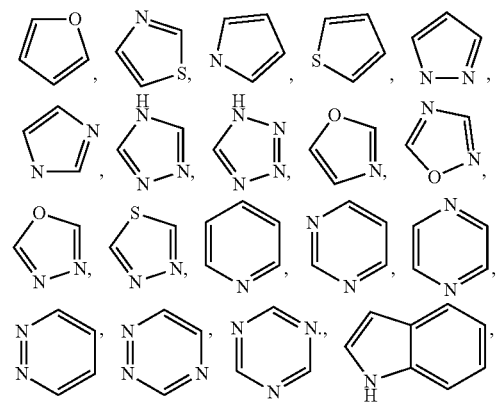

-continued

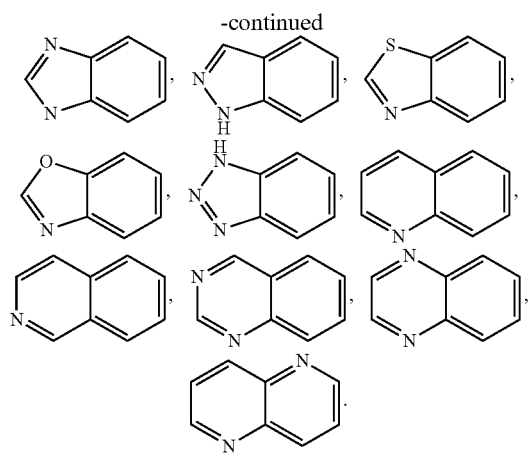

Unless otherwise stated, these heteroaryls may be substituted by one or more groups selected from among methyl, ethyl, iso-propyl, tert-butyl, hydroxy, amino, nitro, alkoxy, fluorine, chlorine, bromine and iodine.

The following are examples of heteroaryl-$C_{1-6}$-alkylenes:

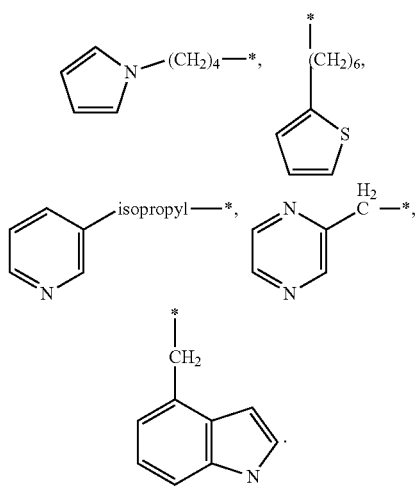

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-haloalkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, $CH_2CF_3$.

By the term "$C_{3-7}$-cycloalkyl" (including those which are part of other groups) are meant cyclic alkyl groups with 3 to 7 carbon atoms, if not specifically defined otherwise. Examples include: cyclopropyl, cyclobutyl, cyclopentyl, cyclohexyl and cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

If not specifically defined otherwise, by the term "$C_{3-10}$-cycloalkyl" are also meant monocyclic alkyl groups with 3 to 7 carbon atoms and also bicyclic alkyl groups with 7 to 10 carbon atoms, or monocyclic alkyl groups which are bridged by at least one $C_{1-3}$-carbon bridge.

By the term "heterocyclic rings" or "heterocycle" are meant, unless stated otherwise, five-, six- or seven-membered, saturated, partially saturated or unsaturated heterocyclic rings which may contain one, two or three heteroatoms selected from among oxygen, sulfur and nitrogen, while the ring may be linked to the molecule through a carbon atom or through a nitrogen atom, if there is one. Although included by the term "heterocyclic rings" or "heterocycles", the term "saturated heterocyclic ring" refers to five-, six- or seven-membered saturated rings. Examples include:

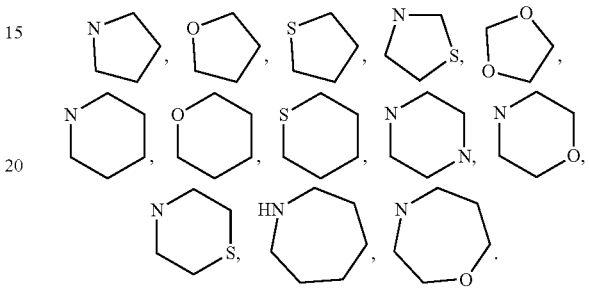

Although included by the term "heterocyclic rings" or "heterocyclic group", the term "partially saturated heterocyclic group" refers to five-, six- or seven-membered partially saturated rings which contain one or two double bonds, without so many double bonds being produced that an aromatic system is formed, unless specifically defined otherwise. Examples include:

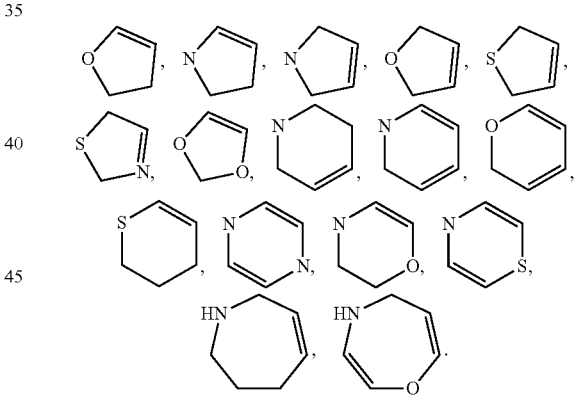

Although included by the term "heterocyclic rings" or "heterocycles", the term "heterocyclic aromatic rings", "unsaturated heterocyclic group" or "heteroaryl" refers to five- or six-membered heterocyclic aromatic groups or 5-10-membered, bicyclic heteroaryl rings which may contain one, two, three or four heteroatoms selected from among oxygen, sulfur and nitrogen, and contain so many conjugated double bonds that an aromatic system is formed, unless not specifically defined otherwise. Examples of five- or six-membered heterocyclic aromatic groups include:

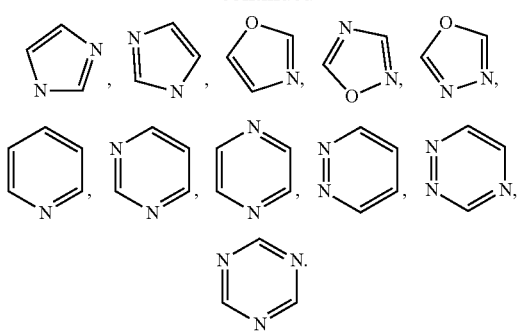

Unless otherwise mentioned, a heterocyclic ring (or heterocycle) may be provided with a keto group. Examples include:

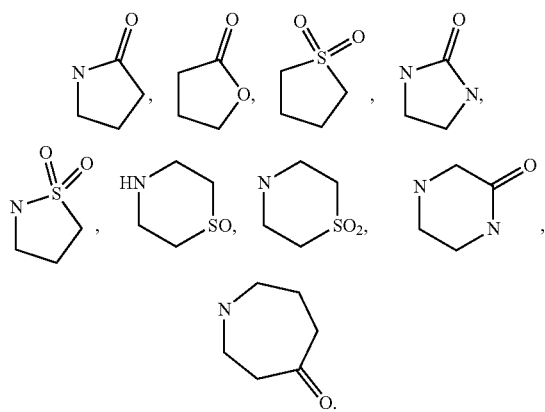

Although covered by the term "cycloalkyl", the term "bicyclic cycloalkyls" generally denotes eight-, nine- or ten-membered bicyclic carbon rings. Examples include:

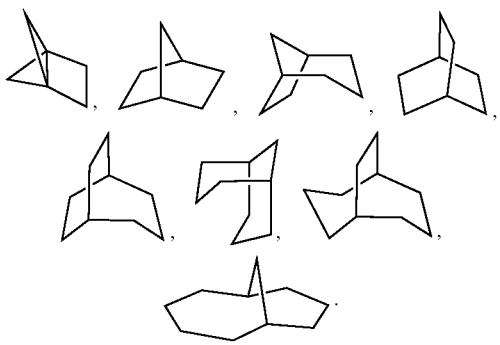

Although already included by the term "heterocycle", the term "bicyclic heterocycles" generally denotes eight-, nine- or ten-membered bicyclic rings which may contain one or more heteroatoms, preferably 1-4, more preferably 1-3, even more preferably 1-2, particularly one heteroatom, selected from among oxygen, sulfur and nitrogen, unless not specifically defined otherwise. The ring may be linked to the molecule through a carbon atom of the ring or through a nitrogen atom of the ring, if there is one. Examples include:

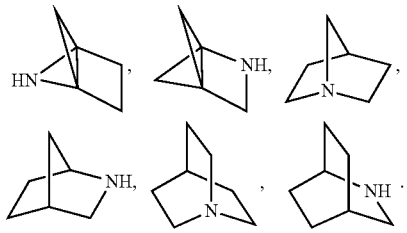

Although already included by the term "aryl", the term "bicyclic aryl" denotes a 5-10 membered, bicyclic aryl ring which contains sufficient conjugated double bonds to form an aromatic system. One example of a bicyclic aryl is naphthyl.

Although already included under "heteroaryl", the term "bicyclic heteroaryl" denotes a 5-10 membered, bicyclic heteroaryl ring which may contain one, two, three or four heteroatoms, selected from among oxygen, sulfur and nitrogen, and contains sufficient conjugated double bonds to form an aromatic system, unless specifically defined otherwise.

Although included by the term "bicyclic cycloalkyls" or "bicyclic aryl", the term "fused cycloalkyl" or "fused aryl" denotes bicyclic rings wherein the bridge separating the rings denotes a direct single bond. The following are examples of a fused, bicyclic cycloalkyl:

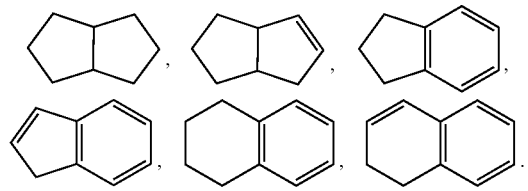

Although included by the term "bicyclic heterocycles" or "bicyclic heteroaryls", the term "fused bicyclic heterocycles" or "fused bicyclic heteroaryls" denotes bicyclic 5-10 membered heterorings which contain one, two, three or four heteroatoms, selected from among oxygen, sulfur and nitrogen and wherein the bridge separating the rings denotes a direct single bond. The "fused bicyclic heteroaryls" moreover contain sufficient conjugated double bonds to form an aromatic system. Examples include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

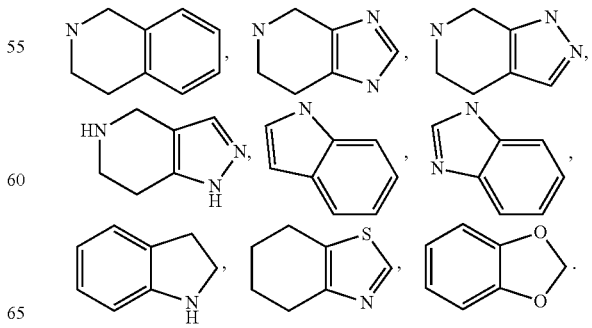

"Halogen" within the scope of the present invention denotes fluorine, chlorine, bromine or iodine. Unless stated to the contrary, fluorine, chlorine and bromine are regarded as preferred halogens.

As mentioned previously, the compounds of formulas (I), (I'), (I"), (II') and (II") may be converted into the salts thereof, particularly for pharmaceutical use into the physiologically and pharmacologically acceptable salts thereof. The phrase "pharmaceutically acceptable" is employed herein to refer to those compounds, materials, compositions, and/or dosage forms which are, within the scope of sound medical judgement, suitable for use in contact with the tissue of human beings and animals without excessive toxicity, irritation, allergic response, or other problem or complication, and commensurate with a reasonable benefit/risk ratio. These salts may be present on the one hand as physiologically and pharmacologically acceptable acid addition salts of the compounds of formulas (I), (I'), (I"), (II') and (II") with inorganic or organic acids. On the other hand, the compound of formulas (I), (I'), (I"), (II') and (II") may be converted by reaction with inorganic bases into physiologically and pharmacologically acceptable salts with alkali or alkaline earth metal cations as counter-ion. The acid addition salts may be prepared for example using hydrochloric acid, hydrobromic acid, sulfuric acid, phosphoric acid, methanesulphonic acid, p-toluenesulfonic acid, acetic acid, fumaric acid, succinic acid, lactic acid, citric acid, tartaric acid or maleic acid. It is also possible to use mixtures of the above-mentioned acids. To prepare the alkali and alkaline earth metal salts of the compounds of formulas (I), (I'), (I"), (II') and (II") it is preferable to use the alkali and alkaline earth metal hydroxides and hydrides, of which the hydroxides and hydrides of the alkali metals, particularly sodium, potassium, magnesium, calcium, zinc and diethanolamine, are preferred, while sodium and potassium hydroxide are particularly preferred.

The invention relates to the compounds in question, optionally in the form of the individual optical isomers, diastereomers, mixtures of diastereomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulfonic acid.

The compounds of formula (I), (I'), (I"), (II') and (II") according to the invention may optionally be present as mixtures of diastereomeric isomers but may also be obtained as pure diastereoisomers. Preferred are the compounds with the specific stereochemistry of formula (I'), (I"), (II') and (II").

4 METHODS OF SYNTHESIS

The compounds according to the invention and their intermediates may be obtained using the methods described in the examples that follow, which may also be combined for this purpose with methods known to those skilled in the art and known from literature.

In particular, the invention provides processes for making compounds of any one of Formulas (I), (I'), (I"), (II') and (II").

Optimal reaction conditions and reaction times may vary depending on the particular reactants used. Unless otherwise specified, solvents, temperature, pressures and other reaction conditions, may be readily selected by one of ordinary skill in the art. Specific procedures are provided in the Synthetic Examples section. Typically, reaction progress may be monitored by thin layer chromatography (TLC) or liquid chromatography mass spectrometry (LC-MS), if desired, and intermediates and products may be purified by chromatography on silica gel, HPLC and/or by recrystallization. The examples which follow are illustrative and, as one skilled in the art will recognize, particular reagents or conditions could be modified as needed for individual compounds without undue experimentation. Starting materials and intermediates used in the methods below are either commercially available or easily prepared from commercially available materials by those skilled in the art.

A compound of any one of Formulas (I), (I'), (I"), (II') and (II") may be prepared by the methods outlined in Schemes 1-3, wherein $R^1$, $R^2$, $R^3$, $R^4$, $R^5$, $R^6$, $R^7$ and G are defined as in claim 1:

Scheme 1

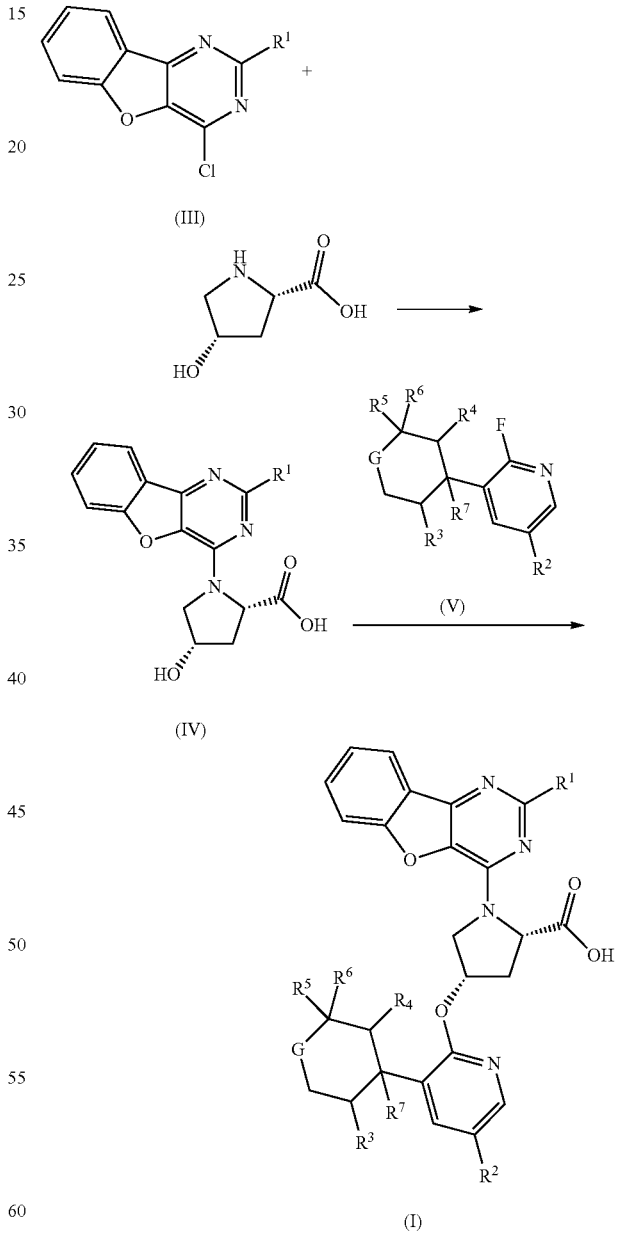

As illustrated in Scheme 1, the reaction of chloro-pyrimidine (III) with (2S,4S)-4-hydroxypyrrolidine-2-carboxylic acid in the presence of a suitable base such as DIPEA, $K_2CO_3$, or NaH in a suitable solvent such as DMSO or DMF provides a hydroxyproline derivative of formula (IV). Reaction of the hydroxyproline derivative (IV) with a pyridine derivative of formula (V) in the presence of a suitable base such as NaH in a suitable solvent such as DMA, DMF or NMP provides a compound of formula (I).

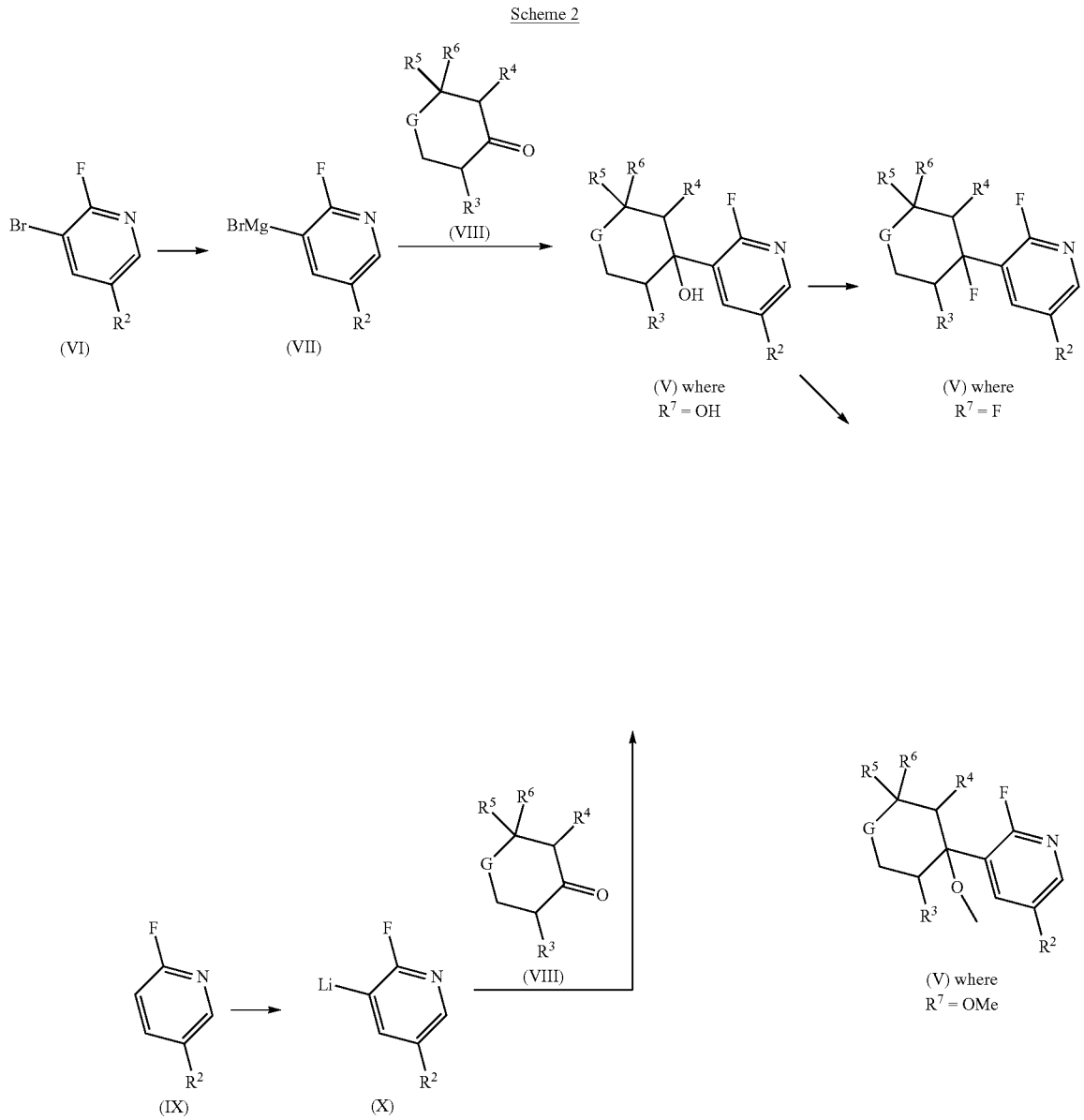

Scheme 2

As illustrated in Scheme 2, the reaction of 3-bromo-2-fluoropyridine derivative (VI) with isopropylmagnesium chloride lithium chloride complex in a suitable solvent such as THF provides the organomagnesium derivative (VII). Reaction of the organomagnesium derivative (VII) in presence of a ketone derivative of formula (VIII) in a solvent such as THF gives the derivative of formula (V) where $R^7$=OH. Alternatively, the reaction of 2-fluoropyridine derivative (IX) with a base such as lithium diisopropylamide in a solvent such as THF provides the organolithium derivative (X). Reaction of the organolithium derivative (X) in the presence of the ketone derivative of formula (VIII) in a solvent such as THF provides a compound of formula (V) where $R^7$=OH.

Substitution of the alcohol functional group ($R^7$=OH) of a compound of formula (V) in presence of fluorinating agents such as bis(2-methoxyethyl) aminosulfur trifluoride (Deoxo-Fluor©) or diethylaminosulfur trifluoride (DAST) in a solvent such as dichloromethane provides a compound of formula (V) where $R^7$=F.

Alkylation of the alcohol functional group ($R^7$=OH) of a compound of formula (V) in the presence of an alkylating reagent such a methyl iodide with a base such as NaH in a solvent such as DMF gives the corresponding compound of formula (V) where $R^7$=OMe.

A compound of formula (III) can be prepared as illustrated in Scheme 3.

Scheme 3

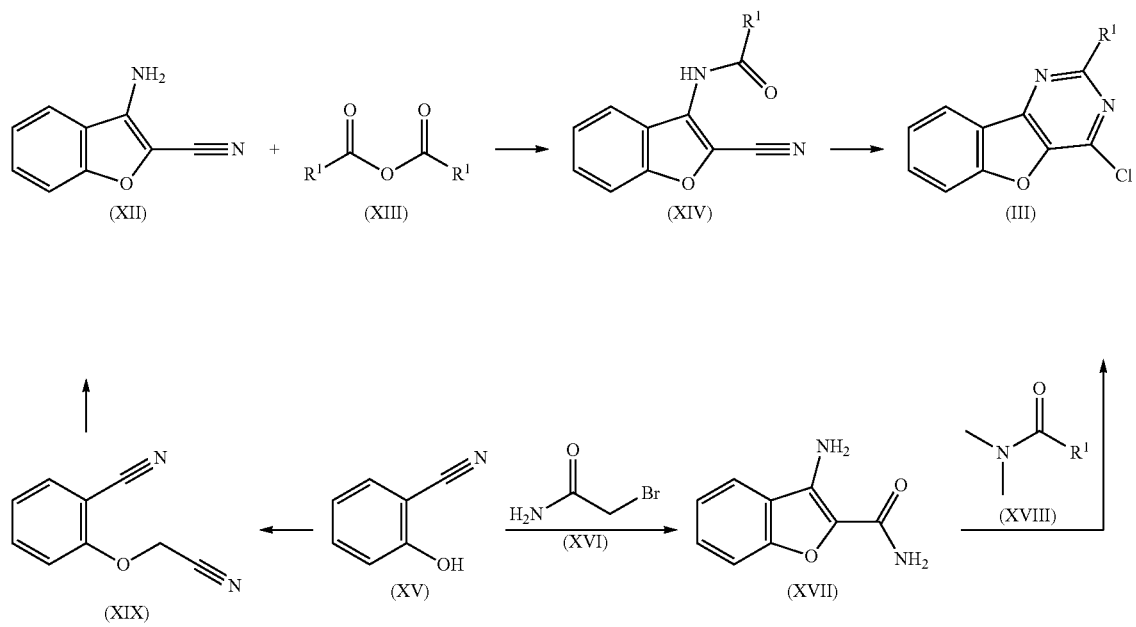

The reaction of 3-amino-1-benzofuran-2-carbonitrile (XII) with an anhydride of formula (XIII) (or the corresponding acid) in a suitable solvent such as pyridine provides amide (XIV). Upon reaction with a suitable chlorination reagent such as phosphorus pentachloride in a suitable solvent such as sulfolane, amide (XIV) cyclizes to form a compound of formula (III).

In an alternative synthetic sequence, 2-hydroxybenzonitrile (XV) reacts with 2-bromoacetamide (XVI) in the presence of a suitable base such as $K_2CO_3$ or KOH in a suitable solvent such as ethanol to provide 3-amino-1-benzofuran-2-carboxamide (XVII). Compound (XVII) reacts with a dimethylamide of formula (XVIII) in the presence of a suitable chlorination reagent such as phosphorus oxychloride and forms a compound of formula (III).

In another alternative synthetic sequence, 2-hydroxybenzonitrile (XV) reacts with bromoacetonitrile in the presence of a suitable base such as $K_2CO_3$ in a suitable solvent such as DMF to yield 2-(cyanomethoxy)benzonitrile (XIX). This compound cyclizes in the presence of a suitable base such as tert-butoxide in a suitable solvent such as THF to form 3-amino-1-benzofuran-2-carbonitrile (XII), and can be converted into a compound of formula (XIV) and subsequently into a compound of formula (III) as described above.

Synthesis of Intermediates

Intermediate 1

Intermediate 1.1 (General Procedure)

N-(2-cyano-1-benzofuran-3-yl)-2,2,2-trifluoroacetamide

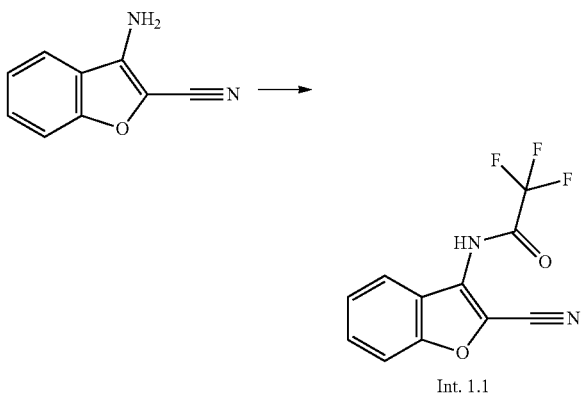

Int. 1.1

TFAA (5.31 g, 25.3 mmol) was added to a mixture of 3-amino-1-benzofuran-2-carbonitrile (4.00 g, 25.3 mmol) in pyridine (40.0 mL) at RT. The mixture was stirred at 25° C. for 12 h, then concentrated under reduced pressure, diluted with 20 mL water and extracted with EtOAc. The combined organic layers were washed with brine, dried over $Na_2SO_4$, filtered and concentrated under reduced pressure. The residue was purified by column chromatography (silica gel; PE/EtOAc=20/1 to 5/1).

ESI-MS: 254.9 [M+H]$^+$ $R_t$ (HPLC): 0.56 min (method A)

The following intermediate was prepared according to the general procedure (INTERMEDIATE 1.1) described above:

| Int. | Starting materials | Structure | ESI-MS | $R_t$ (HPLC) or $R_f$ (TLC): |
|---|---|---|---|---|
| 1.2 | 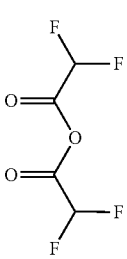 | 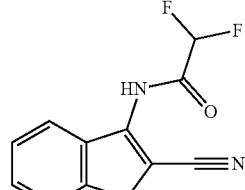 | 237 [M + H]⁺ | $R_f$(TLC): 0.6 (PE/EtOAc = 2/1) |

Intermediate 2

Intermediate 2.1 (General Procedure)

6-Chloro-4-(trifluoromethyl)-8-oxa-3,5-diazatricyclo[7.4.0.0²,⁷]trideca-1(9),2(7),3,5,10,12-hexaene

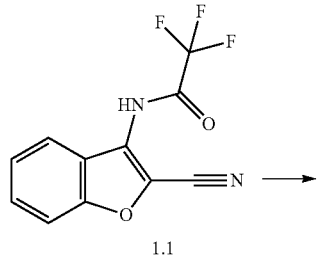

1.1

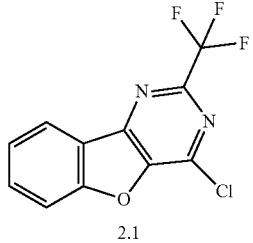

2.1

To a solution of N-(2-cyano-1-benzofuran-3-yl)-2,2,2-trifluoroacetamide (INTERMEDIATE 1.1, 4.00 g, 15.7 mmol) in sulfolane (10.0 mL) was added phosphorus pentachloride (13.1 g, 63.0 mmol). The mixture was stirred at 110° C. for 16 h. After cooling to RT, the reaction mixture was poured into ice water and extracted with EtOAc. The combined organic layers were washed with brine, dried over Na₂SO₄, filtered and concentrated under reduced pressure. The residue was purified by column chromatography (silica gel; PE/EtOAc=20/1 to 10/1).

ESI-MS: 273 [M+H]⁺
$R_t$ (HPLC): 0.71 min (method A)

The following intermediate was prepared according to the general procedure (INTERMEDIATE 2.1) described above:

| Int. | Starting material | Structure | ESI-MS | $R_t$(HPLC) or $R_f$(TLC): |
|---|---|---|---|---|
| 2.2 | 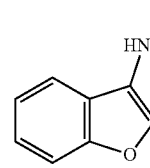 Int. 1.2 | 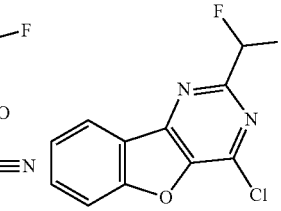 | 255/257 [M + H]⁺ | $R_f$(TLC): 0.6 (PE/EtOAc = 5/1) |

Intermediate 3

Intermediate 3.1 (General Procedure)

(2S,4S)-4-Hydroxy-1-[4-(trifluoromethyl)-8-oxa-3,5-diazatricyclo[7.4.0.0$^{2,7}$]-trideca-1(9),2(7),3,5,10,12-hexaen-6-yl]pyrrolidine-2-carboxylic acid

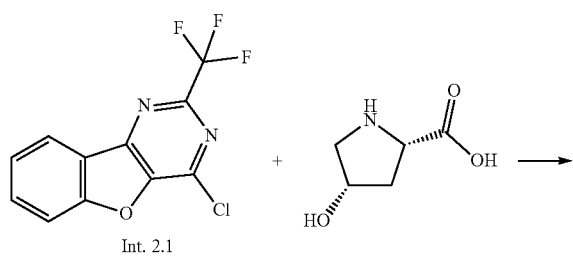

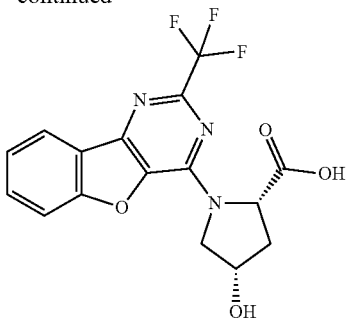

Int. 3.1

To a preheated mixture of (2S,4S)-4-hydroxypyrrolidine-2-carboxylic acid (1.44 g, 11.0 mmol) in DMSO (25.0 mL) at 110° C. was added DIPEA (3.90 g, 30.0 mmol) and 6-chloro-4-(trifluoromethyl)-8-oxa-3,5-diazatricyclo[7.4.0.0$^{2,7}$]trideca-1(9),2(7),3,5,10,12-hexaene (INTERMEDIATE 2.1, 2.73 g, 10.0 mmol). Stirring was continued at 110° C. for 10 min. The heating was removed, and the reaction mixture added dropwise into water and acidified with 4M HCl. The precipitate was filtered and dried.

ESI-MS: 368 [M+H]$^+$

R$_t$ (HPLC): 0.50 min (method A)

The following intermediate was prepared according to the general procedure (INTERMEDIATE 3.1) described above:

| Int. | Starting material | Structure | ESI-MS | R$_t$ (HPLC) [min] (method) | Reaction conditions |
|---|---|---|---|---|---|
| 3.2 | | 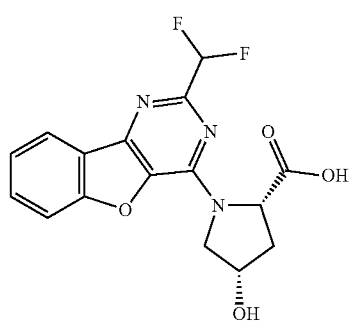 [SMILES: O=C(O)[C@@H]1C[C@H](O)CN1c1nc(C(F)F)nc2c1oc1ccccc12] | 350 [M + H]$^+$ | 0.26 (F) | solvent: DMSO, 110° C., 10 min |

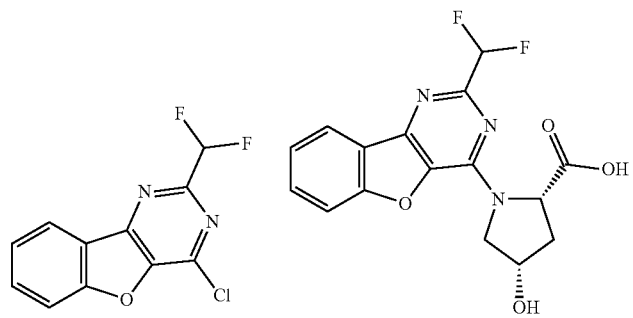

Preparation of Ketone Precursors

Intermediate 4

Methyl 3-[(3-methoxy-3-oxopropyl)sulfanyl]-3-methylbutanoate

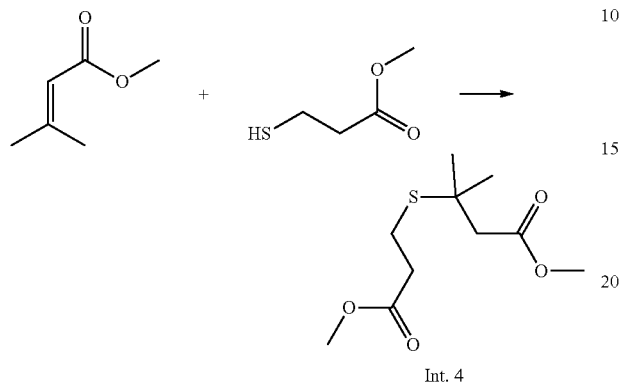

Int. 4

An ice-cooled mixture of 3-methyl-but-2-enoic acid methyl ester (14.2 g, 124 mmol), benzyltrimethylammonium hydroxide solution in MeOH (40% in MeOH, 1.0 g, 6.2 mmol) and piperidine (8.5 g, 99.8 mmol) in MeOH (50 mL) was stirred at 0° C. for 15 min. Thereafter was added dropwise methyl 3-mercaptopropionate (15.0 g, 125 mmol) at 0° C. The reaction mixture was heated to 60° C. and stirred for 24 h. After cooling to RT, diethyl ether (50 mL) was added and the mixture was poured into a 10% aqueous $H_2SO_4$ solution and extracted with diethylether thrice. The combined organic layers were washed with saturated aqueous $NaHCO_3$ solution and brine, dried over sodium sulfate, filtered and concentrated to afford the desired intermediate, which was used as such for the next step.

$R_f$ (TLC): 0.5 (PE/EtOAc=1/0)

$^1$H NMR (300 MHz, Chloroform-d) in ppm: 3.63 (s, 3H), 3.61 (s, 3H), 2.79-2.71 (m, 2H), 2.55-2.46 (m, 4H), 1.37 (s, 6H).

Intermediate 5

Methyl 6,6-dimethyl-4-oxothiane-3-carboxylate

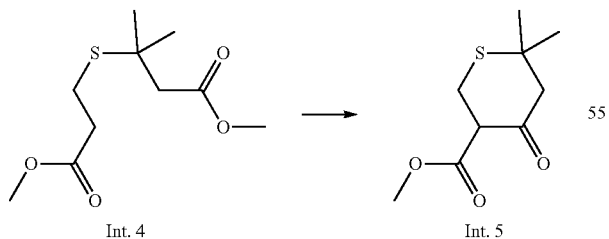

Int. 4    Int. 5

To a solution of LDA (82.3 g, 768 mmol) at −78° C. was added slowly a solution of methyl 3-[(3-methoxy-3-oxopropyl)sulfanyl]-3-methylbutanoate (INTERMEDIATE 4, 60.0 g, 256 mmol) in THF (300 mL). The mixture was stirred at 15° C. for 12 h. The reaction mixture was diluted with 10% aqueous $H_2SO_4$ solution, then extracted with petroleum ether. The organic phase was washed with brine, dried over sodium sulfate, filtered and concentrated under reduced pressure. The crude product was distilled under reduced pressure at 120° C.

$R_f$ (TLC): 0.7 (PE/EtOAc=5/1)

ESI-MS: 203 [M+H]$^+$ $R_t$ (LC-MS): 1.014 min (method X)

Intermediate 6

2,2-Dimethylthian-4-one

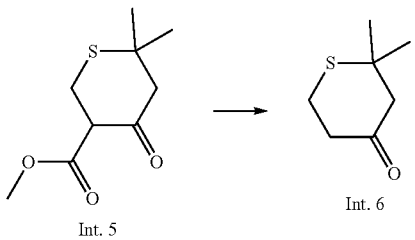

Int. 5    Int. 6

A mixture of methyl 6,6-dimethyl-4-oxothiane-3-carboxylate (INTERMEDIATE 5, 40.0 g, 98.9 mmol) in a 10% aqueous $H_2SO_4$ solution (900 mL) was stirred at 110° C. for 12 h. The reaction mixture was extracted with petroleum ether, and the combined organic layers were washed with saturated aqueous $NaHCO_3$ solution and brine, dried over $Na_2SO_4$, filtered, and concentrated under reduced pressure. The residue was purified by column chromatography on silica gel (petroleum ether/EtOAc, 100:0 to 85:15) to afford the corresponding intermediate.

ESI-MS: 144 [M]$^+$ $R_f$ (TLC): 0.4 (PE/EtOAc=5/1)

Intermediate 7

2,2-Dimethyl-1-I-6-thiane-1,1,4-trione

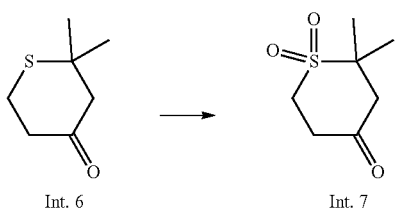

Int. 6    Int. 7

To a mixture of 2,2-dimethylthian-4-one (INTERMEDIATE 6, 9.00 g, 62.4 mmol) in EtOH (90 mL) was added mCPBA (16.2 g, 93.9 mmol). The mixture was stirred at RT for 2 h, then filtered and the filtrate was concentrated under reduced pressure. The mixture was purified by column chromatography on silica gel (petroleum ether/EtOAc, 85:15 to 65:35) to afford the corresponding intermediate.

$R_f$ (TLC): 0.3 (PE/EtOAc=1/1)

$^1$H NMR (300 MHz, Chloroform-d) in ppm: 3.33-3.40 (m, 2H), 2.84-2.97 (m, 2H), 2.81 (s, 2H), 1.45 (s, 6H).

Intermediate 8

2,2,5-Trimethyl-1-I-6-thiane-1,1,4-trione

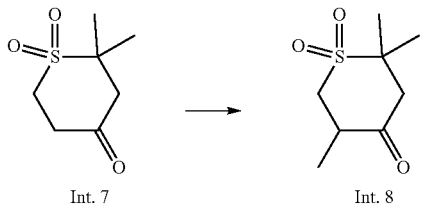

To a solution of LDA (1M in THF/hexanes, 14.8 mL, 14.8 mmol) in 10.0 mL THF, cooled at −78° C., was slowly added a mixture of 2,2-dimethyl-1-I-6-thiane-1,1,4-trione (INTERMEDIATE 7, 2.0 g, 11.4 mmol) and HMPA (2.6 mL, 14.8 mmol) in THF (15 mL), keeping the temperature of the reaction mixture below −60° C. After completed addition, the mixture was stirred at −78° C. for 20 min, after which a solution of methyl iodide (1.4 mL, 22.7 mmol) in THF (10 mL) was added slowly. The reaction mixture was further stirred at −78° C. for 2 h, then allowed to reach RT and stirred at RT for 30 min. The reaction mixture was neutralized at 0° C. by adding an aqueous NH$_4$Cl solution (20 mL) followed by an aqueous 4M HCl solution (10 mL). After phase separation, the organic layer was washed with brine, and the organic phase was dried over Na$_2$SO$_4$, filtered and concentrated under reduced pressure. The crude product was purified by column chromatography on silica gel (CH/EtOAc, 90:10 to 0:100).

ESI-MS: 191 [M+H]$^+$
GC-MS: 3.57 min (method GC01)

Intermediate 9

3-Methylthian-4-one

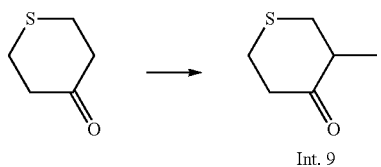

To a mixture of thian-4-one (20.0 g, 172 mmol) and HMPA (39 mL, 224 mmol) in THF (100 mL) at −78° C. was added a LDA solution (2M in THF/heptane, 100 mL, 200 mmol) and the resulting mixture was stirred at −60° C. for 1 h. Then methyl iodide (16.1 mL, 258 mmol) was added dropwise and the mixture was allowed to reach RT while stirring over 4 h. The reaction mixture was neutralized by adding a half-saturated NH$_4$Cl aqueous solution (150 mL), and it was acidified to about pH 5 by adding a 4N HCl aqueous solution. After extraction with EtOAc, the combined organic phases were washed with brine and dried over Na$_2$SO$_4$, filtered and concentrated under reduced pressure. The mixture was purified by column chromatography on silica gel (CH/EtOAc, 6-22% gradient).

ESI-MS: 130 [M]$^+$
R$_f$(TLC): 0.65 (cyclohexane/EtOAc=3/1)

Intermediate 10

3-Methyl-1-I-6-thiane-1,1,4-trione

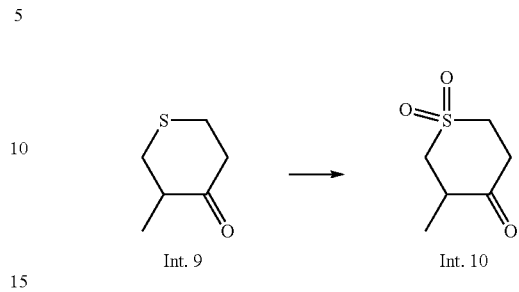

To a mixture of 3-methylthian-4-one (INTERMEDIATE 9, 1.3 g, 8.64 mmol) in 11.0 mL ACN was added a 0.00057M Na$_2$.EDTA aqueous solution (7.5 mL, 0.00428 mmol). To this mixture was added portion-wise over 20 min a mixture of oxone (15.9 g, 51.9 mmol) and NaHCO$_3$ (6.9 g, 82.1 mmol) in deionized water (7.5 mL). The reaction mixture was stirred at RT for 2 days. DCM (80 mL) was added and the mixture was filtered and rinsed with DCM. The filtrate was dried over MgSO$_4$ and concentrated under reduced pressure. The product was used for the next step without further purification.

ESI-MS: 161 [M−H]$^-$
R$_f$(TLC): 0.4 (PE/EtOAc=1/1)

Intermediate 11

8-tert-Butyl 7-methyl (7R)-1,4-dioxa-8-azaspiro[4.5]decane-7,8-dicarboxylate

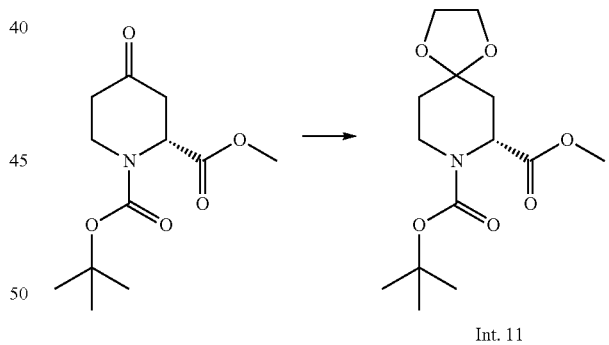

A round bottom flask equipped with a Dean-Stark trap was charged with 1-tert-butyl-2-methyl-(2R)-4-oxopiperidine-1,2-dicarboxylate (3.00 g, 11.7 mmol), 30.0 mL toluene, ethylene glycol (2.30 mL, 41.1 mmol) and p-TOSOH*H$_2$O (220 mg, 1.16 mmol) and the mixture was refluxed for 3 h. The reaction mixture was cooled to RT and washed with sat. NaHCO$_3$-solution. The aqueous phase was extracted with EtOAc and the organic phase was washed with brine, dried over sodium sulfate, filtered and evaporated. The product was used for the next step without further purification.

ESI-MS: 302 [M+H]$^+$
R$_t$ (HPLC): 0.54 min (method A)

Intermediate 12

(7R)-8-[(tert-Butoxy)carbonyl]-1,4-dioxa-8-azaspiro[4.5]decane-7-carboxylic acid

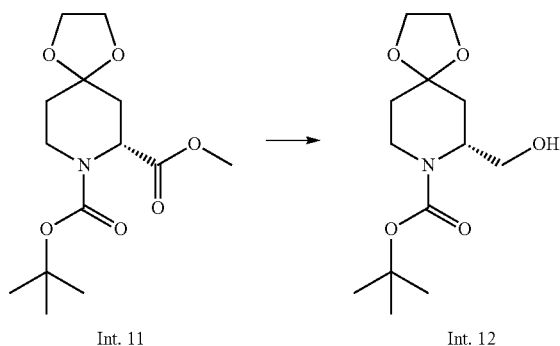 [SMILES: COC(=O)[C@H]1CC2(CCN1C(=O)OC(C)(C)C)OCCO2 ; CC(C)(C)OC(=O)N1CCC2(C[C@@H]1CO)OCCO2]

Int. 11 → Int. 12

LiAlH$_4$ (1M in THF, 8.30 mL, 8.30 mmol) was placed in a round bottom flask under argon atmosphere. A mixture of 8-tert-butyl 7-methyl (7R)-1,4-dioxa-8-azaspiro[4.5]decane-7,8-dicarboxylate (INTERMEDIATE 11, 1.00 g, 3.32 mmol) in 20.0 mL THF was added and the resulting reaction mixture was stirred at RT for 15 min. Water (0.35 mL) was added carefully, followed by 4M aqueous sodium hydride solution (1.05 mL), and again water (1.35 mL). The reaction mixture was stirred at RT for 30 min, then filtered through Celite, washed with THF and concentrated. The residue was purified by column chromatography (silica gel; CH/EtOAc=60/40 to 40/60).

ESI-MS: 274 [M+H]$^+$

R$_t$ (HPLC): 0.43 min (method A)

Intermediate 13

(7R)-1,4-Dioxa-8-azaspiro[4.5]decane-7-carboxylic acid

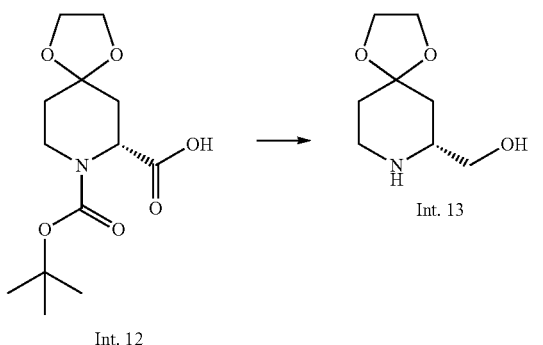 [SMILES: CC(C)(C)OC(=O)N1CCC2(C[C@@H]1C(=O)O)OCCO2 ; OC[C@H]1CC2(CCN1)OCCO2]

Int. 12

To (7R)-8-[(tert-butoxy)carbonyl]-1,4-dioxa-8-azaspiro[4.5]decane-7-carboxylic acid (INTERMEDIATE 12, 270 mg, 0.990 mmol) was added HCl (4M in dioxane, 5.00 mL, 20.0 mmol) and the mixture was stirred at RT for 1 h. The reaction mixture was concentrated, taken up in diethylether and reconcentrated. The residue was used without further purification for the next step.

ESI-MS: 174 [M+H]$^+$

R$_t$ (HPLC): 0.15 min (method A)

Intermediate 14

(8aR)-Hexahydrospiro[[1,3]oxazolo[3,4-a]pyridine-7,2'-[1,3]dioxolan]-3-one

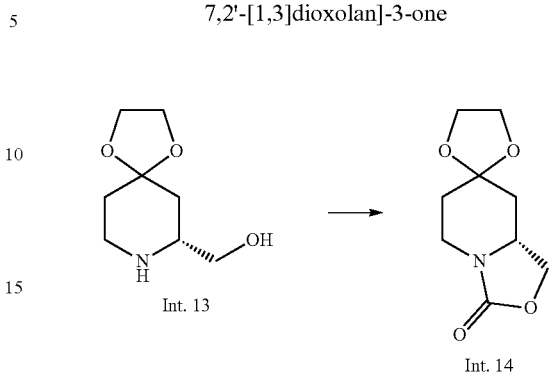

Int. 13 → Int. 14

To (7R)-1,4-dioxa-8-azaspiro[4.5]decane-7-carboxylic acid (INTERMEDIATE 13, 200 mg, 0.95 mmol) in 3.00 mL THF was added DIPEA (332 µL, 1.91 mmol) and 1,1'-carbonyldiimidazole (160 mg, 0.99 mmol) and the mixture was stirred at RT overnight. The reaction mixture was diluted with diethylether and washed with diluted aqueous HCl. The organic phase was washed with brine, dried over sodium sulfate, filtered and evaporated.

ESI-MS: 200 [M+H]$^+$

R$_t$ (HPLC): 0.26 min (method A)

Intermediate 15

(8aR)-Hexahydro-1H-[1,3]oxazolo[3,4-a]pyridine-3,7-dione

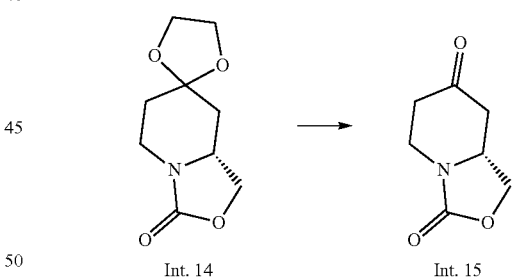

Int. 14 → Int. 15

Concentrated sulfuric acid (750 mL, 14.0 mmol) was added dropwise to a mixture of (8aR)-hexahydrospiro[[1,3]oxazolo[3,4-a]pyridine-7,2'-[1,3]dioxolan]-3-one (INTERMEDIATE 14, 600 mg, 3.01 mmol) in 7.00 mL acetone and 7.00 mL water, and the mixture was stirred at 70° C. overnight. The acetone was removed in vacuo and the residue was partitioned between EtOAc and water. The organic phase was separated, and the aqueous phase was extracted with EtOAc twice. The combined organic phases were washed with brine, dried over sodium sulfate, filtered and concentrated. The residue was azeotroped with n-heptane.

ESI-MS: 156 [M+H]$^+$

R$_t$ (HPLC): 0.14 min (method A)

Intermediate 16

Methyl 2-cyclopropylideneacetate

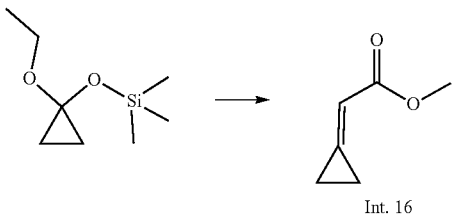
Int. 16

This intermediate was prepared as described in WO 2007/107243, p. 78. A mixture of [(1-ethoxycyclopropyl)oxy]trimethylsilane (2.00 g, 11.5 mmol) in toluene (4.0 mL) was slowly added to a mixture of methyl (triphenylphosphoranylidene)acetate (5.00 g, 15.0 mmol) and benzoic acid (0.200 g, 1.49 mmol) in toluene (28.0 mL). The reaction mixture was stirred at 80° C. for 16 h. Following careful evaporation of the solvent, the mixture was purified by column chromatography on silica gel (PE/DCM, 100:0 to 0:100).

ESI-MS: 112 [M]+

$R_f$ (TLC): 0.66 (CH/EtOAc=70/30)

Intermediate 17

Methyl 3-{[1-(2-methoxy-2-oxoethyl)cyclopropyl]sulfanyl}propanoate

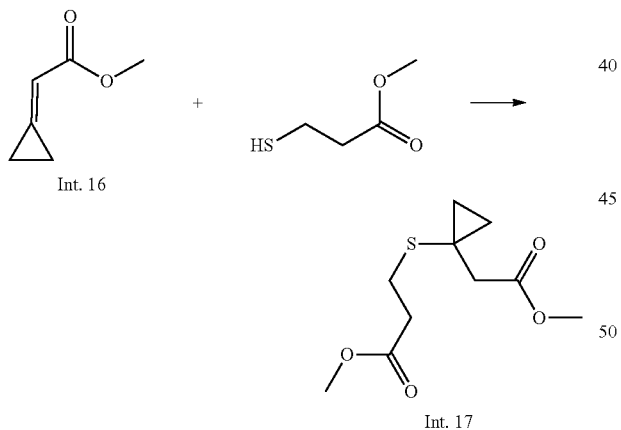
Int. 17

Methyl 3-mercaptopropionate (1.31 g, 10.9 mmol) was added dropwise to a mixture of methyl 2-cyclopropylideneacetate (INTERMEDIATE 16, 1.55 g, 11.5 mmol) and triethylamine (112 mg, 1.09 mmol). The resulting mixture was stirred at 60° C. for 16 h. After reaction completion as monitored by GC/MS, the mixture was diluted with DCM and cyclohexane and purified by column chromatography on silica gel (CH/EtOAC, 93:7 to 40:60).

ESI-MS: 233 [M+H]+

$R_t$ (GC/MS): 3.80 min (method GC01)

$R_f$ (TLC): 0.53 (CH/EtOAc=70/30)

Intermediate 18

Methyl 7-oxo-4-thiaspiro[2.5]octane-6-carboxylate

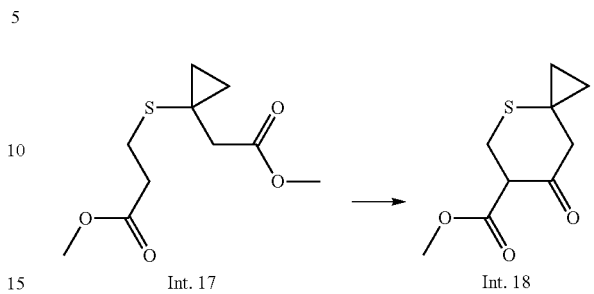
Int. 17    Int. 18

Under argon atmosphere a mixture of aluminum trichloride (2.15 g, 15.3 mmol) and 19.0 mL DCM was cooled to 0° C. Triethylamine (2.15 mL, 15.3 mmol) was added slowly over 5 min. The reaction mixture was cooled to −5° C. with an acetone/ice bath, and a solution of methyl 3-{[1-(2-methoxy-2-oxoethyl)cyclopropyl]-sulfanyl}propanoate (INTERMEDIATE 17, 1.25 g, 5.11 mmol) in 6.00 mL DCM was added slowly over 5 min, while keeping the reaction temperature between −5° C. and 0° C. Upon complete addition of the reagents, the reaction mixture was stirred at 0° C. for 1 h, then at RT for an additional 1.5 h. After reaction completion as monitored by GC/MS, the mixture was poured into water, then acidified with an aqueous 1N $H_2SO_4$ solution. The layers were separated, and the aqueous phase was extracted with DCM. The combined organic phases were washed with water and brine and dried over $Na_2SO_4$, filtered and concentrated under reduced pressure. The residue was purified by column chromatography (silica gel, CH/EtOAC, 93:7 to 40:60) to afford the title compound.

ESI-MS: 201 [M+H]+

$R_t$ (GC/MS): 3.65 min (method GC01)

$R_f$ (TLC): 0.59 (CH/EtOAc=70/30)

Intermediate 19

4-Thiaspiro[2.5]octan-7-one

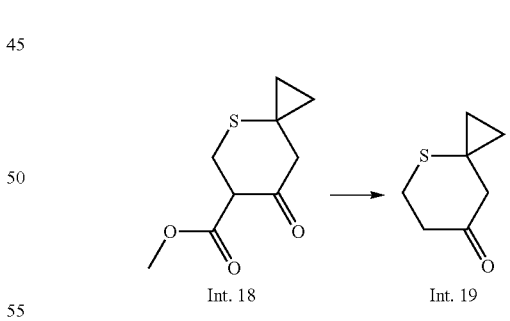
Int. 18    Int. 19

A mixture of methyl 7-oxo-4-thiaspiro[2.5]octane-6-carboxylate (INTERMEDIATE 18, 600 mg, 2.85 mmol) in aqueous 1M $H_2SO_4$ solution (25.0 mL) was stirred for at 110° C. for 5.5 h. The reaction mixture was cooled to RT, neutralized by adding an aqueous saturated $NaHCO_3$ solution and extracted with DCM thrice. The combined organic layers were dried over sodium sulfate, filtered and concentrated under reduced pressure to afford the corresponding intermediate.

ESI-MS: 143 [M−H]−

$R_f$ (TLC): 0.50 (CH/EtOAc=70/30)

Intermediate 20

Methyl 2-(oxetan-3-ylidene)acetate

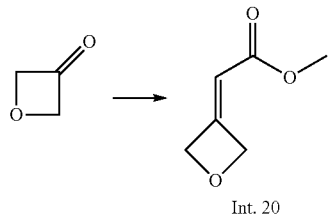

A solution of oxetan-3-one (10.2 g, 142 mmol) in 20.0 mL DCM at 0° C. was added dropwise to a precooled solution of methyl (triphenylphosphoranylidene)acetate (49.7 g, 149 mmol) in 180 mL DCM. After stirring at RT for 90 min, the mixture was concentrated under reduced pressure, diethyl ether (400 mL) was added and the mixture was sonicated at reflux temperature for a few minutes. Subsequently, the mixture was stirred at 0° C. for 15 min, cooled to −15° C. and stirred for 15 min. Then, the suspension was filtered, and the solid was washed with ice-cold diethyl ether thoroughly. The combined filtrates were concentrated under reduced pressure and purified by column chromatography on silica gel (CH/EtOAc, 75:25).

ESI-MS: 129 [M+H]$^+$
$R_t$ (HPLC): 0.26 min (method A)
$R_f$ (TLC): 0.42 (CH/EtOAc=70/30)

Intermediate 21

Methyl 3-{[3-(2-methoxy-2-oxoethyl)oxetan-3-yl]sulfanyl}propanoate

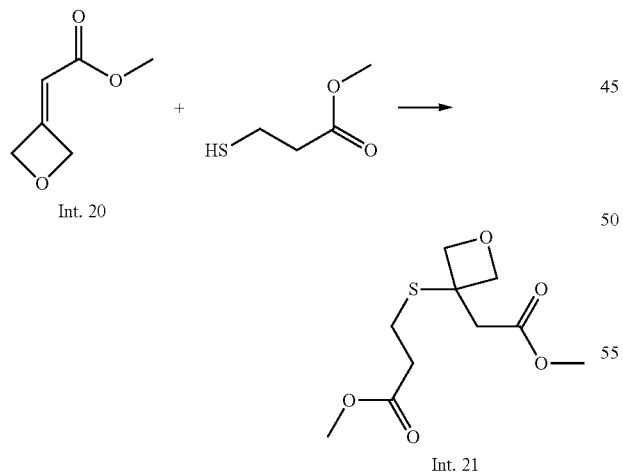

Methyl 3-mercaptopropionate (3.74 g, 29.6 mmol) was added dropwise to a mixture of methyl 2-(oxetan-3-ylidene)acetate (INTERMEDIATE 20, 4.19 g, 31.1 mmol) and triethylamine (302 mg, 2.96 mmol). The resulting mixture was stirred at 60° C. for 16 h. After reaction completion as monitored by GC/MS, the mixture was diluted with DCM and cyclohexane and directly purified by column chromatography on silica gel (CH/EtOAc, 93:7 to 40:60).

ESI-MS: 249 [M+H]$^+$
$R_t$ (GC/MS): 4.21 min (method GC01)
$R_f$ (TLC): 0.15 (CH/EtOAc=70/30)

Intermediate 22

Methyl 8-oxo-2-oxa-5-thiaspiro[3.5]nonane-7-carboxylate

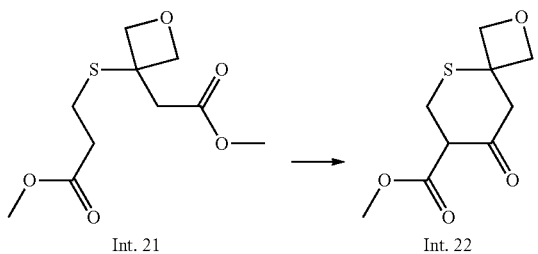

Under argon atmosphere a mixture of aluminum trichloride (17.7 g, 132 mmol) and 173 mL degassed DCM was cooled to 0° C. Triethylamine (18.6 mL, 132 mmol) was added slowly over 20 min. The reaction mixture was cooled to −5° C. with an acetone/ice bath, and a solution of methyl 3-{[3-(2-methoxy-2-oxoethyl)oxetan-3-yl]sulfanyl}-propanoate (INTERMEDIATE 21, 11.5 g, 44.1 mmol) in 58.0 mL DCM was added slowly over 20 min, while keeping the reaction temperature between −5° C. and 0° C. Upon complete addition of the reagents, the reaction mixture was stirred at 0° C. for 1 h, then at RT for an additional 2 h. After reaction completion as monitored by GC/MS, the mixture was poured into water, then acidified with an aqueous 1N H$_2$SO$_4$ solution and stirred for 30 min. The layers were separated, and the aqueous phase was extracted with DCM. The combined organic phases were washed with water and brine and dried over Na$_2$SO$_4$, filtered and concentrated under reduced pressure. The residue was purified by column chromatography on silica gel (CH/EtOAc, 93:7 to 40:60) to afford the title compound.

ESI-MS: 217 [M+H]$^+$
$R_t$ (GC/MS): 3.33 min (method GC01)
$R_f$ (TLC): 0.66 (CH/EtOAc=50/50)

Intermediate 23

2-Oxa-5-thiaspiro[3.5]nonan-8-one

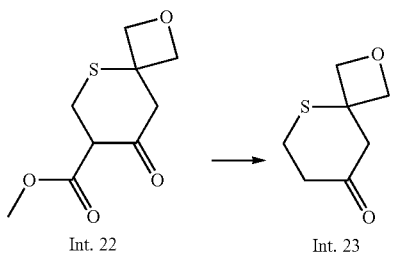

To a solution of methyl 8-oxo-2-oxa-5-thiaspiro[3.5] nonane-7-carboxylate (INTERMEDIATE 22, 1.00 g, 4.39 mmol) in 10.0 mL DMSO was added sodium chloride (282 mg, 4.83 mmol) and deionized water (0.28 mL, 13.2 mmol) and the resulting mixture was immediately heated at 130° C. for 4 h. After cooling to RT, diethylether (100 mL) and a 5% aqueous LiCl solution (100 mL) were added and the mixture was stirred at RT for 10 min. After phase separation, the aqueous layer was extracted with diethylether, and the combined organics were washed with brine, dried over Na$_2$SO$_4$, filtered and concentrated under reduced pressure. The mixture was purified by column chromatography on silica gel (CH/EtOAC, 90:10:12 to 0:100).

ESI-MS: 157 [M−H]$^-$

R$_f$ (TLC): 0.47 (CH/EtOAc=50/50)

Intermediate 24

Methyl 2-cyclobutylideneacetate

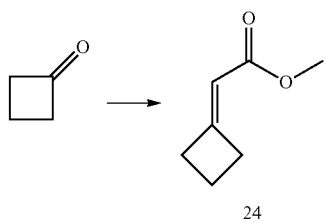

24

This intermediate was prepared as described in EP2192109, p. 52. A mixture containing phosphonoacetic acid methyl ester (7.3 g, 40.0 mmol) and sodium hydride (1.7 g, 38.0 mmol) in THF (120 mL) was stirred at 0° C. for 1 h, then a solution of cyclobutanone (2.1 g, 28.6 mmol) in THF (20 mL) was added dropwise. Following complete addition, the mixture was stirred at RT for 1.5 h. The reaction was neutralized by adding an aqueous saturated NH$_4$Cl solution (100 mL) and the mixture was extracted with hexane. The combined organic layers were washed with brine, dried over Na$_2$SO$_4$, filtered, carefully concentrated under reduced pressure (200 mbar at 45° C. water bath), and purified by column chromatography on silica gel (CH/DCM, 75:25 to 0:100).

ESI-MS: 127 [M+H]$^+$

R$_f$ (TLC): 0.20 (CH/DCM=50/50)

Intermediate 25

Methyl 3-{[1-(2-methoxy-2-oxoethyl)cyclobutyl]sulfanyl}propanoate

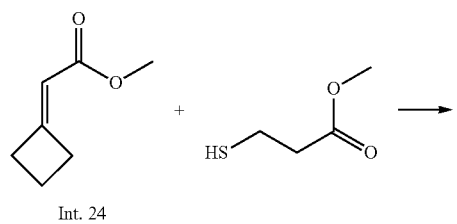

Int. 24

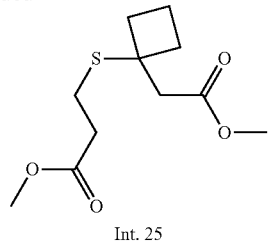

Int. 25

To a mixture containing methyl 2-cyclobutylideneacetate (INTERMEDIATE 24, 3.23 g, 24.3 mmol), piperidine (0.32 mL, 3.23 mmol), methanol (0.322 mL, 7.98 mmol) and benzyl-trimethylammonium hydroxide (40% in MeOH, 0.32 mL, 0.70 mmol) at 0° C. was added methyl 3-mercaptopropionate (2.85 mL, 24.3 mmol). The reaction mixture was warmed at 60° C. for 16 h. After reaction completion as monitored by GC/MS, the mixture was purified by column chromatography on silica gel (CH/EtOAC, 93:7 to 40:60).

ESI-MS: 247 [M+H]$^+$

R$_t$ (GC/MS): 4.12 min (method GC01)

R$_f$ (TLC): 0.49 (CH/EtOAc=70/30)

Intermediate 26

Methyl 8-oxo-5-thiaspiro[3.5]nonane-7-carboxylate

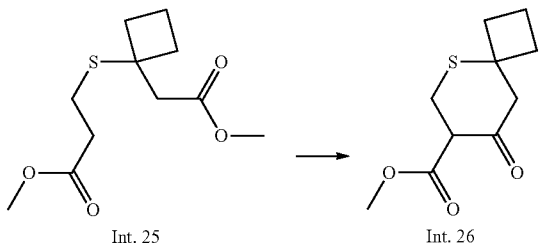

Int. 25    Int. 26

Under argon atmosphere a mixture of aluminum trichloride (7.50 g, 53.5 mmol) and 70.0 mL DCM was cooled to 0° C. Triethylamine (7.51 mL, 53.5 mmol) was added slowly over 10 min. The reaction mixture was cooled to −5° C. with an acetone/ice bath, and a solution of methyl 3-{[1-(2-methoxy-2-oxoethyl)cyclobutyl]sulfanyl}propanoate (INTERMEDIATE 25, 4.6 g, 17.8 mmol) in DCM (22.0 mL) was added slowly over 10 min, while keeping the reaction temperature between −5° C. and 0° C. Upon complete addition of the reagents, the reaction mixture was stirred at 0° C. for 1.5 h, then at RT for 1 h. The mixture was poured into water and acidified with an aqueous 1N H$_2$SO$_4$ solution. The layers were separated, and the aqueous phase was extracted with DCM. The combined organic phases were washed with water and brine and dried over Na$_2$SO$_4$, filtered and concentrated under reduced pressure. The residue was purified by column chromatography on silica gel (CH/EtOAC, 95:5 to 50:50) to afford the title compound.

ESI-MS: 215 [M+H]$^+$

R$_t$ (GC/MS): 3.15 min (method GC01)

R$_f$ (TLC): 0.65 (CH/EtOAc=70/30)

Intermediate 27

5-Thiaspiro[3.5]nonan-8-one

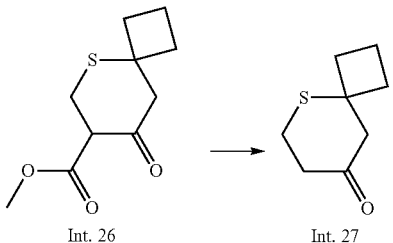

A solution of methyl 8-oxo-5-thiaspiro[3.5]nonane-7-carboxylate (INTERMEDIATE 26, 3.0 g, 13.4 mmol) in aqueous 1N $H_2SO_4$ solution (121 mL, 121 mmol) was stirred at 110° C. for 8 h. The reaction mixture was cooled, neutralized with an aqueous saturated $NaHCO_3$ solution and extracted with DCM. The combined organic phases were washed with brine, dried over $Na_2SO_4$, filtered and concentrated under reduced pressure.

ESI-MS: 155 $[M]^+$
$R_f$ (TLC): 0.56 (CH/EtOAc=70/30)

Intermediate 28

Intermediate 28.01 (General Procedure)

4-(5-Chloro-2-fluoropyridin-3-yl)-3-methyloxan-4-ol

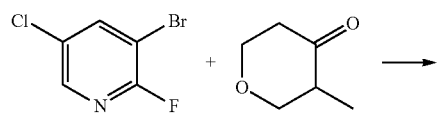

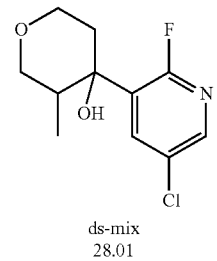

1) Grignard intermediate formation: Under argon, a degassed solution of 3-bromo-5-chloro-2-fluoropyridine (950 mg, 4.29 mmol) in 9.00 mL THF was cooled to −15° C. Isopropylmagnesium chloride lithium chloride complex (4.51 mL, 4.50 mmol) was added dropwise and the mixture was stirred for 10 min at −15° C.

2) Ketone addition: Then, a solution of 3-methyltetrahydropyranone (0.68 mL, 6.00 mmol) in 3.0 mL THF was added dropwise and after completed addition, stirring at −15° C. was continued for 30 min. The reaction mixture was carefully treated with 7.0 mL of 1.0 M aqueous hydrochloric acid at −15° C. Then, the cooling was removed and the mixture was stirred at RT for 10 min. After phase separation, THF was removed under reduced pressure. The aqueous phase was extracted with EtOAc twice. The combined organic phases were washed with water and brine, dried over sodium sulfate, filtered and evaporated. The residue was purified by HPLC (Sunfire, ACN/H2O/TFA) to afford a mixture of cis/trans diastereoisomers.

ESI-MS: 246/248 $[M+H]^+$
$R_t$ (HPLC): 0.42/0.46 min (method A)

The following compounds were prepared according to the general procedure (INTERMEDIATE 28.01) described above, starting from the appropriate aryl halogenide (3-bromo-5-chloro-2-fluoropyridine or 3,5-dibromo-2-fluoropyridine):

| Int. | stereochemistry | Starting material | Structure | ESI-MS | $R_t$ (HPLC) or $R_f$ (TLC) | Reaction conditions * |
|---|---|---|---|---|---|---|
| 28.02 | ds-mix | | 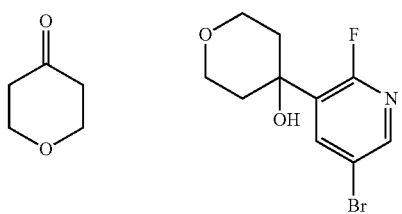 | 290/292 $[M + H]^+$ | $R_t$ (HPLC): 0.43/0.48 min method A | Solvent: THF 1) 10 min, −15° C. 2) 30 min, −15° C. |
| 28.03 | | | 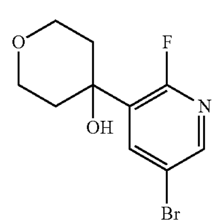 [SMILES: OC1(c2cc(Br)cnc2F)CCOCC1] | 276/278 $[M + H]^+$ | $R_t$ (HPLC): 0.39 min method A | Solvent: THF 1) 30 min, −78° C. 2) 30 min, −78° C. |

-continued

| Int. | stereochemistry | Starting material | Structure | ESI-MS | R$_t$ (HPLC) or R$_f$ (TLC) | Reaction conditions * |
|---|---|---|---|---|---|---|
| 28.04 | ds-mix | | 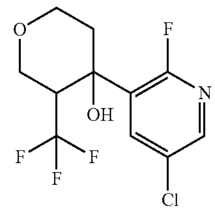 [SMILES: OC1(c2cc(Cl)cnc2F)CCOCC1C(F)(F)F] | — | R$_f$ (TLC): 0.4 (PE/EtOAc = 3/1) | Solvent: THF 1) 10 min, −15° C. 2) 24 h, −30° C. to RT |
| 28.05 | | | 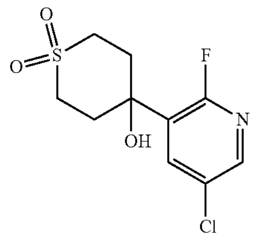 [SMILES: O=S1(=O)CCC(O)(c2cc(Cl)cnc2F)CC1] | 280/282 [M + H]$^+$ | R$_t$ (HPLC): 0.75 min method C | Solvent: THF 1) 10 min, −15° C. 2) 15 min, −15° C. |
| 28.06 | | | 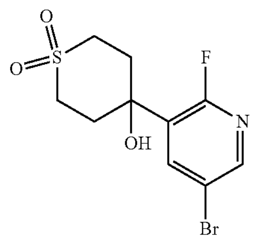 [SMILES: O=S1(=O)CCC(O)(c2cc(Br)cnc2F)CC1] | 324/326 [M + H]$^+$ | R$_t$ (HPLC): 0.36 min method A | Solvent: THF 1) 10 min, −15° C. 2) 30 min, −15° C. |
| 28.07 | rac | Int. 7 | 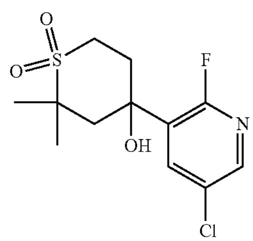 [SMILES: CC1(C)CC(O)(c2cc(Cl)cnc2F)CCS1(=O)=O] | 308 [M + H]$^+$ | R$_t$ (HPLC): 0.82 min method C | Solvent: THF 1) 10 min, −50° C. 2) 10 min, −50° C. |
| 28.08 | ds-mix | Int. 10 | 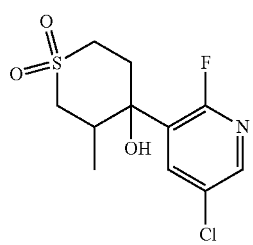 [SMILES: CC1CS(=O)(=O)CCC1(O)c1cc(Cl)cnc1F] | 293/295 [M + H]$^+$ | R$_t$ (HPLC): 0.80 min method C | Solvent: THF 1) 10 min, −50° C. 2) −50° C. to RT |
| 28.09 | | | 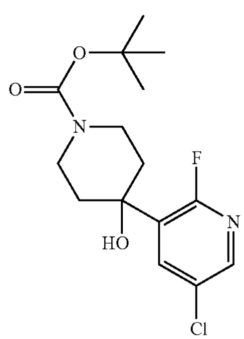 | 274/276 [M + H − tBu]$^+$ | R$_t$ (HPLC): 1.01 min method C | Solvent: THF 1) 10 min, −50° C. 2) −50° C. to RT |

-continued

| Int. | stereochemistry | Starting material | Structure | ESI-MS | $R_t$ (HPLC) or $R_f$ (TLC) | Reaction conditions * |
|---|---|---|---|---|---|---|
| 28.10 | ds-mix | (ketone from 3-methyl-N-Boc-piperidin-4-one) | tert-butyl 4-(5-chloro-2-fluoropyridin-3-yl)-4-hydroxy-3-methylpiperidine-1-carboxylate | 289/291 [M + H − tBu]⁺ | $R_t$ (HPLC): 0.64/0.68 min (A) | Solvent: THF 1) 55 min, −78° C. 2) 0.1 eq LaCl₃·LiCl complex, −65° C. to RT |
| 28.11 | ds-rac | Int. 15 | bicyclic oxazolidinone with 5-chloro-2-fluoropyridin-3-yl and OH | 287/289 [M + H]⁺ | $R_t$ (HPLC): 0.33/0.37 min method A | Solvent: THF 1) 15 min, −10° C. 2) 30 min, −10° C. |
| 28.12 | rac | Int. 19 | thia-spiro[cyclopropane] with 5-chloro-2-fluoropyridin-3-yl and OH | 274/276 [M + H]⁺ | $R_t$ (HPLC): 0.61 min method A | Solvent: THF 1) −78° C. to −15° C., 10 min 2) −15° C. to RT |
| 28.13 | rac | Int. 23 | thia-oxa-spiro with 5-chloro-2-fluoropyridin-3-yl and OH | 290/292 [M + H]⁺ | $R_t$ (HPLC): 0.48 min method A | Solvent: THF 1) 10 min, −78° C. 2) 15 min, −78° C. and 15 min, −15° C. |
| 28.14 | rac | Int. 27 | thia-spiro[cyclobutane] with 5-chloro-2-fluoropyridin-3-yl and OH | 288/290 [M + H]⁺ | $R_t$ (HPLC): 0.64 min (A) | Solvent: THF 1) 1 h, −78° C. and 10 min, RT 2) 30 min, −78° C. to RT |

\* 1) Grignard intermediate formation; 2) ketone addition

Intermediate 29

Intermediate 29.01 and Intermediate 29.02 (General Procedure)

racemic trans 5-Bromo-2-fluoro-3-[4-fluoro-3-methyloxan-4-yl]pyridine and racemic cis 5-Bromo-2-fluoro-3-[4-fluoro-3-methyloxan-4-yl]pyridine

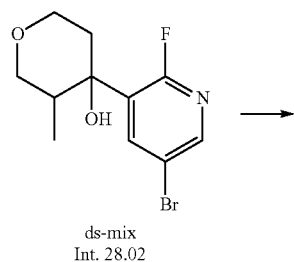

ds-mix
Int. 28.02

→

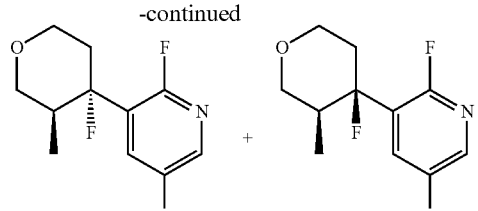

rac-trans  rac-cis
Int. 29.01  Int. 29.02

To a solution of 4-(5-bromo-2-fluoropyridin-3-yl)-3-methyloxan-4-ol (INTERMEDIATE 28.02, 455 mg, 1.57 mmol) in DCM (8.00 mL) at 0° C. was added dropwise bis(2-methoxyethyl) aminosulfur trifluoride (DeoxoFluor) (50% in Toluol, 867 µL, 2.35 mmol). The reaction mixture was stirred at 0° C. for 1 h and then poured into an aqueous NaHCO₃ solution. After phase separation, the aqueous phase was extracted with DCM, and the combined organics were dried over sodium sulfate, filtered and evaporated. The residue was purified by preparative HPLC (Xbridge, ACN/H₂O/TFA) to afford both diastereoisomers Int. 29.01 and Int. 29.02.

Int. 29.01
ESI-MS: 292/294 [M+H]⁺
R$_t$ (HPLC): 0.57 min (method A)
Int. 29.02
ESI-MS: 292/294 [M+H]⁺
R$_t$ (HPLC): 0.62 min (method A)

The following compounds were prepared according to the general procedure (INTERMEDIATE 29.02) described above:

| Int. | Stereo-chemistry | Starting material | Structure | ESI-MS | R$_t$ (HPLC) or R$_f$ (TLC) | Reaction conditions |
|---|---|---|---|---|---|---|
| 29.03 | rac-cis | Int. 28.01 | 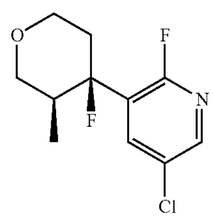 [SMILES: C[C@H]1COCC[C@]1(F)c1cc(Cl)cnc1F] | 248/250 [M + H]⁺ | R$_t$ (HPLC): 0.90 min method Z | Reagent: DeoxoFluor Solvent: DCM 1 h, 0° C. |
| 29.04 | | 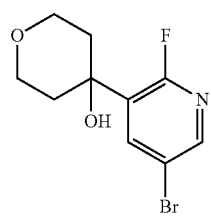 [SMILES: OC1(c2cc(Br)cnc2F)CCOCC1] Int. 28.03 | 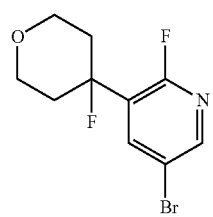 [SMILES: Fc1ncc(Br)cc1C1(F)CCOCC1] | 278/280 [M + H]⁺ | R$_t$ (HPLC): 0.55 min method A | Reagent: DeoxoFluor Solvent: DCM 1 h, 0° C. |

| Int. | Stereo-chemistry | Starting material | Structure | ESI-MS | $R_t$ (HPLC) or $R_f$ (TLC) | Reaction conditions |
|---|---|---|---|---|---|---|
| 29.05 | ds-mix | Int. 28.04 | 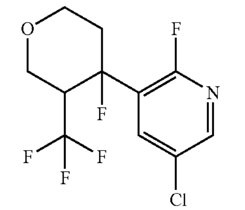 [SMILES: Fc1ncc(Cl)cc1C1(F)CCOCC1C(F)(F)F] | 302/304 [M + H]⁺ | $R_f$ (TLC): 0.7 (PE/EtOAc = 3/1) | Reagent: DAST Solvent: DCM 12 h, RT |
| 29.06 | | Int. 28.05 | 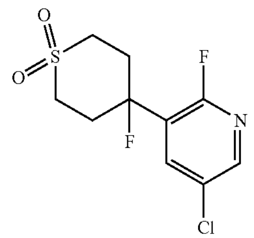 [SMILES: O=S1(=O)CCC(F)(c2cc(Cl)cnc2F)CC1] | 282/284 [M + H]⁺ | $R_t$ (HPLC): 0.43 min method A | Reagent: DeoxoFluor Solvent: DCM 1 h, 0° C. |
| 29.07 | | Int. 28.06 | 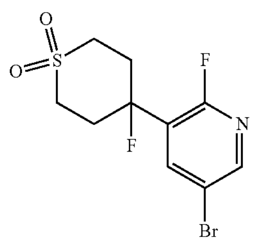 [SMILES: O=S1(=O)CCC(F)(c2cc(Br)cnc2F)CC1] | 326/328 [M + H]⁺ | $R_t$ (HPLC): 0.44 min method A | Reagent: DeoxoFluor Solvent: DCM 1 h, 0° C. |
| 29.08 | | Int. 28.09 | 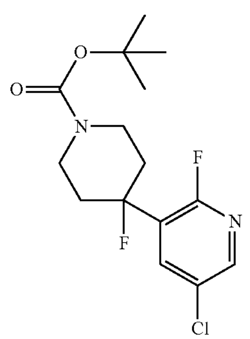 [SMILES: CC(C)(C)OC(=O)N1CCC(F)(c2cc(Cl)cnc2F)CC1] | 277 [M + H − tBu]⁺ | $R_t$ (HPLC): 1.18 min method C | Reagent: DeoxoFluor Solvent: DCM 1 h, 0° C. |
| 29.09 | rac-trans | Int. 28.10 | 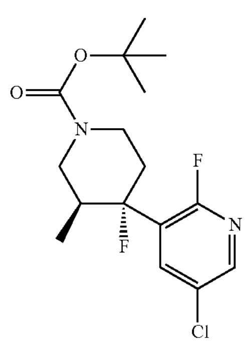 [SMILES: C[C@H]1CN(C(=O)OC(C)(C)C)CC[C@@]1(F)c1cc(Cl)cnc1F] | 291/293 [M + H − tBu]⁺ | $R_t$ (HPLC): 0.75 min method A | Reagent: DAST Solvent: DCM 1 h, 0° C. |

| Int. | Stereo-chemistry | Starting material | Structure | ESI-MS | R$_t$ (HPLC) or R$_f$ (TLC) | Reaction conditions |
|---|---|---|---|---|---|---|
| 29.10 | rac-cis | Int. 28.10 | 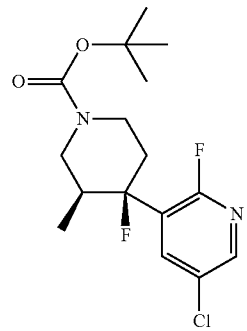 [SMILES: C[C@H]1CN(C(=O)OC(C)(C)C)CC[C@]1(F)c1cc(Cl)cnc1F] | 291/293 [M + H − tBu]⁺ | R$_t$ (HPLC): 0.80 min method A | Reagent: DAST Solvent: DCM 1 h, 0° C. |
| 29.11 | rac | Int. 28.07 | 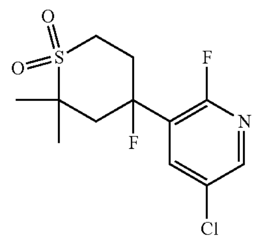 [SMILES: CC1(C)CC(F)(c2cc(Cl)cnc2F)CCS1(=O)=O] | 310/312 [M + H]⁺ | R$_t$ (HPLC): 0.93 min method C | Reagent: DeoxoFluor Solvent: DCM 1 h, 0° C. |
| 29.12 | ds-mix | Int. 28.08 | 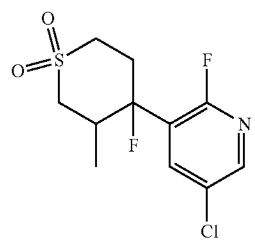 [SMILES: CC1CS(=O)(=O)CCC1(F)c1cc(Cl)cnc1F] | 296/298 [M + H]⁺ | R$_t$ (HPLC): 0.80 min method C | Reagent: DeoxoFluor Solvent: DCM 1 h, 0° C. |
| 29.13 | ds-mix | Int. 28.11 | 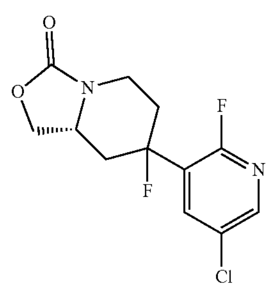 [SMILES: O=C1OC[C@H]2CC(F)(c3cc(Cl)cnc3F)CCN12] | 289/291 [M + H]⁺ | R$_t$ (HPLC): 0.44/0.47 min method A | Reagent: DeoxoFluor Solvent: DCM 3 h, RT |
| 29.14 | rac | Int. 28.12 | 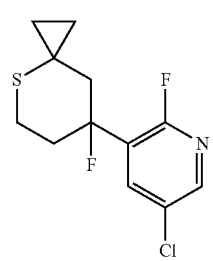 [SMILES: Fc1ncc(Cl)cc1C1(F)CCSC2(CC2)C1] | 276/278 [M + H]⁺ | R$_t$ (HPLC): 0.74 min method A | Reagent: DAST Solvent: DCM 40 min, 0° C. |

-continued

| Int. | Stereo-chemistry | Starting material | Structure | ESI-MS | $R_t$ (HPLC) or $R_f$ (TLC) | Reaction conditions |
|---|---|---|---|---|---|---|
| 29.15 | rac | Int. 28.13 | 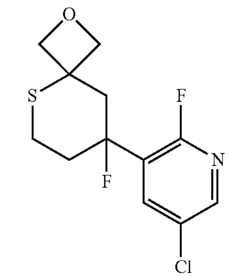 [SMILES: Fc1ncc(Cl)cc1C1(F)CCSC2(COC2)C1] | 292/294 [M + H]⁺ | $R_t$ (HPLC): 0.58 min method A | Reagent: DAST Solvent: DCM 1.5 h, 0° C. |
| 29.16 | rac | Int. 28.14 | 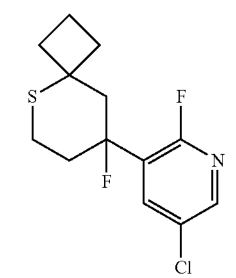 [SMILES: Fc1ncc(Cl)cc1C1(F)CCSC2(CCC2)C1] | 290/292 [M + H]⁺ | $R_t$ (HPLC): 0.78 min method A | Reagent: DAST Solvent: DCM 2 h, 0° C. |

Intermediate 29.18

Racemic trans tert-butyl-4-(5-bromo-2-fluoropyridin-3-yl)-4-fluoro-3-methylpiperidine-1-carboxylate

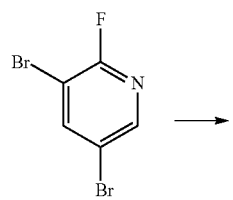

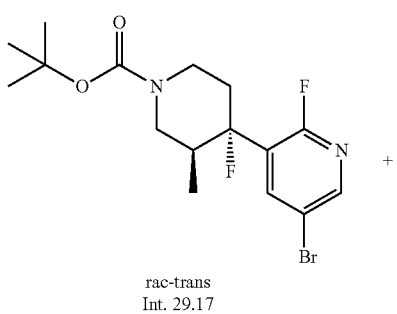

rac-trans
Int. 29.17

+

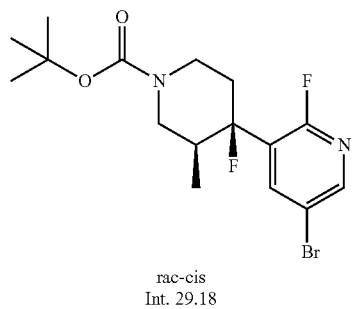

rac-cis
Int. 29.18

These two intermediates were prepared starting from 3,5-dibromo-2-fluoropyridine and N-Boc-3-methyl-4-piperidinone in two synthesis steps followed by HPLC separation according to the preparation of Int. 29.09/29.10.

Int. 29.17
ESI-MS: 335/337 [M+H]⁺
$R_t$ (HPLC): 0.75 min (method A)
Int. 29.18
ESI-MS: 335/337 [M+H]⁺
$R_t$ (HPLC): 0.62 min (method A)

Intermediate 30

Intermediate 30.1 (General Procedure)

2-Fluoro-3-[4-fluoro-3-methyloxan-4-yl]-5-[2-(trimethylsilyl)ethynyl]-pyridine

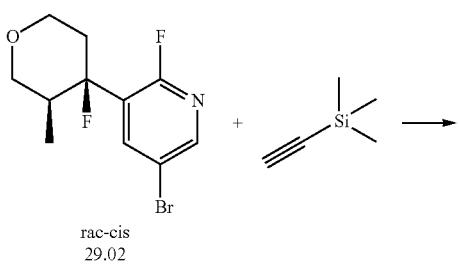

rac-cis
29.02

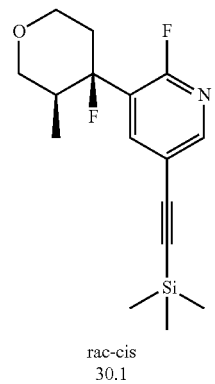

rac-cis
30.1

To a solution of 5-bromo-2-fluoro-3-[4-fluoro-3-methyl-oxan-4-yl]pyridine (INTERMEDIATE 29.02, 175 mg, 0.60 mmol) in THF (3.0 mL) under argon was added DIPEA (813 µL, 4.49 mmol), ethynyltrimethylsilane (356 µL, 2.40 mmol), PdCl$_2$(PPh$_3$)$_2$ (42.0 mg, 0.06 mmol) and copper(I) iodide (34.2 mg, 0.18 mmol). The mixture was stirred at 80° C. for 4 h. The reaction mixture was acidified with TFA, diluted with ACN/H$_2$O, filtered and purified by HPLC (Xbridge, ACN/H2O/TFA).

ESI-MS: 310 [M+H]$^+$
R$_t$ (HPLC): 0.81 min (method A)

The following compounds were prepared according to the general procedure (INTERMEDIATE 30.1) described above:

| Int. | Stereo-chemistry | Starting material | Structure | ESI-MS | R$_t$ (HPLC) [min] (method) | Reaction conditions |
|---|---|---|---|---|---|---|
| 30.2 | rac-trans | Int. 29.01 | 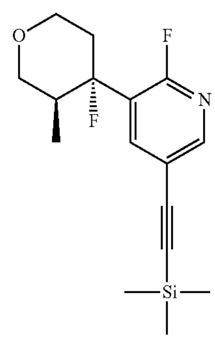 [SMILES: C[C@H]1COCC[C@@]1(F)c1cc(C#C[Si](C)(C)C)cnc1F] | 310 [M + H]$^+$ | 0.78 (A) | THF, 4 h, 80° C. |
| 30.3 | | Int. 29.07 | 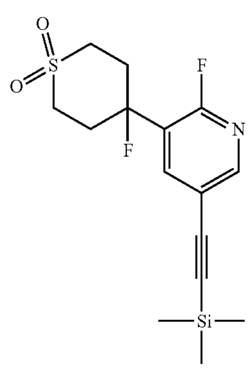 [SMILES: C[Si](C)(C)C#Cc1cnc(F)c(C2(F)CCS(=O)(=O)CC2)c1] | 344 [M + H]$^+$ | 0.67 (A) | THF, 2.5 h, 80° C. |

Intermediate 31

4-(5-Chloro-2-fluoropyridin-3-yl)-4-hydroxy-2,2,5-trimethyl-1-l-6-thiane-1,1-dione

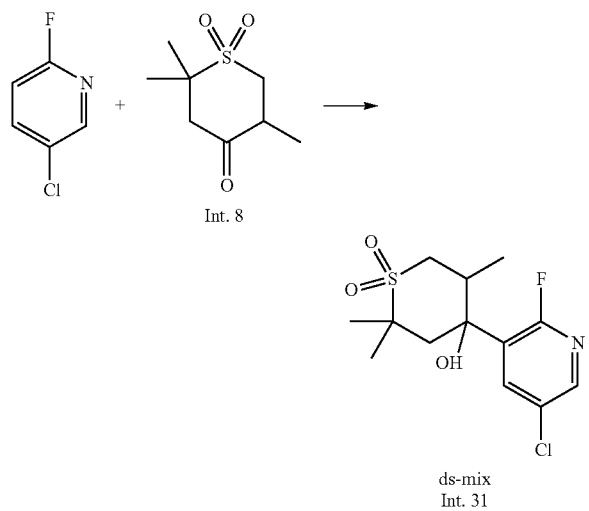

ds-mix
Int. 31

To a solution of 5-chloro-2-fluoropyridine (210 mg, 1.60 mmol) in THF (20 mL) under nitrogen atmosphere pre-cooled at −78° C. was added a LDA solution (2M in THF/heptane, 878 µL, 1.76 mmol) and the mixture was stirred at −78° C. for 20 min. Thereafter was added a solution of 2,2,5-trimethyl-1-l-6-thiane-1,1,4-trione (INTERMEDIATE 8, 305 mg, 0.83 mmol) in 10.0 mL THF and the mixture was stirred at −78° C. for 45 min. The reaction mixture was allowed to reach RT, then it was stirred for further 45 min. The reaction mixture was quenched with an aqueous 1M HCl solution (20 mL), then a saturated NaCl solution (40 mL) and EtOAc (50 mL) were successively added. After phase separation the aqueous phase was extracted with EtOAc. The combined organics were dried, filtered and evaporated. The residue was purified by column chromatography on silica gel (CH/EtOAc=90/10 to 0/100) to afford a mixture of cis/trans diastereoisomers.

ESI-MS: 322/324 [M+H]$^+$
R$_t$ (HPLC): 0.77 min (method B)

Intermediate 32

4-(5-Chloro-2-fluoropyridin-3-yl)-4-methoxy-2,2,5-trimethyl-1-l-6-thiane-1,1-dione

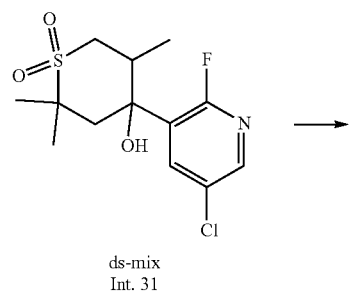

ds-mix
Int. 31

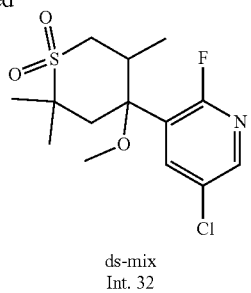

ds-mix
Int. 32

To 4-(5-chloro-2-fluoropyridin-3-yl)-4-hydroxy-2,2,5-trimethyl-1-l-6-thiane-1,1-dione (INTERMEDIATE 31, 107 mg, 0.33 mmol) in 2.5 mL DMF under argon was added NaH (50.8 mg, 1.16 mmol). The reaction mixture was stirred at RT for 5 min, then iodomethane (51.8 µL, 0.830 mmol) was added and the mixture was stirred at RT for 30 min. Another portion of iodomethane (51.8 IL, 0.830 mmol) was added and the mixture was stirred at RT for further 1 h. The mixture was diluted with 10 mL half saturated NaHCO$_3$-solution and extracted with EtOAc. The combined organics were washed with brine, dried, filtered and concentrated. The residue was purified by column chromatography on silica gel (CH/EtOAc=90/10 to 0/100) to afford a mixture of cis/trans diastereoisomers.

ESI-MS: 336/338 [M+H]$^+$
R$_t$ (HPLC): 0.84 min (method C)

Intermediate 33

4-(5-Chloro-2-fluoropyridin-3-yl)-4-fluoro-2,2,5-trimethyl-1-l-6-thiane-1,1-dione

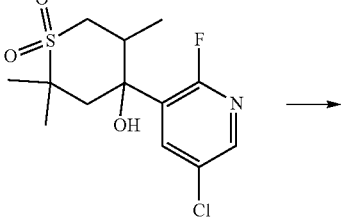

ds-mix
Int. 31

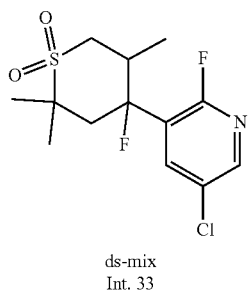

ds-mix
Int. 33

A mixture of 4-(5-chloro-2-fluoropyridin-3-yl)-4-hydroxy-2,2,5-trimethyl-1-l-6-thiane-1,1-dione (INTERMEDIATE 31, 1.25 g, 3.88 mmol) in 20.0 mL dichloromethane was treated with triethylamine trihydrofluoride (633 µL, 3.88 mmol) and subsequently cooled to −78° C. A solution of DAST (2.05 mL, 15.5 mmol) in 10.0 mL DCM was added dropwise. Following complete addition, the reaction mixture was allowed to reach RT over 1 h under vigorous stirring. Another portion of DAST (2.05 mL, 15.5 mmol) was added, then the mixture was stirred for further 1.5 h at RT. The reaction mixture was neutralized at 0° C. by slowly adding a saturated aqueous NaHCO₃-solution (150 mL). The mixture was stirred at RT for 20 min, DCM was added and phases were separated. The organic phase was dried over sodium sulfate, filtered and concentrated. The residue was purified by column chromatography on silica gel (CH/EtOAc=95/5 to 50/50) to afford a mixture of cis/trans diastereoisomers.

ESI-MS: 324/326 [M+H]⁺

$R_t$ (HPLC): 0.87 min (method B)

Intermediate 34

Intermediate 34.1 (General Procedure)

4-Fluoro-4-(2-fluoro-5-{2-[tris(propan-2-yl)silyl]ethynyl}pyridin-3-yl)-2,2,5-trimethyl-1-I-6-thiane-1,1-dione

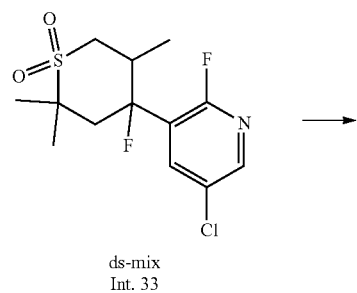

ds-mix
Int. 33

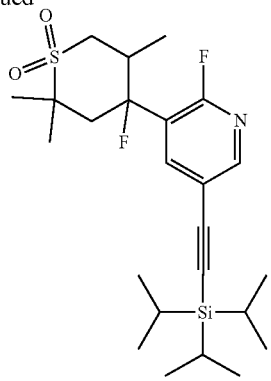

ds-mix
Int. 34.1

To 4-(5-chloro-2-fluoropyridin-3-yl)-4-fluoro-2,2,5-trimethyl-1I6-thiane-1,1-dione (INTERMEDIATE 33, 150 mg, 0.44 mmol) in ACN (2.0 mL) under argon was added cesium carbonate (172 mg, 0.53 mmol), ethynyltris(propan-2-yl)silane (296 µl, 1.32 mmol), Brettphos (20.9 mg, 0.04 mmol) and bis(acetonitrile)dichloropalladium(II) (5.71 mg, 0.02 mmol). The reaction mixture was stirred at 90° C. for 2.5 h, then it was cooled at RT, diluted with 10.0 mL ACN, filtered and evaporated. The residue was purified by column chromatography on silica gel (CH/EtOAc=95/5 to 0/100) to afford a mixture of cis/trans diastereoisomers.

ESI-MS: 470 [M+H]⁺

$R_t$ (HPLC): 1.27 min (method B)

The following compounds were prepared according to the general procedure (INTERMEDIATE 34.1) described above:

| Int. | Stereo-chemistry | Starting materials | Structure | ESI-MS | $R_t$ (HPLC) [min] (method) | Reaction conditions |
|---|---|---|---|---|---|---|
| 34.2 | rac | | 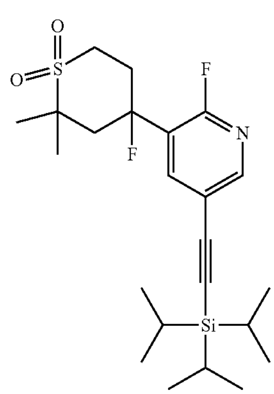 | 456 [M + H]⁺ | 1.25 (B) | Solvent: ACN, 2 h 90° C. |

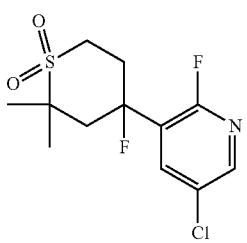 [SMILES: CC1(C)CC(F)(c2cc(Cl)cnc2F)CCS1(=O)=O]

Int. 29.11

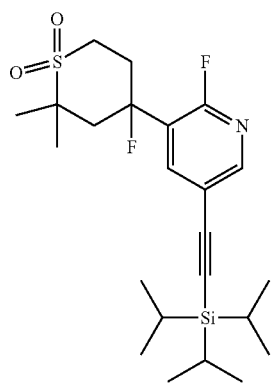 [SMILES: CC(C)[Si](C#Cc1cnc(F)c(C2(F)CCS(=O)(=O)C(C)(C)C2)c1)(C(C)C)C(C)C]

-continued

| Int. | Stereo-chemistry | Starting materials | Structure | ESI-MS | R$_t$ (HPLC) [min] (method) | Reaction conditions |
|---|---|---|---|---|---|---|
| 34.3 | ent | Int. 50.2 | 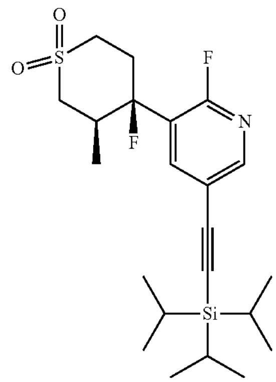 [SMILES: CC(C)[Si](C#Cc1cnc(F)c([C@@]2(F)CCS(=O)(=O)C[C@@H]2C)c1)(C(C)C)C(C)C] | 442 [M + H]$^+$ | 0.95 (A) | Solvent: ACN, 1 h 20 min 90° C. |
| 34.4 | ent | Int. 50.1 | 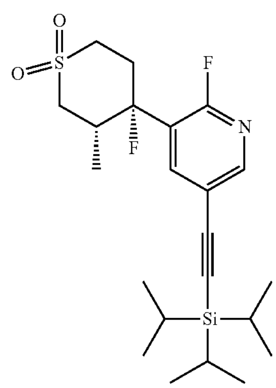 [SMILES: CC(C)[Si](C#Cc1cnc(F)c([C@]2(F)CCS(=O)(=O)C[C@H]2C)c1)(C(C)C)C(C)C] | 442 [M + H]$^+$ | 0.95 (A) | Solvent: ACN, 1 h 20 min 90° C. |
| 34.5 | ent | | 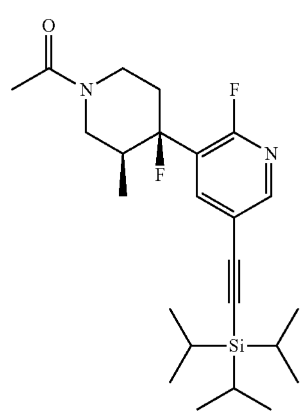 [SMILES: CC(=O)N1CC[C@](F)(c2cc(C#C[Si](C(C)C)(C(C)C)C(C)C)cnc2F)[C@@H](C)C1] | 435 [M + H]$^+$ | 0.98 (A) | Solvent: ACN, 1 h, 90° C. |

Intermediate 35

Intermediate 35.01 and

Intermediate 35.02 (General Procedure)

(2S,4S)-4-({5-chloro-3-[(3R,4S)-4-fluoro-3-methyl-oxan-4-yl]pyridin-2-yl}oxy)-1-[4-(difluoromethyl)-8-oxa-3,5-diazatricyclo[7.4.0.0²,⁷]trideca-1(13),2,4,6,9,11-hexaen-6-yl]pyrrolidine-2-carboxylic acid and (2S,4S)-4-({5-chloro-3-[(3S,4R)-4-fluoro-3-methyl-oxan-4-yl]pyridin-2-yl}oxy)-1-[4-(difluoromethyl)-8-oxa-3,5-diazatricyclo[7.4.0.0²,⁷]trideca-1(13),2,4,6,9,11-hexaen-6-yl]pyrrolidine-2-carboxylic acid

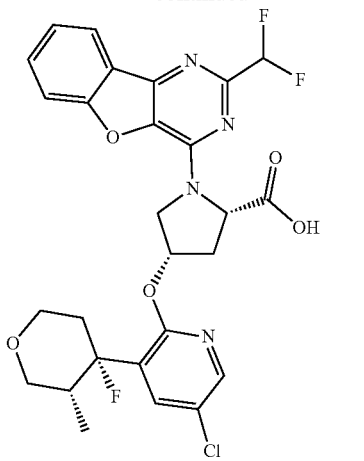

Int. 35.01

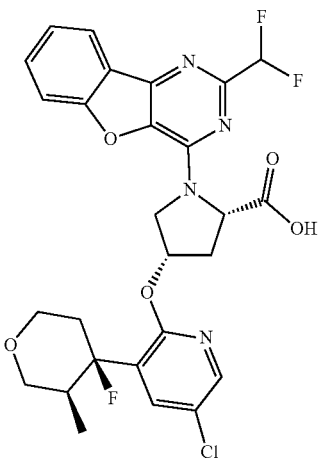

Int. 35.02

Int. 3.2

+

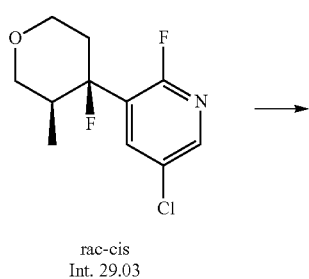

rac-cis
Int. 29.03

→

To a mixture of (2S,4S)-1-[4-(difluoromethyl)-8-oxa-3,5-diazatricyclo[7.4.0.0²,⁷]-trideca-1(9),2(7),3,5,10,12-hexaen-6-yl]-4-hydroxypyrrolidine-2-carboxylic acid (INTERMEDIATE 3.2, 404 mg, 1.10 mmol) in 6.0 mL NMP was added NaH (132 mg, 3.30 mmol) and 5-chloro-2-fluoro-3-[4-fluoro-3-methyloxan-4-yl]pyridine (INTERMEDIATE 29.03, 272 mg, 1.10 mmol). The reaction mixture was stirred at RT for 16 h, then diluted with ACN/water, acidified with TFA, filtered and purified by preparative HPLC (ACN/H₂O/TFA) to afford the two diastereomers Int. 35.01 and Int 35.02. Absolute stereochemistry has been retrospectively assessed by Xray co-crystallization of EXAMPLE 3.01.

Int. 35.01

ESI-MS: 577/579 [M+H]⁺

$R_t$ (HPLC): 0.77 min (method A)

Int. 35.02

ESI-MS: 577/579 [M+H]⁺

$R_t$ (HPLC): 0.78 min (method A)

The following compounds were prepared according to the general procedure (INTERMEDIATE 35) described above:

| Int. | Starting material | Structure | ESI-MS | $R_t$ (HPLC) [min] (method) | Reaction conditions |
|---|---|---|---|---|---|
| 35.03 | Int. 29.04 | 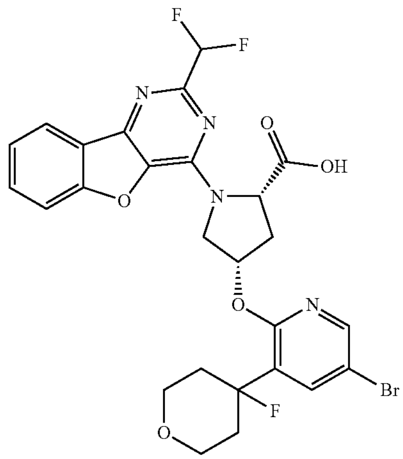 [SMILES: O=C(O)[C@@H]1C[C@H](Oc2ncc(Br)cc2C2(F)CCOCC2)CN1c1nc(C(F)F)nc2c1oc1ccccc12] | 607/609 [M + H]$^+$ | 0.75 (A) | Solvent: DMF, 1 h RT |
| 35.04 | Int. 38.01 | 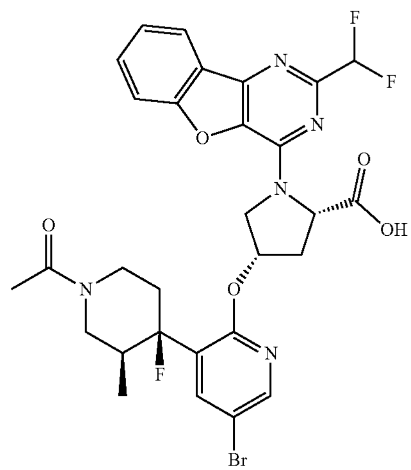 [SMILES: CC(=O)N1CC[C@](F)(c2cc(Br)cnc2O[C@H]2C[C@@H](C(=O)O)N(c3nc(C(F)F)nc4c3oc3ccccc34)C2)[C@@H](C)C1] | 662 [M + H]$^+$ | 0.76 (A) | Solvent: DMF, 2 h RT |

Intermediate 36

Intermediate 36.01

5-Chloro-2-fluoro-3-(4-fluoropiperidin-4-yl)pyridine

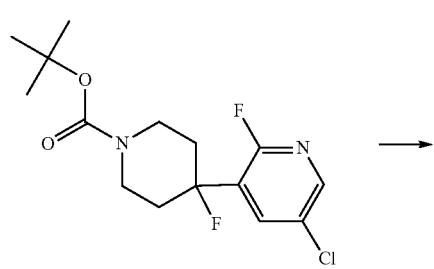

Int 29.08

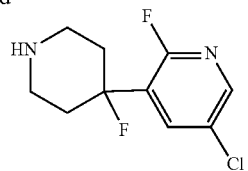

Int. 36.01

To tert-butyl 4-(5-chloro-2-fluoropyridin-3-yl)-4-fluoropiperidine-1-carboxylate (INTERMEDIATE 29.08, 100 mg, 0.30 mmol) in DCM (10 mL) was added TFA (1.0 mL). The reaction mixture was stirred at RT overnight, then it was concentrated and used without further purification for the next step.

ESI-MS: 233/235 [M+H]$^+$ $R_t$ (HPLC): 0.64 min (method C)

The following compounds were prepared according to the general procedure (INTERMEDIATE 36.01) described above:

| Int. | Stereo-chemistry | Starting material | Structure | ESI-MS | $R_t$ (HPLC) [min] (method) | Reaction conditions |
|---|---|---|---|---|---|---|
| 36.02 | rac-cis | Int. 29.10 | 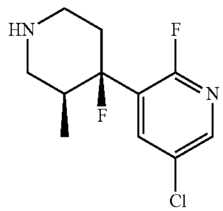 [SMILES: C[C@H]1CNCC[C@]1(F)c1cc(Cl)cnc1F] | 247/249 [M + H]$^+$ | 0.36 (A) | Solvent: 4N HCl in dioxane, 45 min RT |
| 36.03 | | Int. 29.18 | 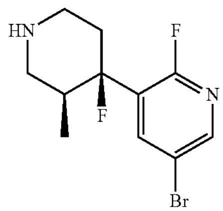 [SMILES: C[C@H]1CNCC[C@]1(F)c1cc(Br)cnc1F] | 291/293 [M + H]$^+$ | 0.36 (A) | Solvent: 4N HCl in dioxane, RT |

Intermediate 37

Intermediate 37.01 (General Procedure)

4-(5-Chloro-2-fluoropyridin-3-yl)-4-fluoropiperidine-1-carbonitrile

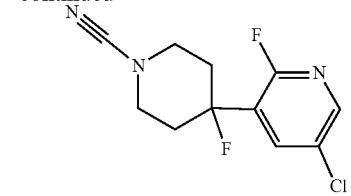

37.01

To a solution of 5-chloro-2-fluoro-3-(4-fluoropiperidin-4-yl)pyridine (INTERMEDIATE 36.01, 100 mg, 0.29 mmol) in DCM (5.0 mL) was added DIPEA (0.40 mL, 2.31 mmol) followed by dropwise addition of cyanogen bromide (3M in DCM, 0.144 mL, 0.43 mmol). The reaction mixture was stirred at RT overnight, then it was diluted with DCM and extracted with water. The combined aqueous phases were extracted with DCM. The combined organics were evaporated and the residue purified by preparative HPLC (ACN/H$_2$O/TFA).

ESI-MS: 258/260 [M+H]$^+$ $R_t$ (HPLC): 0.92 min (method C)

The following compound was prepared according to the general procedure (INTERMEDIATE 37.01) described above:

| Int. | Stereo-chemistry | Starting materials | Structure | ESI-MS | $R_t$ (HPLC) [min] (method) | Reaction conditions |
|---|---|---|---|---|---|---|
| 37.02 | rac-cis | 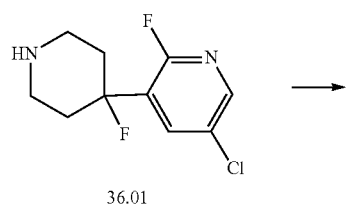<br>Int 36.02 | 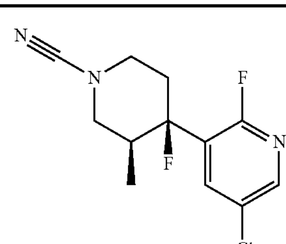 | 272/274 [M + H]$^+$ | 0.59 (A) | Solvent: DCM, DIPEA, 1.5 h RT |

Intermediate 38 racemic cis-1-[4-(5-Chloro-2-fluoropyridin-3-yl)-4-fluoro-3-methylpiperidin-1-yl]ethan-1-one

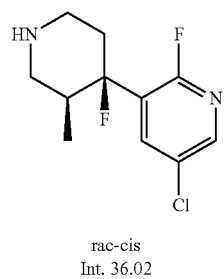

rac-cis
Int. 36.02

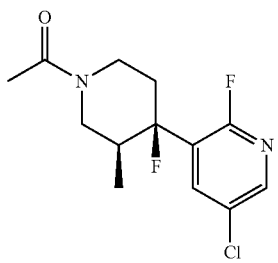

rac-cis
Int. 38

To a solution of 5-chloro-2-fluoro-3-[4-fluoro-3-methylpiperidin-4-yl]pyridine hydrochloride (INTERMEDIATE 36.02, 110 mg, 0.37 mmol) in DCM (4.0 mL) was added acetic anhydride (88.0 µL, 0.89 mmol) and trietylamine (155 µL, 1.11 mmol). The reaction mixture was stirred at RT for 1 h, then neutralized with water and extracted with DCM. The combined organics were dried over Na$_2$SO$_4$, filtered and evaporated.

ESI-MS: 289/291 [M+H]$^+$

R$_t$ (HPLC): 0.55 min (method A)

Intermediate 38.01 racemic cis-1-[4-(5-Bromo-2-fluoropyridin-3-yl)-4-fluoro-3-methylpiperidin-1-yl]ethan-1-one

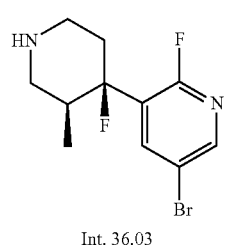

Int. 36.03

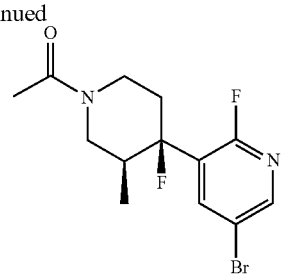

Int. 38.01

To a solution of INTERMEDIATE 36.03 (800 mg, 2.44 mmol) and DIPEA (1.28 ml, 7.33 mmol) in DCM (10 ml) was added acetyl chloride (192 µl, 2.69 mmol). The mixture was stirred for 1 h, then diluted with DCM and extracted with sodium bicarbonate solution. The organic layer was separated, concentrated in vacuo and taken to the next step without further purification.

ESI-MS: 333/335 [M+H]$^+$

R$_t$ (HPLC): 0.53 min (method A)

Intermediate 39 racemic cis-5-Chloro-2-fluoro-3-[4-fluoro-3-methyl-1-(oxetan-3-yl)piperidin-4-yl]pyridine

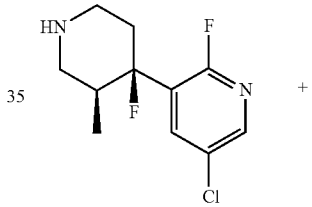

rac-cis
Int. 36.02

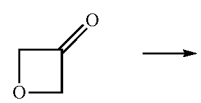

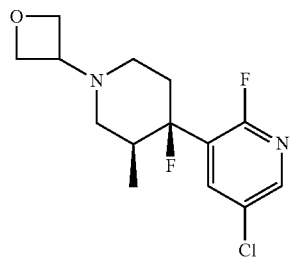

rac-cis
Int. 39

To a solution of 5-chloro-2-fluoro-3-[4-fluoro-3-methylpiperidin-4-yl]pyridine hydrochloride (INTERMEDIATE 36.02, 110 mg, 0.37 mmol) in THF (4.0 mL) was added oxetan-3-one (49.7 lL, 0.85 mmol) and sodium triacetoxyborohydride (234 mg, 1.11 mmol). The reaction mixture was stirred at RT for 1 h, then it was acidified with an aqueous 1N HCl solution (2.0 mL), diluted with water and DCM, and stirred vigorously for 10 min. After phase separation, the aqueous phase was neutralized with an aqueous NaHCO$_3$- solution and extracted with DCM. The combined organics were dried with Na₂SO₄, filtered and evaporated.
ESI-MS: 303 [M+H]⁺
R_t (HPLC): 0.35 min (method A)

Intermediate 40

Intermediate 40.01 and Intermediate 40.02 racemic trans 4-(5-Chloro-2-fluoropyridin-3-yl)-4-methoxy-3-methyl-1-I-6-thiane-1,1-dione and racemic cis 4-(5-Chloro-2-fluoropyridin-3-yl)-4-methoxy-3-methyl-1-I-6-thiane-1,1-dione

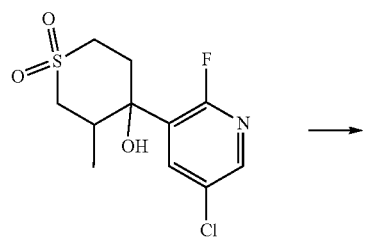

ds-mix
Int. 28.08

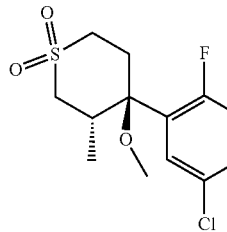

rac-trans
Int. 40.01

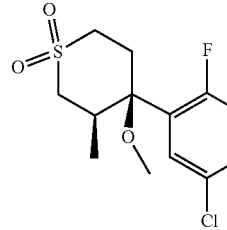

rac-cis
Int. 40.02

To a solution of 4-(5-chloro-2-fluoropyridin-3-yl)-4-hydroxy-3-methyl-1-I-6-thiane-1,1-dione (INTERMEDIATE 28.08, 100 mg, 0.34 mmol) and iodomethane (52.9 IL, 0.85 mmol) in DMF (2.5 mL) was added sodium hydride (52 mg, 1.19 mmol), and the resulting mixture was stirred at RT for 10 min. Ethyl acetate was added and the organic phase was extracted with half saturated aqueous NaHCO₃-solution and brine. The combined organics were dried over Na₂SO₄, filtered and concentrated. The residue was purified by preparative HPLC (ACN/H₂O/NH₃) to afford the cis- and the trans-diastereoisomers as racemic mixtures.

Int. 40.01 (rac-trans)
ESI-MS: 308/310 [M+H]⁺
R_t (HPLC): 0.85 min (method C)

Int. 40.02 (rac-cis):
ESI-MS: 308/310 [M+H]⁺
R_t (HPLC): 0.88 min (method C)

Intermediate 41

1-tert-Butyl 2-methyl (2S,4S)-4-[(3-bromo-5-chloropyridin-2-yl)oxy]pyrrolidine-1,2-dicarboxylate

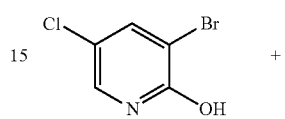

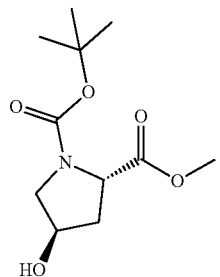

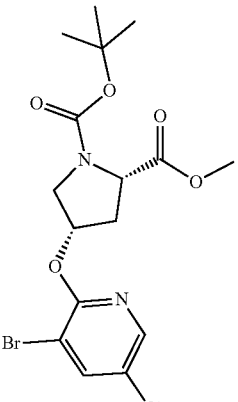

Int. 41

A mixture containing 3-bromo-5-chloropyridin-2-ol (500 mg, 2.40 mmol), 1-tert-butyl-2-methyl-(2S,4R)-4-hydroxy-pyrrolidine-1,2-dicarboxylate (706 mg, 2.88 mmol) and triphenylphosphine (755 mg, 2.88 mmol) in THE (14 mL) was cooled at 0° C. Thereafter DIAD (565 IL, 2.88 mmol) was added dropwise and the reaction mixture was stirred at RT overnight. The volatiles were removed in vacuo, the residue was taken up in DMF/ACN and purified by preparative HPLC (ACN/H₂O/TFA) to afford the corresponding intermediate.

ESI-MS: 435/437 [M+H]⁺
R_t (HPLC): 1.18 min (method C)

Intermediate 42

4,4,5,5-Tetramethyl-2-{3-oxabicyclo[4.1.0]heptan-6-yl}-1,3,2-dioxaborolane

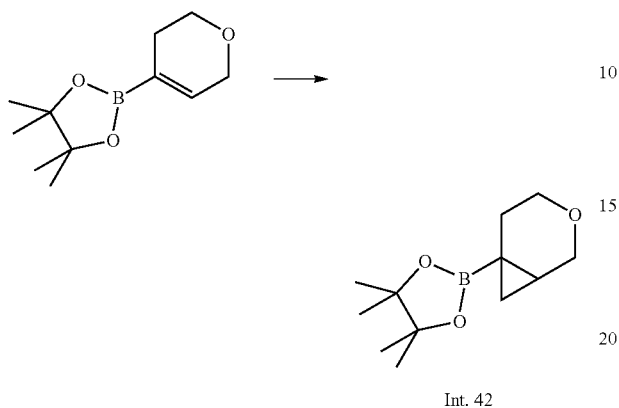

Int. 42

This intermediate was prepared according to a procedure adapted from Hobbs et al., J. Med. Chem. 2019, 62, pp 6972-6984. To a solution of 2-(3,6-dihydro-2H-pyran-4-yl)-4,4,5,5-tetramethyl-1,3,2-dioxaborolane (10.0 g, 47.6 mmol) in DCM (100 mL) cooled to −5° C. was added dropwise a 2M solution of diethyl zinc in toluene (119 mL, 238 mmol). The mixture was further stirred at −5° C. for 5 min, then a solution of chloroiodomethane (84.0 g, 476 mmol) in DCM (100 mL) was added dropwise. This mixture was stirred at −5° C. for 10 min, then stirred at 15° C. for 16 h. The reaction mixture was diluted with water and extracted with EtOAC, and the combined organic layers were washed with brine and dried over Na$_2$SO$_4$, filtered and concentrated under reduced pressure. The crude residue was purified by column chromatography over silica gel (PE/EtOAc: 100:0 to 95:5).

ESI-MS: 224 [M+H]$^+$

R$_t$ (HPLC): 1.02 min (method W)

Intermediate 43

Potassium trifluoro{3-oxabicyclo[4.1.0]heptan-6-yl}boranuide

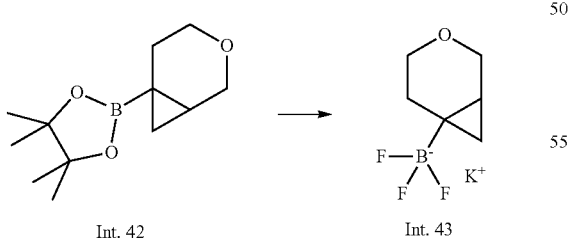

Int. 42          Int. 43

This intermediate was prepared according to a procedure adapted from Hobbs et al., J. Med. Chem. 2019, 62, pp 6972-6984. Under argon atmosphere was prepared a solution of INTERMEDIATE 42 (0.8 g, 3.66 mmol) in 9.3 mL MeOH and 9.3 mL ACN, then an aqueous solution of potassium fluoride (0.9 g, 14.6 mmol) in deionized water (3.4 mL) was added. This suspension was stirred at RT for 10 min. Thereafter was added L-(+)-tartaric acid (1.1 g, 7.32 mmol) followed by THF (0.4 mL) and the mixture was stirred RT for 75 min, then left standing overnight. The precipitate was filtered and washed with ACN. The filtrate was concentrated to dryness, then it was azeotroped three times with toluol and triturated three times with diethyl ether to afford the desired intermediate, which was used directly in the next step without further purification.

ESI-MS: 165 [M−H]$^+$

R$_t$ (HPLC): 1.03 min (method W)

Intermediate 44

1-tert-Butyl 2-methyl (2S,4S)-4-[(5-chloro-3-{3-oxabicyclo[4.1.0]heptan-6-yl}pyridin-2-yl)oxy]-pyrrolidine-1,2-dicarboxylate

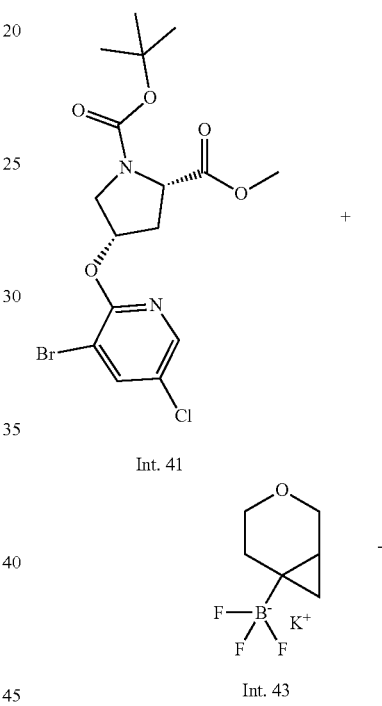

Int. 41

Int. 43

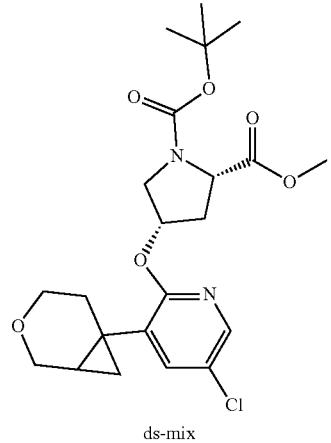

ds-mix
Int. 44

To a solution of 1-tert-butyl-2-methyl (2S,4S)-4-[(3-bromo-5-chloropyridin-2-yl)oxy]pyrrolidine-1,2-dicarboxylate (INTERMEDIATE 41, 300 mg, 0.69 mmol) in dioxane (10 mL) was added successively potassium trifluoro({3-oxabicyclo[4.1.0]-heptan-6-yl})boranuide (INTERMEDIATE 43, 140 mg, 0.69 mmol), Pd(dppf)Cl$_2$ (56.2 mg, 0.07 mmol), K$_2$CO$_3$ (190 mg, 1.38 mmol) and water (500 L). The mixture was stirred at 100° C. overnight. The reaction mixture was purified by preparative HPLC (ACN/H$_2$O/TFA) to afford the corresponding pure intermediate.

ESI-MS: 453/455 [M+H]$^+$
R$_t$ (HPLC): 1.04 min (method C)

Intermediate 45

1-tert-Butyl-2-methyl (2S,4S)-4-[(3-{3-oxabicyclo[4.1.0]heptan-6-yl}-5-{2-[tris(propan-2-yl)silyl]-ethynyl}pyridin-2-yl)oxy]pyrrolidine-1,2-dicarboxylate

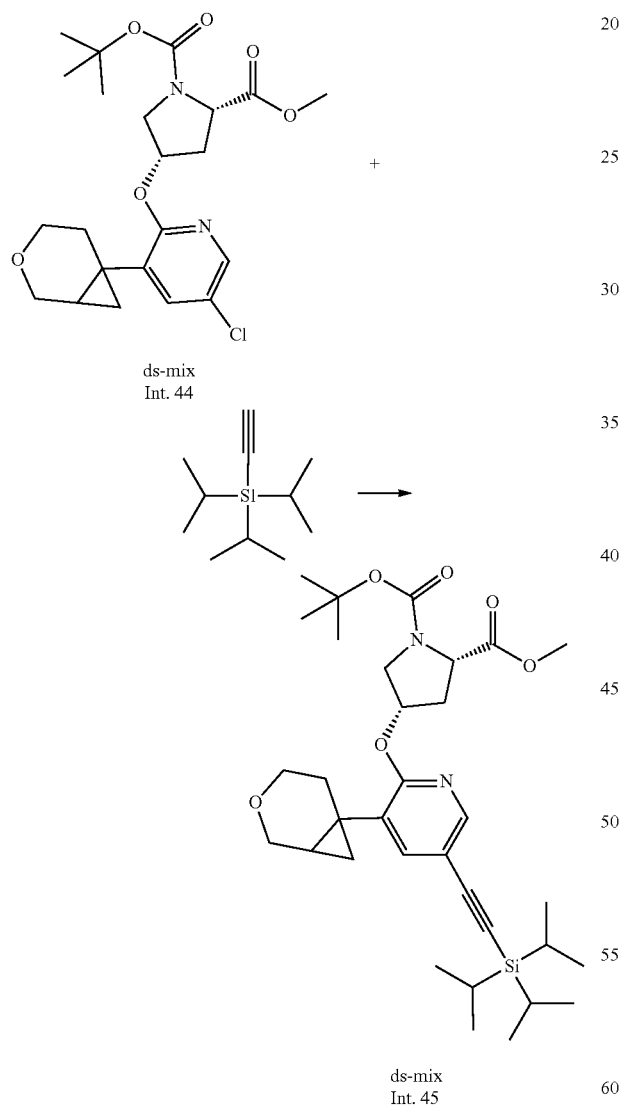

To 1-tert-butyl 2-methyl (2S,4S)-4-[(5-chloro-3-{3-oxabicyclo[4.1.0]heptan-6-yl}pyridin-2-yl)oxy]pyrrolidine-1,2-dicarboxylate (INTERMEDIATE 44, 200 mg, 0.44 mmol) in 4.00 mL ACN was added under argon ethynyltris(propan-2-yl)silane (396 μL, 1.77 mmol), Xphos (21.0 mg, 0.04 mmol), bis(acetonitrile)dichloropalladium(II) (5.73 mg, 0.02 mmol) and cesium carbonate (172 mg, 0.53 mmol). The mixture was stirred at 90° C. for 5 h, then diluted with ACN and purified by column chromatography (silica gel; CH/EtOAc=88/12 to 45/55).

ESI-MS: 599 [M+H]$^+$
R$_t$ (HPLC): 1.31 min (method C)

Intermediate 46

Methyl (2S,4S)-4-[(3-{3-oxabicyclo[4.1.0]heptan-6-yl}-5-{2-[tris(propan-2-yl)silyl]ethynyl}pyridin-2-yl)oxy]pyrrolidine-2-carboxylate

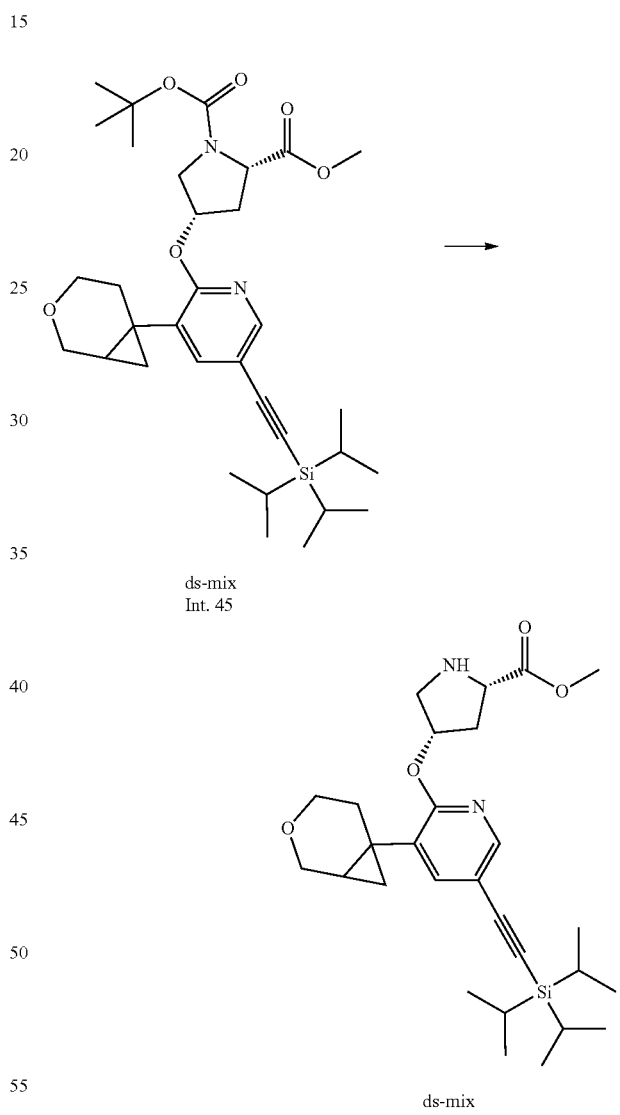

To a solution of 1-tert-butyl-2-methyl (2S,4S)-4-[(3-{3-oxabicyclo[4.1.0]heptan-6-yl}-5-{2-[tris(propan-2-yl)silyl]ethynyl}pyridin-2-yl)oxy]pyrrolidine-1,2-dicarboxylate (INTERMEDIATE 45, 200 mg, 0.33 mmol) in DCM (2.0 mL) was added TFA (130 μL, 1.69 mmol). The mixture was stirred at RT overnight. The reaction mixture was concentrated and used without further purification for the next step.

ESI-MS: 499 [M+H]$^+$
R$_t$ (HPLC): 1.00 min (method C)

Intermediate 47

Methyl-(2S,4S)-4-[(3-{3-oxabicyclo[4.1.0]heptan-6-yl}-5-{2-[tris(propan-2-yl)silyl]ethynyl}pyridin-2-yl)oxy]-1-[4-(trifluoromethyl)-8-oxa-3,5-diazatricyclo-[7.4.0.0$^{2,7}$]trideca-1(13),2(7),3,5,9,11-hexaen-6-yl]pyrrolidine-2-carboxylate

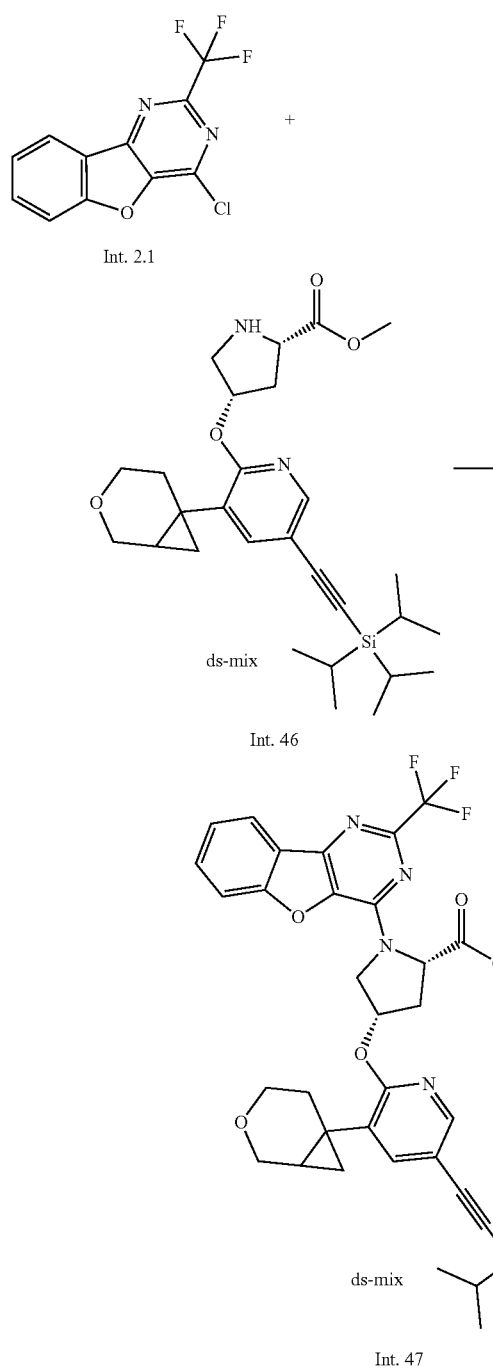

To a solution of 6-chloro-4-(trifluoromethyl)-8-oxa-3,5-diazatricyclo[7.4.0.0$^{2,7}$]trideca-1(9),2,4,6,10,12-hexaene (INTERMEDIATE 2.1, 60.0 mg, 0.22 mmol) in DMF (2.0 mL) was added methyl (2S,4S)-4-[(3-{3-oxabicyclo[4.1.0] heptan-6-yl}-5-{2-[tris(propan-2-yl)silyl]ethynyl}pyridin-2-yl)oxy]-pyrrolidine-2-carboxylate (INTERMEDIATE 46, 110 mg, 0.22 mmol) and K$_2$CO$_3$ (121 mg, 0.88 mmol). The mixture was stirred at RT overnight. The reaction mixture was quenched with ice-water and acidified with TFA. The mixture was stirred at RT for 1 h. EtOAc was added to the mixture and the phases were separated. The organic phase was dried, concentrated in vacuo and used without further purification.

ESI-MS: 735 [M+H]$^+$

R$_t$ (HPLC): 1.33 min (method W)

Intermediate 48

Methyl-(2S,4S)-4-[(5-ethynyl-3-{3-oxabicyclo[4.1.0]heptan-6-yl}pyridin-2-yl)oxy]-1-[4-(trifluoromethyl)-8-oxa-3,5-diazatricyclo[7.4.0.0$^{2,7}$]trideca-1(13),2(7),3,5,9,11-hexaen-6-yl]pyrrolidine-2-carboxylate

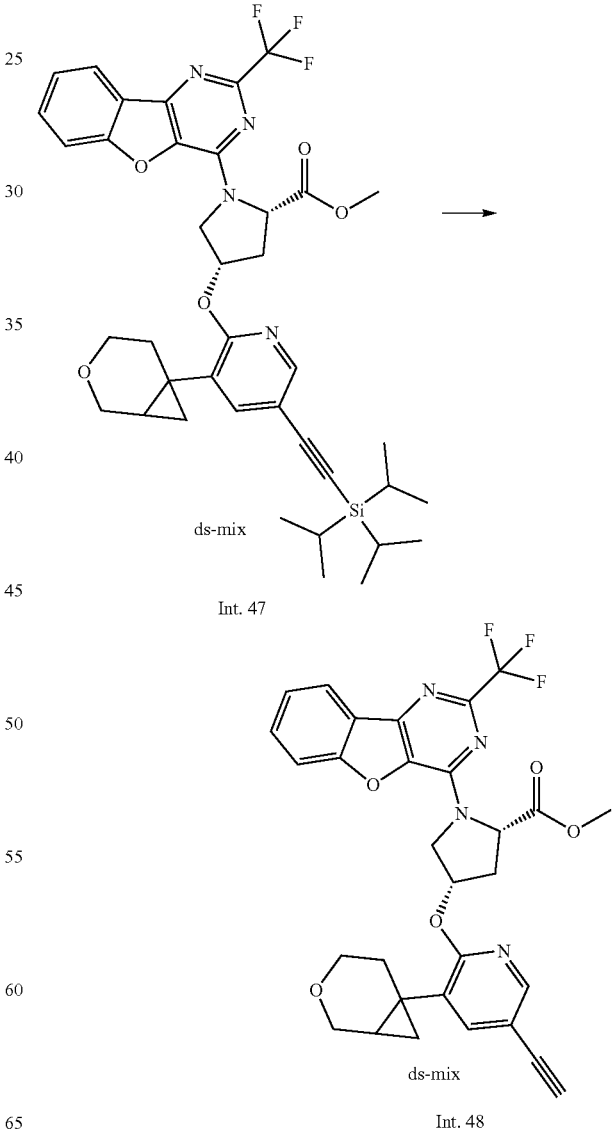

To a solution of methyl (2S,4S)-4-[(3-{3-oxabicyclo[4.1.0]heptan-6-yl}-5-{2-[tris(propan-2-yl)silyl]ethynyl}pyridin-2-yl)oxy]-1-[4-(trifluoromethyl)-8-oxa-3,5-diaza-tricyclo-[7.4.0.0²,]trideca-1(13),2(7),3,5,9,11-hexaen-6-yl]pyrrolidine-2-carboxylate (INTERMEDIATE 47, 90.0 mg, 0.12 mmol) in 2-methyltetrahydrofuran (2.0 mL) was added TBAF (183 µL, 0.18 mmol). The mixture was stirred at RT overnight. The reaction mixture was concentrated and was purified by column chromatography on silica gel (CH/EtOAc=88/12 to 40/60) to afford the corresponding intermediate.

ESI-MS: 579 [M+H]⁺

$R_t$ (HPLC): 1.11 min (method C)

Intermediate 49

Intermediate 49.1 and Intermediate 49.2 racemic trans-4-(5-Chloro-2-fluoropyridin-3-yl)-4-fluoro-3-methyl-1λ⁶-thiane-1,1-dione and racemic cis-4-(5-Chloro-2-fluoropyridin-3-yl)-4-fluoro-3-methyl-1λ⁶-thiane-1,1-dione

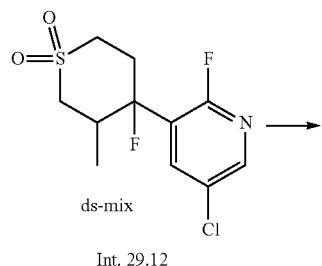

Int. 29.12

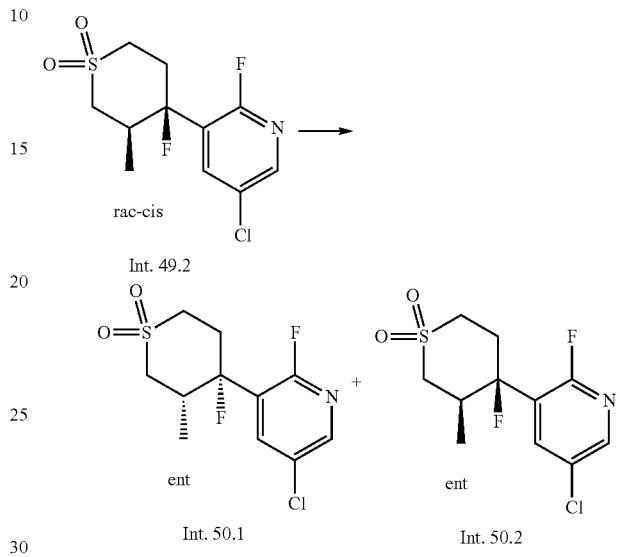

4-(5-chloro-2-fluoropyridin-3-yl)-4-fluoro-3-methyl-1λ⁶-thiane-1,1-dione (INTERMEDIATE 29.12, 277 mg, 0.94 mmol) was purified by preparative RP-HPLC (ACN/H2O/TFA).

Int. 49.1 (rac-trans)

ESI-MS: 296/298 [M+H]⁺

$R_t$ (HPLC): 0.75 min (method C)

Int. 49.2 (rac-cis)

ESI-MS: 296/298 [M+H]⁺

$R_t$ (HPLC): 0.77 min (method C)

Intermediate 50

Intermediate 50.1 and Intermediate 50.2

(3S,4S)-4-(5-chloro-2-fluoropyridin-3-yl)-4-fluoro-3-methyl-1λ⁶-thiane-1,1-dione and (3R,4R)-4-(5-chloro-2-fluoropyridin-3-yl)-4-fluoro-3-methyl-1λ⁶-thiane-1,1-dione Racemic cis-4-(5-chloro-2-fluoropyridin-3-yl)-4-fluoro-3-methyl-1λ⁶-thiane-1,1-dione (INTERMEDIATE 49.2, 830 mg, 2.81 mmol) was purified by chiral SFC to separate both cis enantiomers. Absolute stereochemistry was retrospectively assessed from a cocrystal structure of Example 1.13 bound to human cGAS.

SFC preparative report: Column Chiralpak© IG_20×250 mm_5 µm, Solvents: scCO₂ (90%), MeOH+20 mM NH₃ (10%), BPR: 150 bar, CT: 40° C., Flow: 60 mL/min, Device Sepiatec 1 Prep SFC 100.

Int. 50.1: $R_t$ (SFC): 1.02 min (method E)
Int. 50.2: $R_t$ (SFC): 1.34 min (method E)

Intermediate 51

Intermediate 51.1 and Intermediate 51.2

(4S)-4-(5-Chloro-2-fluoropyridin-3-yl)-4-fluoro-2,2-dimethyl-1λ⁶-thiane-1,1-dione and (4R)-4-(5-Chloro-2-fluoropyridin-3-yl)-4-fluoro-2,2-dimethyl-1λ⁶-thiane-1,1-dione

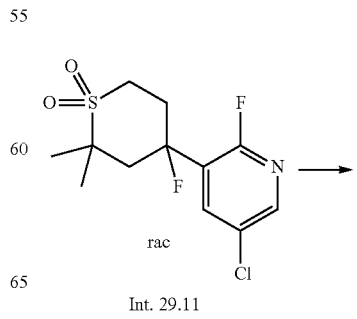

Int. 29.11

Intermediate 52

Intermediate 52.1 (General Procedure)

7-(5-Chloro-2-fluoropyridin-3-yl)-7-fluoro-4-I-6-thiaspiro[2.5]octane-4,4-dione

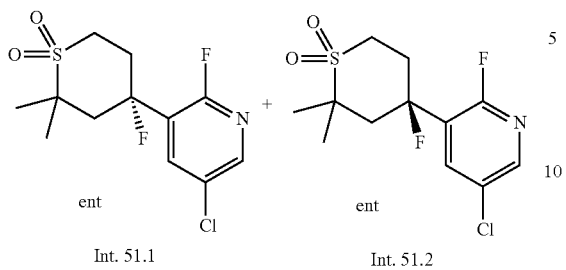

Int. 29.14 → Int. 52.1

4-(5-chloro-2-fluoropyridin-3-yl)-4-fluoro-2,2-dimethyl-1λ⁶-thiane-1,1-dione (INTERMEDIATE 29.11, 100 mg, 0.32 mmol) was purified by chiral SFC to afford the pure diastereomers (Column CHIRAL ART® Cellulose-SC_10× 250 mm_5 μm, solvents: $scCO_2$ (90%), MeOH+20 mM $NH_3$ (10%), BPR: 150 bar, CT: 40° C., Flow: 10 mL/min, Device Mini Gram). Absolute stereochemistry was retrospectively assessed from a cocrystal structure of Example 2.08 bound to human cGAS.

Int. 51.1: $R_t$ (HPLC): 0.84 min (method C)
Int. 51.2: $R_t$ (HPLC): 1.06 min (method C)

To 5-chloro-2-fluoro-3-{7-fluoro-4-thiaspiro[2.5]octan-7-yl}pyridine (INTERMEDIATE 29.14, 100 mg, 0.34 mmol) in 1.00 mL acetic acid was added hydrogen peroxide (30% aq. solution, 173 μL, 1.72 mmol) and the mixture was stirred at RT for 16 h. Again, hydrogen peroxide (30% aq. solution, 173 IL, 1.72 mmol) was added, and the mixture was stirred at RT for 5 h. The reaction mixture was diluted with 1.0 mL acetic acid and stirred at RT for 17 h, then neutralized with saturated aqueous $NaHCO_3$ solution and extracted with DCM. The combined organic phases were dried over sodium sulfate, filtered and evaporated.

ESI-MS: 308/310 [M+H]⁺
$R_t$ (HPLC): 0.51 min (method A)

The following compounds were prepared according to the general procedure (INTERMEDIATE 52.1) described above:

| Int. | Stereochemistry | Starting material | Structure | ESI-MS | $R_t$ (HPLC) [min] (method) | Reaction conditions |
|---|---|---|---|---|---|---|
| 52.2 | rac | | 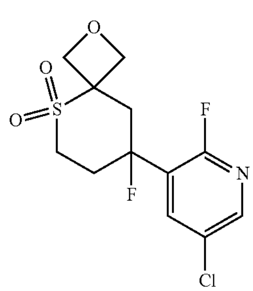 [SMILES: O=S1(=O)CCC(F)(c2cc(Cl)cnc2F)CC12COC2] | 324/326 [M + H]⁺ | 0.45 (A) | Solvent: acetic acid, RT 3.5 h, RT 18 h, RT 7 h |

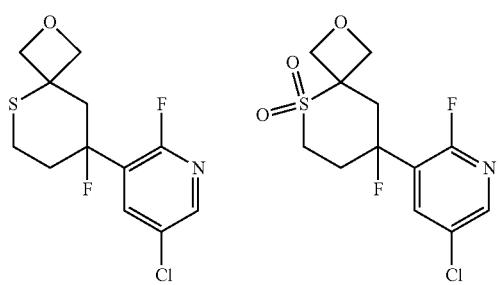

Int. 29.15

-continued

| Int. | Stereochemistry | Starting material | Structure | ESI-MS | $R_t$ (HPLC) [min] (method) | Reaction conditions |
|---|---|---|---|---|---|---|
| 52.3 | rac | Int. 29.16 | 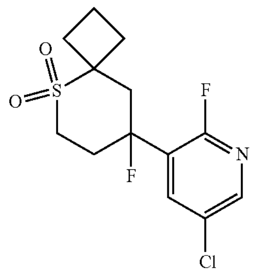 [SMILES: O=S1(=O)CCC(F)(c2cc(Cl)cnc2F)CC12CCC2] | 322/324 [M + H]⁺ | 0.17 (A) | Solvent: acetic acid, RT 24 h, RT 3 h |

Intermediate 53

(2S,4S)-1-[4-(Difluoromethyl)-8-oxa-3,5-diazatricyclo[7.4.0.0²,⁷]trideca-1(9),2(7),3,5,10,12-hexaen-6-yl]-4-({3-[(3S,4R)-4-fluoro-3-methyl oxan-4-yl]-5-(4,4,5,5-tetramethyl-1,3,2-dioxaborolan-2-yl)-pyridin-2-yl}oxy)pyrrolidine-2-carboxylic acid

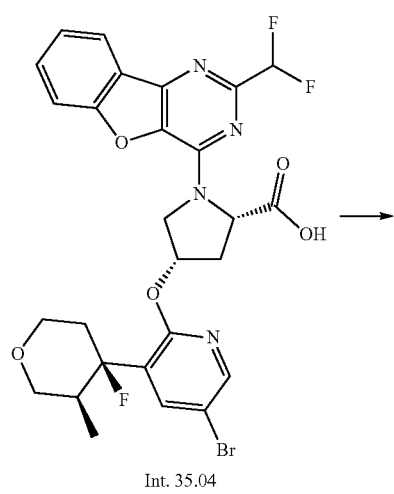

Int. 35.04

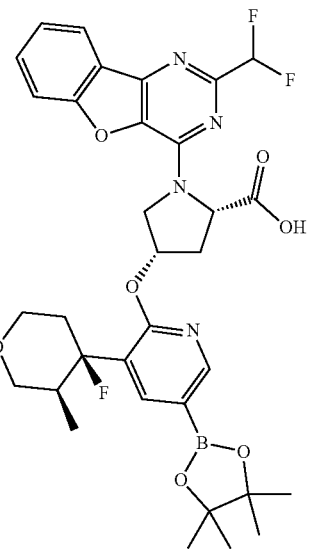

Int. 53

To a degassed mixture of INTERMEDIATE 35.04 (1.50 g, 2.29 mmol), bis-(pinacolato)diboron (675 mg, 2.52 mmol), potassium acetate (475 mg, 4.60 mmol) and dioxane (30 mL) was added (1,1'-bis-(diphenylphosphino)-ferrocen)-dichlorpalladium(II) (175 mg, 0.228 mmol). The mixture was stirred at 90° C. for 3 h. Ice-water was added dropwise, then the product was extracted with diethyl ether/THF. The organic layer was separated, dried with sodium sulfate and concentrated under reduced pressure. The crude product was filtered through silica gel (EtOAc/MeOH=10:1) and evaporated.

ESI-MS: 669 [M+H]⁺

$R_t$ (HPLC): 0.81 min (method A)

Intermediate 60

2-Fluoro-3-[(3S,4R)-4-fluoro-3-methyl-1-(oxetan-3-yl)piperidin-4-yl]-5-(prop-1-yn-1-yl)pyridine

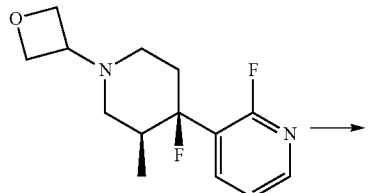

Int. 39

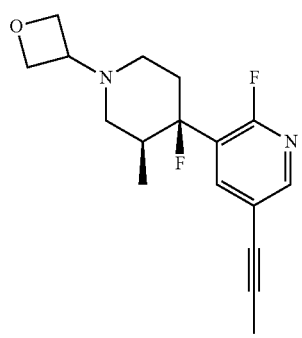

Int. 60

Under argon, propyne (1 mol/L in THF, 1.17 mL, 3.00 eq.), Xphos (18.6 mg, 10 mol %), bis(acetonitrile)palladium (II) dichloride (5.06 mg, 5 mol %) and cesium carbonate (152 mg, 1.20 eq.) were added successively to a degassed solution of racemic cis-5-Chloro-2-fluoro-3-[4-fluoro-3-methyl-1-(oxetan-3-yl)piperidin-4-yl]pyridine (INTERMEDIATE 39, 124 mg, 0.39 mmol) in ACN. The reaction mixture was stirred at 90° C. for 1.5 h, then concentrated and purified by column chromatography on silica gel (CH/EtOAc=80/20 to 0/100).

ESI-MS: 307 [M+H]$^+$

R$_t$ (HPLC): 0.38 min (method A)

Intermediate 61

Racemic cis 1-[4-fluoro-4-[2-fluoro-5-(prop-1-yn-1-yl)pyridin-3-yl]-3-methylpiperidin-1-yl]ethan-1-one

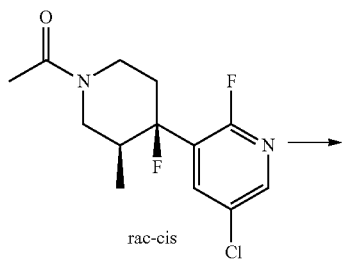

Int. 38

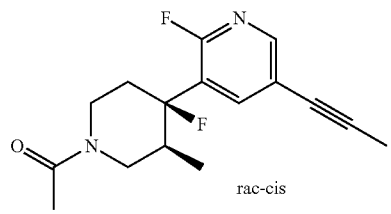

Int. 61

To a degassed solution of racemic cis-1-[4-(5-Chloro-2-fluoropyridin-3-yl)-4-fluoro-3-methylpiperidin-1-yl]ethan-1-one (INTERMEDIATE 38, 166 mg, 0.500 mmol) in anhydrous ACN (3.0 mL) were added successively propyne (1 mol/L in THF, 1.50 mL, 1.50 mmol), Xphos (23.8 mg, 0.050 mmol), bis(acetonitrile)palladium(II) dichloride (6.5 mg, 0.025 mmol) and cesium carbonate (195 mg, 0.600 mmol). The mixture was stirred for at 90° C. 1 h, then cooled to RT, diluted with ACN, filtered and evaporated to dryness. The crude product was purified by silica gel chromatography (CH/EtOAc 20%→100%)

ESI-MS: 293 [M+H]$^+$

R$_t$ (HPLC): 0.55 min (method A)

Preparation of Final Compounds

Example 1.01 (General Route)

(2S,4S)-4-({5-Chloro-3-[(3S,4R)-4-hydroxy-3-methyloxan-4-yl]pyridin-2-yl}oxy)-1-[4-(difluoromethyl)-8-oxa-3,5-diazatricyclo[7.4.0.0$^{2,7}$]trideca-1(13),2,4,6,9,11-hexaen-6-yl]pyrrolidine-2-carboxylic acid

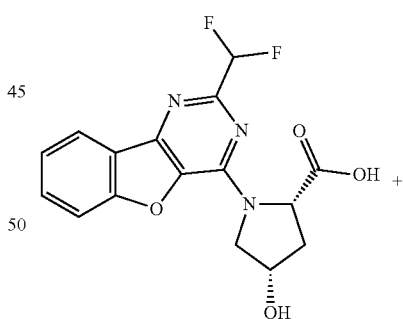

Int. 3.2

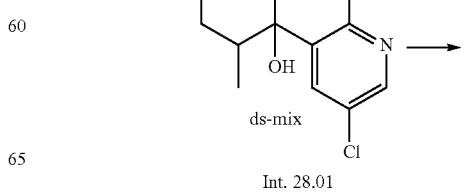

Int. 28.01

-continued

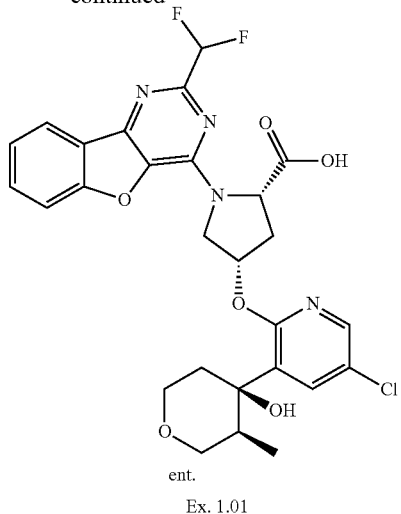

Ex. 1.01

To (2S,4S)-1-[4-(difluoromethyl)-8-oxa-3,5-diazatricyclo[7.4.0.0¹]trideca-1(9),2(7),3,5,10,12-hexaen-6-yl]-4-hydroxypyrrolidine-2-carboxylic acid (INTERMEDIATE 3.2, 147 mg, 0.40 mmol) in 2.00 mL DMA was added NaH (48.0 mg, 1.20 mmol) and the mixture was stirred at RT for 30 min. A mixture of 4-(5-chloro-2-fluoropyridin-3-yl)-3-methyloxan-4-ol (INTERMEDIATE 28.01, 147 mg, 0.60 mmol) in 2.00 mL DMA was added and the reaction mixture was stirred at RT for 1 h, then diluted with ACN/water, acidified with TFA, filtered and purified by RP-HPLC (XBridge C-18, ACN/H2O/TFA) to afford the crude product as a mixture of all four diasteroisomers. After purification under SFC conditions (column: BEH_2-EP, 10×250 mm, 5 μm; MeOH/$CO_2$=10/90, CT: 40° C., BPR: 120 bar, Flow: 10 mL/min) EXAMPLE 1.01 was obtained as pure enantiomer. Absolute stereochemistry was assessed from a cocrystal of EXAMPLE 1.01 bound to human cGAS.

ESI-MS: 575 $[M+H]^+$ $R_t$ (HPLC): 2.27 min (method I)

The following compounds were prepared according to the general procedure (EXAMPLE 1.01) described above:

| Ex. | Starting materials | Structure | ESI-MS | $R_t$ (HPLC) [min] (method) | Reaction conditions |
|---|---|---|---|---|---|
| 1.02 | Int. 3.2 + Int. 30.1 | 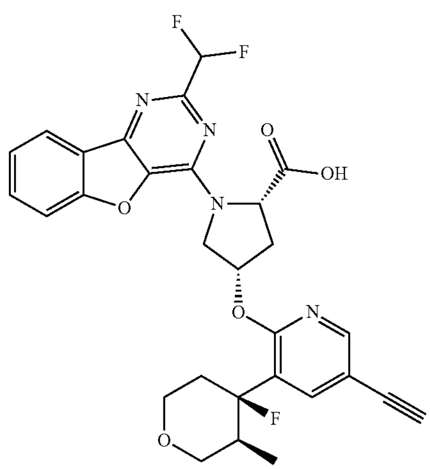 [SMILES: C#Cc1cnc(O[C@H]2C[C@@H](C(=O)O)N(c3nc(C(F)F)nc4c3oc3ccccc34)C2)c([C@@]2(F)CCOC[C@@H]2C)c1] | 567 $[M + H]^+$ | 0.54 (D) | NMP, RT, 1 h RP-HPLC: XBridge C-18; SFC: MeOH (20 mM $NH_3$)/$CO_2$; column: Torus-2-PIC, 10 × 250 mm, 5 μm; CT: 40° C.; BPR: 120 bar, Flow: 10 mL/min |
| 1.03 | Int. 3.2 + Int. 30.2 | 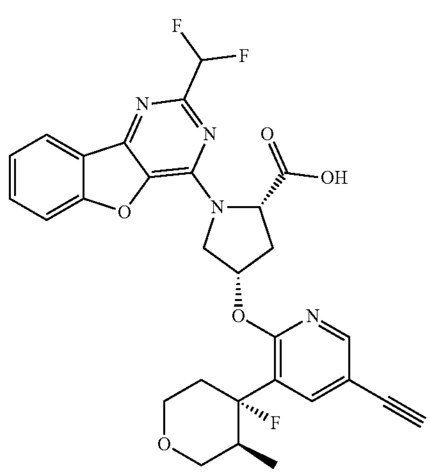 [SMILES: C#Cc1cnc(O[C@H]2C[C@@H](C(=O)O)N(c3nc(C(F)F)nc4c3oc3ccccc34)C2)c([C@]2(F)CCOC[C@@H]2C)c1] | 567 $[M + H]^+$ | 3.10 (G) | NMP, RT, 1 h RP-HPLC: XBridge C-18; SFC: IPA (20 mM $NH_3$)/$CO_2$ = 25/75; column: Chiralpak ® IG, 10 × 250 mm, 5 μm; CT: 40° C.; BPR: 140 bar, Flow: 10 mL/min |

| Ex. | Starting materials | Structure | ESI-MS | R$_t$ (HPLC) [min] (method) | Reaction conditions |
|---|---|---|---|---|---|
| 1.04 | Int. 3.1 + 30.2 | 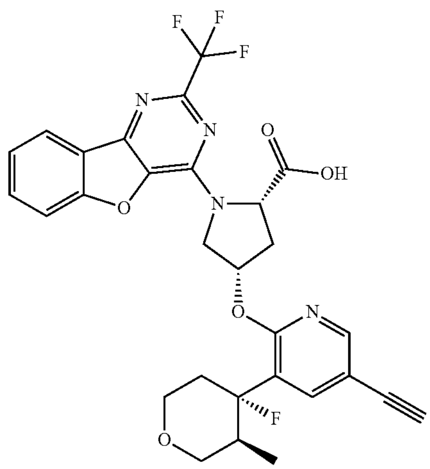 [SMILES: C#Cc1cnc(O[C@H]2C[C@@H](C(=O)O)N(c3nc(C(F)(F)F)nc4c3oc3ccccc34)C2)c([C@]2(F)CCOC[C@@H]2C)c1] | 585 [M + H]$^+$ | 1.17 (K) | NMP, RT, 1 h RP-HPLC: XBridge C-18; SFC: IPA (20 mM NH$_3$)/CO$_2$ = 20/80; column: CHIRAL ART ® Amylose-AC_N_10 × 250 mm, 5 μm; CT: 40° C.; BPR: 150 bar, Flow: 10 mL/min |
| 1.05 | Int. 3.2 + Int. 32 | 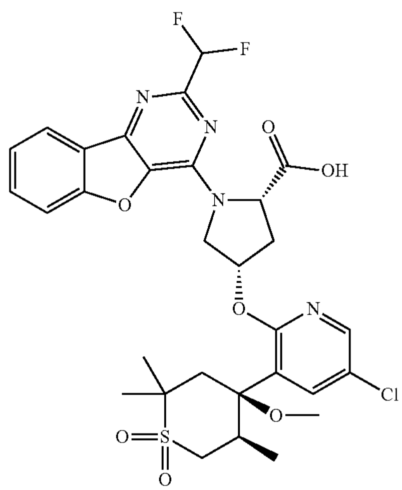 [SMILES: CO[C@]1(c2cc(Cl)cnc2O[C@H]2C[C@@H](C(=O)O)N(c3nc(C(F)F)nc4c3oc3ccccc34)C2)CC(C)(C)S(=O)(=O)C[C@@H]1C] | 665 [M + H]$^+$ | 1.87 (M) | DMF, RT, 2 h RP-HPLC: Agilent Zorbax SB C-18; SFC: IPA (20 mM NH$_3$)/CO$_2$ = 30/70; column: CHIRAL ART ® Amylose-C_neo_20 × 250 mm, 5 μm; CT: 40° C.; BPR: 150 bar, Flow: 10 mL/min |
| 1.06 | Int. 3.1 + Int. 33 | 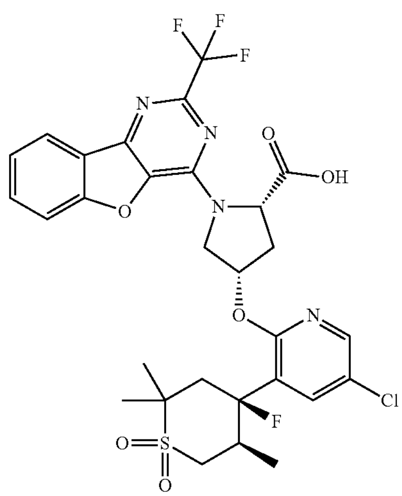 [SMILES: C[C@H]1CS(=O)(=O)C(C)(C)C[C@]1(F)c1cc(Cl)cnc1O[C@H]1C[C@@H](C(=O)O)N(c2nc(C(F)(F)F)nc3c2oc2ccccc23)C1] | 671 [M + H]$^+$ | 2.93 (N) | DMF, RT, 2 h RP-HPLC: Waters Sunfire C-18; SFC: MeOH (20 mM NH$_3$)/CO$_2$ = 20/80; column: CHIRAL ART ® Cellulose-SC 20 × 250 mm, 5 μm; CT: 40° C.; BPR: 150 bar, Flow: 10 mL/min |

-continued

| Ex. | Starting materials | Structure | ESI-MS | R$_t$ (HPLC) [min] (method) | Reaction conditions |
|---|---|---|---|---|---|
| 1.07 | Int. 3.1 + Int. 33 | 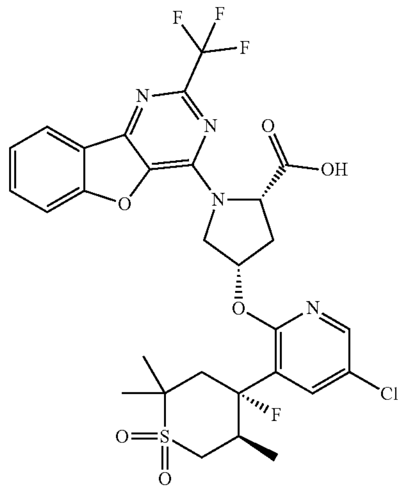 [SMILES: C[C@H]1CS(=O)(=O)C(C)(C)C[C@@]1(F)c1cc(Cl)cnc1O[C@H]1C[C@@H](C(=O)O)N(c2nc(C(F)(F)F)nc3c2oc2ccccc23)C1] | 671 [M + H]$^+$ | 3.41 (N) | DMF, RT, 2 h RP-HPLC: Waters Sunfire C-18; SFC: MeOH (20 mM NH$_3$)/CO$_2$ = 20/80; column: CHIRAL ART ® Cellulose-SC 20 × 250 mm, 5 μm; CT: 40° C.; BPR: 150 bar, Flow: 10 mL/min |
| 1.08 | Int. 3.1 + Int. 34.1 | 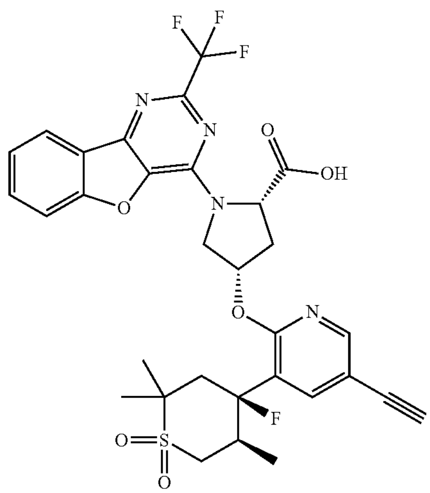 [SMILES: C#Cc1cnc(O[C@H]2C[C@@H](C(=O)O)N(c3nc(C(F)(F)F)nc4c3oc3ccccc34)C2)c([C@@]2(F)CC(C)(C)S(=O)(=O)C[C@@H]2C)c1] | 661 [M + H]$^+$ | 2.06 (M) | NMP, 40° C., 2 h RP-HPLC: Agilent Zorbax SB C-18; SFC: IPA (20 mM NH$_3$)/CO$_2$ = 30/70; column: CHIRAL ART ® Amylose-C_neo_20 × 250 mm, 5 μm; CT: 40° C.; BPR: 150 bar, Flow: 10 mL/min |
| 1.09 | Int. 3.2 + Int. 34.1 | 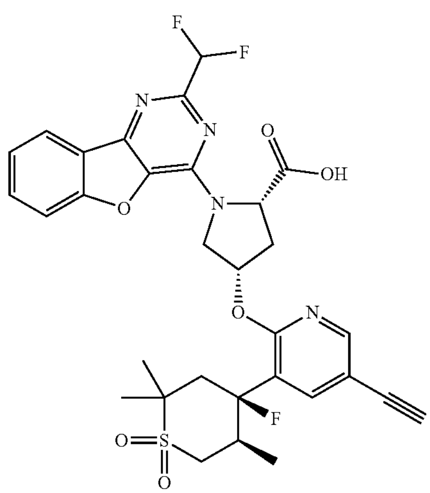 [SMILES: C#Cc1cnc(O[C@H]2C[C@@H](C(=O)O)N(c3nc(C(F)F)nc4c3oc3ccccc34)C2)c([C@@]2(F)CC(C)(C)S(=O)(=O)C[C@@H]2C)c1] | 643 [M + H]$^+$ | 3.07 (O) | NMP, 40° C., 2 h RP-HPLC: Agilent Zorbax SB C-18; SFC: MeOH (20 mM NH$_3$)/CO$_2$ = 25/75; column: CHIRAL ART ® Cellulose-SC 10 × 250 mm, 5 μm; CT: 40° C.; BPR: 150 bar, Flow: 10 mL/min |

| Ex. | Starting materials | Structure | ESI-MS | R$_t$ (HPLC) [min] (method) | Reaction conditions |
|---|---|---|---|---|---|
| 1.10 | Int. 3.2 + Int. 34.1 | 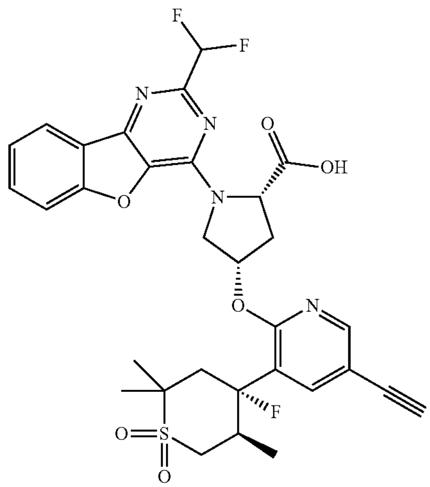 [SMILES: C#Cc1cnc(O[C@H]2C[C@@H](C(=O)O)N(c3nc(C(F)F)nc4c3oc3ccccc34)C2)c([C@]2(F)CC(C)(C)S(=O)(=O)C[C@@H]2C)c1] | 643 [M + H]$^+$ | 3.63 (O) | NMP, 40° C., 2 h RP-HPLC: Agilent Zorbax SB C-18; SFC: MeOH (20 mM NH$_3$)/CO$_2$ = 25/75; column: CHIRAL ART® Cellulose-SC 10 × 250 mm, 5 µm; CT: 40° C.; BPR: 150 bar, Flow: 10 mL/min |
| 1.11 | Int. 3.2 + Int. 49.1 | 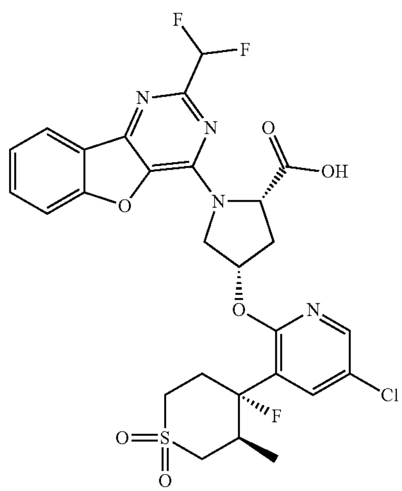 [SMILES: C[C@H]1CS(=O)(=O)CC[C@@]1(F)c1cc(Cl)cnc1O[C@H]1C[C@@H](C(=O)O)N(c2nc(C(F)F)nc3c2oc2ccccc23)C1] | 625 [M + H]$^+$ | 3.56 (Q) | DMF, RT, 30 min SFC: MeOH (20 mM NH$_3$)/CO$_2$; column: Torus-2-PIC, 10 × 250 mm, 5 µm; CT: 40° C.; BPR: 120 bar, Flow: 10 mL/min |
| 1.12 | Int. 3.2 + Int. 49.2 | 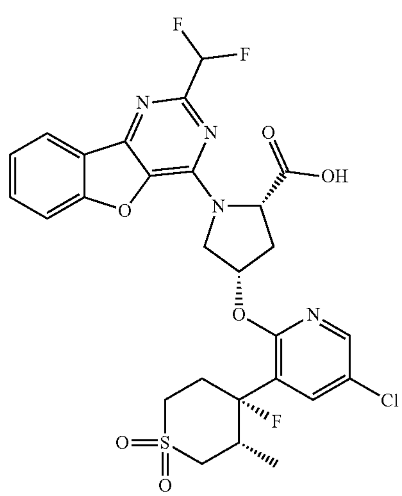 [SMILES: C[C@@H]1CS(=O)(=O)CC[C@@]1(F)c1cc(Cl)cnc1O[C@H]1C[C@@H](C(=O)O)N(c2nc(C(F)F)nc3c2oc2ccccc23)C1] | 625 [M + H]$^+$ | 3.45 (P) | DMF, RT, 1 h SFC: MeOH (20 mM NH$_3$)/CO$_2$ = 30/70; column: CHIRAL ART® Cellulose-SC 10 × 250 mm, 5 µm; CT: 40° C.; BPR: 150 bar, Flow: 10 mL/min |

-continued

| Ex. | Starting materials | Structure | ESI-MS | R$_t$ (HPLC) [min] (method) | Reaction conditions |
|---|---|---|---|---|---|
| 1.13 | Int. 3.2 + Int. 49.2 | 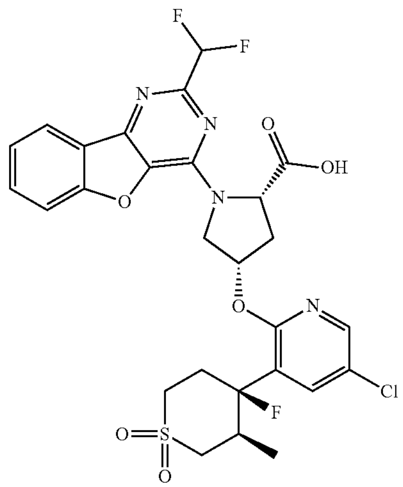 [SMILES: C[C@H]1CS(=O)(=O)CC[C@]1(F)c1cc(Cl)cnc1O[C@H]1C[C@@H](C(=O)O)N(c2nc(C(F)F)nc3c2oc2ccccc23)C1] | 625 [M + H]$^+$ | 3.17 (P) | DMF, RT, 1 h SFC: MeOH (20 mM NH$_3$)/CO$_2$ = 30/70; column: CHIRAL ART ® Cellulose-SC 10 × 250 mm, 5 μm; CT: 40° C.; BPR: 150 bar, Flow: 10 mL/min |
| 1.14 | Int. 3.1 + Int. 34.2 | 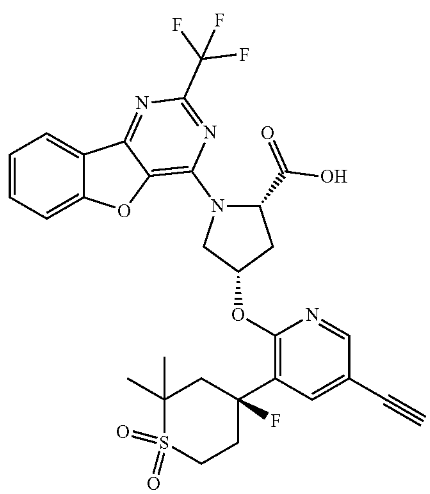 [SMILES: C#Cc1cnc(O[C@H]2C[C@@H](C(=O)O)N(c3nc(C(F)(F)F)nc4c3oc3ccccc34)C2)c([C@]2(F)CCS(=O)(=O)C(C)(C)C2)c1] | 647 [M + H]$^+$ | 4.36 (Q) | NMP, RT, overnight SFC: MeOH (20 mM NH$_3$)/CO$_2$ = 35/65; column: Chiralpak@ IG 10 × 250 mm, 5 μm; CT: 40° C.; BPR: 150 bar, Flow: 10 mL/min |
| 1.15 | Int. 3.2 + Int. 34.2 | 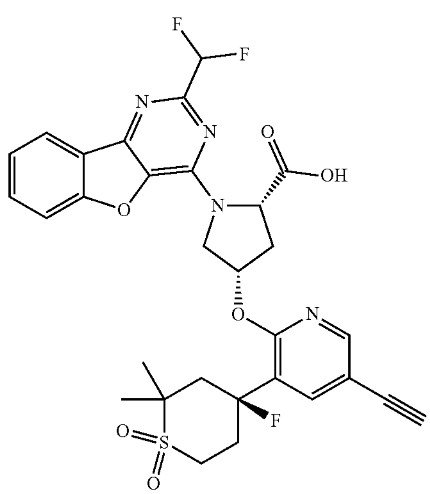 [SMILES: C#Cc1cnc(O[C@H]2C[C@@H](C(=O)O)N(c3nc(C(F)F)nc4c3oc3ccccc34)C2)c([C@]2(F)CCS(=O)(=O)C(C)(C)C2)c1] | 629 [M + H]$^+$ | 4.61 (R) | NMP, RT, overnight SFC: MeOH (20 mM NH$_3$)/CO$_2$ = 40/60; column: Chiralpak@ IG 10 × 250 mm, 5 μm; CT: 40° C.; BPR: 150 bar, Flow: 10 mL/min |

-continued

| Ex. | Starting materials | Structure | ESI-MS | R$_t$ (HPLC) [min] (method) | Reaction conditions |
|---|---|---|---|---|---|
| 1.16 | Int. 3.2 + Int. 33 | 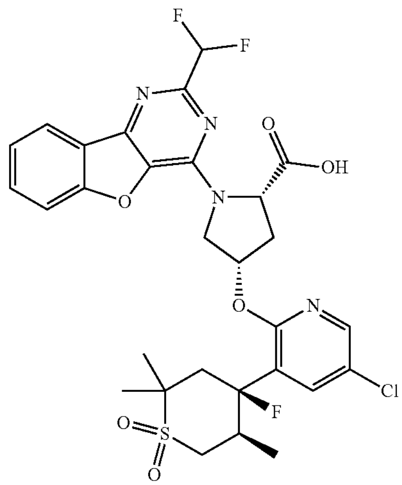 [SMILES: C[C@H]1CS(=O)(=O)C(C)(C)C[C@]1(F)c1cc(Cl)cnc1O[C@H]1C[C@@H](C(=O)O)N(c2nc(C(F)F)nc3c2oc2ccccc23)C1] | 653 [M + H]$^+$ | 2.62 (K) | DMF, RT, 2 h RP-HPLC: Agilent Zorbax SB C-18; SFC: MeOH (20 mM NH$_3$)/CO$_2$ = 20/80; column: CHIRAL ART ® Cellulose-SC 10 × 250 mm, 5 μm; CT: 40° C.; BPR: 150 bar, Flow: 10 mL/min |
| 1.17 | Int. 3.2 + Int. 52.1 | 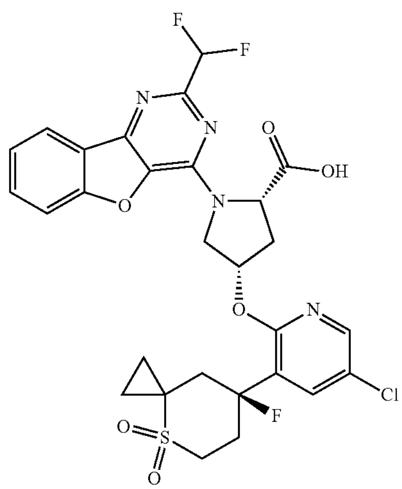 [SMILES: O=C(O)[C@@H]1C[C@H](Oc2ncc(Cl)cc2[C@]2(F)CCS(=O)(=O)C3(CC3)C2)CN1c1nc(C(F)F)nc2c1oc1ccccc12] | 637 [M + H]$^+$ | 4.09 (O) | NMP, RT 1 h RP-HPLC: XBridge C-18; SFC: MeOH (20 mM NH$_3$)/CO$_2$ = 25/75; column: CHIRAL ART ® Cellulose-SC 10 × 250 mm, 5 μm; CT: 40° C.; BPR: 150 bar, Flow: 10 mL/min |
| 1.18 | Int. 3.2 + Int. 52.1 | 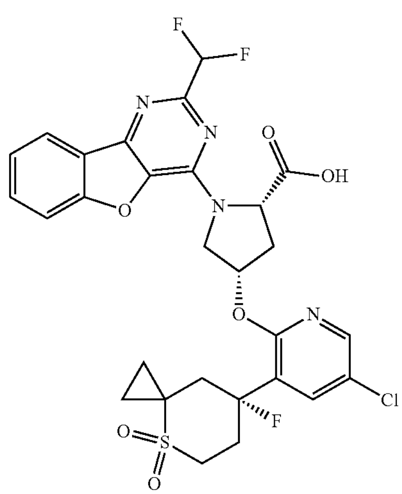 [SMILES: O=C(O)[C@@H]1C[C@H](Oc2ncc(Cl)cc2[C@@]2(F)CCS(=O)(=O)C3(CC3)C2)CN1c1nc(C(F)F)nc2c1oc1ccccc12] | 637 [M + H]$^+$ | 4.47 (O) | NMP, RT 1 h RP-HPLC: XBridge C-18; SFC: MeOH (20 mM NH$_3$)/CO$_2$ = 25/75; column: CHIRAL ART ® Cellulose-SC 10 × 250 mm, 5 μm; CT: 40° C.; BPR: 150 bar, Flow: 15 mL/min |

-continued

| Ex. | Starting materials | Structure | ESI-MS | R_t (HPLC) [min] (method) | Reaction conditions |
|---|---|---|---|---|---|
| 1.19 | Int. 3.2 + Int. 52.2 | 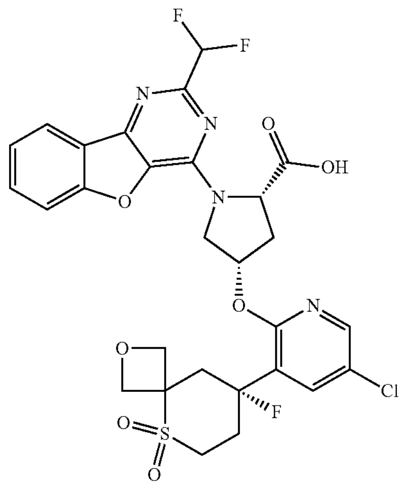 [SMILES: O=C(O)[C@@H]1C[C@H](Oc2ncc(Cl)cc2[C@@]2(F)CCS(=O)(=O)C3(COC3)C2)CN1c1nc(C(F)F)nc2c1oc1ccccc12] | 653 [M + H]⁺ | 1.49 (Y) | NMP, RT 1.5 h RP-HPLC: XBridge C-18; SFC: EtOH (20 mM NH$_3$)/CO$_2$ = 40/60; column: Chiralpak@ IG 10 × 250 mm, 5 μm; CT: 40° C.; BPR: 150 bar, Flow: 60 mL/min |
| 1.20 | Int. 3.2 + Int. 52.2 | 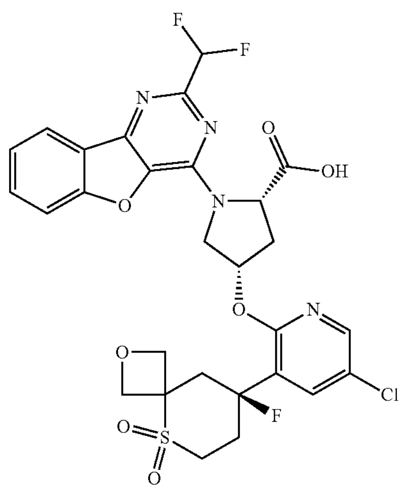 [SMILES: O=C(O)[C@@H]1C[C@H](Oc2ncc(Cl)cc2[C@]2(F)CCS(=O)(=O)C3(COC3)C2)CN1c1nc(C(F)F)nc2c1oc1ccccc12] | 653 [M + H]⁺ | 2.38 (Y) | NMP, RT, 1.5 h RP-HPLC: XBridge C-18; SFC: EtOH (20 mM NH$_3$)/CO$_2$ = 40/60; column: Chiralpak@ IG 10 × 250 mm, 5 μm; CT: 40° C.; BPR: 150 bar, Flow: 60 mL/min |
| 1.21 | Int. 3.2 + Int. 52.3 | 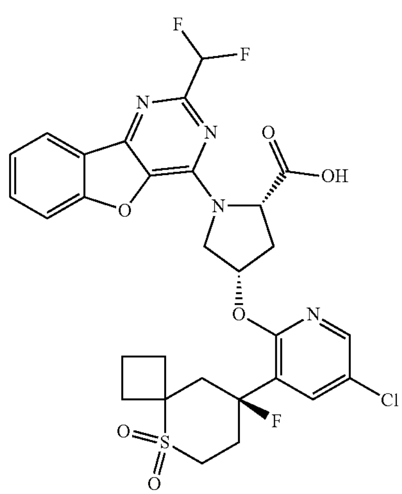 [SMILES: O=C(O)[C@@H]1C[C@H](Oc2ncc(Cl)cc2[C@]2(F)CCS(=O)(=O)C3(CCC3)C2)CN1c1nc(C(F)F)nc2c1oc1ccccc12] | 651 [M + H]⁺ | 2.23 (Y) | NMP, RT, 1.5 h RP-HPLC: XBridge C-18; SFC: EtOH (20 mM NH$_3$)/CO$_2$ = 40/60; column: Chiralpak@ IG 10 x 250 mm, 5 μm; CT: 40° C.; BPR: 150 bar, Flow: 15 mL/min |

| Ex. | Starting materials | Structure | ESI-MS | R$_t$ (HPLC) [min] (method) | Reaction conditions |
|---|---|---|---|---|---|
| 1.22 | Int. 3.2 + Int. 38 | 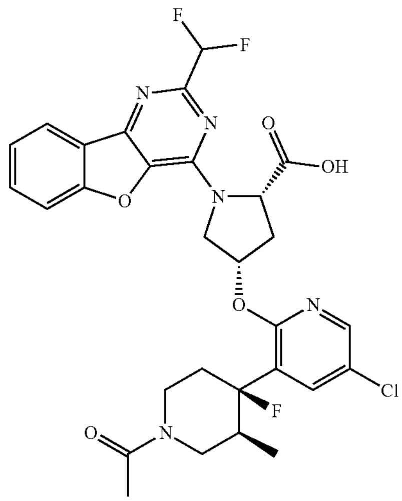 [SMILES: CC(=O)N1CC[C@](F)(c2cc(Cl)cnc2O[C@H]2C[C@@H](C(=O)O)N(c3nc(C(F)F)nc4c3oc3ccccc34)C2)[C@@H](C)C1] | 618 [M + H]$^+$ | 3.27 (U) | NMP, RT, 2 h RP-HPLC: XBridge C-18; SFC: MeOH (20 mM NH$_3$)/CO$_2$; column: Torus-DEA, CT: 40° C.; BPR: 120 bar |
| 1.23 | Int. 3.2 + Int. 39 | 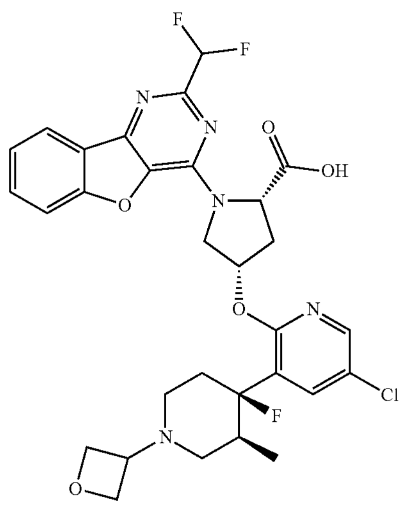 [SMILES: C[C@H]1CN(C2COC2)CC[C@]1(F)c1cc(Cl)cnc1O[C@H]1C[C@@H](C(=O)O)N(c2nc(C(F)F)nc3c2oc2ccccc23)C1] | 632 [M + H]$^+$ | 2.36 (T) | Solvent: NMP, RT 2 h RP-HPLC: XBridge C-18; SFC: MeOH (20 mM NH$_3$)/CO$_2$; column: BEH; CT: 40° C.; BPR: 120 bar |
| 1.24 | Int. 3.2 + Int. 37.02 | 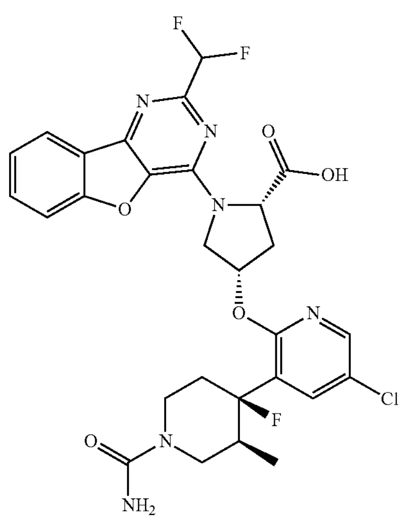 [SMILES: C[C@H]1CN(C(N)=O)CC[C@]1(F)c1cc(Cl)cnc1O[C@H]1C[C@@H](C(=O)O)N(c2nc(C(F)F)nc3c2oc2ccccc23)C1] | 619/621 [M + H]$^+$ | 3.37 (L) | Solvent: NMP, RT 2 h RP-HPLC: XBridge C-18; SFC: MeOH (20 mM NH$_3$)/CO$_2$; column: Torus-2-PIC; CT: 40° C.; BPR: 120 bar |

-continued

| Ex. | Starting materials | Structure | ESI-MS | R$_t$ (HPLC) [min] (method) | Reaction conditions |
|---|---|---|---|---|---|
| 1.25 | Int. 3.2 + Int. 29.05 | 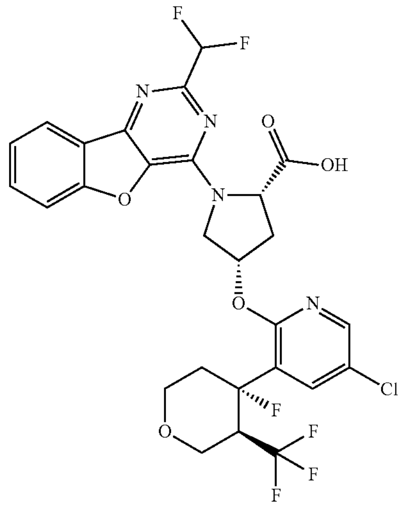 [SMILES: O=C(O)[C@@H]1C[C@H](Oc2ncc(Cl)cc2[C@]2(F)CCOC[C@@H]2C(F)(F)F)CN1c1nc(C(F)F)nc2c1oc1ccccc12] | 631/633 [M + H]$^+$ | 2.27 (V) | Solvent: DMA, RT 1 h |

RP-HPLC: Sunfire C-18;
SFC: MeOH (20 mM NH$_3$)/CO$_2$;
column: BEH_2-EP; CT: 40° C.;
BPR: 120 bar Example 2.01 (General Route)

(2S,4S)-4-{[5-Chloro-3-(4-fluoro-1,1-dioxo-1-I-6-thian-4-yl)pyridin-2-yl]oxy}-1-[4-(difluoromethyl)-8-oxa-3,5-diazatricyclo[7.4.0.0$^{2,7}$]trideca-1(13),2,4,6,9,11-hexaen-6-yl]pyrrolidine-2-carboxylic acid

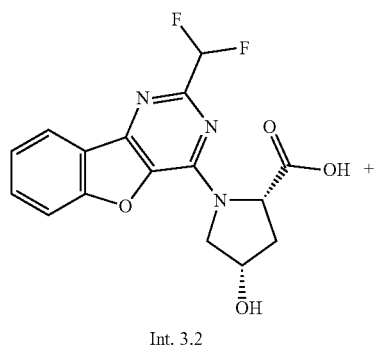

Int. 3.2

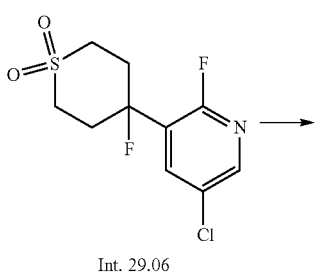

Int. 29.06

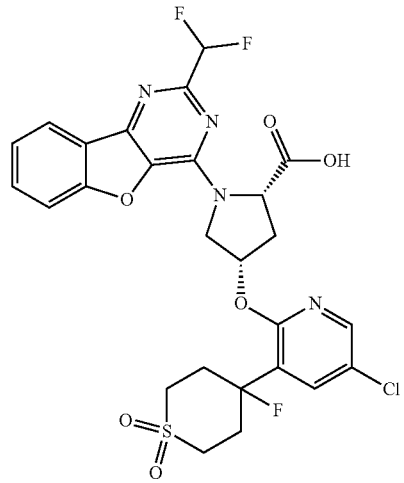

Ex. 2.01

To (2S,4S)-1-[4-(difluoromethyl)-8-oxa-3,5-diazatricyclo[7.4.0.0$^1$]trideca-1(9),2(7),3,5,10,12-hexaen-6-yl]-4-hydroxypyrrolidine-2-carboxylic acid (INTERMEDIATE 3.2, 18.4 mg, 0.05 mmol) in 2.00 mL DMA was added 4-(5-chloro-2-fluoropyridin-3-yl)-4-fluoro-1-I-6-thiane-1,1-dione (INTERMEDIATE 29.06, 14.1 mg, 0.05 mmol) and NaH (6.00 mg, 0.15 mmol). The reaction mixture was stirred for 16 h at RT, then diluted with ACN/water, acidified with TFA, filtered and purified by HPLC (ACN/H2O/TFA).

ESI-MS: 611 [M+H]$^+$

R$_t$ (HPLC): 0.97 min (method H)

The following compounds were prepared according to the general procedure (EXAMPLE 2.01) described above:

| Ex. | Starting materials | Structure | ESI-MS | R$_t$ (HPLC) [min] (method) | Reaction conditions |
|---|---|---|---|---|---|
| 2.02 | Int 3.1 + Int. 29.06 | 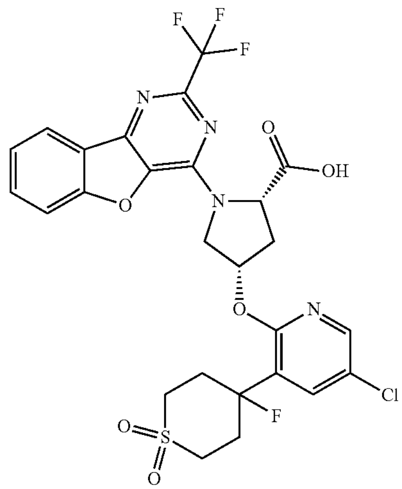 [SMILES: O=C(O)[C@@H]1C[C@H](Oc2ncc(Cl)cc2C2(F)CCS(=O)(=O)CC2)CN1c1nc(C(F)(F)F)nc2c1oc1ccccc12] | 629 [M + H]$^+$ | 1.04 (H) | DMA, RT, 1 h |
| 2.03 | Int 3.2 + Int. 30.3 | 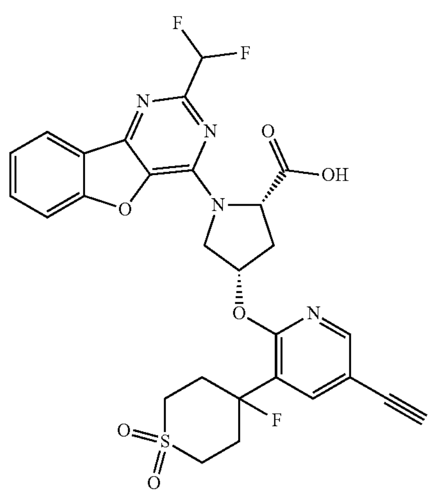 [SMILES: C#Cc1cnc(O[C@H]2C[C@@H](C(=O)O)N(c3nc(C(F)F)nc4c3oc3ccccc34)C2)c(C2(F)CCS(=O)(=O)CC2)c1] | 601 [M + H]$^+$ | 0.93 (J) | NMP, RT, 2 h |
| 2.04 | Int. 3.2 + Int. 29.07 | 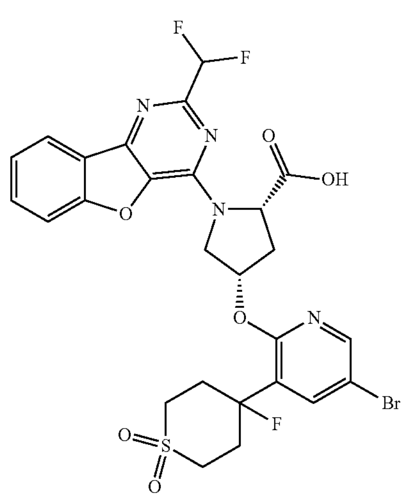 [SMILES: O=C(O)[C@@H]1C[C@H](Oc2ncc(Br)cc2C2(F)CCS(=O)(=O)CC2)CN1c1nc(C(F)F)nc2c1oc1ccccc12] | 655 [M + H]$^+$ | 0.52 (D) | DMA, RT, 1 h |

-continued

| Ex. | Starting materials | Structure | ESI-MS | R_t (HPLC) [min] (method) | Reaction conditions |
|---|---|---|---|---|---|
| 2.05 | Int. 3.2 + Int. 37.1 | 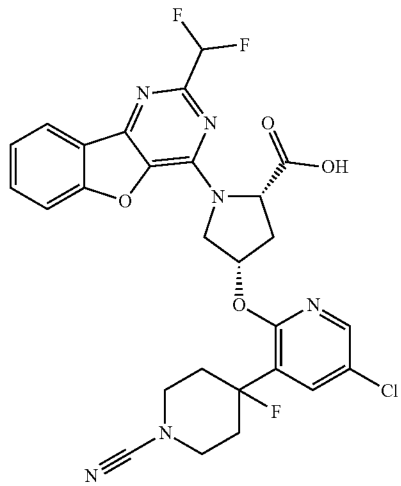 [SMILES: N#CN1CCC(F)(c2cc(Cl)cnc2O[C@H]2C[C@@H](C(=O)O)N(c3nc(C(F)F)nc4c3oc3ccccc34)C2)CC1] | 587 [M + H]⁺ | 1.12 (C) | DMF, RT, 1 h |
| 2.06 | Int. 3.2 + Int. 40.02 | 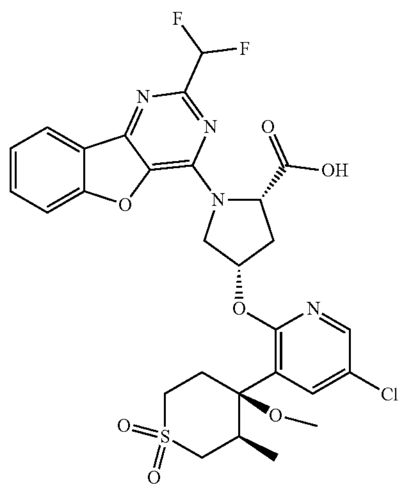 [SMILES: CO[C@]1(c2cc(Cl)cnc2O[C@H]2C[C@@H](C(=O)O)N(c3nc(C(F)F)nc4c3oc3ccccc34)C2)CCS(=O)(=O)C[C@@H]1C] | 637 [M + H]⁺ | 1.01 (W) | DMF, RT, 1 h |
| 2.07 | Int 3.1 + Int. 30.3 | 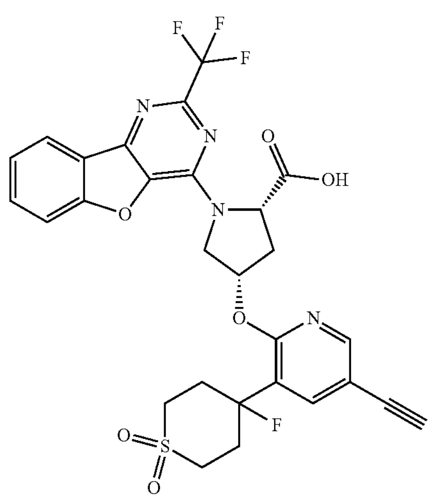 [SMILES: C#Cc1cnc(O[C@H]2C[C@@H](C(=O)O)N(c3nc(C(F)(F)F)nc4c3oc3ccccc34)C2)c(C2(F)CCS(=O)(=O)CC2)c1] | 619 [M + H]⁺ | 1.02 (J) | NMP, RT, 1 h |

-continued

| Ex. | Starting materials | Structure | ESI-MS | R$_t$ (HPLC) [min] (method) | Reaction conditions |
|---|---|---|---|---|---|
| 2.08 | Int. 3.2 + Int. 51.1 | 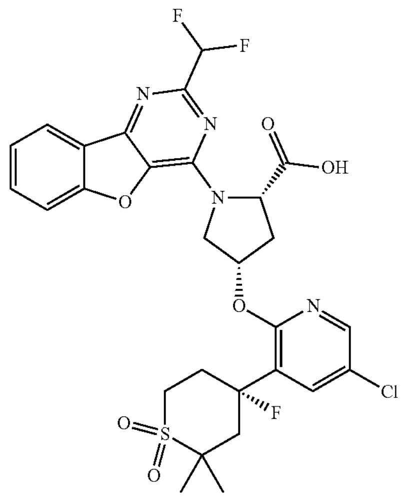 [SMILES: CC1(C)C[C@](F)(c2cc(Cl)cnc2O[C@H]2C[C@@H](C(=O)O)N(c3nc(C(F)F)nc4c3oc3ccccc34)C2)CCS1(=O)=O] | 639 [M + H]$^+$ | 1.00 (W) | DMF, RT, 1 h |
| 2.09 | Int. 3.1 + Int. 51.1 | 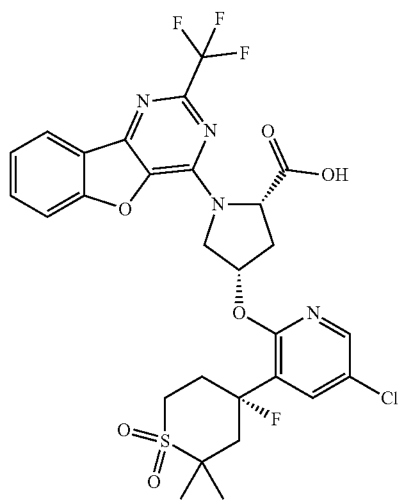 [SMILES: CC1(C)C[C@](F)(c2cc(Cl)cnc2O[C@H]2C[C@@H](C(=O)O)N(c3nc(C(F)(F)F)nc4c3oc3ccccc34)C2)CCS1(=O)=O] | 657 [M + H]$^+$ | 1.04 (W) | DMF, RT, 1 h |
| 2.10 | Int. 3.1 + Int. 49.2 | 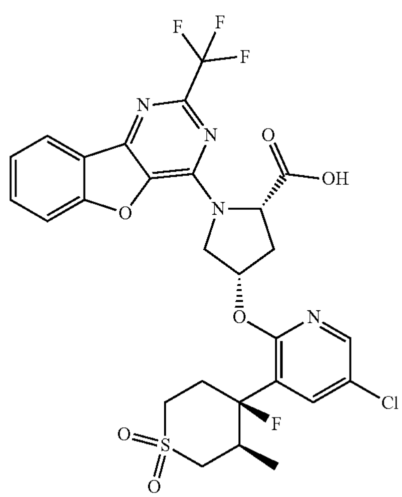 [SMILES: C[C@H]1CS(=O)(=O)CC[C@]1(F)c1cc(Cl)cnc1O[C@H]1C[C@@H](C(=O)O)N(c2nc(C(F)(F)F)nc3c2oc2ccccc23)C1] | 643 [M + H]$^+$ | 0.56 (D) | NMP, RT, 1 h |

-continued

| Ex. | Starting materials | Structure | ESI-MS | R$_t$ (HPLC) [min] (method) | Reaction conditions |
|---|---|---|---|---|---|
| 2.11 | Int. 3.2 + Int. 34.3 | 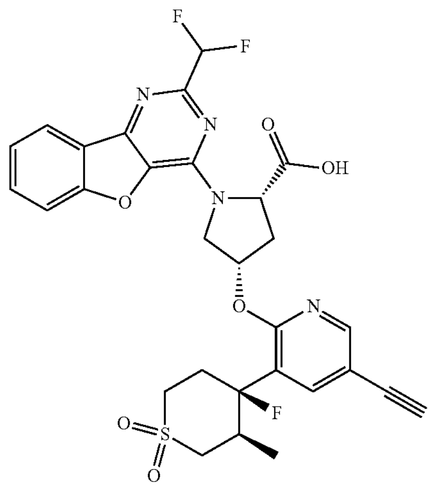 [SMILES: C#Cc1cnc(O[C@H]2C[C@@H](C(=O)O)N(c3nc(C(F)F)nc4c3oc3ccccc34)C2)c([C@@]2(F)CCS(=O)(=O)C[C@@H]2C)c1] | 615 [M + H]$^+$ | 0.66 (A) | DMF, 60° C., 15 min |
| 2.12 | Int. 3.1 + Int. 34.3 | 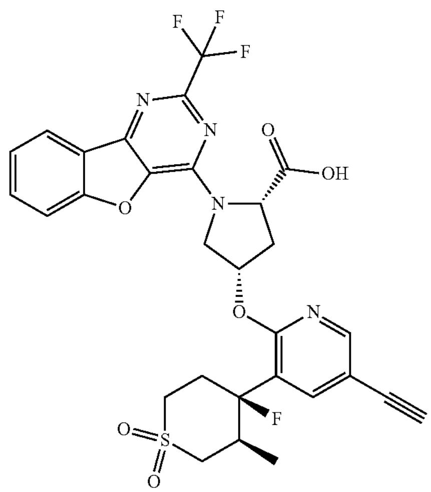 [SMILES: C#Cc1cnc(O[C@H]2C[C@@H](C(=O)O)N(c3nc(C(F)(F)F)nc4c3oc3ccccc34)C2)c([C@@]2(F)CCS(=O)(=O)C[C@@H]2C)c1] | 633 [M + H]$^+$ | 1.13 (W) | DMF, RT, 45 min |
| 2.13 | Int. 3.2 + Int. 29.13 | 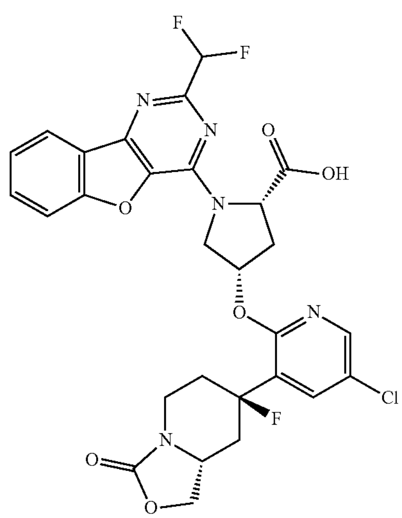 [SMILES: O=C(O)[C@@H]1C[C@H](Oc2ncc(Cl)cc2[C@@]2(F)CCN3C(=O)OC[C@H]3C2)CN1c1nc(C(F)F)nc2c1oc1ccccc12] | 616/618 [M + H]$^+$ | 0.69 (A) | DMF, RT, 1 h |

-continued

| Ex. | Starting materials | Structure | ESI-MS | R$_t$ (HPLC) [min] (method) | Reaction conditions |
|---|---|---|---|---|---|
| 2.14 | Int. 3.2 + Int. 34.4 | 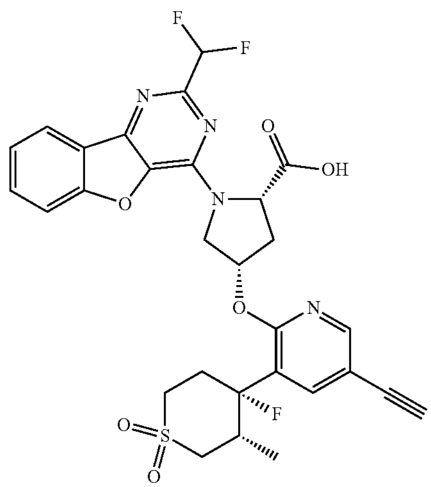 [SMILES: C#Cc1cnc(O[C@H]2C[C@@H](C(=O)O)N(c3nc(C(F)F)nc4c3oc3ccccc34)C2)c([C@]2(F)CCS(=O)(=O)C[C@H]2C)c1] | 615 [M + H]$^+$ | 0.68 (A) | DMF, 60° C., 15 min |
| 2.15 | Int. 3.1 + Int. 34.4 | 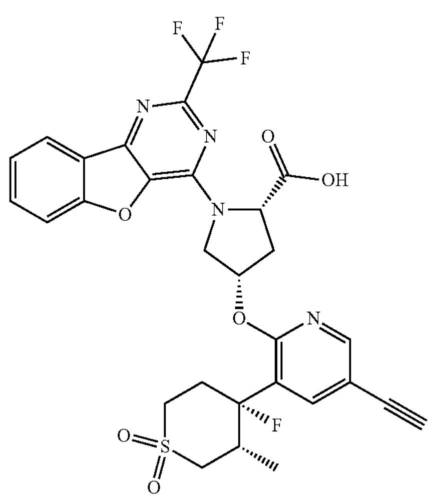 [SMILES: C#Cc1cnc(O[C@H]2C[C@@H](C(=O)O)N(c3nc(C(F)(F)F)nc4c3oc3ccccc34)C2)c([C@]2(F)CCS(=O)(=O)C[C@H]2C)c1] | 633 [M + H]$^+$ | 0.73 (A) | DMF, 60° C., 15 min |
| 2.16 | Int. 3.2 + Int. 29.02 | 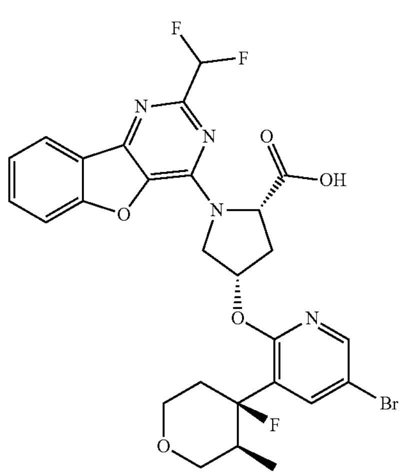 [SMILES: C[C@H]1COCC[C@]1(F)c1cc(Br)cnc1O[C@H]1C[C@@H](C(=O)O)N(c2nc(C(F)F)nc3c2oc2ccccc23)C1] | 621 [M + H]$^+$ | 1.16 (H) | NMP, RT, 16 h |

-continued

| Ex. | Starting materials | Structure | ESI-MS | R$_t$ (HPLC) [min] (method) | Reaction conditions |
|---|---|---|---|---|---|
| 2.17 | Int. 3.1 + Int. 60 | 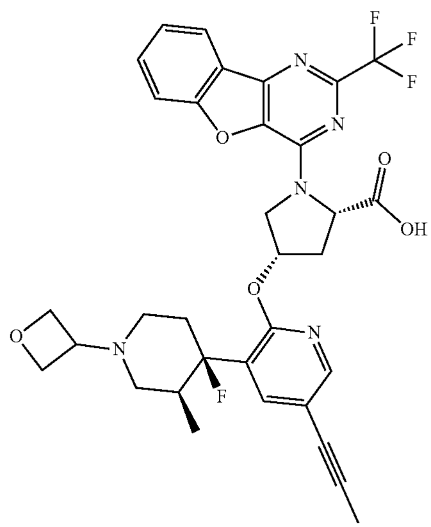 [SMILES: CC#Cc1cnc(O[C@H]2C[C@@H](C(=O)O)N(c3nc(C(F)(F)F)nc4c3oc3ccccc34)C2)c([C@@]2(F)CCN(C3COC3)C[C@@H]2C)c1] | 654 [M + H]$^+$ | 0.88 (H) | NMP, 50° C., 10 min |
| 2.18 | Int. 3.2 + Int. 60 | 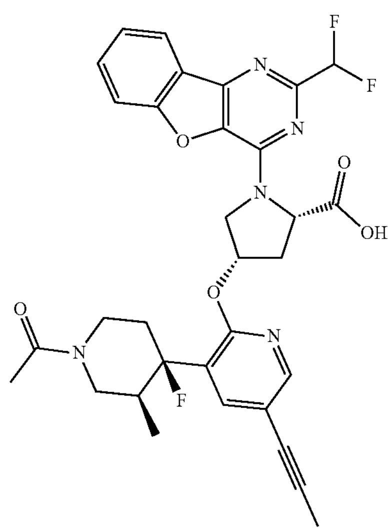 [SMILES: CC#Cc1cnc(O[C@H]2C[C@@H](C(=O)O)N(c3nc(C(F)F)nc4c3oc3ccccc34)C2)c([C@@]2(F)CCN(C(C)=O)C[C@@H]2C)c1] | 622 [M + H]$^+$ | 1.12 (Z) | NMP, 50° C., 10 min |
| 2.19 | Int. 3.1 + Int. 34.5 | 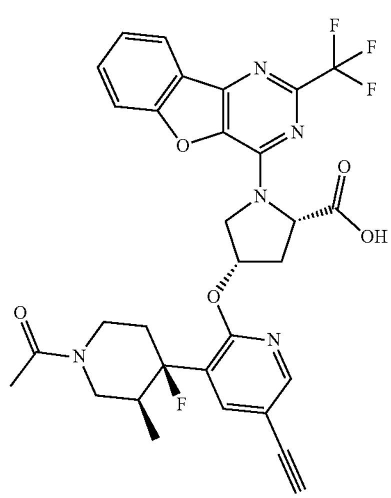 [SMILES: C#Cc1cnc(O[C@H]2C[C@@H](C(=O)O)N(c3nc(C(F)(F)F)nc4c3oc3ccccc34)C2)c([C@@]2(F)CCN(C(C)=O)C[C@@H]2C)c1] | 626 [M + H]$^+$ | 1.12 (H) | NMP, 50° C., 10 min |

| Ex. | Starting materials | Structure | ESI-MS | R$_t$ (HPLC) [min] (method) | Reaction conditions |
|---|---|---|---|---|---|
| 2.20 | Int. 3.2 + Int. 34.5 | 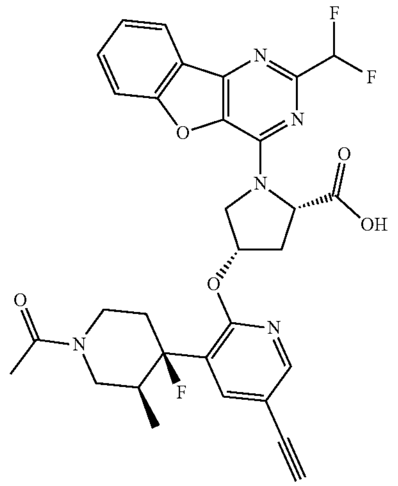 [SMILES: C#Cc1cnc(O[C@H]2C[C@@H](C(=O)O)N(c3nc(C(F)F)nc4c3oc3ccccc34)C2)c([C@@]2(F)CCN(C(C)=O)C[C@@H]2C)c1] | 608 [M + H]$^+$ | 1.04 (H) | NMP, 50° C., 10 min |

Example 3.01 (General Route)

(2S,4S)-1-[4-(Difluoromethyl)-8-oxa-3,5-diazatricyclo[7.4.0.0$^{2,7}$]trideca-1(13),2,4,6,9,11-hexaen-6-yl]-4-({3-[(3S,4R)-4-fluoro-3-methyloxan-4-yl]-5-(1-methyl-1H-pyrazol-4-yl)pyridin-2-yl}oxy)pyrrolidine-2-carboxylic acid

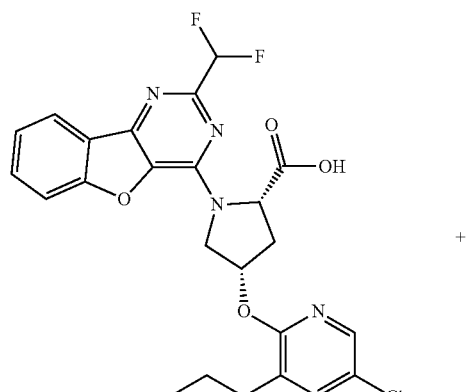

Int. 35.01

+

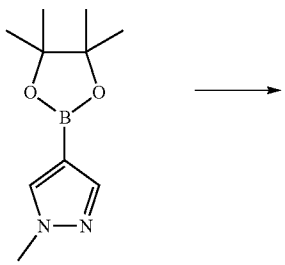

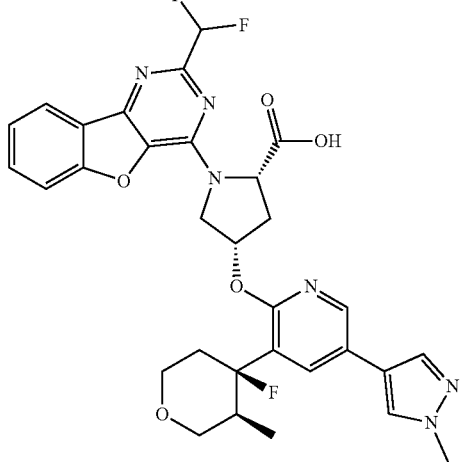

Ex. 3.01

To (2S,4S)-4-({5-chloro-3-[(3S,4R)-4-fluoro-3-methyloxan-4-yl]pyridin-2-yl}oxy)-1-[4-(difluoromethyl)-8-oxa-3,5-diazatricyclo[7.4.0.0$^{2,7}$]trideca-1(13),2,4,6,9,11-hexaen-6-yl]pyrrolidine-2-carboxylic acid (INTERMEDIATE 35.01, 50.0 mg, 0.09 mmol) in 2.00 mL dioxane was added 1-methyl-4-(4,4,5,5-tetramethyl-1,3,2-dioxaborolan-2-yl)-1H-pyrazole (63.0 mg, 0.30 mmol) sodium carbonate solution (0.11 mL, 0.22 mmol), Xphos 3$^{rd}$ gen (7.00 mg, 0.01 mmol) and Tetrakis (10.0 mg, 0.01 mmol). This mixture was stirred for at 100° C. for 4 h. After cooling down to RT, the reaction mixture was diluted with water and extracted three times with DCM. The organic phases were dried using an ISOLUTE © phase separator and concentrated under reduced pressure. The residue was dissolved with ACN/DMSO/TFA, filtered and purified by HPLC (ACN/H2O/TFA).
ESI-MS: 623 [M+H]$^+$
R$_t$ (HPLC): 0.66 min (method A)
The following compound was prepared according to the general procedure (EXAMPLE 3.01) described above:

| Ex. | Starting materials | Structure | ESI-MS | R$_t$ (HPLC) [min] (method) | Reaction conditions |
|---|---|---|---|---|---|
| 3.02 | Int. 35.01 + 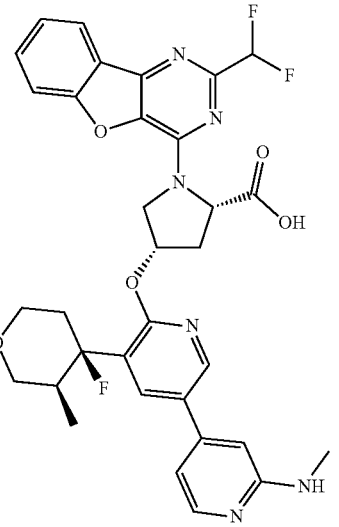 | 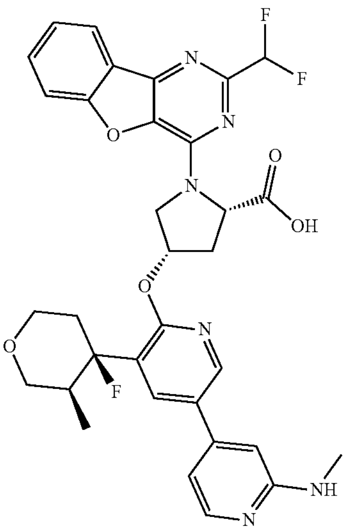 [SMILES: CNc1cc(-c2cnc(O[C@H]3C[C@@H](C(=O)O)N(c4nc(C(F)F)nc5c4oc4ccccc45)C3)c([C@@]3(F)CCOC[C@@H]3C)c2)ccn1] | 649 [M + H]$^+$ | 0.43 (F) | Solvent: dioxane, 100° C., 2 h |
| 3.03 | Int. 35.04 + 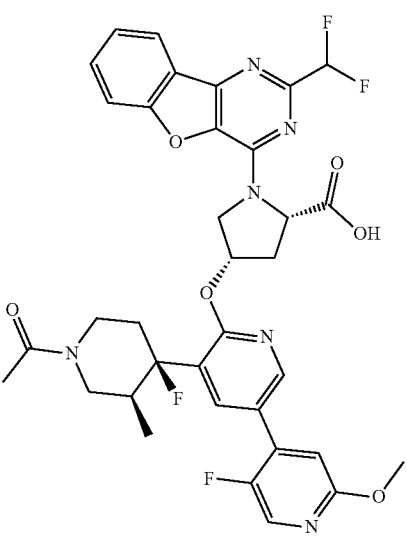 | 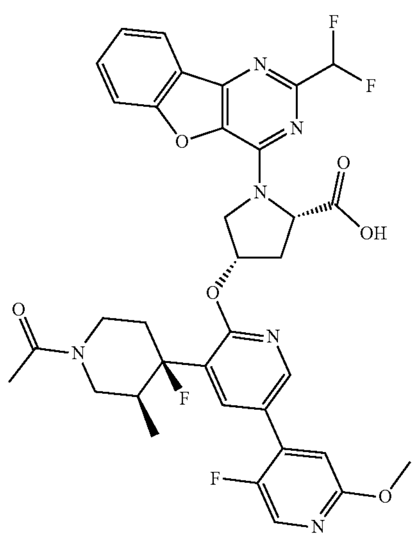 [SMILES: COc1cc(-c2cnc(O[C@H]3C[C@@H](C(=O)O)N(c4nc(C(F)F)nc5c4oc4ccccc45)C3)c([C@@]3(F)CCN(C(C)=O)C[C@@H]3C)c2)c(F)cn1] | 709 [M + H]$^+$ | 1.13 (H) | Solvent: dioxane, 100° C., 2 h |
| 3.04 | Int. 35.04 + 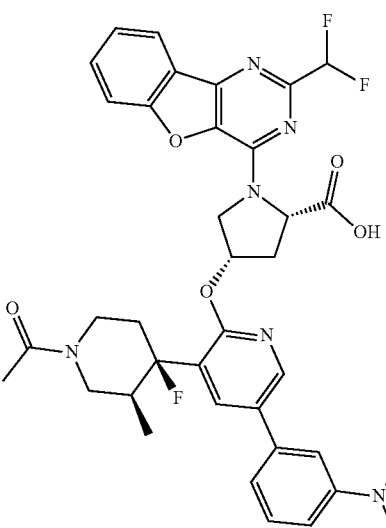 | 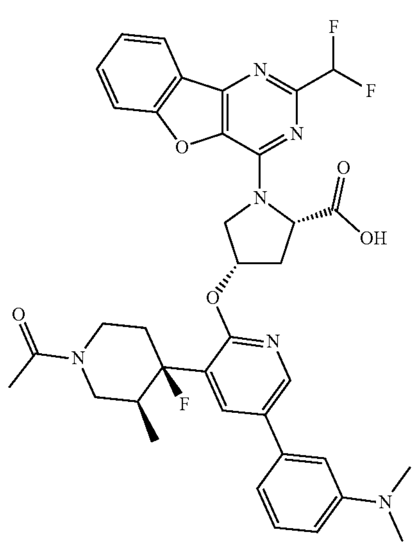 [SMILES: CC(=O)N1CC[C@](F)(c2cc(-c3cccc(N(C)C)c3)cnc2O[C@H]2C[C@@H](C(=O)O)N(c3nc(C(F)F)nc4c3oc3ccccc34)C2)[C@@H](C)C1] | 703 [M + H]$^+$ | 0.82 (H) | Solvent: dioxane, 100° C., 2 h |

Example 4.01 (General Route)

(2S,4S)-4-[(5-ethynyl-3-{3-oxabicyclo[4.1.0]heptan-6-yl}pyridin-2-yl)oxy]-1-[4-(trifluoromethyl)-8-oxa-3,5-diazatricyclo[7.4.0.0$^{2,7}$]trideca-1(13),2,4,6,9,11-hexaen-6-yl]pyrrolidine-2-carboxylic acid

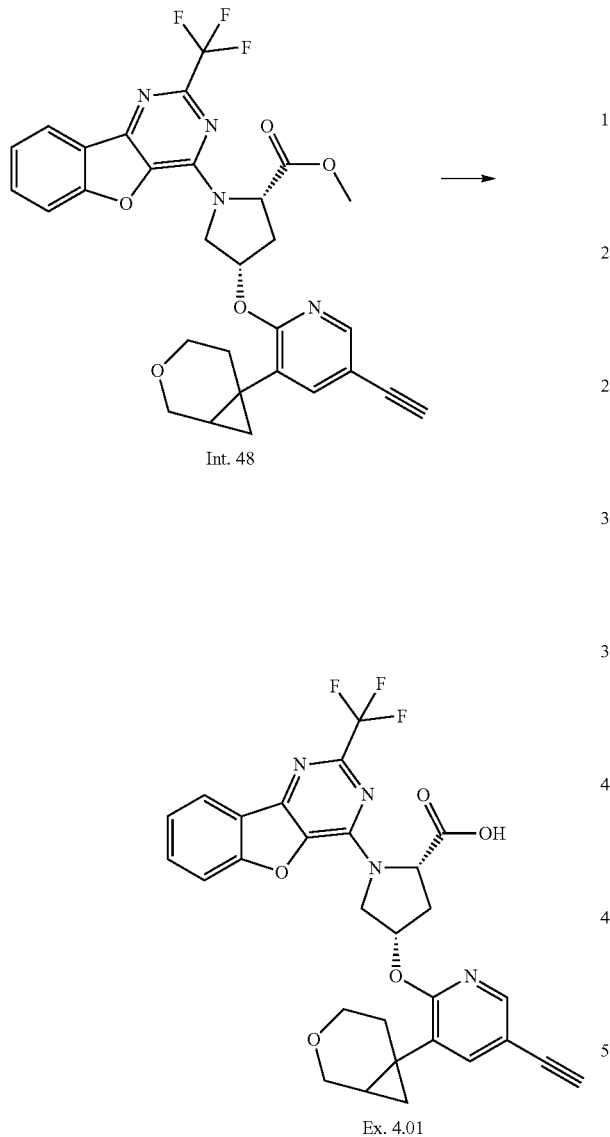

Int. 48

Ex. 4.01

To methyl (2S,4S)-4-[(5-ethynyl-3-{3-oxabicyclo[4.1.0]heptan-6-yl}pyridin-2-yl)oxy]-1-[4-(trifluoromethyl)-8-oxa-3,5-diazatricyclo[7.4.0.0$^{2,7}$]trideca-1(13),2,4,6,9,11-hexaen-6-yl]pyrrolidine-2-carboxylate (INTERMEDIATE 48, 40.0 mg, 0.07 mmol) in 1.50 mL methanol was added lithium hydroxide (2.0 mol/L, 450 mL, 0.90 mmol) and the reaction mixture was stirred at 50° C. for 2 h. The reaction mixture was concentrated under reduced pressure and the residue was purified by HPLC (ACN/H2O/TFA).

ESI-MS: 565 [M+H]$^+$

R$_t$ (HPLC): 1.03 min (method W)

Example 5.01 (General Route)

(2S,4S)-4-{[5-(4-chloro-1H-pyrazol-1-yl)-3-(4-fluorooxan-4-yl)pyridin-2-yl]oxy}-1-[4-(difluoromethyl)-8-oxa-3,5-diazatricyclo[7.4.0.0$^{2,7}$]trideca-1(13),2,4,6,9,11-hexaen-6-yl]pyrrolidine-2-carboxylic acid

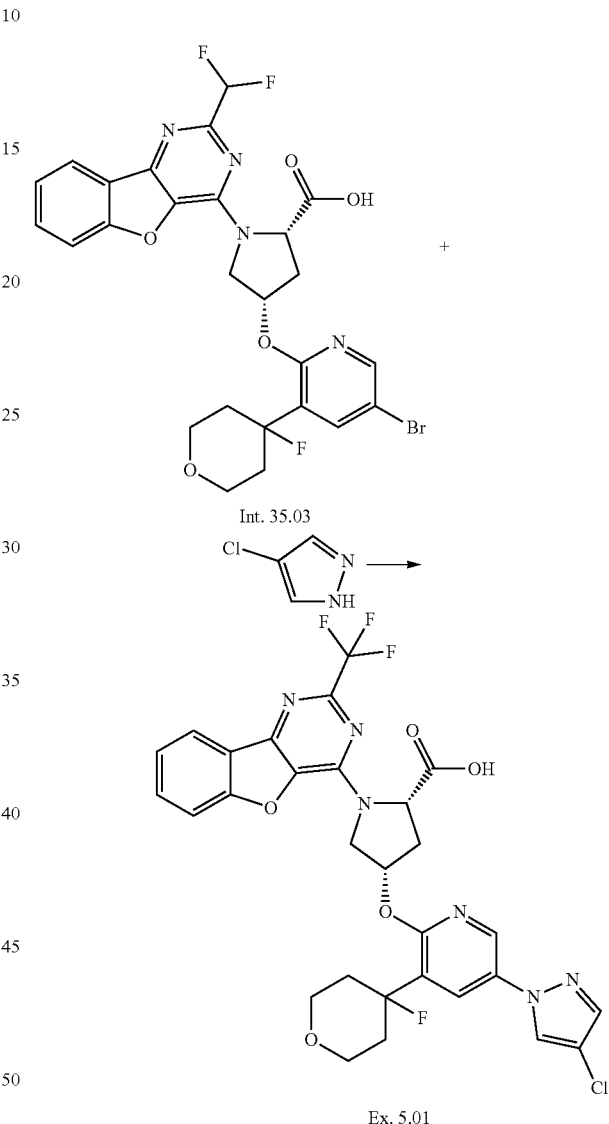

Int. 35.03

Ex. 5.01

To 4-chloro-1H-pyrazole (7.69 mg, 0.08 mmol) was added under inert atmosphere a solution of (2S,4S)-4-{[5-bromo-3-(4-fluorooxan-4-yl)pyridin-2-yl]oxy}-1-[4-(difluoromethyl)-8-oxa-3,5-diazatricyclo[7.4.0.0$^{2,7}$]trideca-1(13),2,4,6,9,11-hexaen-6-yl]pyrrolidine-2-carboxylic acid (INTERMEDIATE 35.03, 30.4 mg, 0.05 mmol) in 1.00 mL dioxane, followed by Li(HMDS) (1 mol/L in THF, 125 μL, 0.13 mmol) and tBu-Brett-Phos (3.91 mg, 0.01 mmol). This reaction mixture was stirred at 100° C. overnight. After cooling down to RT, the mixture was filtered, diluted with water and ACN and purified by HPLC (ACN/H2O/TFA).

ESI-MS: 629 [M+H]$^+$

R$_t$ (HPLC): 1.09 min (method J)

Example 6.01 (General Route)

(2S,4S)-4-({5-[1-(Difluoromethyl)-1H-pyrazol-4-yl]-3-[(3S,4R)-4-fluoro-3-methyloxan-4-yl]pyridin-2-yl}oxy)-1-[4-(difluoromethyl)-8-oxa-3,5-diazatricyclo[7.4.0.0$^{2,7}$]trideca-1(9),2(7),3,5,10,12-hexaen-6-yl]pyrrolidine-2-carboxylic acid

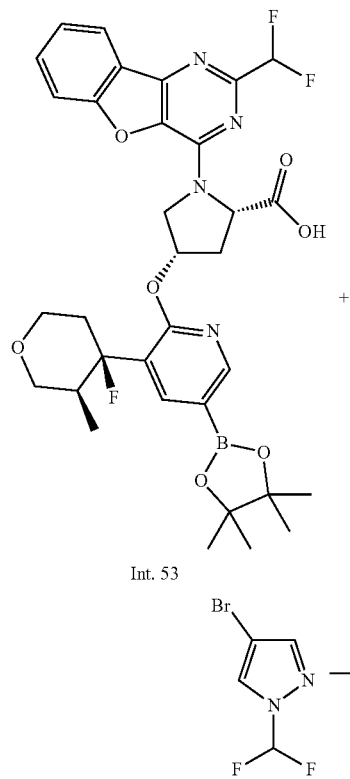

Int. 53

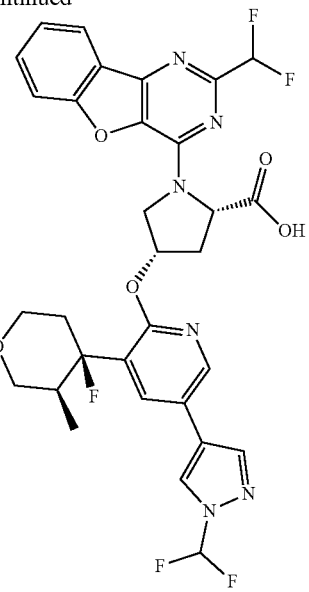

Ex. 6.01

To a solution of (2S,4S)-1-[4-(difluoromethyl)-8-oxa-3,5-diazatricyclo[7.4.0.0$^{2,7}$]trideca-1(9),2(7),3,5,10,12-hexaen-6-yl]-4-({3-[(3S,4R)-4-fluoro-3-methyloxan-4-yl]-5-(4,4,5,5-tetramethyl-1,3,2-dioxaborolan-2-yl)-pyridin-2-yl}oxy)pyrrolidine-2-carboxylic acid (INTERMEDIATE 53, 50 mg, 0.075 mmol) in dioxane (3.0 ml) under nitrogen atmosphere were added 4-bromo-1-(difluoromethyl)-1H-pyrazole (39 mg, 0.20 mmol), potassium carbonate (2.0 mol/L aqueous solution, 0.20 mL, 0.40 mmol), and Xphos 3rd gen (6.33 mg, 0.00748 mmol). The mixture was heated at 100° C. for 2 h. The mixture was diluted with DMF, filtrated and the crude product purified my preparative HPLC (C18 column, ACN, H2O-TFA, 60° C.).

ESI-MS: 709 [M+H]$^+$
$R_t$ (HPLC): 1.02 (method H)

The following compounds were prepared according to the general procedure (EXAMPLE 6.01) described above:

| Ex. | Starting materials | Structure | ESI-MS | $R_t$ (HPLC) [min] (method) | Reaction conditions |
|---|---|---|---|---|---|
| 6.02 | Int. 53 + <br> (pyridine-boronic acid with methoxy) | (structure shown) | 650 [M + H]$^+$ | 0.60 (A) | Dioxane, 90° C., 3.5 h |

-continued

| Ex. | Starting materials | Structure | ESI-MS | R$_t$ (HPLC) [min] (method) | Reaction conditions |
|---|---|---|---|---|---|
| 6.03 | Int. 53 + | 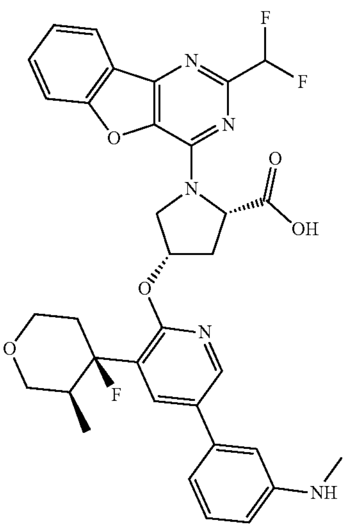 [SMILES: CNc1cccc(-c2cnc(O[C@H]3C[C@@H](C(=O)O)N(c4nc(C(F)F)nc5c4oc4ccccc45)C3)c([C@@]3(F)CCOC[C@@H]3C)c2)c1] | 648 [M + H]$^+$ | 0.84 (H) | Dioxane, 80° C., 2 h |
| 6.04 | Int. 53 + | 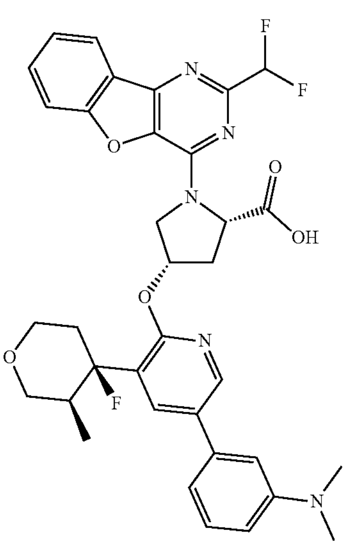 [SMILES: C[C@H]1COCC[C@]1(F)c1cc(-c2cccc(N(C)C)c2)cnc1O[C@H]1C[C@@H](C(=O)O)N(c2nc(C(F)F)nc3c2oc2ccccc23)C1] | 662 [M + H]$^+$ | 0.63 (D) | Dioxane, 80° C., 2 h |

143

Prodrug P01 (General Route)

Methyl (2S,4S)-4-({5-cyano-3-[(3R,4R)-4-fluoro-3-methyl-1,1-dioxo-1-I-6-thian-4-yl]pyridin-2yl}oxy)-1-[4-(trifluoromethyl)-8-oxa-3,5-diazatricyclo[7.4.0.0$^{2,7}$]trideca-1(13),2,4,6,8,11-hexaen-6-yl]pyrrolidine-2-carboxylate

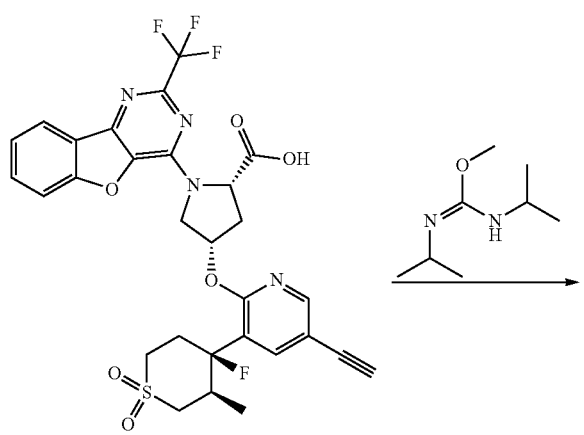

Ex. 2.14

144

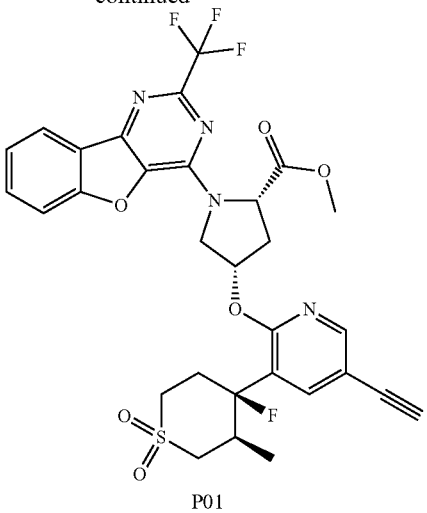

P01

To (2S,4S)-4-({5-cyano-3-[(3R,4R)-4-fluoro-3-methyl-1,1-dioxo-1-I-6-thian-4-yl]pyridin-2-yl}oxy)-1-[4-(trifluoromethyl)-8-oxa-3,5-diazatricyclo[7.4.0.0$^{2,7}$]trideca-1(13),2,4,6,9,11-hexaen-6-yl]pyrrolidine-2-carboxylic acid (EXAMPLE 2.14, 15.0 mg, 0.02 mmol) in 1.00 mL THF was added (E)-N,N'-bis(propan-2-yl)methoxy-methanimidamide (43.1 µL, 0.23 mmol) and was stirred at RT for 62 h. The reaction mixture was diluted with water and ACN and purified by HPLC (ACN/H2O/TFA).

ESI-MS: 647 [M+H]$^+$
R$_t$ (HPLC): 0.99 min (method H)

The following compounds were prepared according to the general procedure (PRODRUG P01) described above:

| Prodrug No. | Starting material | Structure | ESI-MS | R$_t$ (HPLC) [min] (method) | Reaction conditions |
|---|---|---|---|---|---|
| P02 | Ex. 1.14 | 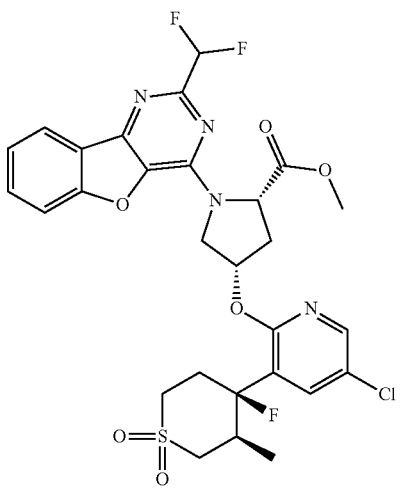 [SMILES: COC(=O)[C@@H]1C[C@H](Oc2ncc(Cl)cc2[C@@]2(F)CCS(=O)(=O)C[C@@H]2C)CN1c1nc(C(F)F)nc2c1oc1ccccc12] | 639 [M + H]$^+$ | 1.09 (H) | Solvent: THF, RT 48 h |

-continued

| Prodrug No. | Starting material | Structure | ESI-MS | R$_t$ (HPLC) [min] (method) | Reaction conditions |
|---|---|---|---|---|---|
| P03 | Ex. 1.5 | 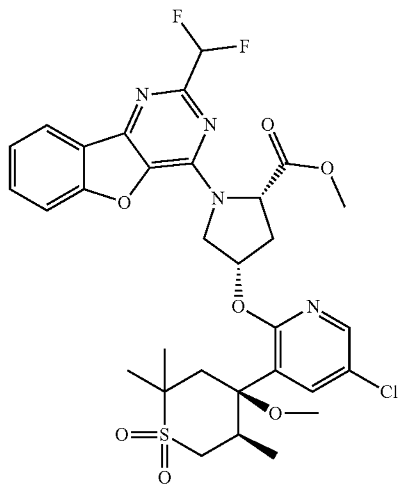 [SMILES: COC(=O)[C@@H]1C[C@H](Oc2ncc(Cl)cc2[C@@]2(OC)CC(C)(C)S(=O)(=O)C[C@@H]2C)CN1c1nc(C(F)F)nc2c1oc1ccccc12] | 679 [M + H]$^+$ | 1.17 (H) | Solvent: THF, RT, 62 h |

General Technical Remarks

The terms "ambient temperature" and "room temperature" are used interchangeably and designate a temperature of about 20° C., e.g. 15 to 25° C.

As a rule, $^1$H NMR spectra and/or mass spectra have been obtained of the compounds prepared. Unless otherwise stated, all chromatographic operations were performed at room temperature.

List of Abbreviations

ACN acetonitrile
aq. Aqueous
Brettphos 2-(dicyclohexylphosphino)-3,6-dimethoxy-2'-4'-6'-triisopropyl-1,1'-biphenyl
BPR back pressure regulator
° C. degree Celsius
CH cyclohexane
CT column temperature
DA diode array
DAST diethylaminosulfur trifluoride
DBU diazabicyclo[5.4.0]undec-7-ene
DCM dichloromethane
Deoxo-Fluor© bis-(2-methoxyethyl)-aminosulfur trifluoride
DIAD diisopropyl azodicarboxylate
DIPEA diisopropylethylamine
DMA dimethylacetamide
DMAP 4-dimethylaminopyridine
DMF N,N-dimethylformamide
ds-mix diastereoisomeric mixture of cis/trans
ent enantiopure
ESI-MS electrospray ionisation mass spectrometry
EtOAc ethyl acetate
eq equivalent
Ex. EXAMPLE
FA formic acid
GC/MS gas chromatography-mass spectrometry
h hour
HCl hydrochloric acid
HATU [dimethylamino-(1,2,3-triazolo[4,5-b]pyridin-3-yloxy)-methylene]-dimethyl-ammonium hexafluorophosphate
HMPA hexamethylphosphoramide
HPLC high performance liquid chromatography
Int. INTERMEDIATE
IPA isopropyl alcohol
K$_2$CO potassium carbonate
KOH Potassium hydroxide
L Liter
LDA lithium diisopropylamide
LiAlH$_4$ lithium aluminium hydride
LiHMDS lithium hexamethyldisilazide
mCPBA meta-chloroperbenzoic acid
MeOH methanol
min minute(s)
mL milliliter
MS mass spectrum
NH$_3$ ammonia
NH$_4$OH solution of NH$_3$ in water
NMP N-methy-2-pyrrolidone
PE petroleum ether
PdCl$_2$(PPh$_3$)$_2$ bis(triphenylphosphine)palladium(II)dichloride
Pd(dppf)Cl$_2$ (1,1'-bis-(diphenylphosphino)-ferrocen)-dichlorpalladium (II)
Pd(PPh$_3$)$_4$ tetrakis(triphenylphosphine)palladium(0)
Pd(OH)$_2$/C Palladium hydroxide on carbon 20%
psi pound per square inch
pTsOH*H$_2$O p-Toluenesulfonic acid monohydrate
rac racemic mixture or racemate
rac-cis racemic mixture of cis diastereoisomer
rac-trans racemic mixture of trans diastereoisomer
RT room temperature (about 20° C.)
R$_t$ retention time (in minutes)
scCO$_2$ supercritical carbon dioxide
TBAF tetrabutylammoniumfluorid
tBu-Brett-Phos 2-(di-tert-butylphosphino)-2',4',6'-triisopropyl-3,6-dimethoxy-1,1'-biphenyl
TEAF triethylammonium formate
Tetrakis tetrakis(triphenylphosphine)-palladium-(0)

TFA trifluoroacetic acid
TFAA trifluoroacetic acid anhydride
TH F tetrahydrofuran
Xphos 2-dicyclohexylphosphin-2',4',6'-triisopropylbiphenyl
Xphos 3$^{rd}$ gen (2-Dicyclohexylphosphino-2',4',6'-triisopropyl-1,1'-biphenyl)[2-(2'-amino-1,1'-biphenyl)]palladium(II) methanesulfonate
Ziram Dimethyldithiocarbamic acid zinc salt Analytical Methods (HPLC/SFC):

Method A

| time (min) | Vol % water (incl. 0.1% TFA) | Vol % I | Flow [mL/min] |
| --- | --- | --- | --- |
| 0.00 | 99 | 1 | 1.6 |
| 0.02 | 99 | 1 | 1.6 |
| 1.00 | 0 | 100 | 1.6 |
| 1.10 | 0 | 100 | 1.6 | column: Xbridge BEH C18_2.1 × 30 mm, 1.7 μm;
CT: 60° C.

Method B

| time (min) | Vol % water (incl. 0.1% TFA) | Vol % I | Flow [mL/min] |
| --- | --- | --- | --- |
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 | column: Stable Bond (Agilent) 1.8 μm; 3.0 × 30 mm;
CT: 60° C.

Method C (SFC)

| time (min) | Vol. % scCO$_2$ | Vol % MeOH 20 mM NH$_3$ | Flow [mL/min] |
| --- | --- | --- | --- |
| 0.00 | 90 | 10 | 2.0 |
| 4.00 | 90 | 10 | 2.0 | column: CHIRAL ART Cellulose_SC (YMC) 3.0 μm; 3.0 × 100 mm;
CT: 40° C., BP: 2175 PSI, Instrument: Agilent 1260 Infinity II SFC with DAD Method D

| time (min) | Vol. % water (incl. 0.1% NH$_4$OH) | Vol. % I | Flow [mL/min] |
| --- | --- | --- | --- |
| 0.00 | 95 | 5 | 1.5 |
| 1.30 | 0 | 100 | 1.5 |
| 1.50 | 0 | 100 | 1.5 |
| 1.60 | 95 | 5 | 1.5 | column: Xbridge C18_3.0 × 30 mm_2.5 μm (Waters);
CT: 60° C.

Method E(SFC

| time (min) | Vol. % scCO$_2$ | Vol. % MeOH 20 mM NH$_3$ | Flow [mL/min] |
| --- | --- | --- | --- |
| 0.00 | 90 | 10 | 2.0 |
| 4.00 | 90 | 10 | 2.0 | column: Chiralpak IG (Daicel) 3.0 μm; 3.0 × 100 mm;
CT: 40° C.

Method E (SFC)

| time (min) | Vol % water (incl. 0.1% NH3) | Vol % I | Flow [mL/min] |
| --- | --- | --- | --- |
| 0.00 | 95 | 5 | 1.3 |
| 0.02 | 95 | 5 | 1.3 |
| 1.00 | 0 | 100 | 1.3 |
| 1.30 | 0 | 100 | 1.3 | column: Xbridge BEH (Waters) C18_2.1 × 30 mm, 2.5 μm;
CT: 60° C.

Method G (SFC)

| time (min) | Vol % scCO$_2$ | Vol % IPA 20 mM NH$_3$ | Flow [mL/min] |
| --- | --- | --- | --- |
| 0.00 | 75 | 25 | 4.0 |
| 10.0 | 75 | 25 | 4.0 | column: Chiralpak IG (Daicel) 4.6 × 250 mm, 5 μm;
CT: 40° C.

Method H

| time (min) | Vol. % water (incl. 0.1% TFA) | Vol. % I | Flow [mL/min] |
| --- | --- | --- | --- |
| 0.00 | 95 | 5 | 1.5 |
| 1.30 | 0 | 100 | 1.5 |
| 1.50 | 0 | 100 | 1.5 |
| 1.60 | 95 | 5 | 1.5 | column: Sunfire C18 (Waters) 2.5 μm; 3.0 × 30 mm;
CT: 60° C.

Method I (SFC)

| time (min) | Vol. % scCO$_2$ | Vol. % MeOH | Flow [mL/min] |
| --- | --- | --- | --- |
| 0.00 | 97 | 3 | 1.3 |
| 2.50 | 55 | 45 | 1.3 |
| 3.50 | 55 | 45 | 1.3 |
| 3.51 | 97 | 3 | 1.3 |
| 4.00 | 97 | 3 | 1.3 | column: Acquity UPC2 BEH 2-EP (Waters) 3.0 × 100 mm, 1.7 μm;
CT: 30° C.

Method J

| time (min) | Vol. % water (incl. 0.1% TFA) | Vol. % I | Flow [mL/min] |
| --- | --- | --- | --- |
| 0.00 | 95 | 5 | 1.5 |
| 1.30 | 0 | 100 | 1.5 |
| 1.50 | 0 | 100 | 1.5 |
| 1.60 | 95 | 5 | 1.5 | column: Sunfire C18 (Waters) 2.5 μm; 3.0 × 30 mm;
CT: 60° C.

Method K (SFC)

| time (min) | Vol. % scCO$_2$ | Vol. % IPA 20 mM NH$_3$ | Flow [mL/min] |
| --- | --- | --- | --- |
| 0.00 | 80 | 20 | 2.0 |
| 4.00 | 80 | 20 | 2.0 | column: Chiral Art Amylos-C Neo (YMC) 3.0 μm; 3.0 × 100 mm;
CT: 40° C.

Method L (SFC)

| time (min) | Vol. % scCO$_2$ | Vol. % methanol | Flow [mL/min] |
|---|---|---|---|
| 0.00 | 97 | 3 | 1.3 |
| 2.50 | 55 | 45 | 1.3 |
| 3.50 | 55 | 45 | 1.3 |
| 3.51 | 97 | 3 | 1.3 |
| 4.00 | 97 | 3 | 1.3 | column: Acquity UPC2 Torus 2-PIC (Waters) 1.7 µm; 3.0 × 100 mm; CT: 30° C.

Method M (SFC)

| time (min) | Vol. % scCO$_2$ | Vol % IPA 20 mM NH$_3$ | Flow [mL/min] |
|---|---|---|---|
| 0.00 | 70 | 30 | 2.0 |
| 4.00 | 70 | 30 | 2.0 | column: Chiral Art Amylos-C Neo (YMC) 3.0 µm; 3.0 × 100 mm; CT: 40° C.

Method N (SFC)

| time (min) | Vol. % scCO$_2$ | Vol % MeOH 20 mM NH$_3$ | Flow [mL/min] |
|---|---|---|---|
| 0.00 | 80 | 20 | 4.0 |
| 10.00 | 80 | 20 | 4.0 | column: CHIRAL ART Cellulose_SC (YMC) 5.0 µm; 4.6 × 250 mm; CT: 40° C.

Method O (SFC)

| time (min) | Vol. % scCO$_2$ | Vol % MeOH 20 mM NH$_3$ | Flow [mL/min] |
|---|---|---|---|
| 0.00 | 75 | 25 | 4.0 |
| 10.00 | 75 | 25 | 4.0 | column: CHIRAL ART Cellulose_SC (YMC) 5.0 µm; 4.6 × 250 mm; CT: 40° C.

Method P (SFC)

| time (min) | Vol. % scCO$_2$ | Vol % MeOH 20 mM NH$_3$ | Flow [mL/min] |
|---|---|---|---|
| 0.00 | 70 | 30 | 4.0 |
| 10.00 | 70 | 30 | 4.0 | column: CHIRAL ART Cellulose_SC (YMC) 5.0 µm; 4.6 × 250 mm; CT: 40° C.

Method Q (SFC)

| time (min) | Vol % scCO$_2$ | Vol % MeOH 20 mM NH$_3$ | Flow [mL/min] |
|---|---|---|---|
| 0.00 | 65 | 35 | 4.0 |
| 10.0 | 65 | 35 | 4.0 | column: Chiralpak IG (Daicel) 4.6 × 250 mm, 5 µm; CT: 40° C.

Method R (SFC)

| time (min) | Vol % scCO$_2$ | Vol % MeOH 20 mM NH$_3$ | Flow [mL/min] |
|---|---|---|---|
| 0.00 | 60 | 40 | 4.0 |
| 10.0 | 60 | 40 | 4.0 | column: Chiralpak IG (Daicel) 4.6 × 250 mm, 5 µm; CT: 40° C.

Method S (SFC)

| time (min) | Vol % scCO$_2$ | Vol % MeOH 20 mM NH$_3$ | Flow [mL/min] |
|---|---|---|---|
| 0.00 | 60 | 40 | 2.0 |
| 4.0 | 60 | 40 | 2.0 | column: Chiralpak IG (Daicel) 3.0 × 100 mm, 3 µm; CT: 40° C.

Method T (SFC)

| time (min) | Vol % csCO2 | Vol % MeOH | Flow [mL/min] |
|---|---|---|---|
| 0.00 | 97 | 3 | 1.3 |
| 2.50 | 55 | 45 | 1.3 |
| 3.50 | 55 | 45 | 1.3 |
| 3.51 | 97 | 3 | 1.3 |
| 4.00 | 97 | 3 | 1.3 | column: Acquity UPC2 BEH (Waters) 3.0 × 100 mm, 1.7 µm; CT: 30° C.

Method U (SFC)

| time (min) | Vol % scCO2 | Vol % MeOH | Flow [mL/min] |
|---|---|---|---|
| 0.00 | 97 | 3 | 1.3 |
| 2.50 | 55 | 45 | 1.3 |
| 3.50 | 55 | 45 | 1.3 |
| 3.51 | 97 | 3 | 1.3 |
| 4.00 | 97 | 3 | 1.3 | column: Acquity UPC2 Torus DEA (Waters) 3.0 × 100 mm, 1.7 µm; CT: 30° C.

Method V (SFC)

| time (min) | Vol % scCO$_2$ | Vol % MeOH 20 mM NH$_3$ | Flow [mL/min] |
|---|---|---|---|
| 0.00 | 95 | 5 | 2.0 |
| 3.60 | 40 | 60 | 2.0 |
| 4.00 | 40 | 60 | 2.0 | column: Lux Cellulose-4 (Phenomenex) 3.0 × 100 mm, 3 µm; CT: 40° C.

Method W

| time (min) | Vol % water (incl. 0.1% TFA) | Vol % I | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 | column: Sunfire C18_3.0 × 30 mm_2.5 µm (Waters); CT: 60° C.

Method X

| time (min) | Vol % water + 0.04%(v/v)TFA | Vol % ACN + 0.02%(v/v)TFA | Flow [mL/min] |
|---|---|---|---|
| 0.00 | 95 | 5 | 1.0 |
| 1.00 | 5 | 95 | 1.0 |
| 1.80 | 0 | 100 | 1.0 |
| 1.81 | 95 | 5 | 1.2 |
| 2.00 | 95 | 5 | 1.2 | column: Kinetex C18 30 × 2.1 mm, 5 µm; CT: 40° C., Instrument: Agilent 1200 & G6120B Method Z

| time (min) | Vol % water (incl. 0.1% TFA) | Vol % I | Flow [mL/min] |
|---|---|---|---|
| 0.0 | 95 | 5 | 1.5 |
| 1.3 | 0 | 100 | 1.5 |
| 1.5 | 0 | 100 | 1.5 | column: Sunfire C18_3.0 × 30 mm_2.5 µm (Waters Aquity); CT: 60° C.

Method GC01

| time (min) | % Sol [Helium] | Temp [° C.] | Flow [mL/min] |
|---|---|---|---|
| 0.00 | 100 | 50 | 2.1 |
| 1.00 | 100 | 50 | 2.1 |
| 2.80 | 100 | 170 | 2.1 |
| 6.00 | 100 | 320 | 2.1 |
| 8.50 | 100 | 320 | 2.1 |

Device: Agilent GC 7890A with FI- and MS-Detector, Column: Optima 5HT, 15 m × 0.25 m × 0.25 µm Column producer: Macherey-Nagel, Injector temperature: 280° C. Temperature Ion source: 300° C. Temperature Quadrupole: 150° C.

5 EXAMPLES

5.1 Example Compounds

The following Example compounds of formulas (I), (I'), (I"), (II') and (II") as summarized in Table 1 have been synthesized and tested with respect to their pharmacological properties regarding their potency to inhibit cGAS activity.

In particular the "biochemical (in vitro) IC50-values" with regard to cGAS-inhibition (hcGAS IC50), the "IC50-value with regard to the inhibition of IFN induction in virus-stimulated THP1 cells" (THP$_{(vir)}$ IC50), the "IC50-value with regard to the inhibition of IFN induction in cGAMP-stimulated THP1 cells" (THP$_{(CGAMP)}$ IC50) and the "IC50-value with regard to inhibition of IFN induction in dsDNA-stimulated human whole blood" (hWB IC50) has been experimentally determined according to the assay methods as described in section 6 below. The results are summarized in Table 1.

The Example compounds of formulas (I), (I'), (I"), (II') and (II") as summarized in Table 1 show at the same time the following three properties:
- a satisfying "biochemical (in vitro) IC50-value with regard to cGAS inhibition" (with a hcGAS IC50 of 100 nM, preferably of 50 nM, in particular of 10 nM),
- a satisfying "cellular IC50-value regarding cGAS inhibition" (with a THP1$_{(vir)}$ IC50 of 1 µM, preferably of 500 nM, more preferably of 100 nM, in particular of 50 nM) and
- a satisfying selectivity for cGAS-inhibition (with a ratio THP1$_{(CGAMP)}$IC50/THP1$_{(vir)}$IC50 of ≥10, more preferably ≥50, more preferably ≥500, in particular ≥1000).

Additionally, the Example compounds of formulas (I), (I'), (I"), (II') and (II") also show acceptable IC50-values with regard to inhibition of IFN induction in dsDNA-stimulated human whole blood (hWB IC50).

TABLE 1

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 1.01 | 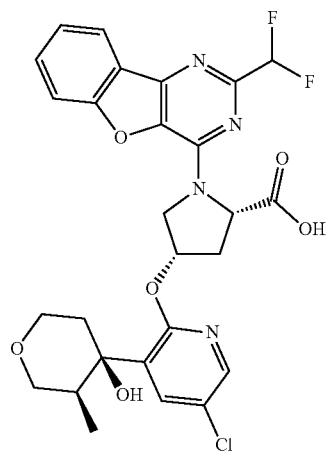 [SMILES: C[C@H]1COCC[C@]1(O)c1cc(Cl)cnc1O[C@H]1C[C@@H](C(=O)O)N(c2nc(C(F)F)nc3c2oc2ccccc23)C1] | 5 | 530 | >16600 | >31 | |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 1.02 | 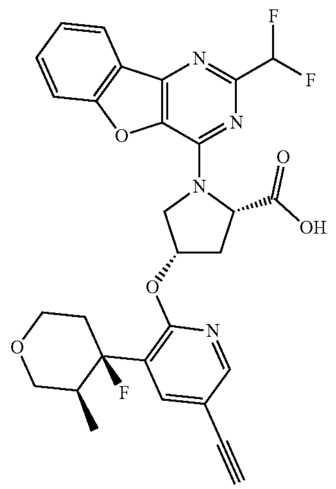 [SMILES: C#Cc1cnc(O[C@H]2C[C@@H](C(=O)O)N(c3nc(C(F)F)nc4c3oc3ccccc34)C2)c([C@@]2(F)CCOC[C@@H]2C)c1] | 3 | 351 | 18922 | 54 | 103 |
| 1.03 | 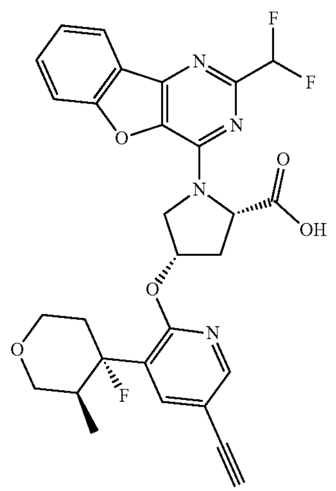 [SMILES: C#Cc1cnc(O[C@H]2C[C@@H](C(=O)O)N(c3nc(C(F)F)nc4c3oc3ccccc34)C2)c([C@]2(F)CCOC[C@@H]2C)c1] | 2 | 283 | >16599 | >59 | 137 |
| 1.04 | 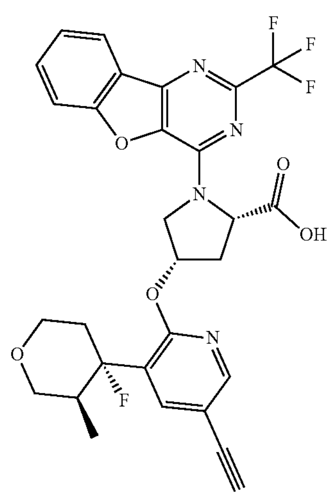 [SMILES: C#Cc1cnc(O[C@H]2C[C@@H](C(=O)O)N(c3nc(C(F)(F)F)nc4c3oc3ccccc34)C2)c([C@]2(F)CCOC[C@@H]2C)c1] | 4 | 378 | 24920 | 66 | 648 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 1.05 | 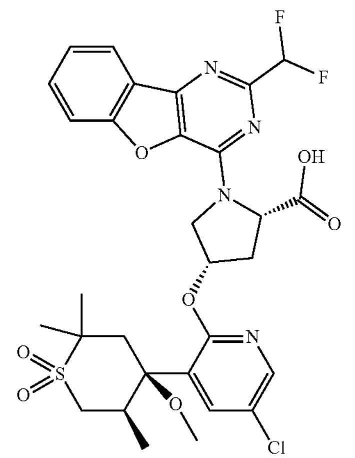 [SMILES: CO[C@]1(c2cc(Cl)cnc2O[C@H]2C[C@@H](C(=O)O)N(c3nc(C(F)F)nc4c3oc3ccccc34)C2)CC(C)(C)S(=O)(=O)C[C@@H]1C] | 2 | 44 | 13188 | 298 | 135 |
| 1.06 | 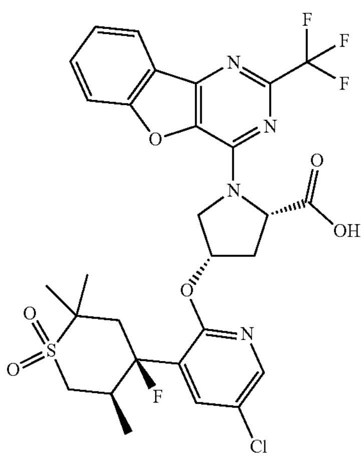 [SMILES: C[C@H]1CS(=O)(=O)C(C)(C)C[C@]1(F)c1cc(Cl)cnc1O[C@H]1C[C@@H](C(=O)O)N(c2nc(C(F)(F)F)nc3c2oc2ccccc23)C1] | 5 | 12 | 5822 | 479 | 24 |
| 1.07 | 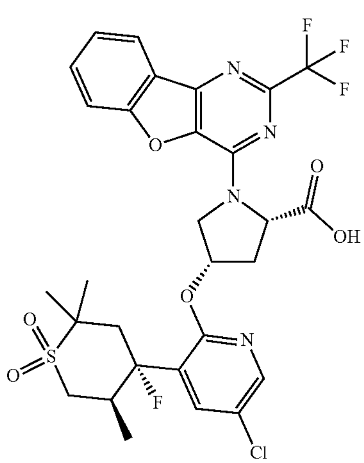 [SMILES: C[C@H]1CS(=O)(=O)C(C)(C)C[C@@]1(F)c1cc(Cl)cnc1O[C@H]1C[C@@H](C(=O)O)N(c2nc(C(F)(F)F)nc3c2oc2ccccc23)C1] | 69 | 216 | 3676 | 17 | 213 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 1.08 | 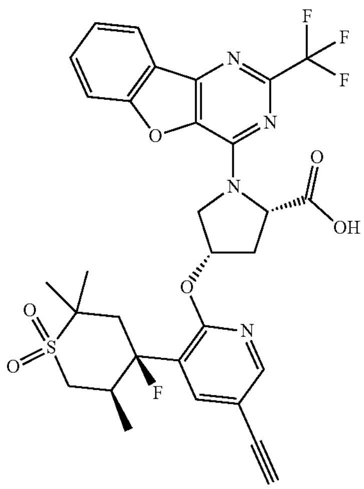 [SMILES: C#Cc1cnc(O[C@H]2C[C@@H](C(=O)O)N(c3nc(C(F)(F)F)nc4c3oc3ccccc34)C2)c([C@@]2(F)CC(C)(C)S(=O)(=O)C[C@@H]2C)c1] | 4 | 4 | 13932 | 3275 | 16 |
| 1.09 | 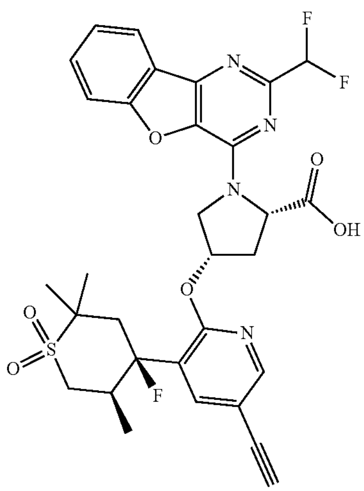 [SMILES: C#Cc1cnc(O[C@H]2C[C@@H](C(=O)O)N(c3nc(C(F)F)nc4c3oc3ccccc34)C2)c([C@@]2(F)CC(C)(C)S(=O)(=O)C[C@@H]2C)c1] | 4 | <5 | 15822 | >2935 | 4 |
| 1.10 | 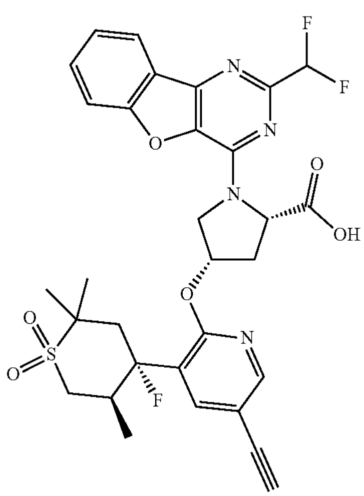 [SMILES: C#Cc1cnc(O[C@H]2C[C@@H](C(=O)O)N(c3nc(C(F)F)nc4c3oc3ccccc34)C2)c([C@]2(F)CC(C)(C)S(=O)(=O)C[C@@H]2C)c1] | 40 | 82 | 2245 | 28 | 70 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 1.11 | 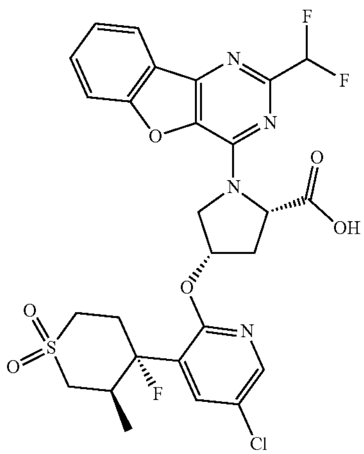 [SMILES: C[C@H]1CS(=O)(=O)CC[C@@]1(F)c1cc(Cl)cnc1O[C@H]1C[C@@H](C(=O)O)N(c2nc(C(F)F)nc3c2oc2ccccc23)C1] | 2 | 731 | >16611 | >23 | 194 |
| 1.12 | 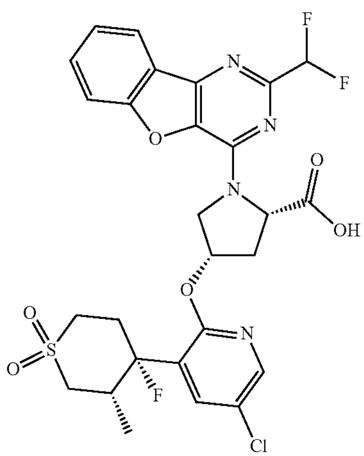 [SMILES: C[C@@H]1CS(=O)(=O)CC[C@@]1(F)c1cc(Cl)cnc1O[C@H]1C[C@@H](C(=O)O)N(c2nc(C(F)F)nc3c2oc2ccccc23)C1] | 9 | 314 | 15335 | 49 | 270 |
| 1.13 | 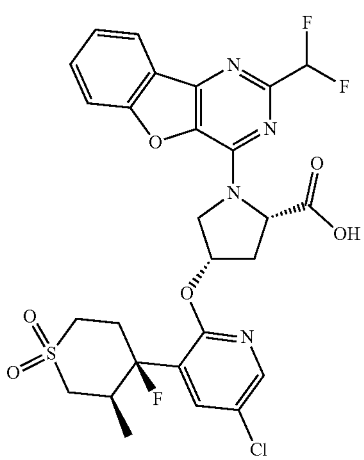 [SMILES: C[C@H]1CS(=O)(=O)CC[C@]1(F)c1cc(Cl)cnc1O[C@H]1C[C@@H](C(=O)O)N(c2nc(C(F)F)nc3c2oc2ccccc23)C1] | 2 | 6 | 22502 | 3491 | 6 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 1.14 | 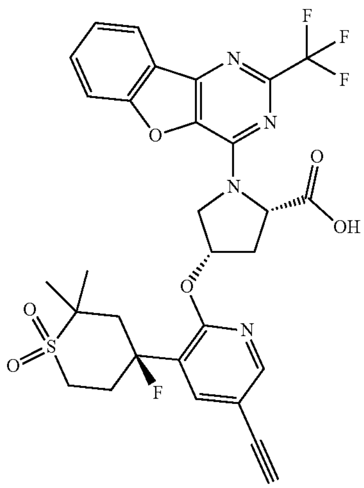 [SMILES: C#Cc1cnc(O[C@H]2C[C@@H](C(=O)O)N(c3nc(C(F)(F)F)nc4c3oc3ccccc34)C2)c([C@]2(F)CCS(=O)(=O)C(C)(C)C2)c1] | 9 | 42 | 5280 | 127 | 53 |
| 1.15 | 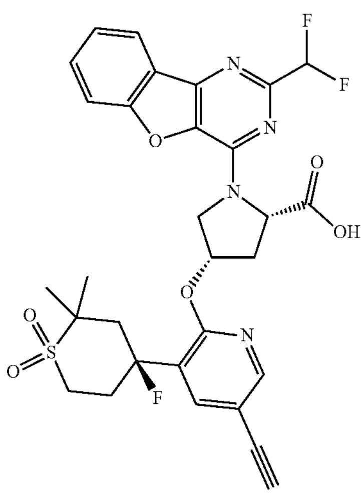 [SMILES: C#Cc1cnc(O[C@H]2C[C@@H](C(=O)O)N(c3nc(C(F)F)nc4c3oc3ccccc34)C2)c([C@]2(F)CCS(=O)(=O)C(C)(C)C2)c1] | 6 | 11 | 10200 | 963 | 22 |
| 1.16 | 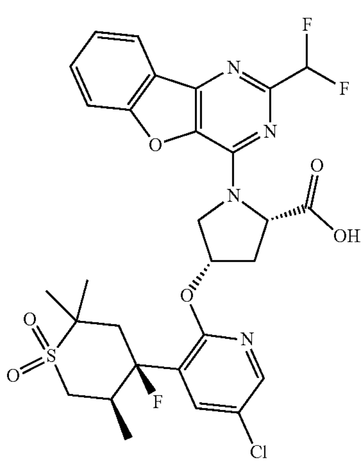 [SMILES: C[C@H]1CS(=O)(=O)C(C)(C)C[C@]1(F)c1cc(Cl)cnc1O[C@H]1C[C@@H](C(=O)O)N(c2nc(C(F)F)nc3c2oc2ccccc23)C1] | 5 | 8 | 8237 | 1055 | 6 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 1.17 | 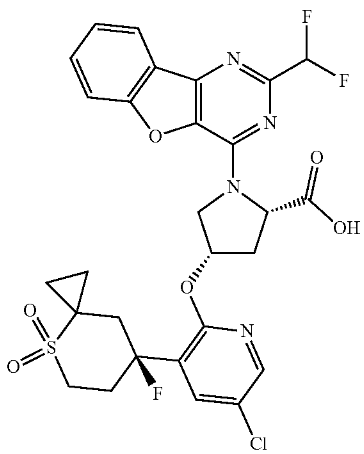 [SMILES: O=C(O)[C@@H]1C[C@H](Oc2ncc(Cl)cc2[C@]2(F)CCS(=O)(=O)C3(CC3)C2)CN1c1nc(C(F)F)nc2c1oc1ccccc12] | 3 | 54 | 22148 | 412 | 45 |
| 1.18 | 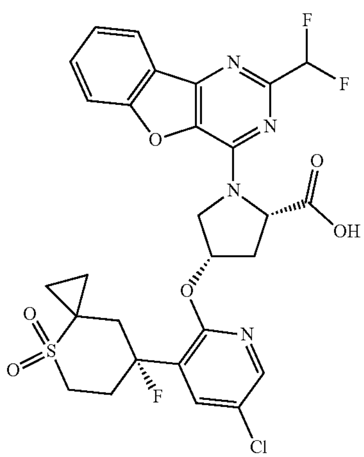 [SMILES: O=C(O)[C@@H]1C[C@H](Oc2ncc(Cl)cc2[C@@]2(F)CCS(=O)(=O)C3(CC3)C2)CN1c1nc(C(F)F)nc2c1oc1ccccc12] | 9 | 535 | 10870 | 20 | 287 |
| 1.19 | 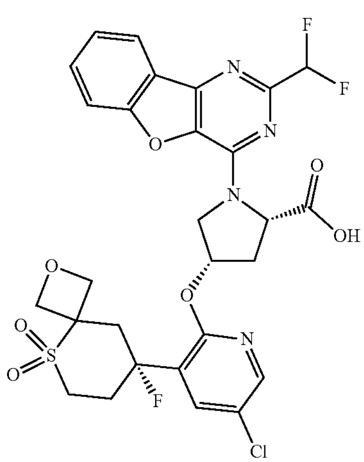 [SMILES: O=C(O)[C@@H]1C[C@H](Oc2ncc(Cl)cc2[C@@]2(F)CCS(=O)(=O)C3(COC3)C2)CN1c1nc(C(F)F)nc2c1oc1ccccc12] | 5 | 566 | 13976 | 25 | 316 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 1.20 | 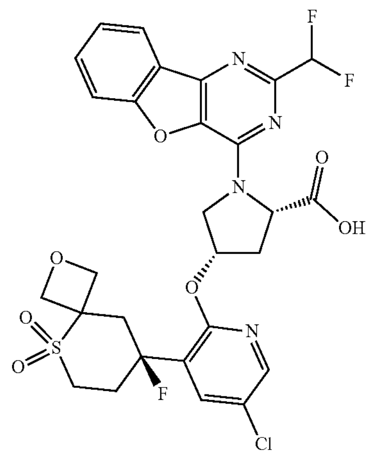 [SMILES: O=C(O)[C@@H]1C[C@H](Oc2ncc(Cl)cc2[C@]2(F)CCS(=O)(=O)C3(COC3)C2)CN1c1nc(C(F)F)nc2c1oc1ccccc12] | 3 | 139 | 15484 | 111 | 55 |
| 1.21 | 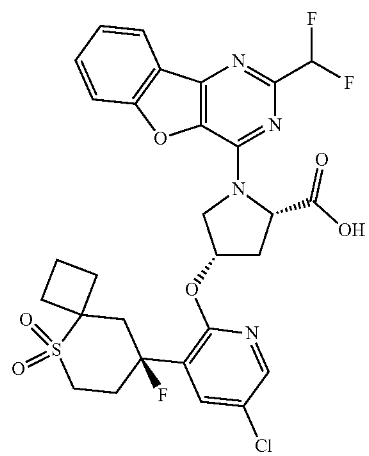 [SMILES: O=C(O)[C@@H]1C[C@H](Oc2ncc(Cl)cc2[C@]2(F)CCS(=O)(=O)C3(CCC3)C2)CN1c1nc(C(F)F)nc2c1oc1ccccc12] | 5 | 126 | 9282 | 74 | 76 |
| 1.22 | 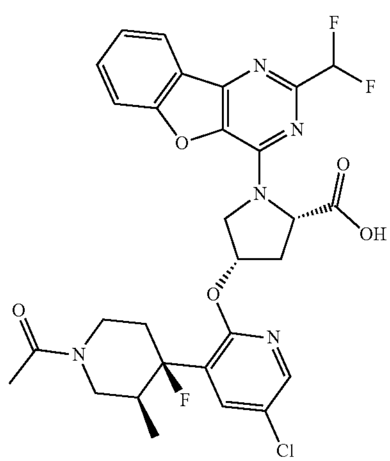 [SMILES: CC(=O)N1CC[C@](F)(c2cc(Cl)cnc2O[C@H]2C[C@@H](C(=O)O)N(c3nc(C(F)F)nc4c3oc3ccccc34)C2)[C@@H](C)C1] | 4 | 85 | 16070 | 189 | 114 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 1.23 | 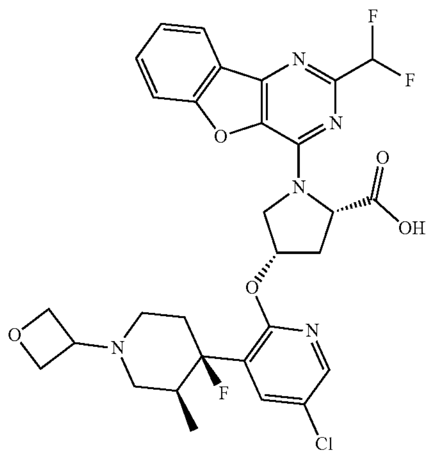 [SMILES: C[C@H]1CN(C2COC2)CC[C@]1(F)c1cc(Cl)cnc1O[C@H]1C[C@@H](C(=O)O)N(c2nc(C(F)F)nc3c2oc2ccccc23)C1] | 15 | 185 | 8404 | 45 | 165 |
| 1.24 | 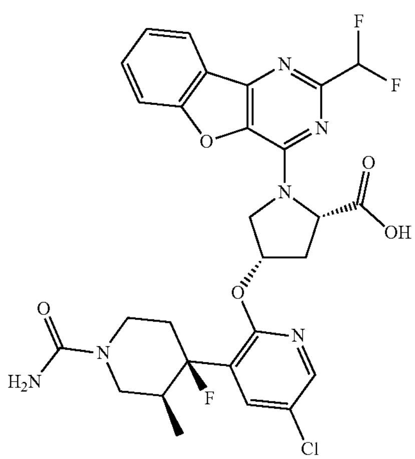 [SMILES: C[C@H]1CN(C(N)=O)CC[C@]1(F)c1cc(Cl)cnc1O[C@H]1C[C@@H](C(=O)O)N(c2nc(C(F)F)nc3c2oc2ccccc23)C1] | 7 | 248 | 21832 | 88 | 479 |
| 1.25 | 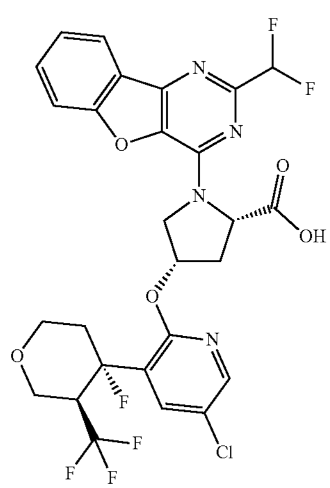 [SMILES: O=C(O)[C@@H]1C[C@H](Oc2ncc(Cl)cc2[C@]2(F)CCOC[C@@H]2C(F)(F)F)CN1c1nc(C(F)F)nc2c1oc1ccccc12] | 10 | 712 | 13538 | 19 | 502 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 2.01 | 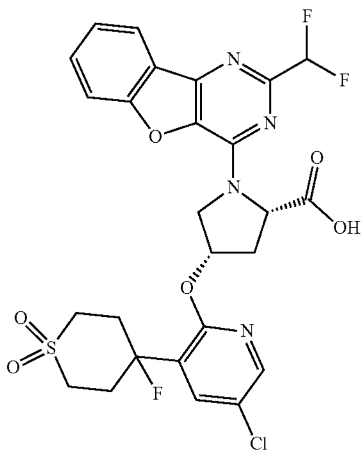 [SMILES: O=C(O)[C@@H]1C[C@H](Oc2ncc(Cl)cc2C2(F)CCS(=O)(=O)CC2)CN1c1nc(C(F)F)nc2c1oc1ccccc12] | 3 | 179 | >16612 | >93 | |
| 2.02 | 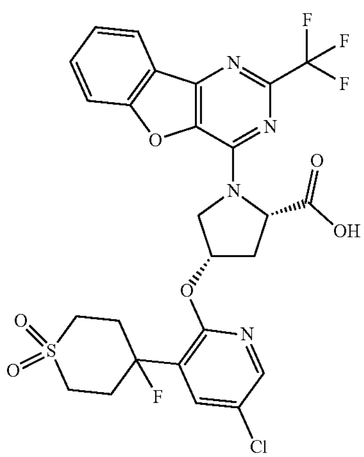 [SMILES: O=C(O)[C@@H]1C[C@H](Oc2ncc(Cl)cc2C2(F)CCS(=O)(=O)CC2)CN1c1nc(C(F)(F)F)nc2c1oc1ccccc12] | 4 | 540 | >16620 | >31 | 89 |
| 2.03 | 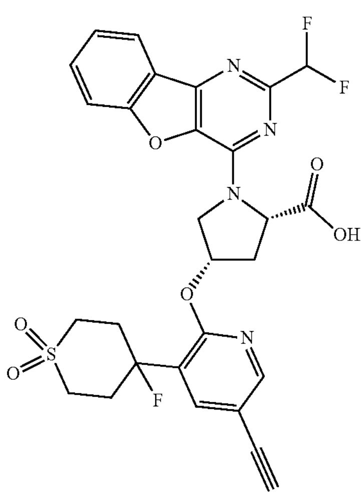 [SMILES: C#Cc1cnc(O[C@H]2C[C@@H](C(=O)O)N(c3nc(C(F)F)nc4c3oc3ccccc34)C2)c(C2(F)CCS(=O)(=O)CC2)c1] | 2 | 112 | >16611 | >148 | 40 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 2.04 | 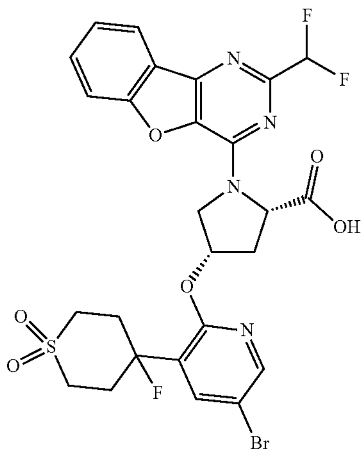 [SMILES: O=C(O)[C@@H]1C[C@H](Oc2ncc(Br)cc2C2(F)CCS(=O)(=O)CC2)CN1c1nc(C(F)F)nc2c1oc1ccccc12] | 5 | 638 | >16619 | >26 | 115 |
| 2.05 | 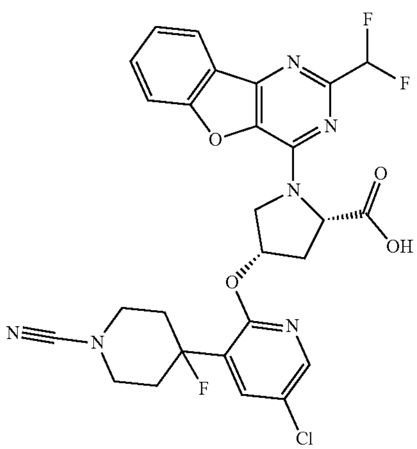 [SMILES: N#CN1CCC(F)(c2cc(Cl)cnc2O[C@H]2C[C@@H](C(=O)O)N(c3nc(C(F)F)nc4c3oc3ccccc34)C2)CC1] | 6 | 718 | 16748 | 23 | 945 |
| 2.06 | 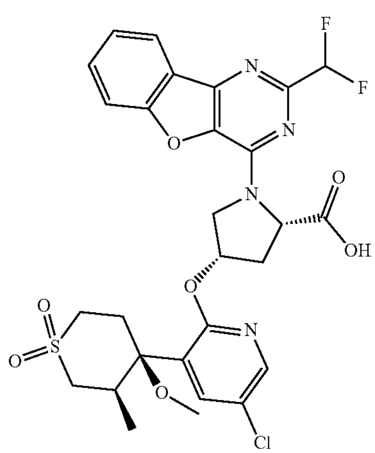 [SMILES: CO[C@]1(c2cc(Cl)cnc2O[C@H]2C[C@@H](C(=O)O)N(c3nc(C(F)F)nc4c3oc3ccccc34)C2)CCS(=O)(=O)C[C@@H]1C] | 8 | 314 | 14568 | 46 | 287 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 2.07 | 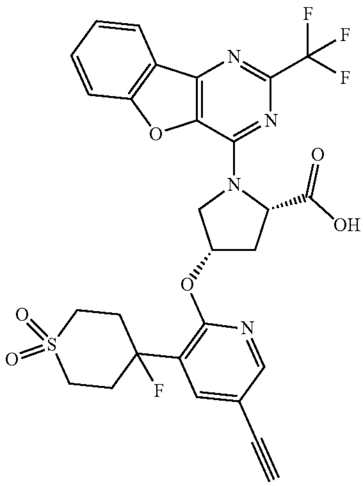 [SMILES: C#Cc1cnc(O[C@H]2C[C@@H](C(=O)O)N(c3nc(C(F)(F)F)nc4c3oc3ccccc34)C2)c(C2(F)CCS(=O)(=O)CC2)c1] | 2 | 688 | >16624 | >24 | 97 |
| 2.08 | 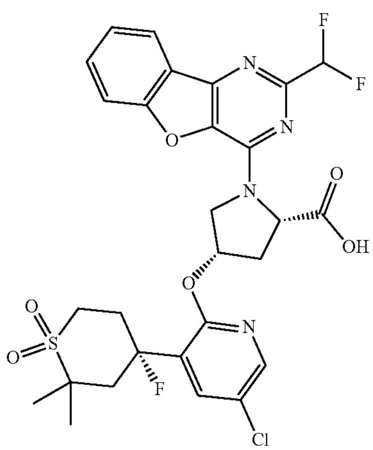 [SMILES: CC1(C)C[C@](F)(c2cc(Cl)cnc2O[C@H]2C[C@@H](C(=O)O)N(c3nc(C(F)F)nc4c3oc3ccccc34)C2)CCS1(=O)=O] | 5 | 25 | 11999 | 479 | 28 |
| 2.09 | 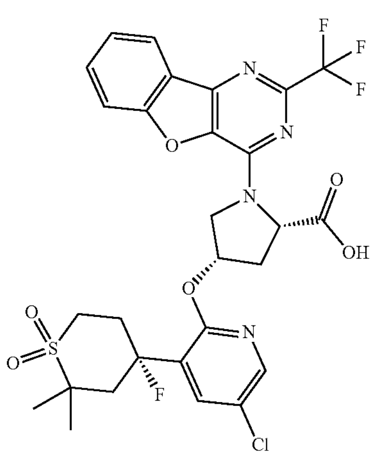 [SMILES: CC1(C)C[C@](F)(c2cc(Cl)cnc2O[C@H]2C[C@@H](C(=O)O)N(c3nc(C(F)(F)F)nc4c3oc3ccccc34)C2)CCS1(=O)=O] | 11 | 168 | 5494 | 33 | 90 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 2.10 | 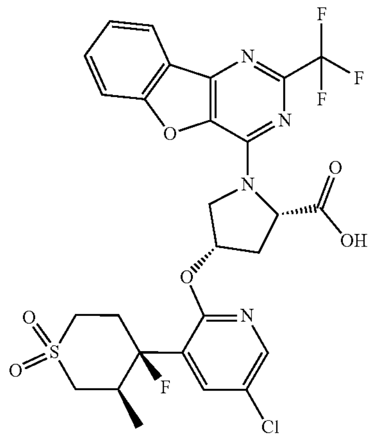 [SMILES: C[C@H]1CS(=O)(=O)CC[C@]1(F)c1cc(Cl)cnc1O[C@H]1C[C@@H](C(=O)O)N(c2nc(C(F)(F)F)nc3c2oc2ccccc23)C1] | 3 | 4 | 18848 | 4605 | 15 |
| 2.11 | 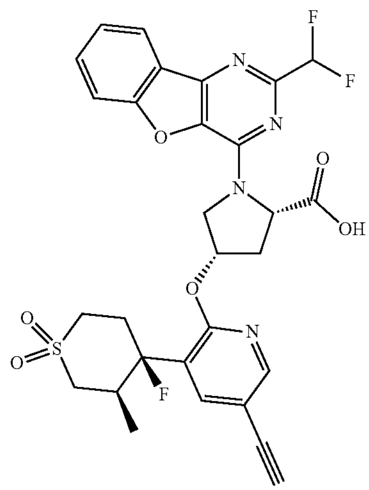 [SMILES: C#Cc1cnc(O[C@H]2C[C@@H](C(=O)O)N(c3nc(C(F)F)nc4c3oc3ccccc34)C2)c([C@@]2(F)CCS(=O)(=O)C[C@@H]2C)c1] | 2 | 4 | >16623 | >3829 | 3 |
| 2.12 | 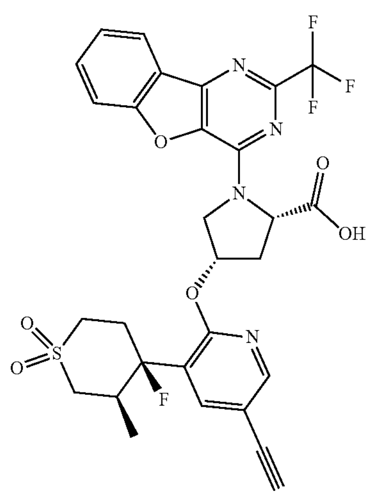 [SMILES: C#Cc1cnc(O[C@H]2C[C@@H](C(=O)O)N(c3nc(C(F)(F)F)nc4c3oc3ccccc34)C2)c([C@@]2(F)CCS(=O)(=O)C[C@@H]2C)c1] | 3 | 8 | 21781 | 2619 | 8 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 2.13 | 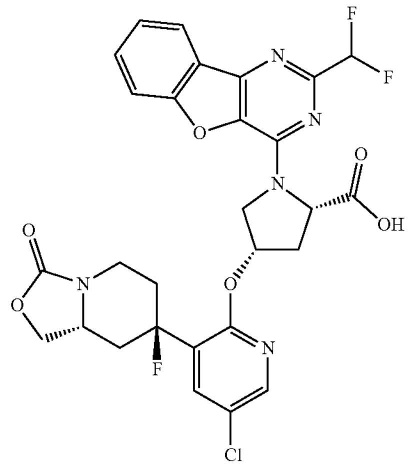 [SMILES: O=C(O)[C@@H]1C[C@H](Oc2ncc(Cl)cc2[C@@]2(F)CCN3C(=O)OC[C@H]3C2)CN1c1nc(C(F)F)nc2c1oc1ccccc12] | 7 | 818 | >16601 | >20 | 582 |
| 2.14 | 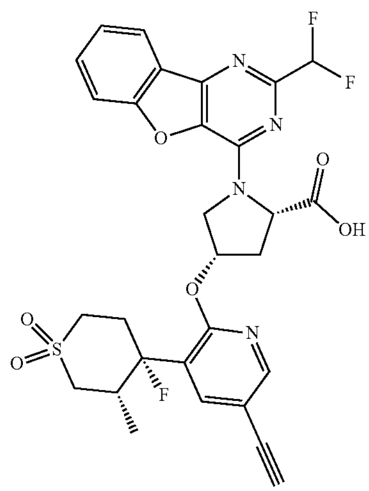 [SMILES: C#Cc1cnc(O[C@H]2C[C@@H](C(=O)O)N(c3nc(C(F)F)nc4c3oc3ccccc34)C2)c([C@]2(F)CCS(=O)(=O)C[C@H]2C)c1] | 5 | 248 | 7756 | 31 | 124 |
| 2.15 | 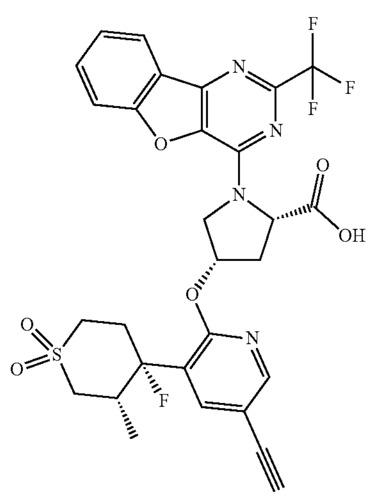 [SMILES: C#Cc1cnc(O[C@H]2C[C@@H](C(=O)O)N(c3nc(C(F)(F)F)nc4c3oc3ccccc34)C2)c([C@]2(F)CCS(=O)(=O)C[C@H]2C)c1] | 6 | 207 | 10276 | 50 | 291 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 2.16 | 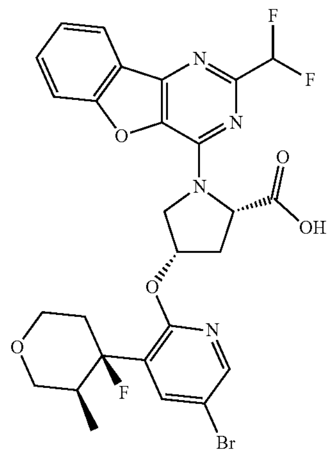 [SMILES: C[C@H]1COCC[C@]1(F)c1cc(Br)cnc1O[C@H]1C[C@@H](C(=O)O)N(c2nc(C(F)F)nc3c2oc2ccccc23)C1] | 4 | 125 | >16628 | 133 | 325 |
| 2.17 | 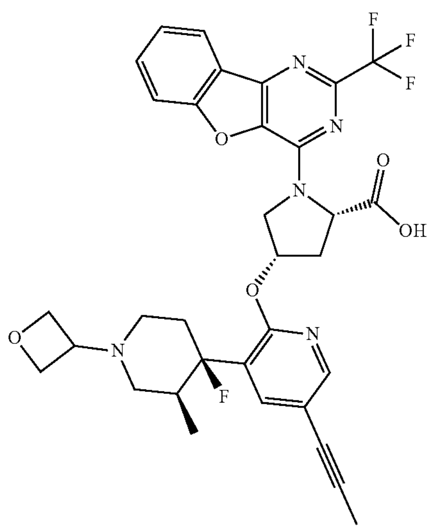 [SMILES: CC#Cc1cnc(O[C@H]2C[C@@H](C(=O)O)N(c3nc(C(F)(F)F)nc4c3oc3ccccc34)C2)c([C@@]2(F)CCN(C3COC3)C[C@@H]2C)c1] | 96 | 382 | 3921 | 10 | 287 |
| 2.18 | 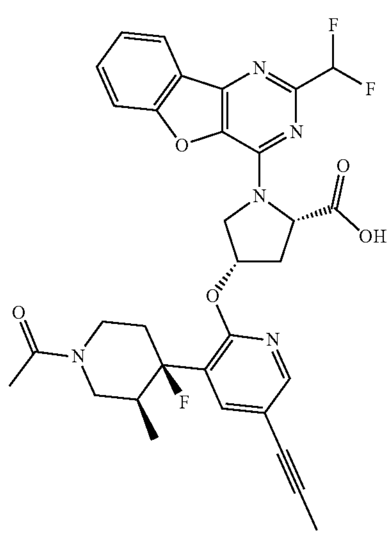 [SMILES: CC#Cc1cnc(O[C@H]2C[C@@H](C(=O)O)N(c3nc(C(F)F)nc4c3oc3ccccc34)C2)c([C@@]2(F)CCN(C(C)=O)C[C@@H]2C)c1] | 13 | 59 | 12633 | 215 | 97 |

TABLE 1-continued
Pharmacological properties of the Example compounds of the invention
| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 2.19 | 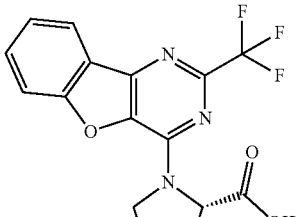 | 5 | 23 | 9962 | 435 | 57 |
| 2.20 | 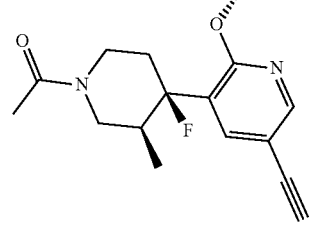 | 4 | 17 | 9888 | 583 | 25 |
| 3.01 | 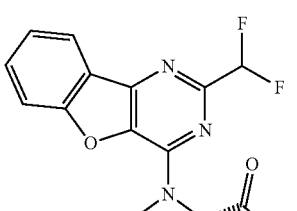 | 2 | 81 | >16596 | >205 | 51 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 3.02 | 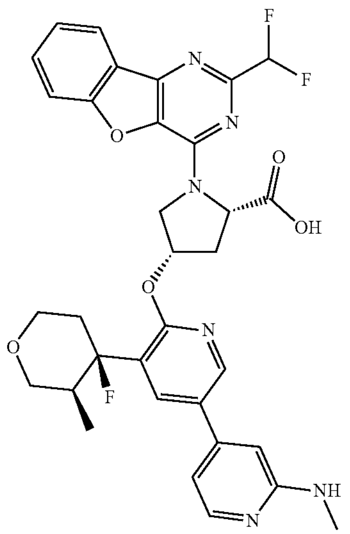 [SMILES: CNc1cc(-c2cnc(O[C@H]3C[C@@H](C(=O)O)N(c4nc(C(F)F)nc5c4oc4ccccc45)C3)c([C@@]3(F)CCOC[C@@H]3C)c2)ccn1] | 2 | 23 | 4710 | 201 | 53 |
| 3.03 | 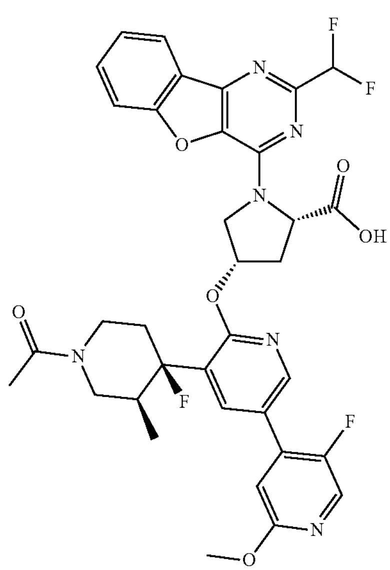 [SMILES: COc1cc(-c2cnc(O[C@H]3C[C@@H](C(=O)O)N(c4nc(C(F)F)nc5c4oc4ccccc45)C3)c([C@@]3(F)CCN(C(C)=O)C[C@@H]3C)c2)c(F)cn1] | 12 | 18 | 10361 | 568 | 53 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 3.04 | 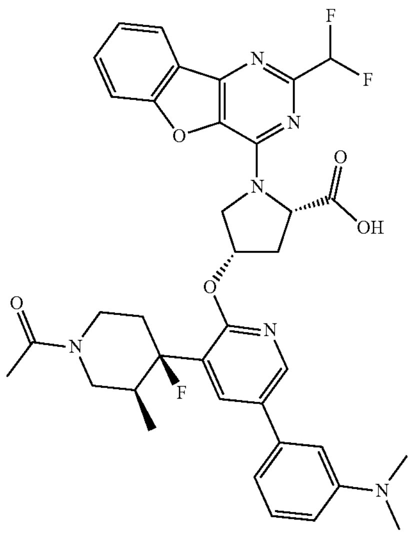 [SMILES: CC(=O)N1CC[C@](F)(c2cc(-c3cccc(N(C)C)c3)cnc2O[C@H]2C[C@@H](C(=O)O)N(c3nc(C(F)F)nc4c3oc3ccccc34)C2)[C@@H](C)C1] | 29 | 16 | 10467 | 650 | 46 |
| 4.01 | 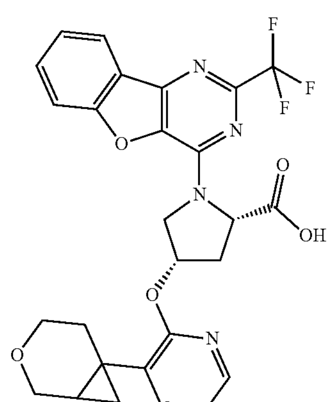 | 8 | 784 | >16596 | >21 | 1499 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 5.01 | 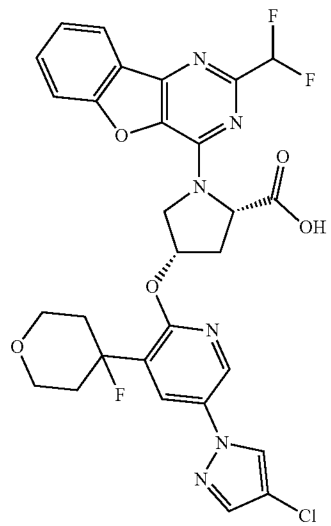 [SMILES: O=C(O)[C@@H]1C[C@H](Oc2ncc(-n3cc(Cl)cn3)cc2C2(F)CCOCC2)CN1c1nc(C(F)F)nc2c1oc1ccccc12] | 12 | 1,001 | >16610 | >17 | 2886 |
| 6.01 | 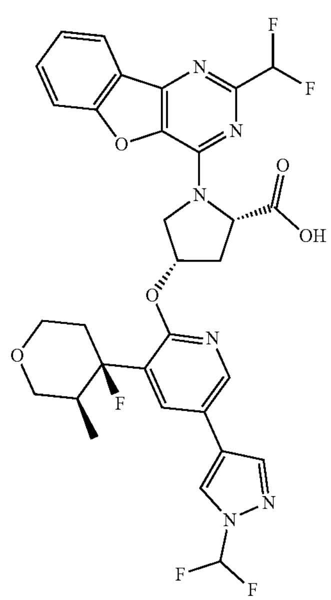 [SMILES: C[C@H]1COCC[C@]1(F)c1cc(-c2cnn(C(F)F)c2)cnc1O[C@H]1C[C@@H](C(=O)O)N(c2nc(C(F)F)nc3c2oc2ccccc23)C1] | 5 | 35 | >9994 | >289 | 82 |

TABLE 1-continued
Pharmacological properties of the Example compounds of the invention
| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 6.02 | 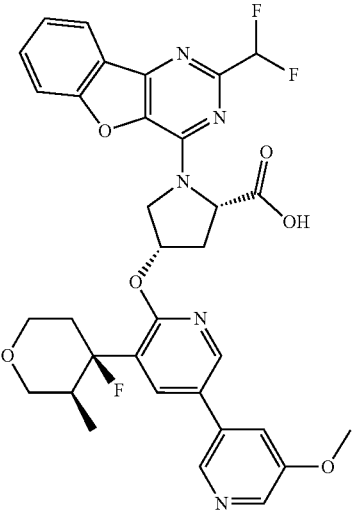 [SMILES: COc1cncc(-c2cnc(O[C@H]3C[C@@H](C(=O)O)N(c4nc(C(F)F)nc5c4oc4ccccc45)C3)c([C@@]3(F)CCOC[C@@H]3C)c2)c1] | 6 | 5 | >16619 | >3212 | 45 |
| 6.03 | 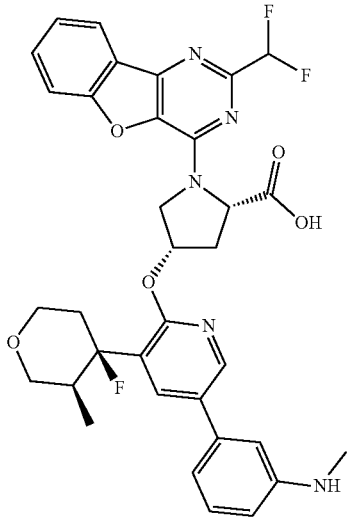 [SMILES: CNc1cccc(-c2cnc(O[C@H]3C[C@@H](C(=O)O)N(c4nc(C(F)F)nc5c4oc4ccccc45)C3)c([C@@]3(F)CCOC[C@@H]3C)c2)c1] | 10 | 35 | 9508 | 276 | 38 |

TABLE 1-continued

Pharmacological properties of the Example compounds of the invention

| Exam. No. | Structure | hcGAS IC50 [nM] | THP1$_{(vir)}$ IC50 [nM] | THP1$_{(cGAMP)}$ IC50 [nM] | Ratio THP$_{(cGAMP)}$ IC50/THP$_{(vir)}$ IC50 | hWB IC50 [nM] |
|---|---|---|---|---|---|---|
| 6.04 | [structure] | 17 | 21 | 7682 | 371 | 75 |

5.2 Comparison of the Example Compounds with Prior Art Compounds

5.2.1 Compounds of WO 2020/142729

In WO 2020/142729 cGAS-inhibitors with partially similar structures have been disclosed. On page 44 and 45 of WO 2020/142729 the "biochemical (in vitro) IC50-values" with regard to cGAS-inhibition (corresponding to "hcGAS IC50") have been disclosed. Hereby compounds with a "biochemical (in vitro) IC50-value" of less than 100 nM had been designated into "group A", compounds with a "biochemical (in vitro) IC50-value" of greater than 100 nM and less than 500 nM had been designated into "group B", compounds with a "biochemical (in vitro) IC50-value" of greater than 500 nM and less than 1 μM had been designated into "group C", compounds with a "biochemical (in vitro) IC50-value" of greater than 1 μM and less than 10 μM had been designated into "group D" and compounds with a "biochemical (in vitro) IC50-value" of greater than 10 μM had been designated into "group E" (see page 44 of WO 2020/142729).

On page 45 of WO 2020/142729 it is disclosed that only compound No. 25 could be designated to "group A" having a "biochemical (in vitro) IC50-value" of less than 100 nM. All other example compounds of WO 2020/142729 show "biochemical (in vitro) IC50-values" of greater than 100 nM.

5.2.2 Comparison Between the Examples of the Invention and the Examples of WO 2020/142729

Selected prior art compounds of WO 2020/142729 have been synthesized and then have been tested with respect to their pharmacological properties regarding their potency to inhibit the cGAS/STING pathway. In particular the "biochemical (in vitro) IC50-values" with regard to cGAS-inhibition (hcGAS IC50), the "cellular IC50-values with regard to inhibition of IFN induction in virus-stimulated THP1 cells" (THP1$_{(vir)}$ IC50), the "cellular IC50-value with regard to inhibition of IFN induction in cGAMP-stimulated THP1 cells" (THP1$_{(cGAMP)}$ IC50) and the "IC50-value with regard to inhibition of IFN induction in human whole blood" (hWB) have been experimentally determined for the structurally closest examples of WO 2020/142729 according to the assay methods as described in section 6 below (see Table 2).

TABLE 2

Pharmacological properties of a selection of Example compounds from WO 2020/142729

| Example No. (as disclosed in WO 2020/142729) | Structure | hcGAS IC50 [nM] | THP1$_{(vir)}$ IC50 [nM] | THP1$_{(cGAMP)}$ IC50 [nM] | hWB IC50 [nM] |
|---|---|---|---|---|---|
| 15 | [structure] | 2700 | >17000 | >17000 | — |

TABLE 2-continued

Pharmacological properties of a selection of Example compounds from WO 2020/142729

| Example No. (as disclosed in WO 2020/142729) | Structure | hcGAS IC50 [nM] | THP1$_{(vir)}$ IC50 [nM] | THP1$_{(cGAMP)}$ IC50 [nM] | hWB IC50 [nM] |
|---|---|---|---|---|---|
| 25 | 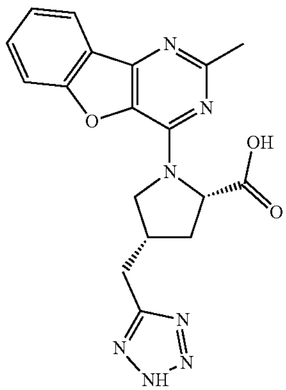 [SMILES: Cc1nc(N2C[C@@H](Cc3nn[nH]n3)C[C@H]2C(=O)O)c2oc3ccccc3c2n1] | 55 | >17000 | >17000 | >9992 |
| 28 | 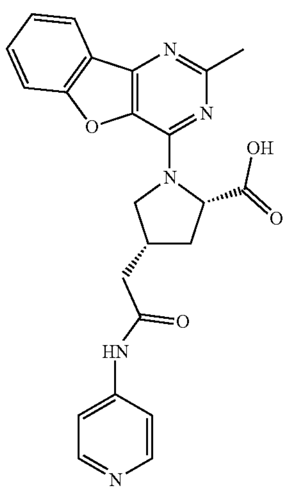 [SMILES: Cc1nc(N2C[C@@H](CC(=O)Nc3ccncc3)C[C@H]2C(=O)O)c2oc3ccccc3c2n1] | 630 | >32000 | >17000 | >9990 |
| 38 | 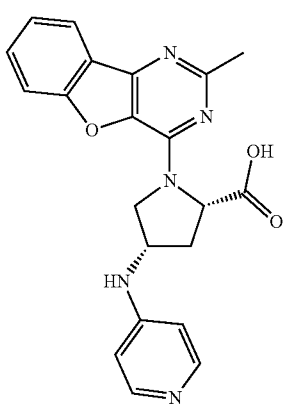 [SMILES: Cc1nc(N2C[C@@H](Nc3ccncc3)C[C@H]2C(=O)O)c2oc3ccccc3c2n1] | 3000 | >17000 | >17000 | >9990 |

TABLE 2-continued

Pharmacological properties of a selection of Example compounds from WO 2020/142729

| Example No. (as disclosed in WO 2020/142729) | Structure | hcGAS IC50 [nM] | THP1$_{(vir)}$ IC50 [nM] | THP1$_{(cGAMP)}$ IC50 [nM] | hWB IC50 [nM] |
|---|---|---|---|---|---|
| 58 | 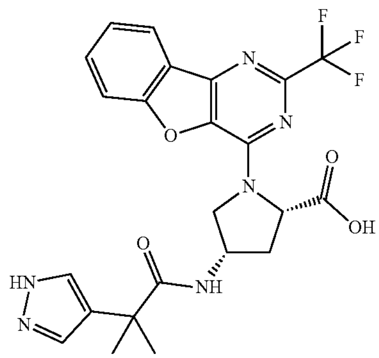 [SMILES: CC(C)(C(=O)N[C@H]1C[C@@H](C(=O)O)N(c2nc(C(F)(F)F)nc3c2oc2ccccc23)C1)c1cn[nH]c1] | 320 | 21000 | 23000 | >9982 |

The pharmacological properties for the Example compounds of the invention as summarized in Table 1 and the respective pharmacological properties for the compounds of WO 2020/142729 can be compared to each other, since they were experimentally determined according to the identical assay procedures as described in section 6 below.

From data as shown in Table 2 it is clear that all example compounds of WO 2020/142729 show "biochemical (in vitro) IC50-values" (=hcGAS IC50) that are significantly larger than 100 nM—with the only exception of Example No. 25 of WO 2020/142729 (in WO 2020/142729 designated in "Group A" having a "biochemical (in vitro) IC50-value" (=hcGAS IC50) of less than 100 nM). In contrast to that the Example compounds of the invention all have "biochemical (in vitro) IC50-values" (hcGAS IC50) of less than 100 nM. However, Example No. 25 of WO 2020/142729 which has a "biochemical (in vitro) IC50-value" (hcGAS IC50) of 55 nM, does not at all comply with the selection criterium of a "satisfying cellular inhibitory potency" shown by a THP1$_{(vir)}$ IC50 of lower than 1 μM, because THP1$_{(vir)}$ IC50 for Example No. 25 of WO 2020/142729 is 17 μM.

5.3 Prodrugs

It is known that esters of active agents with a carboxylic acid group may represent viable prodrugs which may i.e. show an improved oral absorption/bioavailability compared to the respective active agent. Frequently used prodrugs of active agents with a carboxylic acid group are for example methyl esters, ethyl esters, iso-propyl esters etc. (see Beaumont et al., Current Drug Metabolism, 2003, Vol. 4, Issue 6, 461-485).

Further, Nakamura et al., Bioorganic & Medicinal Chem., Vol. 15, Issue 24, p. 7720-7725 (2007), describes that also N-acylsulfonamide derivatives and N-acylsulfonylurea derivatives of a specific active agent with a free carboxylic acid group have the potential of being a viable prodrug.

Additionally, experimental hints have been found that also the methyl esters of the example compounds of formulas (I), (I'), (I"), (II') and (II") represent viable prodrugs of the cGAS inhibitors of formulas (I), (I'), (I"), (II') and (II").

Compounds P01, P02 and P03 are methyl esters of the Example compounds 2.12, 1.13 and 1.05, respectively and therefore may represent viable prodrugs of the respective Example compounds.

P01, P02 and P03 have been synthesized and tested for their pharmacological properties with respect to their potency to inhibit the cGAS/STING pathway. Subsequently, the experimentally determined pharmacological properties of prodrugs P01, P02 and P03 have been compared to the corresponding pharmacological properties of the respective Example compounds 2.12, 1.13 and 1.05 as summarized in Table 3.

This comparison between the Example compound and its corresponding prodrug shows that the hcGAS IC50-values for the Example compounds are always around or even smaller than 10 nM, whereas the hcGAS IC50-values for the corresponding prodrugs are always extremely large, that means generally larger than at least 7000 nM. That large difference between an Example compound on the one hand and its corresponding prodrug on the other hand is never observed for the respective THP1$_{(vir)}$IC50-values which always stay in the same range between the Example compound and its corresponding prodrug (see Table 3 for instance for Example No. 2.12 and its respective prodrug P01).

One possible explanation for that observation is that the example compounds (which represent the "drugs") all have a free carboxyl group which seems to be crucial for inhibition of cGAS activity, whereas in all "prodrugs" the carboxyl group is masked by a carboxy-methyl ester group. Consequently, the prodrugs lose their inhibitory potency in the "in vitro human cGAS enzyme assay" (see section 6.1 below), because in this assay intracellular enzymes that cleave the carboxy-methyl ester group are absent. Therefore the prodrugs show extremely large "biochemical (in vitro) IC50-values" (=hcGAS IC50) in this "in vitro human cGAS enzyme assay", whereas the corresponding Example compounds (which represent the drugs or active agents) show small "biochemical (in vitro) IC50-values" (=hcGAS IC50).

In the "human cGAS cell and the counter cell assay" (see section 6.2 below) endogenous cellular enzymes that cleave the carboxy-methyl ester group are present. Consequently not only the Example compounds themselves (that means the drugs or active agents themselves) show small THP1$_{(vir)}$ IC50-values, but also the corresponding prodrugs show relatively small "THP1$_{(vir)}$IC50-values", because in this "human cGAS cell assay" the methyl ester of the prodrugs can be cleaved by endogenous intracellular enzymes into the corresponding drug/active agent that shows inhibitory potency again.

This explanation together with the measurements as shown in Table 3 imply that methyl ester derivatives of the compounds of formulas (I), (I'), (I''), (II') and (II'') really seem to represent viable prodrugs of the compounds of formulas (I), (I'), (I''), (II') and (II'') which themselves have no inhibitory potency regarding the in vitro human biochemical cGAS inhibition. However, upon cleavage of the methyl ester by endogenous intracellular enzymes the compounds of formulas (I), (I'), (I''), (II') and (II'') (the active agents) are formed, that exhibit again an inhibitory potency regarding the cGAS/STING pathway.

TABLE 3

Comparison between selected Example compound of the invention (= active agents) and their respective methyl ester prodrugs:

| Example No./ Prodrug No. | Structure | hcGAS IC50 [nM] | THP1$_{(vir)}$ IC50 [nM] | THP1$_{(cGAMP)}$ IC50 [nM] | hWB IC50 [nM] |
| --- | --- | --- | --- | --- | --- |
| P01 (Prodrug of Ex. 2.12) | 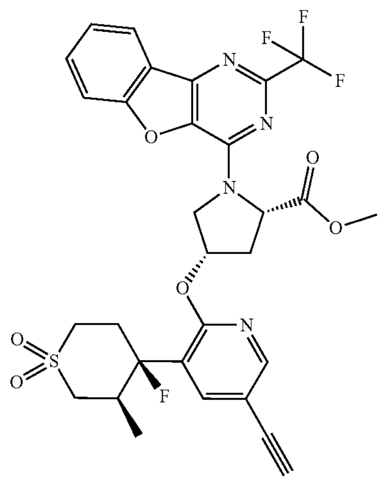 [SMILES: C#Cc1cnc(O[C@H]2C[C@@H](C(=O)OC)N(c3nc(C(F)(F)F)nc4c3oc3ccccc34)C2)c([C@@]2(F)CCS(=O)(=O)C[C@@H]2C)c1] | 19147 | 11 | >16612 | 67 |
| Ex. 2.12 | 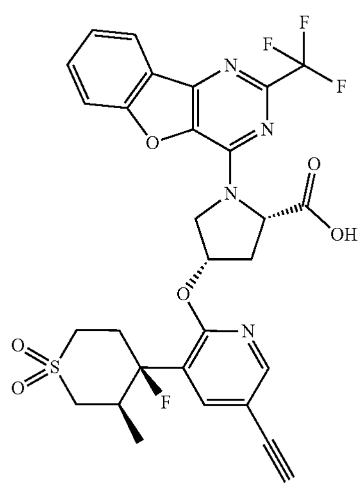 | 3 | 8 | 21781 | 8 |

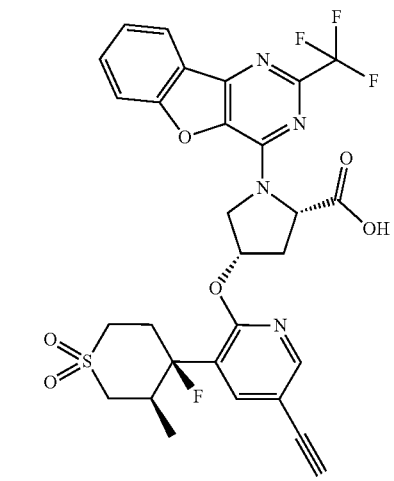 [SMILES: C#Cc1cnc(O[C@H]2C[C@@H](C(=O)O)N(c3nc(C(F)(F)F)nc4c3oc3ccccc34)C2)c([C@@]2(F)CCS(=O)(=O)C[C@@H]2C)c1]

TABLE 3-continued
Comparison between selected Example compound of the invention (= active agents) and their respective methyl ester prodrugs:
| Example No./ Prodrug No. | Structure | hcGAS IC50 [nM] | THP1$_{(vir)}$ IC50 [nM] | THP1$_{(cGAMP)}$ IC50 [nM] | hWB IC50 [nM] |
|---|---|---|---|---|---|
| P02 (prodrug of Ex. 1.13) | 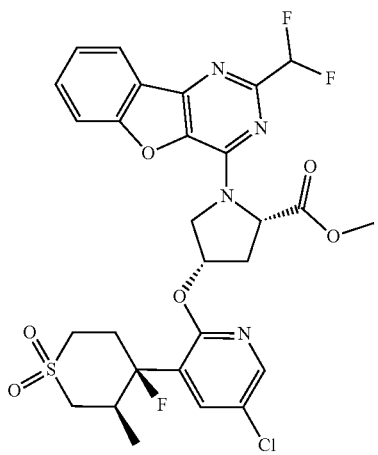 [SMILES: COC(=O)[C@@H]1C[C@H](Oc2ncc(Cl)cc2[C@@]2(F)CCS(=O)(=O)C[C@@H]2C)CN1c1nc(C(F)F)nc2c1oc1ccccc12] | >9954 | 29 | >16620 | 140 |
| Ex. 1.13 | 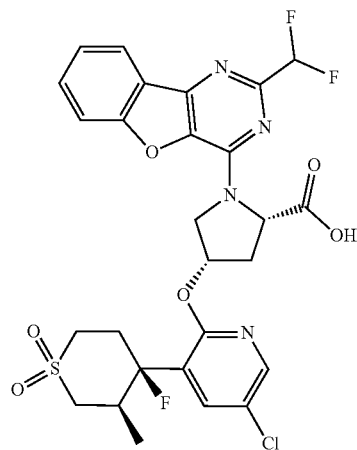 [SMILES: C[C@H]1CS(=O)(=O)CC[C@]1(F)c1cc(Cl)cnc1O[C@H]1C[C@@H](C(=O)O)N(c2nc(C(F)F)nc3c2oc2ccccc23)C1] | 2 | 6 | 22502 | 6 |
| P03 (prodrug of Ex. 1.05) | 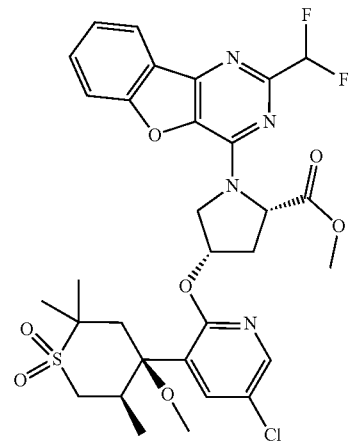 [SMILES: COC(=O)[C@@H]1C[C@H](Oc2ncc(Cl)cc2[C@@]2(OC)CC(C)(C)S(=O)(=O)C[C@@H]2C)CN1c1nc(C(F)F)nc2c1oc1ccccc12] | 7253 | 202 | 20592 | 1994 |

TABLE 3-continued

Comparison between selected Example compound of the invention (= active agents) and their respective methyl ester prodrugs:

| Example No./Prodrug No. | Structure | hcGAS IC50 [nM] | THP1$_{(vir)}$ IC50 [nM] | THP1$_{(cGAMP)}$ IC50 [nM] | hWB IC50 [nM] |
|---|---|---|---|---|---|
| Ex. 1.05 | 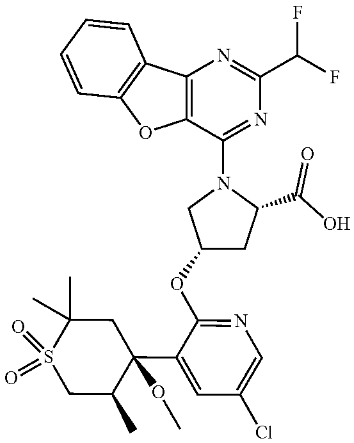 [SMILES: CO[C@]1(c2cc(Cl)cnc2O[C@H]2C[C@@H](C(=O)O)N(c3nc(C(F)F)nc4c3oc3ccccc34)C2)CC(C)(C)S(=O)(=O)C[C@@H]1C] | 2 | 44 | 13188 | 135 |

6 BIOLOGICAL EXPERIMENTS

The activity of the compounds of the invention may be demonstrated using the following in vitro cGAS enzyme and cell assays:

6.1 Method: Human cGAS Enzyme Assay (hcGAS IC50 (In Vitro))

Human cGAS enzyme was incubated in the presence of a 45 base pair double stranded DNA to activate the enzyme and GTP and ATP as substrates. Compound activity was determined by measuring the effect of compounds on the formation of the product of the enzyme reaction, cGAMP, which is measured by a mass spectrometry method.

Enzyme Preparation:

Human cGAS (amino acid 1-522) with an N-terminal 6×-His-tag and SUMO-tag was expressed in *E. coli* BL21 (DE3) pLysS (Novagen) cells for 16 h at 18° C. Cells were lysed in buffer containing 25 mM Tris (pH 8), 300 mM NaCl, 10 mM imidazole, 10% glycerol, protease inhibitor cocktail (cOmplete™, EDTA-free, Roche) and DNase (5 µg/mL). The cGAS protein was isolated by affinity chromatography on Ni-NTA agarose resin and further purified by size exclusion chromatography using a Superdex 200 column (GE Healthcare) equilibrated in 20 mM Tris (pH 7.5), 500 mM KCl, and 1 mM TCEP. Purified protein was concentrated to 1.7 mg/mL and stored at −80° C.

Assay Method

Compounds were delivered in 10 mM DMSO solution, serially diluted and transferred to the 384 well assay plate (Greiner #781201) using an Echo acoustic dispenser. Typically, 8 concentrations were used with the highest concentration at 10 µM in the final assay volume followed by ~1:5 dilution steps. DMSO concentration was set to 1% in the final assay volume. The 384 well assay plate contained 22 test compounds (column 1-22), and DMSO in column 23 and 24.

After the compound transfer, 15 µL of the enzyme-DNA-working solution (12 nM cGAS, 0.32 µM 45 base pair DNA in assay buffer, 10 mM Tris pH 7.5/10 mM KCl/5 mM MgCl2/1 mM DTT) were added to each well from column 1-23 via a MultiDrop Combi dispenser. In column 24, 15 µl of assay buffer without enzyme/DNA were added as a low control.

The plates were then pre-incubated for 60 min at room temperature.

Following that, 10 µL of GTP (ThermoFisher #R0461)-ATP (Promega #V915B) mix in assay buffer were added to the assay plate (columns 1-24, 30 µM final concentration each) using a Multidrop Combi.

The plates were incubated again for 90 min at room temperature.

Following the incubation, the reaction was stopped by 80 µL of 0.1% formic acid in assay buffer containing 5 nM cyclic-di-GMP (Sigma #SML1228) used as internal standard for the mass spectrometry. The total volume/well was 105 µL.

Rapidfire MS Detection

The plates were centrifuged at 4000 rpm, 4° C., for 5 min.

The RapidFire autosampler was coupled to a binary pump (Agilent 1290) and a Triple Quad 6500 (ABSciex, Toronto, Canada). This system was equipped with a 10 µL loop, C18 [12 IL bed volume] cartridge (Agilent, Part No. G9210A) containing 10 mM NH4Ac (aq) water (pH7.4) as eluent A (pump 1 at 1.5 mL/min, pump 2 at 1.25 mL/min) and 10 mM NH4Ac in v/v/v 47.5/47.5/5 ACN/MeOH/H2O (pH7.4) as eluent B (pump 3 at 1.25 mL/min). Aspiration time: 250 ms; Load time: 3000 ms; Elute time: 3000 ms; Wash volume: 500 µL.

The MS was operated in positive ion mode with HESI ion source, with a source temperature of 550° C., curtain gas=35, gas 1=65, and gas 2=80. Unit mass resolution in SRM mode. The following transitions and MS parameters (DP: declustering potential and CE: collision energy) for cGAMP and DicGMP were determined:

Analyte: cGAMP at 675.1/524, DP=130, CE=30 and

Internal standard: cyclic-di-GMP at 690.1/540, DP=130, CE=30.

The formation of cGAMP was monitored and evaluated as ratio to cyclic-di-GMP.

Data Evaluation and Calculation:

For data evaluation and calculation, the measurement of the low control was set as 0% control and the measurement of the high control was set as 100% control. The IC50 values were calculated using the standard 4 parameter logistic regression formula. Calculation: $[y=(a-d)/(1+(x/c)^b)+d]$, a=low value, d=high value; x=conc M; c=1C50 M; b=slope

6.2 Method: Human cGAS Cell Assay and cGAMP Stimulated Counter Cell Assay (THP1$_{(vir)}$ IC50 and THP1$_{(cGAMP)}$ IC50)

THP1-Dual™ cells (InvivoGen #thpd-nfis) expressing IRF dependent Lucia luciferase reporter were used as basis for both assays. For the detection of cellular cGAS activity cells were stimulated by a baculovirus (pFastbac-1, Invitrogen, no coding insert) infection that delivers the cGAS enzyme stimulating double-stranded DNA (measurement of THP1$_{(vir)}$ IC50).

For the counter assay, cells were stimulated by cGAMP (SigmaAldrich #SML1232) to activate the identical pathway independent and directly downstream of cGAS (measurement of THP1$_{(cAMP)}$ IC50). Pathway activity was monitored by measuring the Lucia luciferase activity induced by either DNA stimulated cGAS enzyme activity (measurement of THP1$^{(vir)}$ IC50) or by cGAMP directly (measurement of THP1$_{(cAMP)}$ IC50, counter assay).

Assay Method

Compounds were delivered in 10 mM DMSO solution, serially diluted and transferred to the 384 well assay plate (Greiner #781201) using an Echo acoustic dispenser. Typically, 8 concentrations were used with the highest concentration at 10 μM in the final assay volume followed by ~1:5 dilution steps. DMSO concentration was set to 1% in the final assay volume. The 384 well assay plate contained 21 test compounds (column 1-22), and DMSO in column 23 and 24.

Cells, cultivated according to manufacturer conditions, were harvested by centrifugation at 300 g/10 min and were then resuspended and diluted to 1.66E5 cells/ml in fresh cell culture medium (RPMI 1640 (Gibco #A10491-01), 10% FCS (Gibco #10500), 1× GlutaMax (Gibco #35050-061),1× Pen/Strep solution (Gibco #15140-122), 100 μg/ml Normocin (InvivoGen #ant-nr), 100 μg/ml Zeocin (InvivoGen #ant-zn), 10 μg/ml Blasticidin S (Life Technologies #A11139-03)). The baculovirus solution was then added 1:200 (may have varied according to virus batch) to the cells (measurement of THP1$_{(vir)}$ IC50). Alternatively, for the counter assay cGAMP was added to the cells at a final concentration of 10 μM (measurement of THP1$_{(cAMP)}$ IC50).

30 μL of the cell/virus-mix were added to each well of the compound plate from column 1-23 via MultiDrop Combi dispenser (5000 cells/well). In column 24, 30 μl/5000 cells/well without virus were added as a low control.

The plates were then incubated for 18 h at 37° C. in a humidified incubator.

Following that, 15 μL of QuantiLuc detection reagent (InvivoGen #rep-qlcg5) were added to each well using a MultiDrop Combi. Measurement was done immediately after the addition using an EnVision reader (US-luminescence read-mode).

Data Evaluation and Calculation:

For data evaluation and calculation, the measurement of the low control was set as 0% control and the measurement of the high control was set as 100% control. The IC50 values were calculated using the standard 4 parameter logistic regression formula. Calculation: $[y=(a-d)/(1+(x/c)^b)+d]$, a=low value, d=high value; x=conc M; c=1C50 M; b=slope

6.3 Method: Human Whole Blood Assay (Human WB IC50)

For the detection of cellular cGAS activity human whole blood was stimulated by transfection with double stranded DNA. Pathway activity was monitored by measuring the IFNα2α production.

Assay Method

Compounds were delivered as 10 mM DMSO solution and serially diluted and transferred to the 96-well cell culture plate (Corning #3595), prefilled with 20 μl OptiMEM (Gibco, #11058-021) in each well, using an Echo acoustic dispenser. Typically, 8 concentrations were used with the highest concentration at 10 μM in the final assay volume followed by ~1:5 dilution steps. DMSO concentration was set to 0.1% in the final assay volume. The 96-well assay plate contained 10 test compounds, and DMSO in control wells.

Collection of human whole blood from 3 or more healthy donors (male or female, no medication for 7 days except contraceptive and thyroxine) as Na-Citrate blood (e.g. 3.8% in Monovettes from Sarstedt) was conducted in parallel. Whole blood was kept at room temperature for a maximum of 3 hours after collection until use in the assay.

160 μl of the whole blood samples was transferred to each well of the 96-well assay plates filled with compound/OptiMEM. All assay plates were prepared as duplicates with blood from different donors. Blood plates were kept at room temperature for 60 minutes and continuous shaking with 450 rpm, covered with the lid, but not sealed.

DNA-Fugene mix (Herring DNA, Sigma Aldrich #D6898-1G, Fugene (5×1 mL), Promega #E2312) was prepared in OptiMEM and incubated for 10 min at RT (125 ng DNA/20 μl and Fugene ratio 9.6:1). 20 μl of the DNA Fugene mix was added to each well, resulting in 125 ng DNA/well/200 μl, and Fugene Ratio 9.6:1. 20 μl OptiMEM and 9.6:1 Fugene was added to all low control wells.

After covering assay plates with aera seals and the lid, blood plates were kept at room temperature for 30 minutes and continuous shaking with 450 rpm, followed by an overnight incubation of 22 h at 37° C. in the incubator, without shaking.

For the detection of IFNα-2α in human plasma, the biotinylated capture antibody (Antibody set IFNA2, Meso Scale Diagnostics #B21VH-3, including coating and capture antibody) was diluted 1:17.5 in Diluent 100 (Meso Scale Diagnostics #R50AA-4), according to the manufacturer's directions. U-Plex MSD GOLD 96-well Small Spot Strepavidin SECTOR Plates (Meso Scale Diagnostics #L45SA-5) were coated with 25 μl diluted capture antibody. Coated plates were incubated for 60 min at room temperature under continuous shaking at 700 rpm. MSD IFNα-2a plates were washed three times with 150 μl wash buffer (1×HBSS, 0.05% Tween).

After blocking the plates with 100 μl block solution/well (1×HBSS with 0.2% Tween, 2% BSA) for 60 min at room temperature and continuous shaking at 700 rpm, plates were emptied as dry as possible by dumping just before continuing with the human plasma.

Whole Blood assay plates were centrifuged at 1600 rpm for 10 minutes. 25 μl of supernatant was transferred with a pipetting robot from each whole blood plate to the corresponding IFNα-2a plate.

Plates were sealed with microplate seals and kept at room temperature again under continuous shaking at 700 rpm for two hours.

Next MSD IFNα-2a plates were washed three times with 150 μl wash buffer (1×HBSS, 0.05% Tween), before adding 25 μl MSD SULFO-TAG IFNα-2a Antibody solution (1:100 diluted in Diluent 3 (Meso Scale Diagnostics #R50AP-2) to each well of the plates.

Afterwards plates were sealed with microplate seals and kept at room temperature again under continuous shaking at 700 rpm for two hours. Finally, MSD IFNα-2α plates were washed three times with 150 μl wash buffer (1×HBSS, 0.05% Tween). 150 μl 2× Read buffer was added to each well and plates were immediately measured with the MSD Sector S600 Reader using the vendor barcode.

Data Evaluation and Calculation:

For data evaluation and calculation, % control calculation of each well was based on the mean of high (DNA stimulated control) and mean of low (unstimulated control) controls by using the following formula:

[counts(sample)−counts(low))/(counts(high)−counts(low))]*100

The IC50 values were calculated using the standard 4 parameter logistic regression formula. Calculation: [y=(a−d)/(1+(x/c)^b)+d], a=low value; d=high value; x=conc M; c=1C50 M; b=slope

7 Indications

As has been found, the compounds of formulas (I), (I'), (I"), (II') and (II") are characterized by their range of applications in the therapeutic field. Particular mention should be made of those applications for which the compounds of formulas (I), (I'), (I"), (II') and (II") according to the invention are preferably used on the basis of their pharmaceutical activity as cGAS inhibitors. While the cGAS pathway is important for host defense against invading pathogens, such as viral infection and invasion by some intracellular bacteria, cellular stress and genetic factors may also cause production of aberrant cellular dsDNA, e.g. by nuclear or mitochondrial leakage, and thereby trigger autoinflammatory responses. Consequently, cGAS inhibitors have a strong therapeutic potential to be used in the treatment of diverse autoinflammatory and autoimmune diseases.

An et al., Arthritis Rheumatol. 2017 April; 69(4):800-807, disclosed that cGAS expression in peripheral blood mononuclear cells (PBMCs) was significantly higher in patients with the autoimmune disease systemic lupus erythematosus (SLE) than in normal controls. Targeted measurement of cGAMP by tandem mass spectrometry detected cGAMP in 15% of the tested SLE patients, but none of the normal or rheumatoid arthritis controls. Disease activity was higher in SLE patients with cGAMP versus those without cGAMP. Whereas higher cGAS expression may be a consequence of exposure to type I interferon (IFN), detection of cGAMP in SLE patients with increased disease activity indicates potential involvement of the cGAS pathway in disease expression.

Park et al., Ann Rheum Dis. 2018 October; 77(10):1507-1515, also discloses the involvement of the cGAS pathway in the development of SLE.

Thim-Uam et al., iScience 2020 Sep. 4; 23(9), 101530 (doi: 10.1016/j.isci.2020.101530), discloses that the STING pathway mediates lupus via the activation of conventional dendritic cell maturation and plasmacytoid dendritic cell differentiation.

Gao et al., Proc. Natl. Acad. Sci. USA. 2015 Oct. 20; 112(42):E5699-705, describes that the activation of cGAS by self-DNA leads to certain autoimmune diseases such as interferonopathies.

Tonduti et al., Expert Rev. Clin. Immunol. 2020 February; 16(2):189-198 discloses that cGAS inhibitors have particular therapeutic potential in Aicardi-Goutières syndrome which is a lupus-like severe autoinflammatory immune-mediated disorder.

In Yu et al., Cell 2020 Oct. 29; 183(3):636-649, the link between TDP-43 triggered mitochondrial DNA and the activation of the cGAS/STING pathway in amyotrophic lateral sclerosis (ALS) is described.

Ryu et al., Arthritis Rheumatol. 2020 November; 72(11): 1905-1915, also shows that bioactive plasma mitochondrial DNA is associated with disease progression in specific fibrosing diseases such as systemic sclerosis (SSc) or interstitial lung diseases (ILDs), progressive fibrosing interstitial lung diseases (PF-ILDs), and idiopathic pulmonary fibrosis (IPF).

In Schuliga et al., Clin. Sci. (Lond). 2020 Apr. 17; 134(7):889-905, it is described that self-DNA perpetuates IPF lung fibroblast senescence in a cGAS-dependent manner.

Additional scientific hints linking the cause for other fibrosing diseases such as non-alcoholic steatotic hepatitis (NASH) with the cGAS/STING pathway have been described in Yu et al., J. Clin. Invest. 2019 Feb. 1; 129(2): 546-555, and in Cho et al., Hepatology. 2018 October; 68(4): 1331-1346.

Nascimento et al., Sci. Rep. 2019 Oct. 16; 9(1):14848, discloses that self-DNA release and STING-dependent sensing drives inflammation to due to cigarette smoke in mice hinting at a link between the cGAS-STING pathway and chronic obstructive pulmonary disease (COPD).

Ma et al., Sci. Adv. 2020 May 20; 6(21):eaaz6717, discloses that ulcerative colitis and inflammatory bowel disease (IBD) may be restrained by controlling cGAS-mediated inflammation.

Gratia et al., J. Exp. Med. 2019 May 6; 216(5):1199-1213, shows that Bloom syndrome protein restrains innate immune sensing of micronuclei by cGAS. Consequently cGAS-inhibitors have a therapeutic potential in treating Bloom's syndrome.

Kerur et al., Nat. Med. 2018 January; 24(1):50-61, describes that cGAS plays a significant role in noncanonical-inflammasome activation in age-related macular degeneration (AMD).

Further, the cGAS inhibitors of formulas (I), (I'), (I"), (II') and (II") also have a therapeutic potential in the treatment of cancer (see Hoong et al., Oncotarget. 2020 Jul. 28; 11(30): 2930-2955, and Chen et al., Sci. Adv. 2020 Oct. 14; 6(42): eabb8941).

Additionally, the cGAS inhibitors of formulas (I), (I'), (I"), (II') and (II") have also a therapeutic potential in the treatment of heart failure (Hu et al., Am. J. Physiol. Heart Circ. Physiol. 2020 Jun. 1; 318(6):H1525-H1537).

Further scientific hints at a correlation between Parkinsons disease and the cGAS/STING pathway (Sliter et al., Nature. 2018 September; 561(7722):258-262) and between Sjogren's syndrome and the cGAS/STING pathway (Papinska et al., J. Dent. Res. 2018 July; 97(8):893-900) exist.

Furthermore, cGAS inhibitors of formula (I) (I'), (I"), (II') and (II") have also a therapeutic potential in the treatment of COVID-19/SARS-CoV-2 infections as shown in Di Domizio et al., Nature. 2022 Jan. 19. doi: 10.1038/s41586-022-

04421-w: "The cGAS-STING pathway drives type I IFN immunopathology in COVID-19", and in Neufeldt et al., Commun Biol. 2022 Jan. 12; 5(1):45. doi: 10.1038/s42003-021-02983-5: "SARS-CoV-2 infection induces a pro-inflammatory cytokine response through cGAS-STING and NF-kappaB".

Additionally, cGAS inhibitors of formula (I) (I'), (I"), (II') and (II") have a therapeutic potential in the treatment of renal inflammation and renal fibrosis as shown in Chung et al., Cell Metab. 2019 30:784-799: "Mitochondrial Damage and Activation of the STING Pathway Lead to Renal Inflammation and Fibrosis", and in Maekawa et al., Cell Rep. 2019 29:1261-1273: "Mitochondrial Damage Causes Inflammation via cGAS-STING Signaling in Acute Kidney Injury".

Furthermore, cGAS inhibitors of formula (I) (I'), (I"), (II') and (II") have a therapeutic potential in the treatment of cancer as shown in Bakhoum et el., Nature. 2018 Jan. 25; 553(7689):467-472: "Chromosomal instability drives metastasis through a cytosolic DNA response", and in Liu et al., Nature. 2018 November; 563(7729):131-136: "Nuclear cGAS suppresses DNA repair and promotes tumorigenesis".

Additionally, cGAS inhibitors of formula (I) (I'), (I"), (II') and (II") have a therapeutic potential in the treatment of dysmetabolism, because $STING^{gt}$ animals show reduced macrophage infiltration in adipose tissue upon subchronic high caloric intake (HFD) and $STING^{gt}$ and IRF3-deficiency leads to a decrease in blood glucose and insulin and reduced body weight (Mao et al, Arterioscler Thromb Vasc Biol, 2017; 37 (5): 920-929).

Furthermore, cGAS inhibitors of formula (I) (I'), (I"), (II') and (II") have a therapeutic potential in the treatment of vascular diseases and leads to vascular repair/regeneration, because the release of mitochondrial DNA into the cytosol of endothelial cells results in cGAS/STING pathway activation and suppression of endothelial proliferation. Further, knockout of the cGAS gene restores endothelial repair/regeneration in a mouse model of inflammatory lung injury (Huang et al, Immunity, 2020, March 2017; 52 (3): 475-486.e5. doi: 10.1016/j.immuni.2020, 02.002).

Additionally, cGAS inhibitors of formula (I) (I'), (I"), (II') and (II") have a therapeutic potential in the treatment of age-related and obesity-related cardiovascular diseases (Hamann et al, Immun Ageing, 2020, March 14; 17: 7; doi: 10.1186/s12979-020-00176-y.eCollection 2020).

Consequently the compounds of formulas (I), (I'), (I"), (II') and (II") as cGAS inhibitors can be used in the therapy of autoinflammatory and autoimmune diseases such as systemic lupus erythematosus (SLE), interferonopathies, Aicardi-Goutieres syndrome, age-related macular degeneration (AMD), amyotrophic lateral sclerosis (ALS), inflammatory bowel disease (IBD), chronic obstructive pulmonary disease (COPD), Bloom's syndrome, Sjogren's syndrome and Parkinson disease.

Additionally the compounds of formulas (I), (I'), (I"), (II') and (II") as cGAS inhibitors can be used in the therapy of fibrosing disease such as systemic sclerosis (SSc), interferonopathies, non-alcoholic steatotic hepatitis (NASH), interstitial lung disease (ILD), preferably progressive fibrosing interstitial lung disease (PF-ILD), in particular idiopathic pulmonary fibrosis (IPF).

Further, the compounds of formulas (I), (I'), (I"), (II') and (II") as cGAS inhibitors can be used in the therapy of age-related macular degeneration (AMD), heart failure, COVID-19/SARS-CoV-2 infection, renal inflammation, renal fibrosis, dysmetabolism, vascular diseases, cardiovascular diseases and cancer.

8 COMBINATIONS

The compounds of formulas (I), (I'), (I"), (II') and (II") may be administered to the patient alone or in combination with one or more other pharmacologically active agents.

In a preferred embodiment of the invention the compounds of formulas (I), (I'), (I"), (II') and (II") may be combined with one or more pharmacologically active agents selected from the group of anti-inflammatory agents, anti-fibrotic agents, anti-allergic agents/anti-histamines, bronchodilators, beta 2 agonists/betamimetics, adrenergic agonists, anticholinergic agents, methotrexate, mycophenolate mofetil, leukotriene modulators, JAK inhibitiors, anti-interleukin antibodies, non-specific immunotherapeutics such as interferones or other cytokines/chemokines, cytokine/chemokine receptor modulators (i.e. cytokine receptor agonists or antagonists), Toll-like receptor agonists (=TLR agonists), immune checkpoint regulators, anti-TNF antibodies such as Adalimumab (Humira™), and anti-BAFF agents (such as Belimumab and Etanercept).

Anti-fibrotic agents are preferably selected from Pirfenidone and tyrosine kinase inhibitors such as Nintedanib, wherein Nintedanib is preferred in particular.

Preferred examples of anti-inflammatory agents are NSAIDs and corticosteroids.

NSAIDs are preferably selected from ibuprofen, naproxen, diclofenac, meloxicam, celecoxib, acetylsalicylic acid (Aspirin™), indomethacin, mefenamic acid and etoricoxib.

Corticosteroids are preferably selected from Flunisolide, Beclomethasone, Triamcinolone, Budesonide, Fluticasone, Mometasone, Ciclesonide, Rofleponide and Dexametasone.

Antiallergic agents/anti-histamines are preferably selected from Epinastine, Cetirizine, Azelastine, Fexofenadine, Levocabastine, Loratadine, Ebastine, Desloratidine and Mizolastine.

Beta 2 agonists/betamimetics may be either long acting beta 2 Agonists (LABAs) or short acting beta agonists (SABAs). Particularly preferred beta 2 agonists/betamimetics are selected from Bambuterol, Bitolterol, Carbuterol, Clenbuterol, Fenoterol, Formoterol, Hexoprenalin, Ibuterol, Pirbuterol, Procaterol, Reproterol, Salmeterol, Sulfonterol, Terbutalin, Tolubuterol, Olodaterol, and Salbutamol, in particular Olodaterol.

Anticholinergic agents are preferably selected from ipratropium salts, tiotropium salts, glycopyrronium salts, and theophylline, wherein tiotropium bromide is preferred in particular.

Leukotriene modulators are preferably selected from Montelukast, Pranlukast, Zafirlukast, Ibudilast and Zileuton.

JAK inhibitors are preferably selected from Baricitinib, Cerdulatinib, Fedratinib, Filgotinib, Gandotinib, Lestaurtinib, Momelotinib, Pacritinib, Peficitinib, Ruxolitinib, Tofacitinib, and Upadacitinib.

Anti-interleukin antibodies are preferably selected from anti-IL23 antibodies such as Risankizumab, anti-IL17 antibodies, anti-IL1 antibodies, anti-IL4 antibodies, anti-IL13 antibodies, anti-IL-5 antibodies, anti-IL-6 antibodies such as Tocilizumab (Actemra™), anti-IL-12 antibodies, anti-IL-15 antibodies.

9 FORMULATIONS

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, intrasternal, and subcutaneous injection or infusion. Inhalation refers to administration into the patient's lungs whether inhaled through the mouth or through the nasal passages. Topical administration includes application to the skin. The compounds of the invention may be administered via eye drops to treat Sjogren's syndrome.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatin capsule), as a solution or suspension. When administered by inhalation the active substance combination may be given as a powder, as an aqueous or aqueous-ethanolic solution or using a propellant gas formulation.

Preferably, therefore, pharmaceutical formulations are characterized by the content of one or more compounds of formulas (I), (I'), (I"), (II') and (II") according to the preferred embodiments above.

It is particularly preferable if the compounds of formulas (I), (I'), (I"), (II') and (II") are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example kollidone or shellac, gum arabic, talc, titanium dioxide or sugar. To achieve delayed release or prevent incompatibilities the core may also consist of a number of layers. Similarly, the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavor enhancer, e.g. a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatin capsules. Suitable suppositories may be made for example by mixing with carriers provided for this purpose, such as neutral fats or polyethylene glycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatin and the like. Moreover, lubricants such as magnesium stearate, sodium lauryl sulphate and talc may be used at the same time for the tableting process. In the case of aqueous suspensions, the active substances may be combined with various flavor enhancers or colorings in addition to the excipients mentioned above.

The invention claimed is:
1. A compound of formula (I),

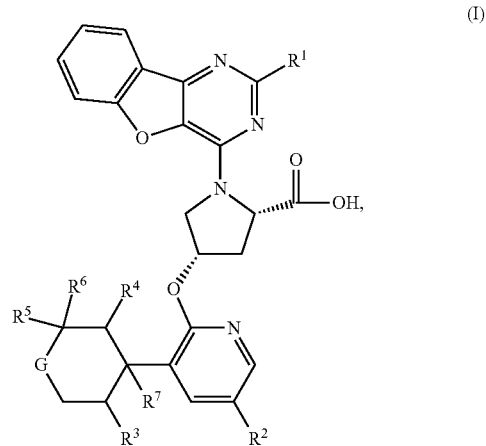

wherein
$R^1$ is selected from methyl, ethyl, halomethyl and halogen,
wherein
G is selected from $SO_2$, S, O, N, and $NR^8$,
wherein
$R^2$ is selected from H, halogen, cyclopropyl, $C_{1-3}$-alkyl, $C_{2-5}$-alkynyl and CN,
or wherein $R^2$ is a cyclic group selected from the group consisting of a phenyl or a five- to six-membered heteroaryl with 1, 2, 3 or 4 heteroatoms, each independently selected from N, S and O, wherein this cyclic group is substituted by one or two, identical or different substituents $R^{10}$,
wherein
$R^3$ is selected from H, methyl and —$CF_3$,
$R^4$ is selected from H, methyl and —$CF_3$,
$R^5$ is selected from H, methyl, —CN, -methylene-OH and —$CF_3$,
or $R^5$ may be absent,
$R^6$ is selected from H, methyl, —CN, -methylene-OH and —$CF_3$,
$R^7$ is selected from hydrogen, halogen, methyl, —O-methyl and —OH, R⁸ is selected from CN, H, methyl, —CO—NH₂, —CO—(C₁₋₃-alkyl), cycloalkyl and oxetane, wherein each $R^{10}$ is independently selected from the group consisting of hydrogen, halogen, haloalkyl, -methyl, -ethyl, —NH—CO-methyl, —N(CH₃)₂, —CH₂—OH, —NH(CH₃), —O—CH₃ and —CN, or wherein $R^5$ and $R^6$ together form a ring selected from oxetane, tetrahydrofurane, cyclopropane and cyclobutane, or in the case that G is NR⁸, then, while $R^5$ is absent, $R^8$ and $R^6$ and the C-atoms in between form an annulated five-membered aromatic or non-aromatic heterocycle comprising two heteroatoms each independently selected from N and O, whereby this five-membered annulated heterocycle may optionally be substituted by an oxo-group, or $R^7$ and $R^3$ together with the C-atoms in between form an annulated cyclopropane ring;

or a prodrug or pharmaceutically acceptable salt thereof.

2. The compound of formula (I') according to claim 1

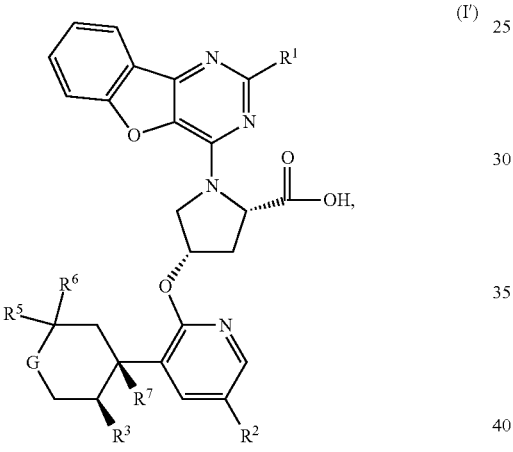
(I')

or of formula (I")

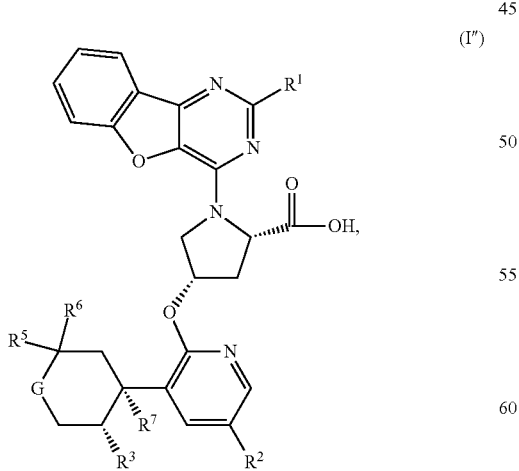
(I")

wherein $R^1$, $R^2$, $R^3$, $R^5$, $R^6$, $R^7$, $R^8$, $R^9$, $R^{10}$ and G are defined as in claim 1;

or a prodrug or pharmaceutically acceptable salt thereof.

3. The compound of formula (II') according to claim 1,

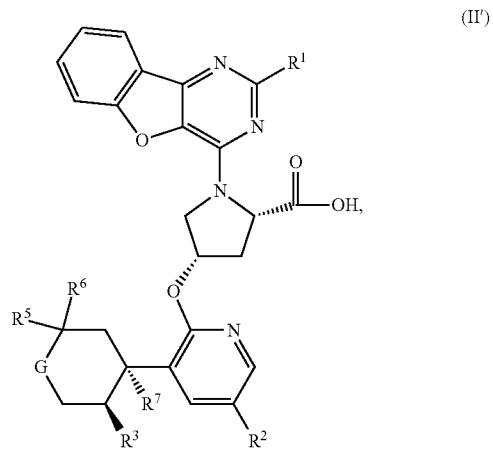
(II')

or of formula (II")

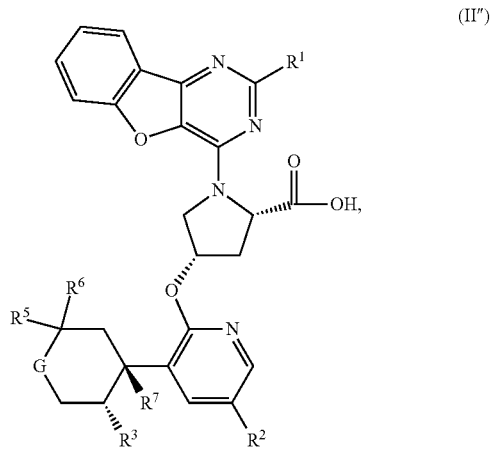
(II")

wherein $R^1$, $R^2$, $R^3$, $R^5$, $R^6$, $R^7$, $R^8$, $R^9$, $R^{10}$ and G are defined as in claim 1;

or a prodrug or pharmaceutically acceptable salt thereof.

4. The compound of formula (I) according to claim 1, wherein

G is selected from SO₂, O and NR⁸, and wherein

R⁸ is selected from CN, H, methyl, —CO—NH₂, —CO-methyl and oxetane, and wherein $R^2$ is selected from H, halogen, 1-propynyl and ethynyl, or wherein $R^2$ is a cyclic group selected from the group consisting of a five- to six-membered heteroaryl with 1 or 2 heteroatoms selected from N, S and O selected from the group consisting of pyridinyl and pyrazolyl, wherein this cyclic group is substituted by one or two, identical or different substituents $R^{10}$ selected from the group consisting of halogen, methyl and —NH(CH₃);

or a prodrug or pharmaceutically acceptable salt thereof.

5. The compound of formula (I) according to claim 1, wherein $R^1$ is halomethyl;

or a prodrug or pharmaceutically acceptable salt thereof.

6. The compound of formula (I) according to claim 5, wherein $R^1$ is a fluoromethyl selected from the group consisting of —$CF_3$, —$CHF_2$ and —$CH_2F$;
or a prodrug or pharmaceutically acceptable salt thereof.

7. The compound of formula (I) according to claim 1, wherein $R^3$ is methyl and $R^4$ is hydrogen;
or a prodrug or pharmaceutically acceptable salt thereof.

8. The compound of formula (I) according to claim 1, wherein $R^7$ is halogen;
or a prodrug or pharmaceutically acceptable salt thereof.

9. The compound of formula (I) according to claim 8, wherein $R^7$ is F;
or a prodrug or pharmaceutically acceptable salt thereof.

10. The compound of formula (I) according to claim 1, wherein G is selected from the group consisting of O and $SO_2$
and wherein $R^7$ is F;
or a prodrug or pharmaceutically acceptable salt thereof.

11. The compound of formula (I) according to claim 10, wherein $R^2$ is selected from ethynyl, 1-propynyl and halogen;
or a prodrug or pharmaceutically acceptable salt thereof.

12. The compound of formula (I) according to claim 11, wherein $R^3$ is methyl and $R^4$ is hydrogen;
or a prodrug or pharmaceutically acceptable salt thereof.

13. The compound of formula (I) according to claim 1, wherein
$R^1$ is fluoromethyl,
G is $SO_2$,
$R^7$ is F,
and wherein
$R^5$ and $R^6$ are either both methyl or both hydrogen
or wherein $R^5$ and $R^6$ form together a ring selected from the group consisting of oxetane, cyclopropane and cyclobutane;
or a prodrug or pharmaceutically acceptable salt thereof.

14. The compound of formula (I) according to claim 13, wherein $R^3$ is methyl and $R^4$ is hydrogen;
or a prodrug or pharmaceutically acceptable salt thereof.

15. The compound of formula (I) according to claim 13, wherein
$R^5$ and $R^6$ are either both methyl
or wherein $R^5$ and $R^6$ form together a ring selected from the group consisting of oxetane, cyclopropane and cyclobutane;
or a prodrug or pharmaceutically acceptable salt thereof.

16. The compound of formula (I) according to claim 1, wherein
G is O,
$R^1$ is fluoromethyl,
$R^7$ is selected from F, —O-methyl and —OH, and
$R^5$ and $R^6$ are both hydrogen;
or a prodrug or pharmaceutically acceptable salt thereof.

17. The compound of formula (I) according to claim 16, wherein $R^3$ is methyl and $R^4$ is hydrogen;
or a prodrug or pharmaceutically acceptable salt thereof.

18. The compound of formula (I) according to claim 1, wherein $R^2$ is selected from the group consisting of H, ethynyl, 1-propynyl and halogen;
or a prodrug or pharmaceutically acceptable salt thereof.

19. The compound of formula (I) according to claim 1, wherein $R^3$ is methyl and $R^4$ is hydrogen,
wherein $R^7$ is F,
wherein $R^5$ and $R^6$ are both hydrogen,
and wherein $R^2$ is a cyclic group selected from the group consisting of a five- to six-membered heteroaryl with 1 or 2 heteroatoms selected from N, S and O selected from the group consisting of pyridine and pyrazole,
wherein this cyclic group is substituted by one or two, identical or different substituents $R^{10}$ selected from the group consisting of halogen, methyl and —$NH(CH_3)$;
or a prodrug or pharmaceutically acceptable salt thereof.

20. The compound of formula (I) according to claim 1, which is selected from the group consisting of

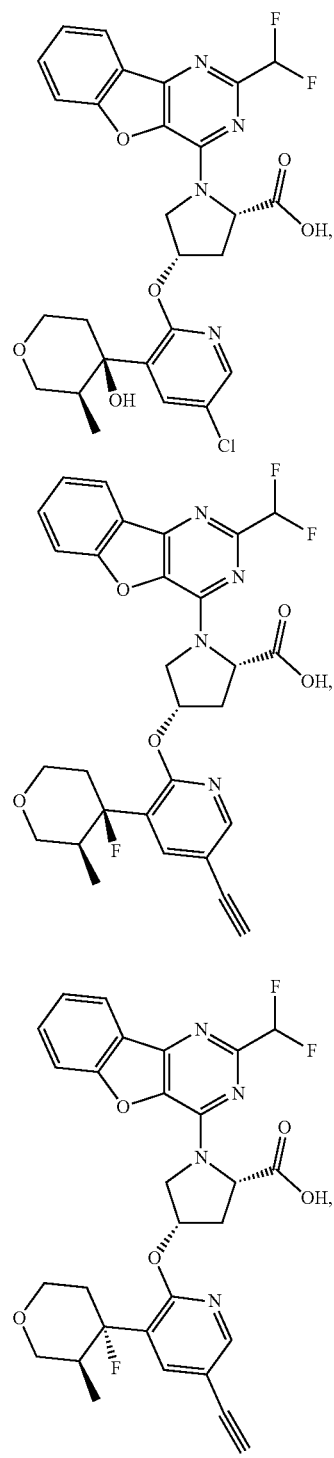

215
-continued
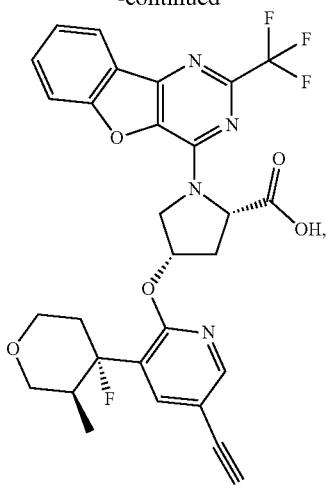
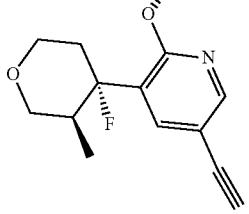
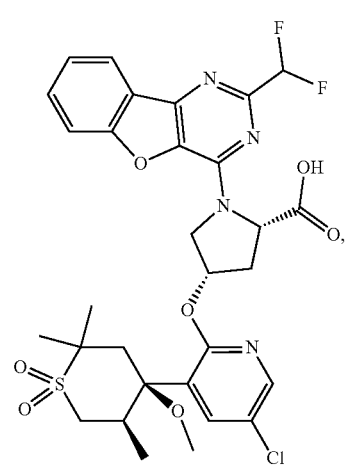
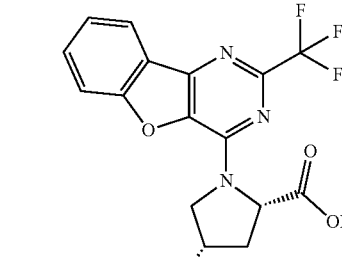
216
-continued
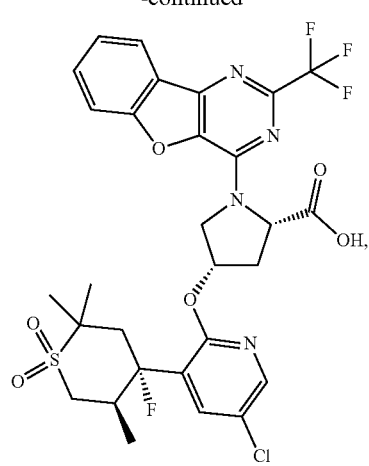
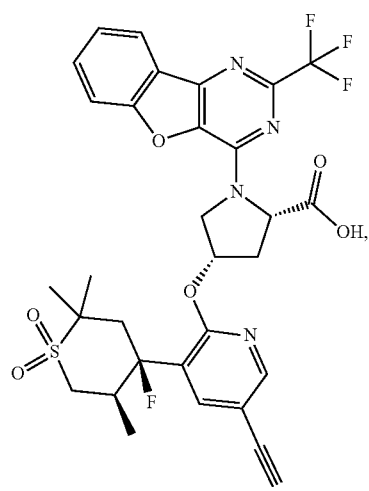
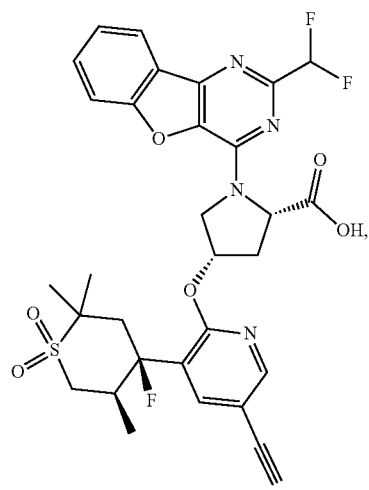

217
-continued
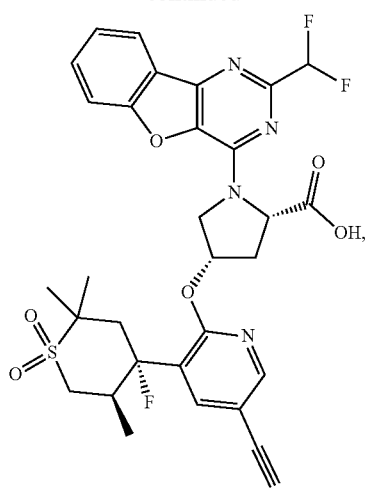
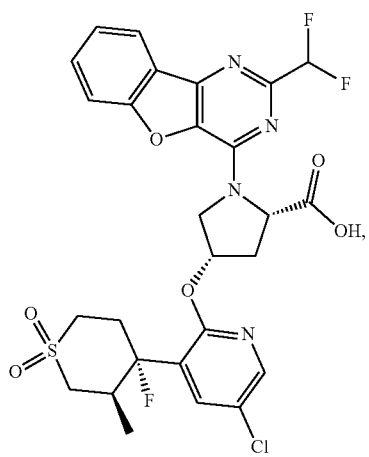
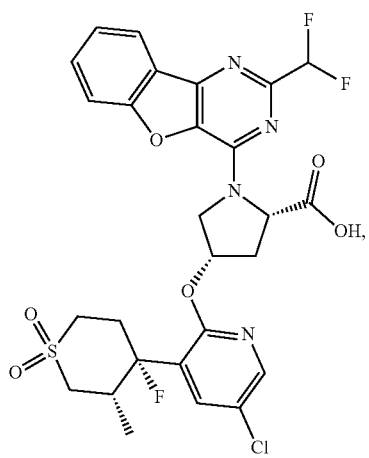
218
-continued
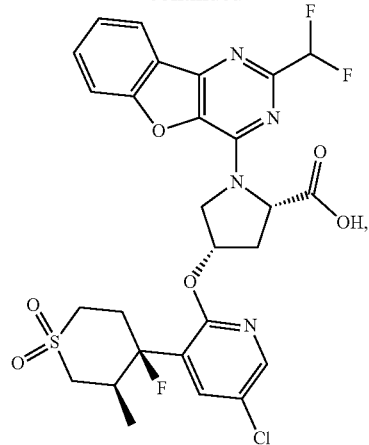
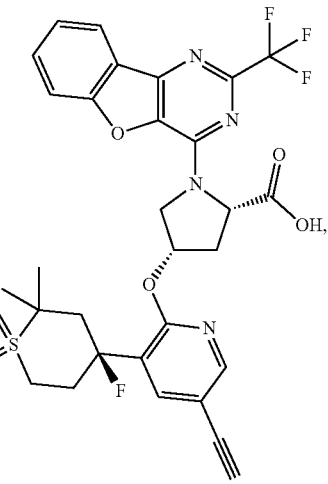
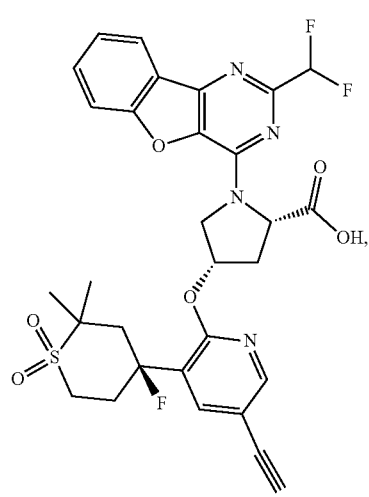

219
-continued
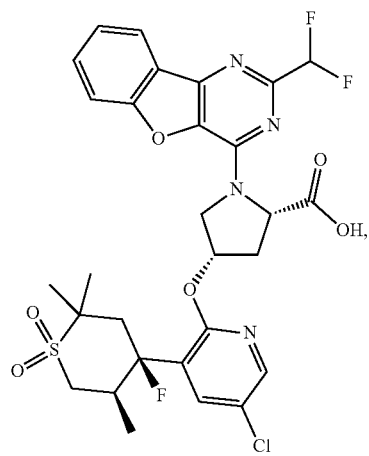
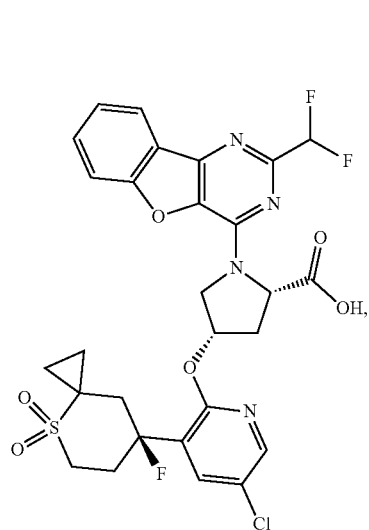
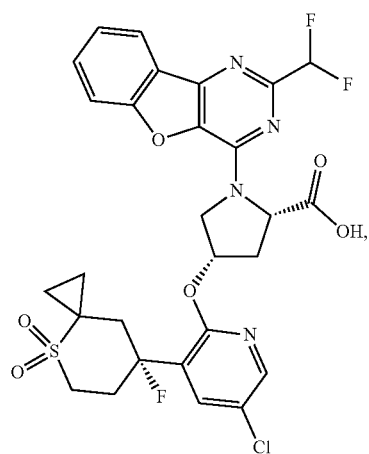
220
-continued
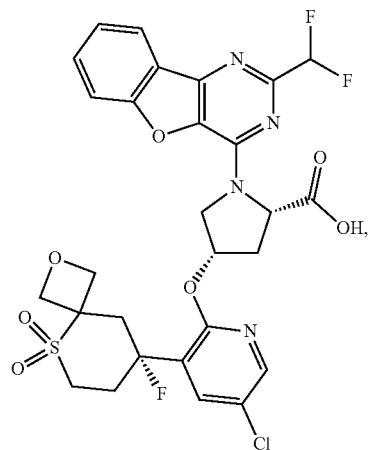
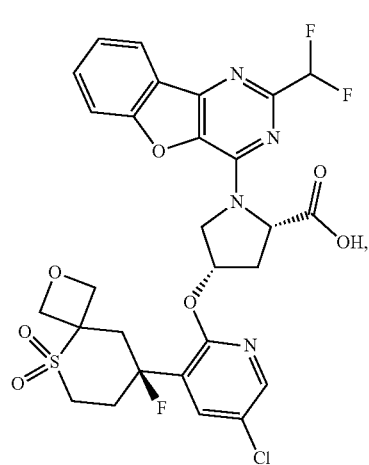
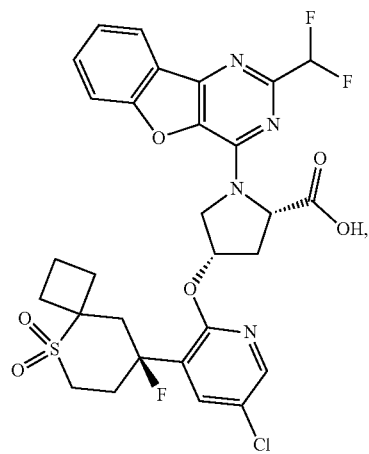

221
-continued
222
-continued
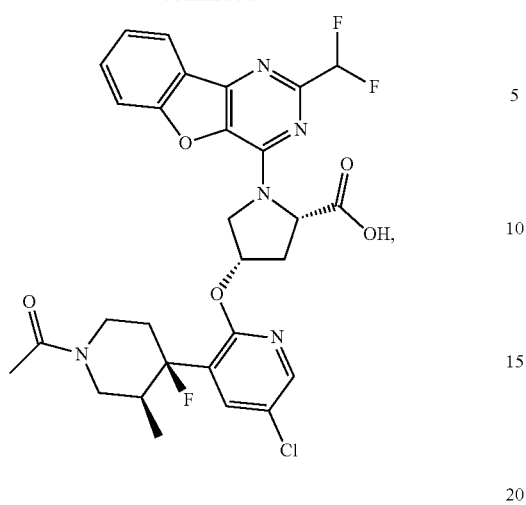
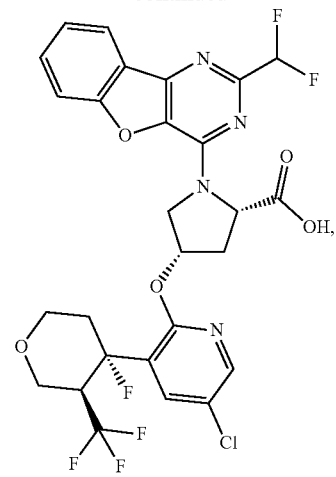
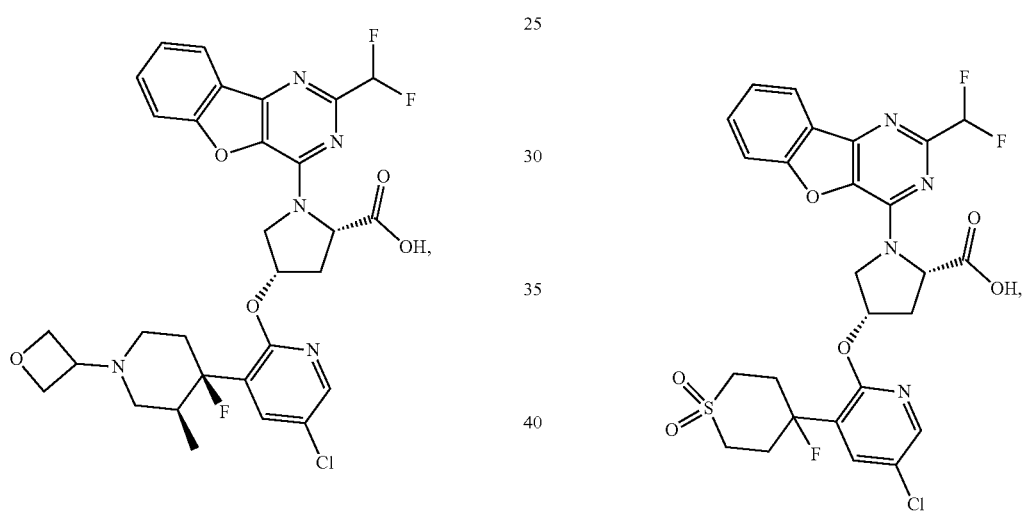
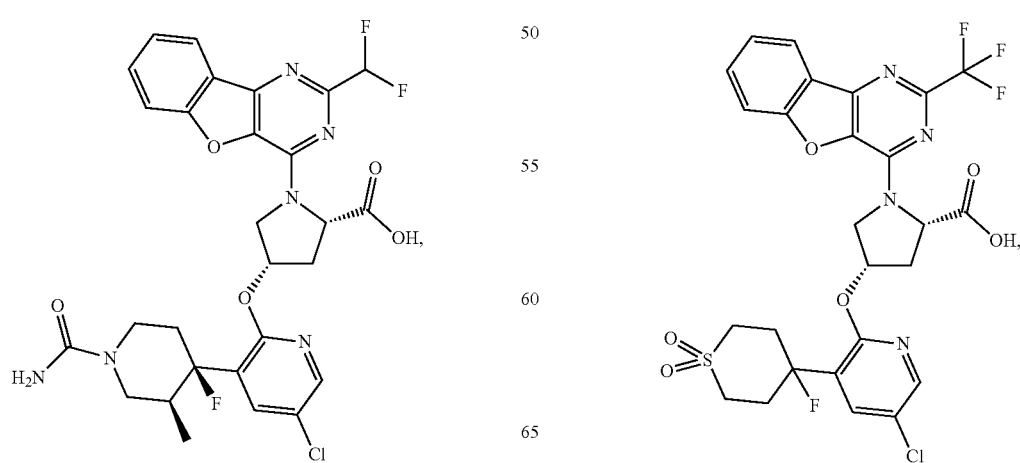

223
-continued
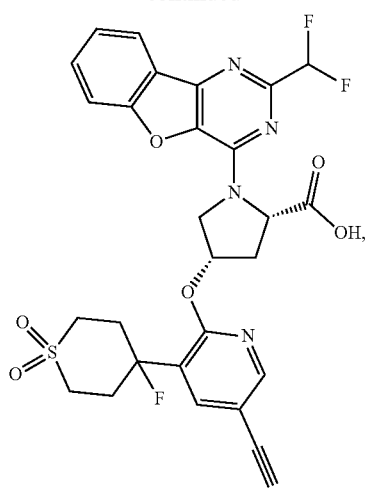
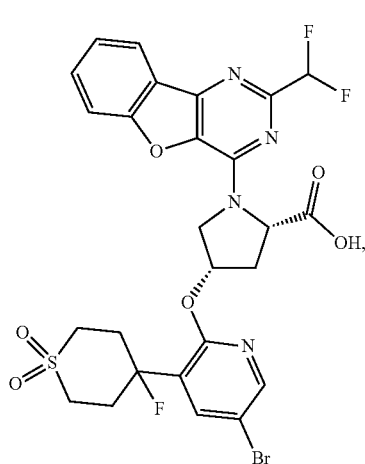
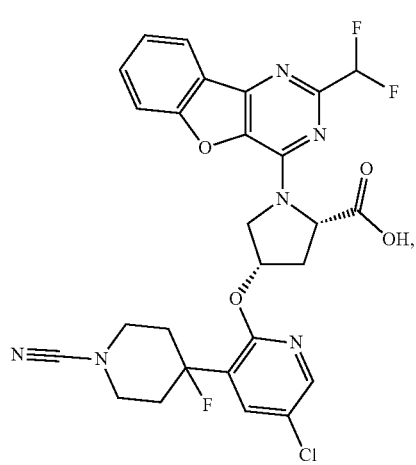
224
-continued
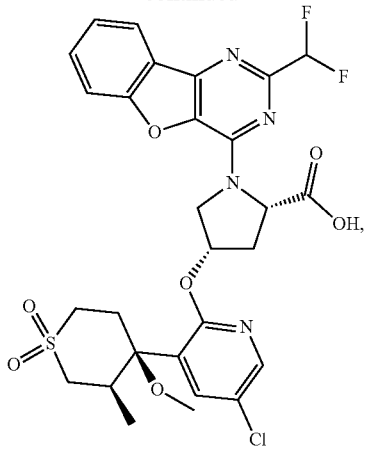
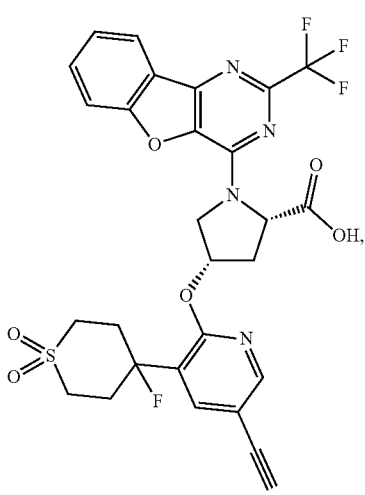
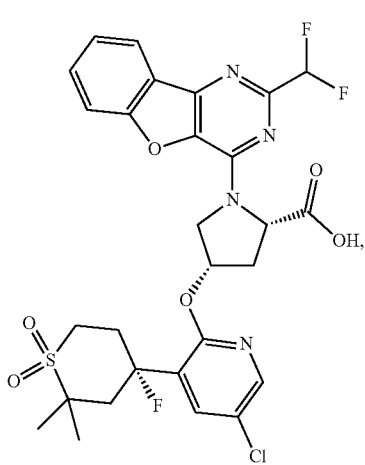

225
-continued
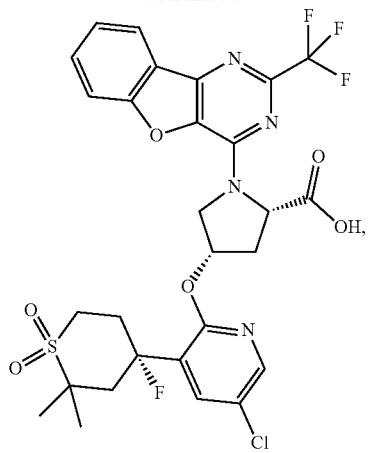
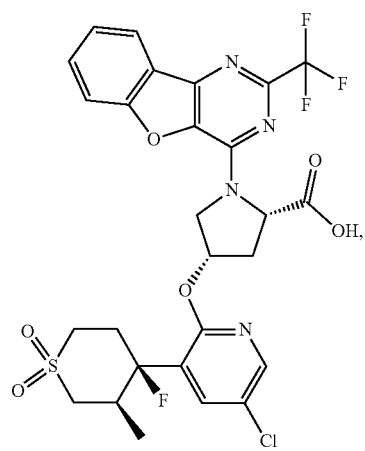
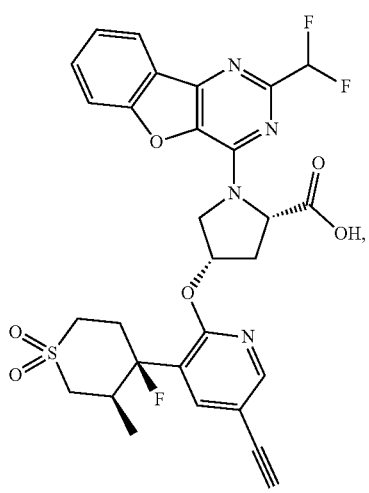
226
-continued
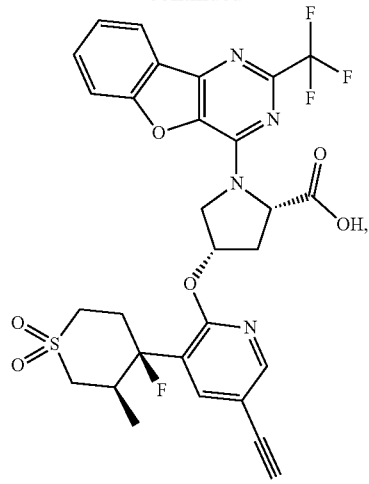
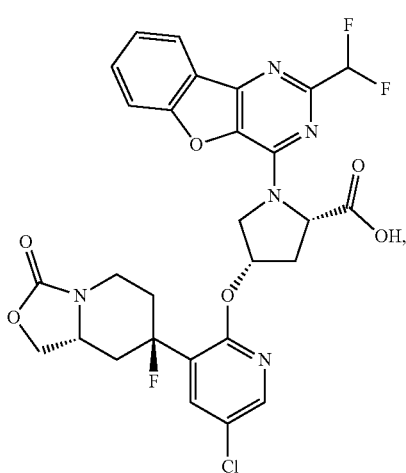
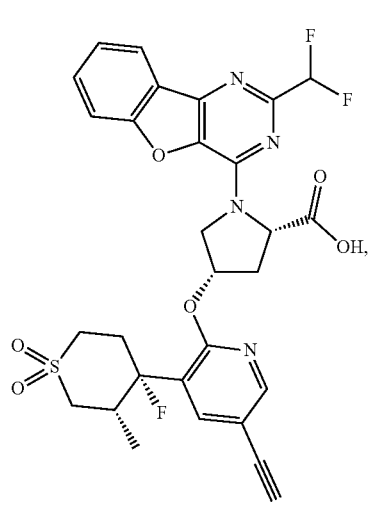

227
-continued
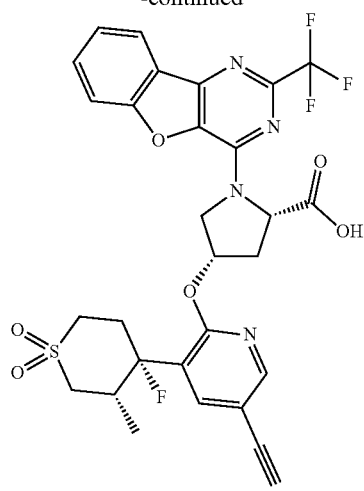
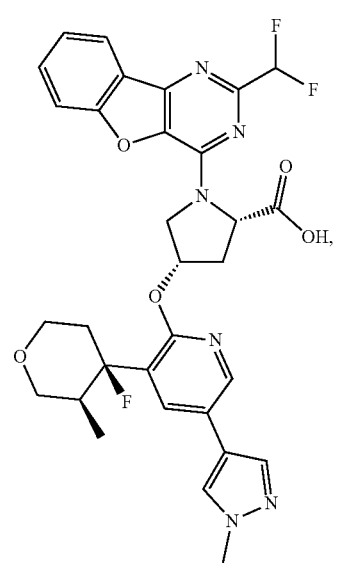
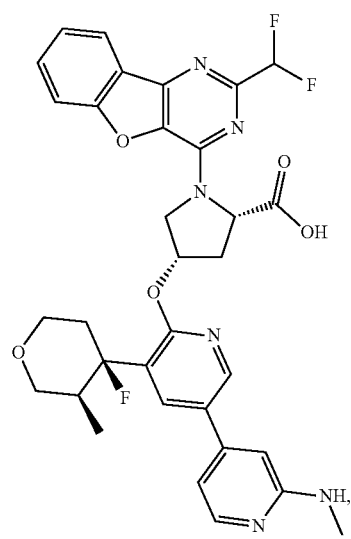
228
-continued
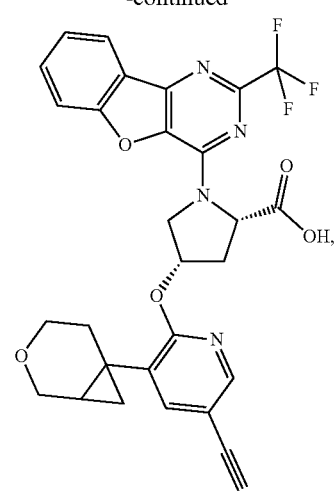
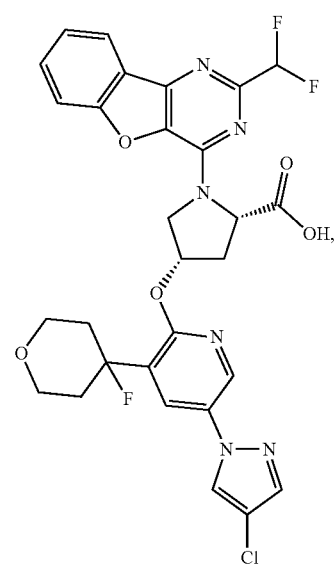
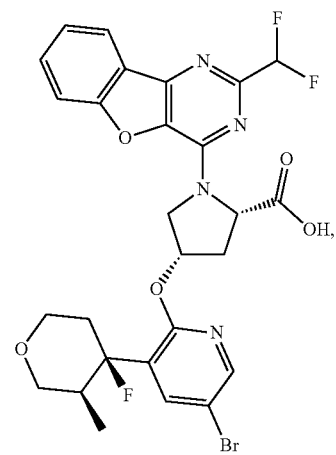

229
-continued
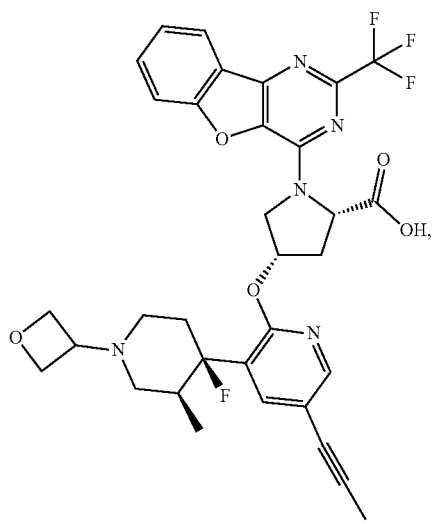
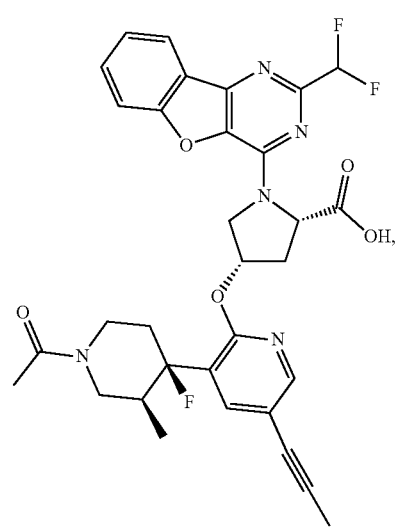
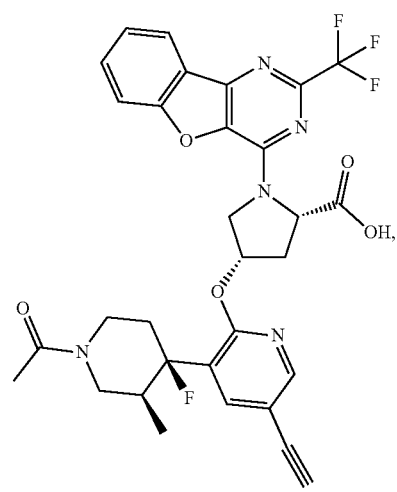
230
-continued
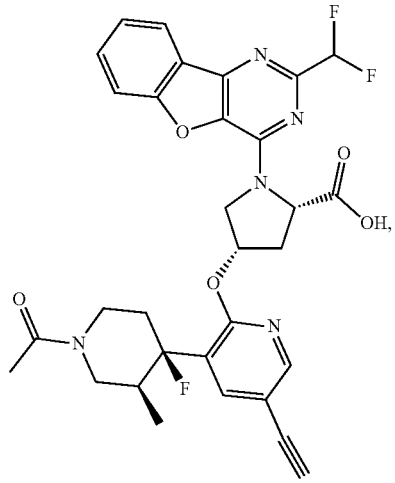
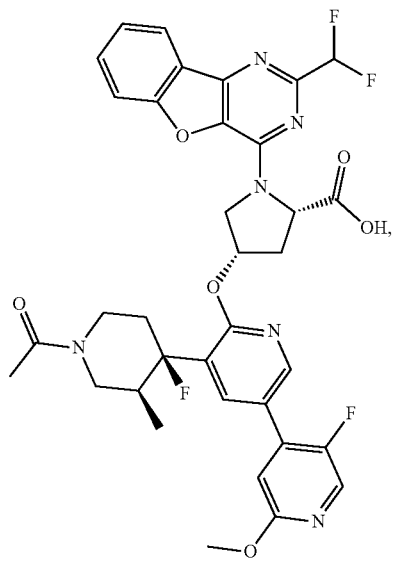
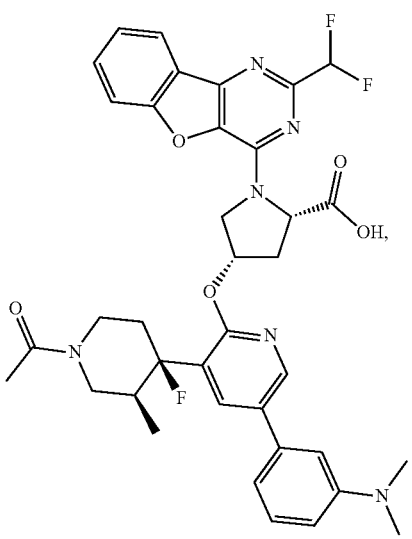

231
-continued
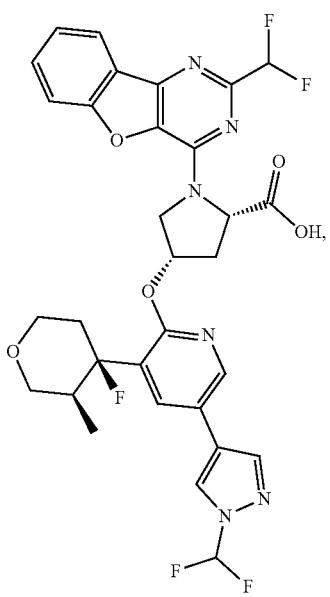
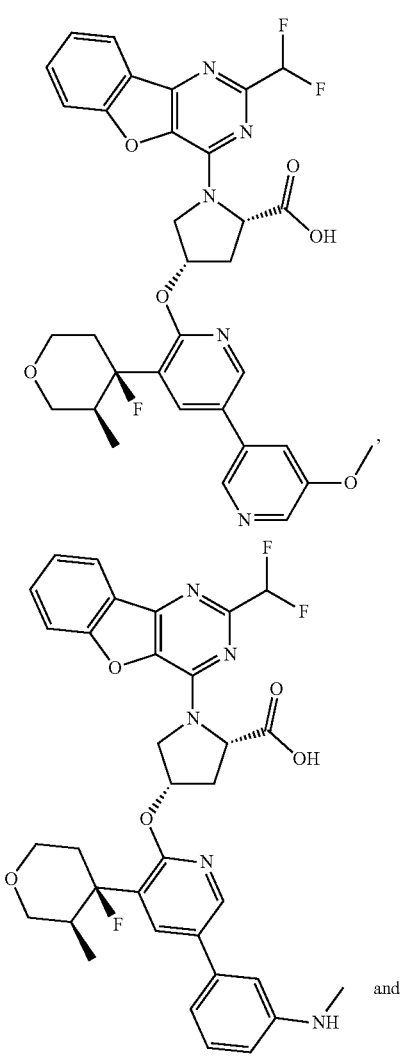
and
232
-continued
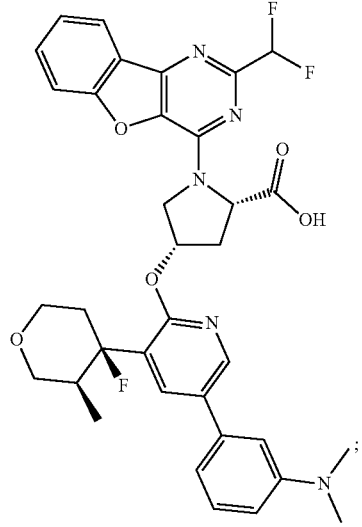 [SMILES: C[C@H]1COCC[C@]1(F)c1cc(-c2cccc(N(C)C)c2)cnc1O[C@H]1C[C@@H](C(=O)O)N(c2nc(C(F)F)nc3c2oc2ccccc23)C1]
and a prodrug or pharmaceutically acceptable salt thereof.
21. An intermediate of formula (IV)
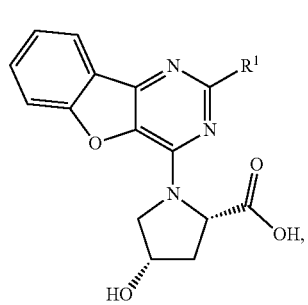
(IV)
wherein
R$^1$ is selected from methyl, ethyl, halomethyl and halogen.
22. A prodrug of any of the compounds of formula (I) as defined in claim 1 which falls into the scope of formula (A),
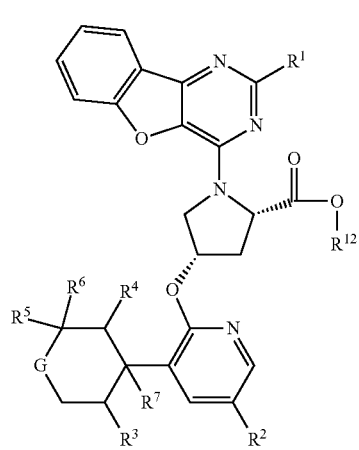
(A)
wherein R$^{12}$ C$_{1-4}$-alkyl, aryl, —CH$_2$-aryl or NH—SO$_2$—C$_{1-3}$-alkyl.

23. The prodrug of formula (A) according to claim 22, wherein $R^{12}$ is methyl.

24. The compound of formula (I) according to claim 1, which is

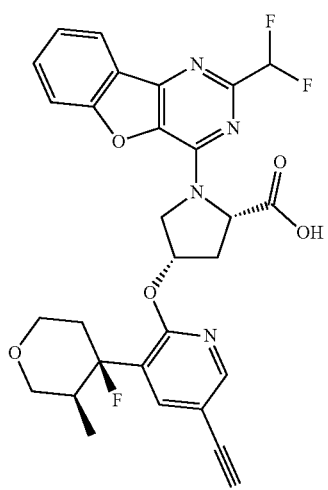 [SMILES: C#Cc1cnc(O[C@H]2C[C@@H](C(=O)O)N(c3nc(C(F)F)nc4c3oc3ccccc34)C2)c([C@@]2(F)CCOC[C@@H]2C)c1]

or a pharmaceutically acceptable salt thereof.

25. The compound of formula (I) according to claim 1, which is

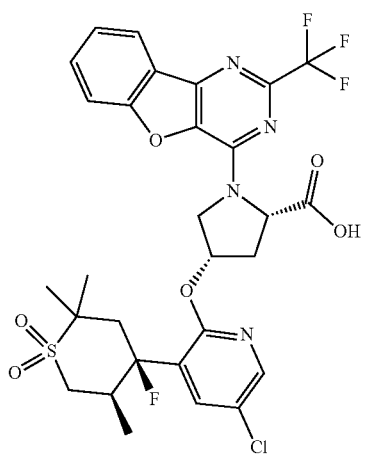 [SMILES: C[C@H]1CS(=O)(=O)C(C)(C)C[C@]1(F)c1cc(Cl)cnc1O[C@H]1C[C@@H](C(=O)O)N(c2nc(C(F)(F)F)nc3c2oc2ccccc23)C1]

or a pharmaceutically acceptable salt thereof.

26. The compound of formula (I) according to claim 1, which is

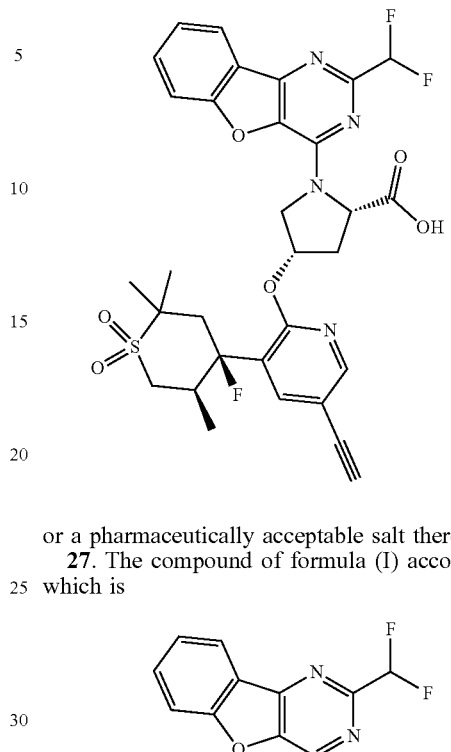

or a pharmaceutically acceptable salt thereof.

27. The compound of formula (I) according to claim 1, which is

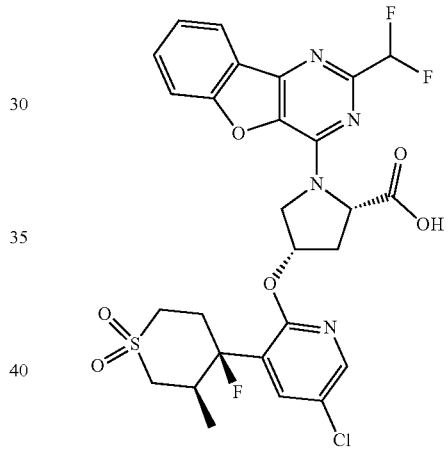

or a pharmaceutically acceptable salt thereof.

28. The compound of formula (I) according to claim 1, which is

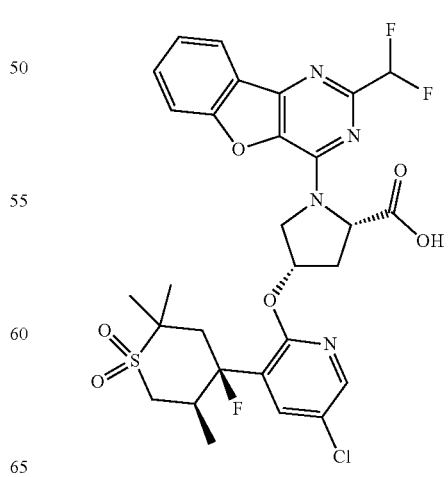

or a pharmaceutically acceptable salt thereof.

29. The compound of formula (I) according to claim 1, which is

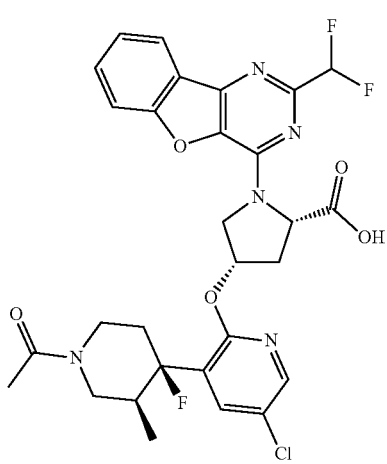 [SMILES: CC(=O)N1CC[C@](F)(c2cc(Cl)cnc2O[C@H]2C[C@@H](C(=O)O)N(c3nc(C(F)F)nc4c3oc3ccccc34)C2)[C@@H](C)C1]

or a pharmaceutically acceptable salt thereof.

30. The compound of formula (I) according to claim 1, which is

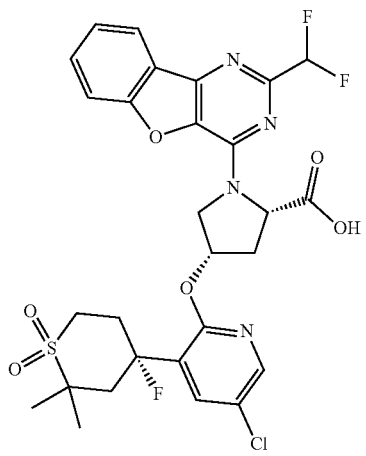 [SMILES: CC1(C)C[C@](F)(c2cc(Cl)cnc2O[C@H]2C[C@@H](C(=O)O)N(c3nc(C(F)F)nc4c3oc3ccccc34)C2)CCS1(=O)=O]

or a pharmaceutically acceptable salt thereof.

31. The compound of formula (I) according to claim 1, which is

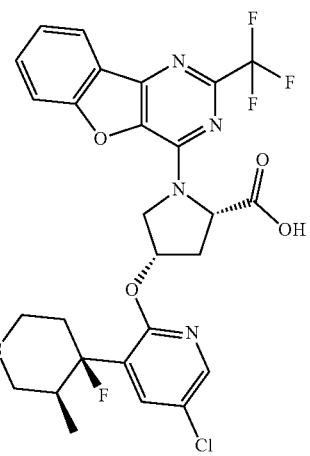

or a pharmaceutically acceptable salt thereof.

32. The compound of formula (I) according to claim 1, which is

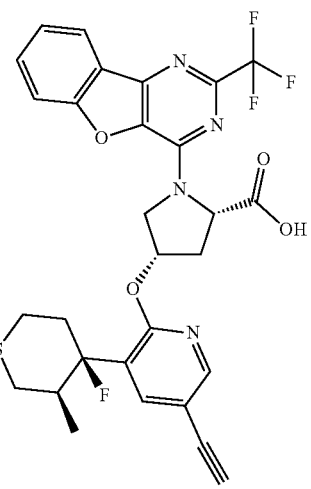

or a pharmaceutically acceptable salt thereof.

33. The compound of formula (I) according to claim 1, which is

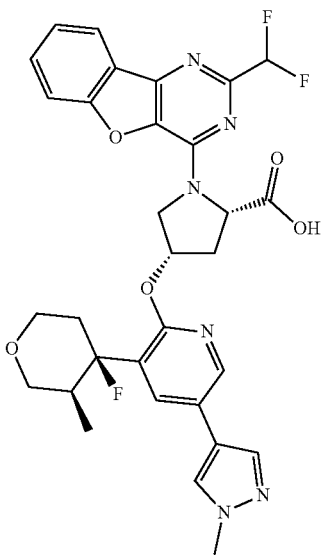 [SMILES: C[C@H]1COCC[C@]1(F)c1cc(-c2cnn(C)c2)cnc1O[C@H]1C[C@@H](C(=O)O)N(c2nc(C(F)F)nc3c2oc2ccccc23)C1]

or a pharmaceutically acceptable salt thereof.

34. A pharmaceutical composition comprising a compound of formula (I) according to claim 1 and optionally one or more pharmaceutically acceptable carriers and/or excipients.

35. A pharmaceutical composition comprising a compound of formula (I) according to claim 1 in combination with one or more active agents selected from the group consisting of anti-inflammatory agents, anti-fibrotic agents, anti-allergic agents/anti-histamines, bronchodilators, beta 2 agonists/betamimetics, adrenergic agonists, anticholinergic agents, methotrexate, mycophenolate mofetil, leukotriene modulators, JAK inhibitors, anti-interleukin antibodies, non-specific immunotherapeutics, cytokine/chemokine receptor modulators, toll-like receptor agonists, immune checkpoint regulators, an anti-TNF antibody and an anti-BAFF antibody.

36. The pharmaceutical composition according to claim 35, wherein the compound of formula (I) is combined with one or more anti-fibrotic agents selected from the group consisting of Pirfenidon and Nintedanib.

37. The pharmaceutical composition according to claim 35, wherein the compound of formula (I) is combined with one or more anti-inflammatory agents selected from the group consisting of NSAIDs and corticosteroids.

38. The pharmaceutical composition according to claim 35, wherein the compound of formula (I) is combined with one or more active agents selected from the group of bronchodilators, beta 2 agonists/betamimetics, adrenergic agonists and anticholinergic agents.

39. The pharmaceutical composition according to claim 35, wherein the compound of formula (I) is combined with one or more anti-interleukin antibodies selected from the group consisting of anti-IL-23, anti-IL-17 antibodies, anti-IL-1 antibodies, anti-IL-4 antibodies, anti-IL-13 antibodies, anti-1L-5 antibodies, anti-IL-6 antibodies, anti-IL-12 antibodies and anti-IL-15 antibodies.

40. A method of treating in a subject a disease that can be treated by the inhibition of cGAS, said method comprising administering to the subject a compound of formula (I) according to claim 1.

41. A method of treating in a subject a disease selected from the group consisting of systemic lupus erythematosus (SLE), interferonopathies, Aicardi-Goutieres syndrome, age-related macular degeneration (AMD), amyotrophic lateral sclerosis (ALS), inflammatory bowel disease (IBD), chronic obstructive pulmonary disease (COPD), Bloom's syndrome, Sjogren's syndrome, Parkinsons disease, heart failure and cancer, systemic sclerosis (SSc), non-alcoholic steatotic hepatitis (NASH), interstitial lung disease (ILD), progressive fibrosing interstitial lung disease (PF-ILD) and idiopathic pulmonary fibrosis (IPF), said method comprising administering to the subject a compound of formula (I) according to claim 1.

42. A method of treating in a subject a disease selected from the group consisting of systemic lupus erythematosus (SLE), interferonopathies, Aicardi-Goutieres syndrome, age-related macular degeneration (AMD), amyotrophic lateral sclerosis (ALS), inflammatory bowel disease (IBD), chronic obstructive pulmonary disease (COPD), Bloom's syndrome, Sjogren's syndrome and Parkinsons disease, said method comprising administering to the subject a compound of formula (I) according to claim 1.

43. A method of treating in a subject a fibrosing disease selected from the group consisting of systemic sclerosis (SSc), non-alcoholic steatohepatitis (NASH), interferonopathies, interstitial lung disease (ILD), progressive fibrosing interstitial lung disease (PF-ILD) and idiopathic pulmonary fibrosis (IPF), said method comprising administering to the subject a compound of formula (I) according to claim 1.

44. A method of treating in a subject a disease selected from the group consisting of age-related macular degeneration (AMD), heart failure, COVID-19/SARS-CoV-2 infection, renal inflammation, renal fibrosis, dysmetabolism, vascular diseases, cardiovascular diseases and cancer, said method comprising administering to the subject a compound of formula (I) according to claim 1.

45. A method of treating in a subject a disease selected from the group consisting of interferonopathies, systemic sclerosis (SSc), and non-alcoholic steatotic hepatitis (NASH), said method comprising administering to the subject a compound selected from the group consisting of:

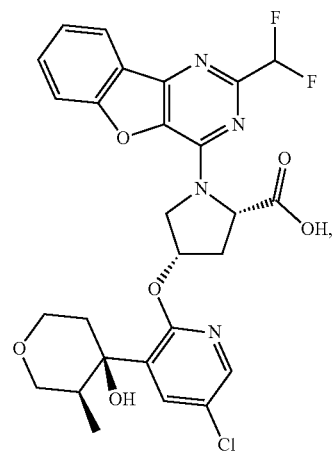

239
-continued
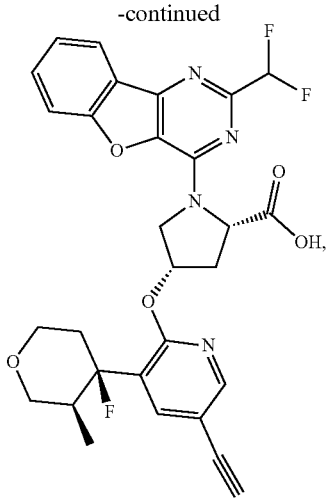
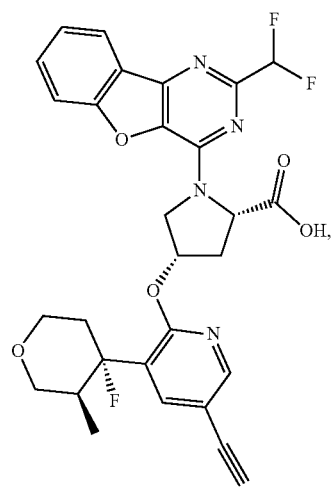
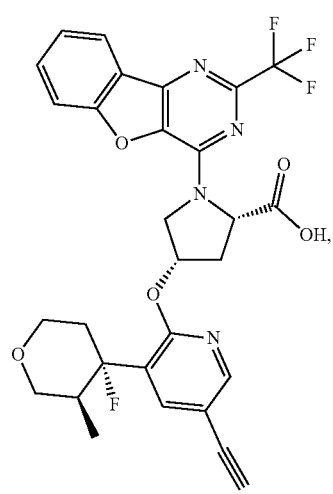
240
-continued
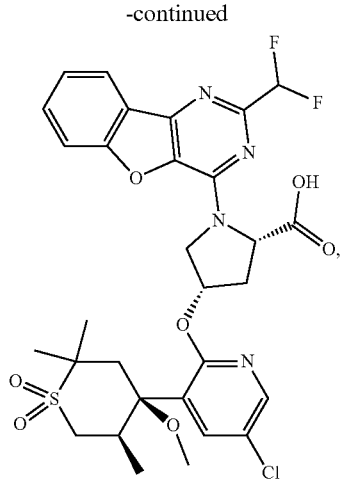
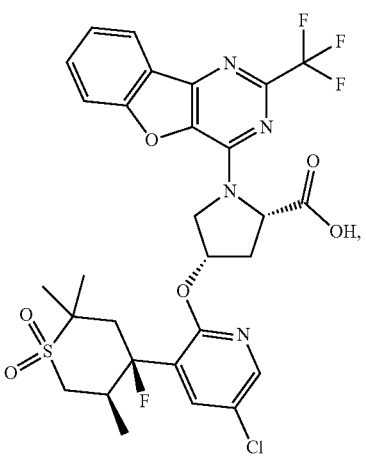
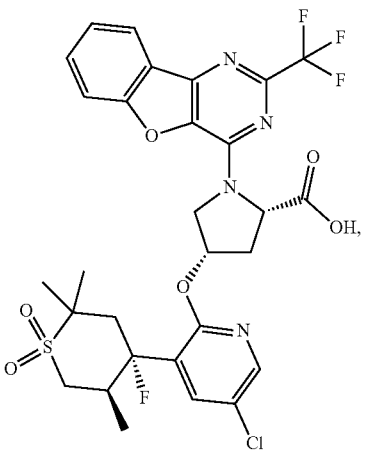

241
-continued
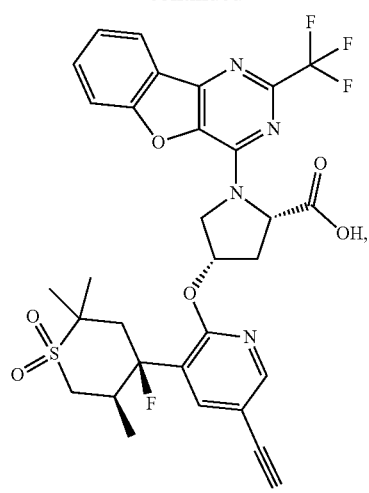
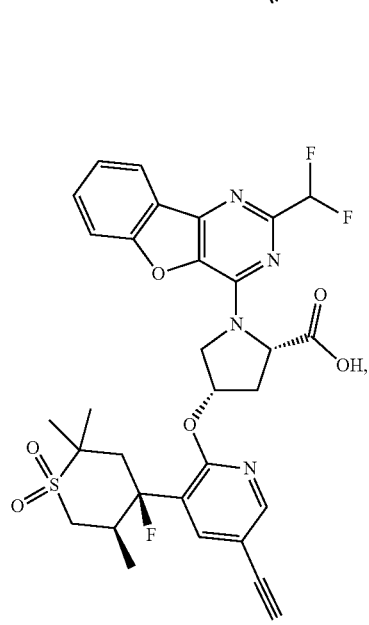
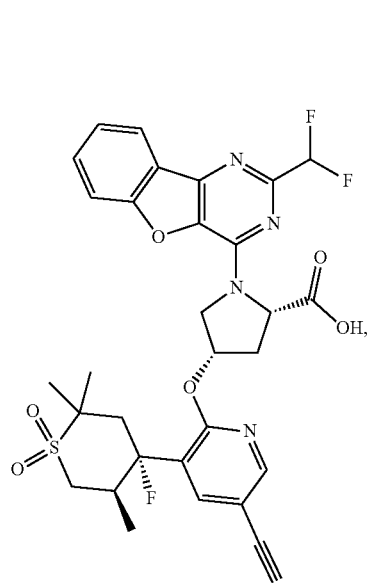
242
-continued
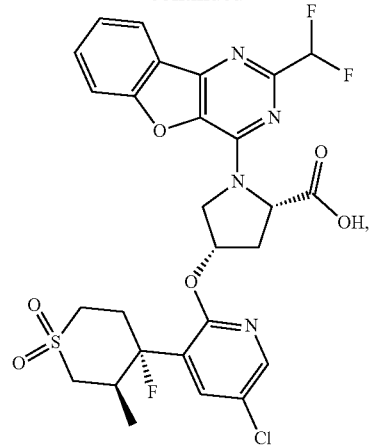
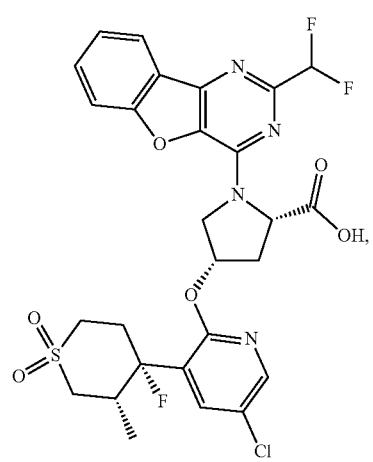
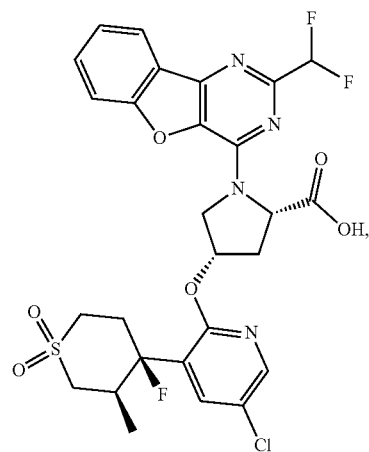

243
-continued
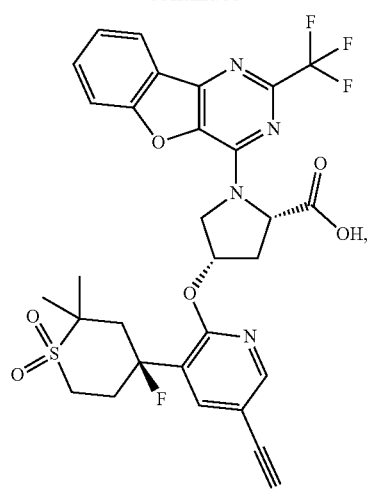
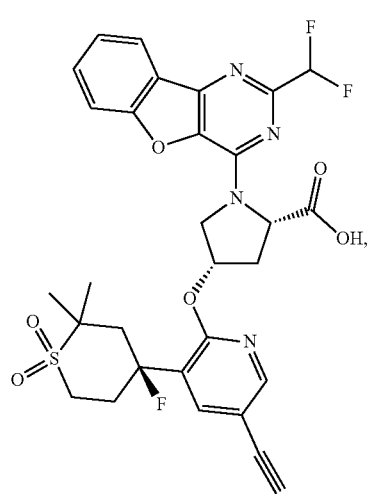
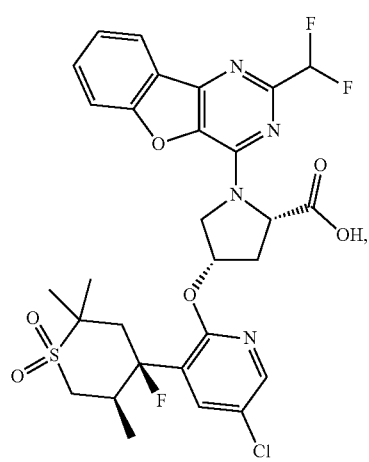
244
-continued
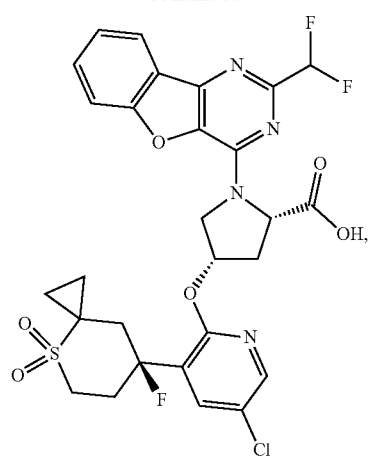
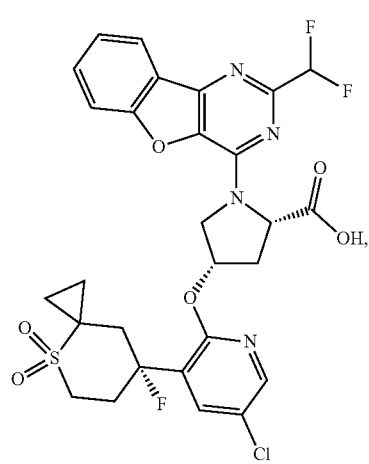
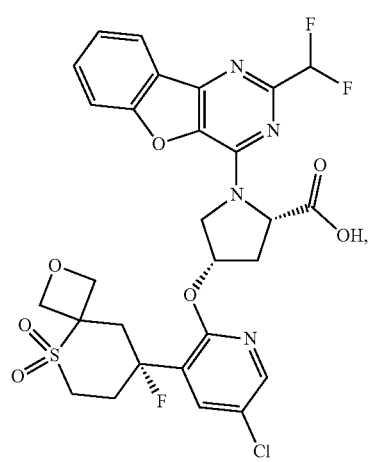

245
-continued
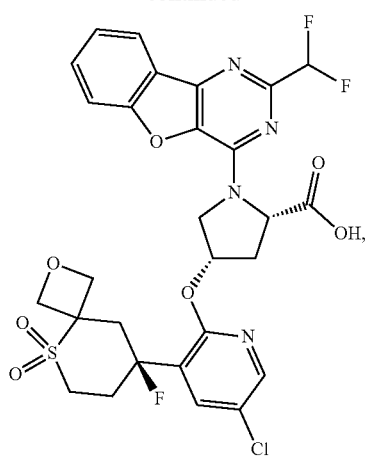
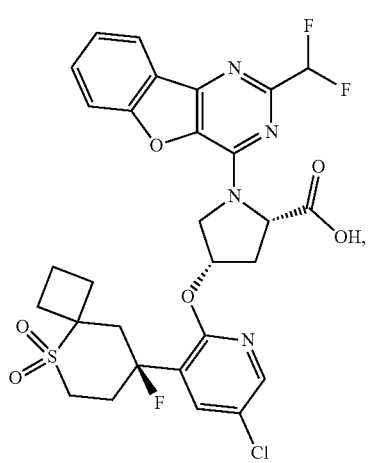
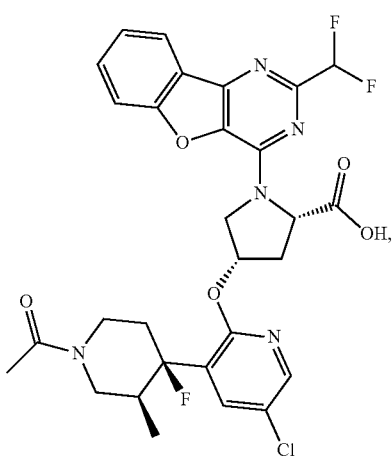
246
-continued
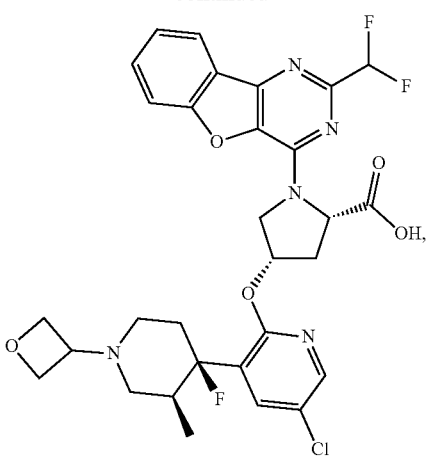
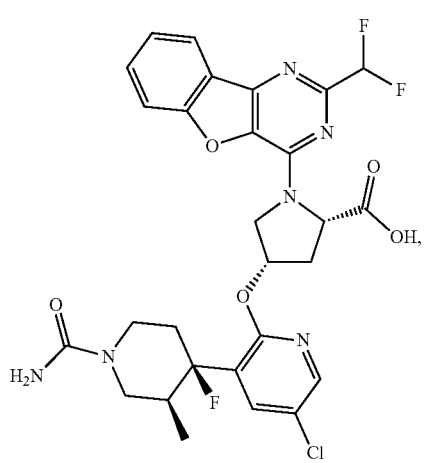
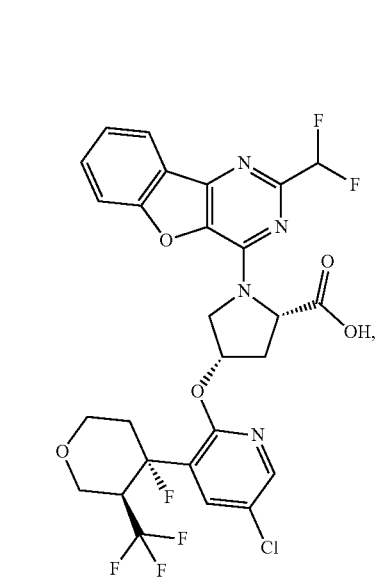

247
-continued
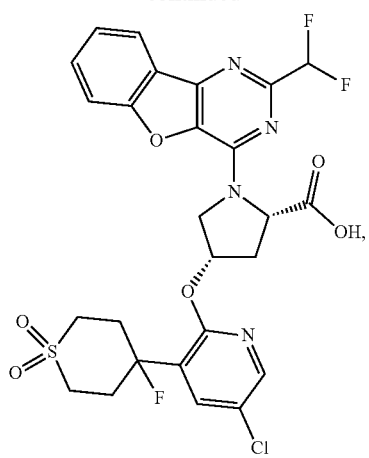
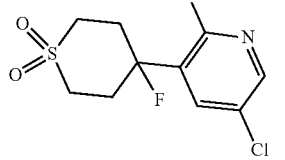
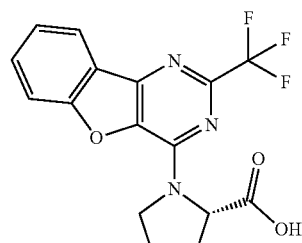
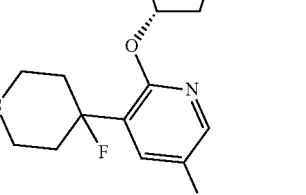
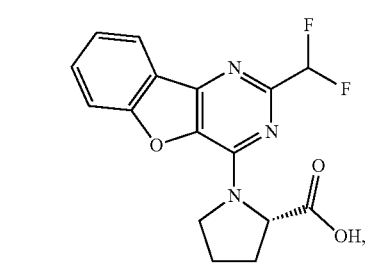
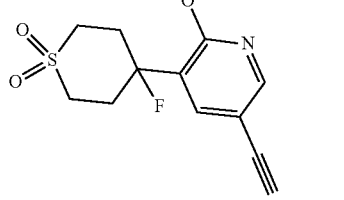
248
-continued
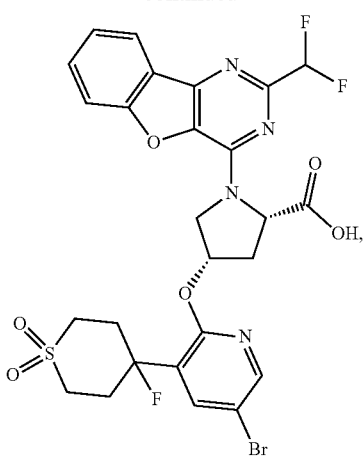
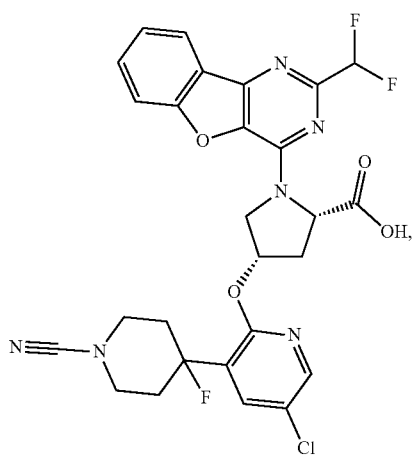
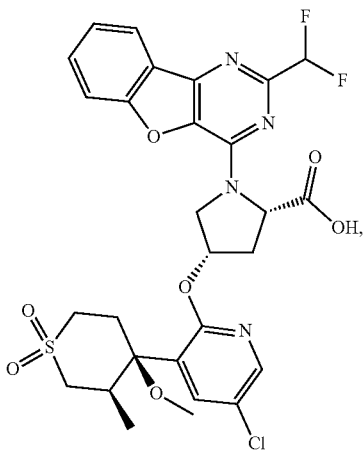

249
-continued
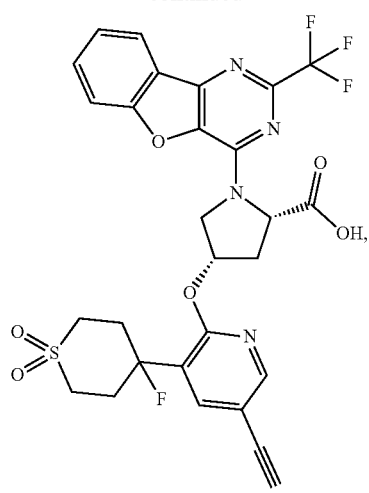
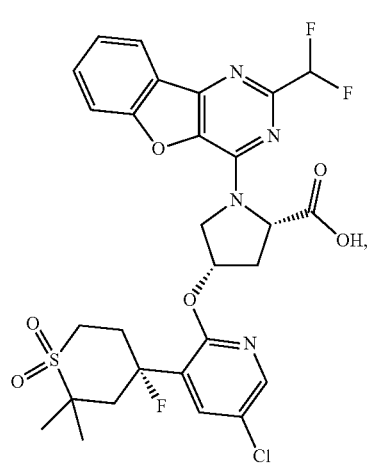
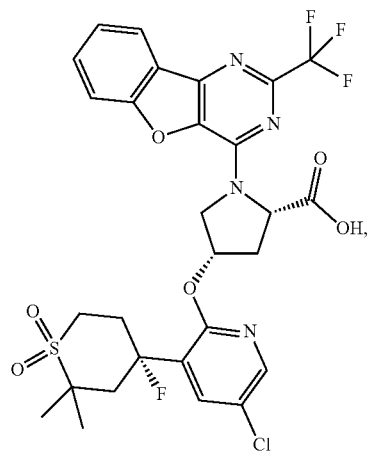
250
-continued
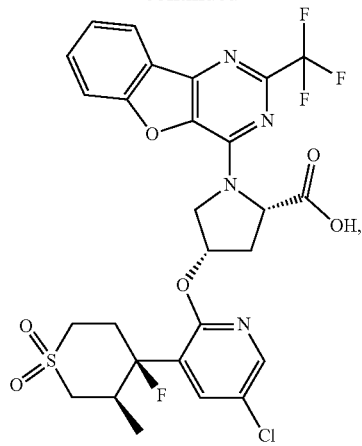
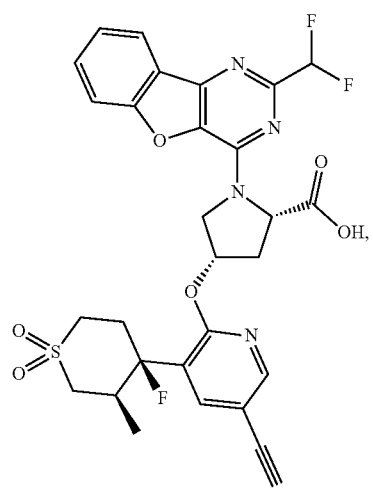
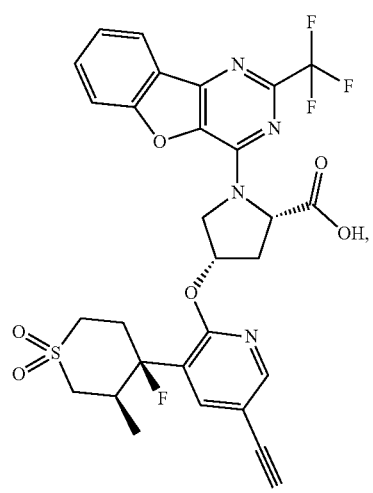

251
-continued
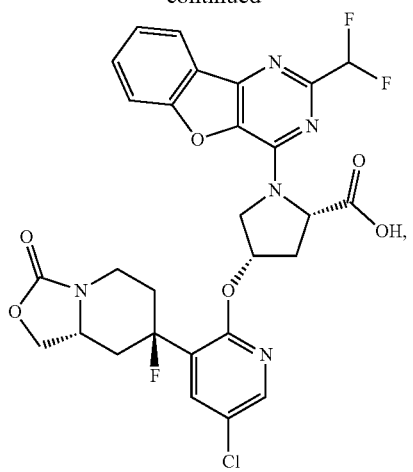
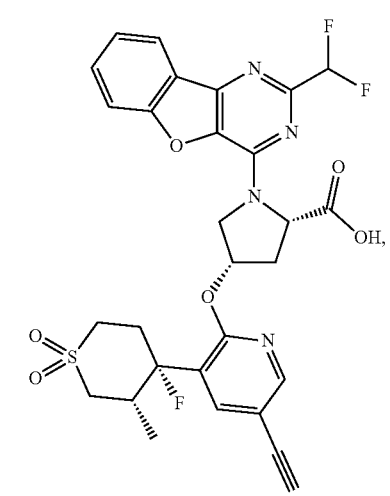
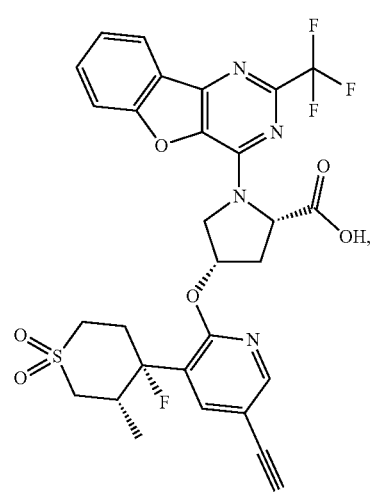
252
-continued
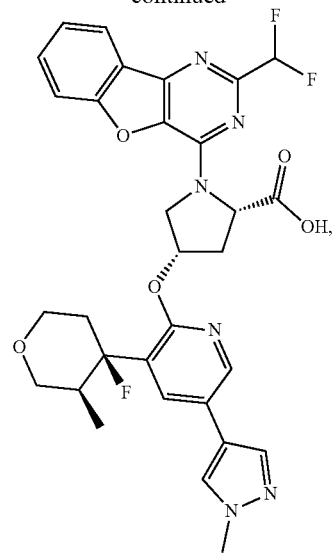
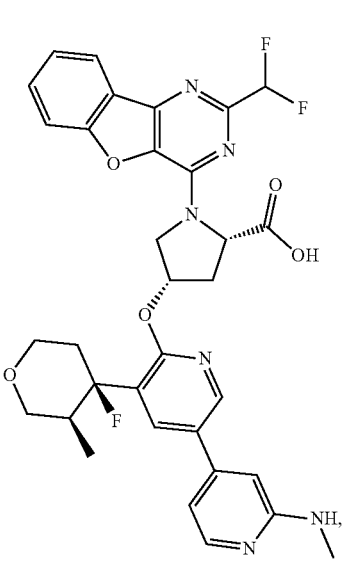
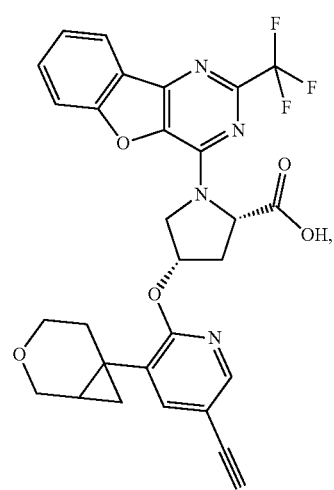

253
-continued
254
-continued
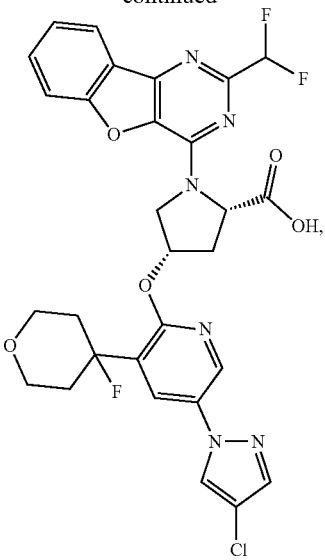
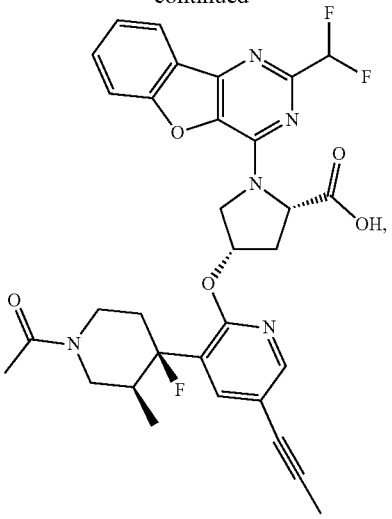

255
-continued
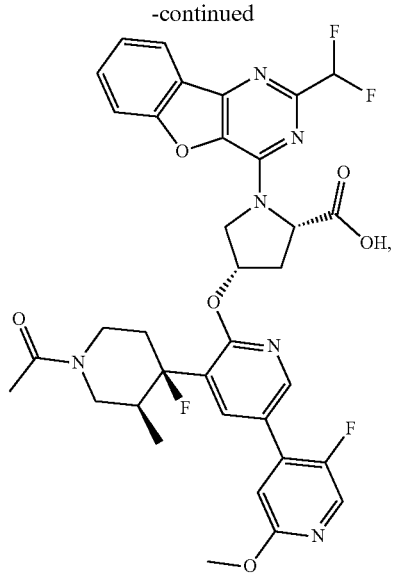
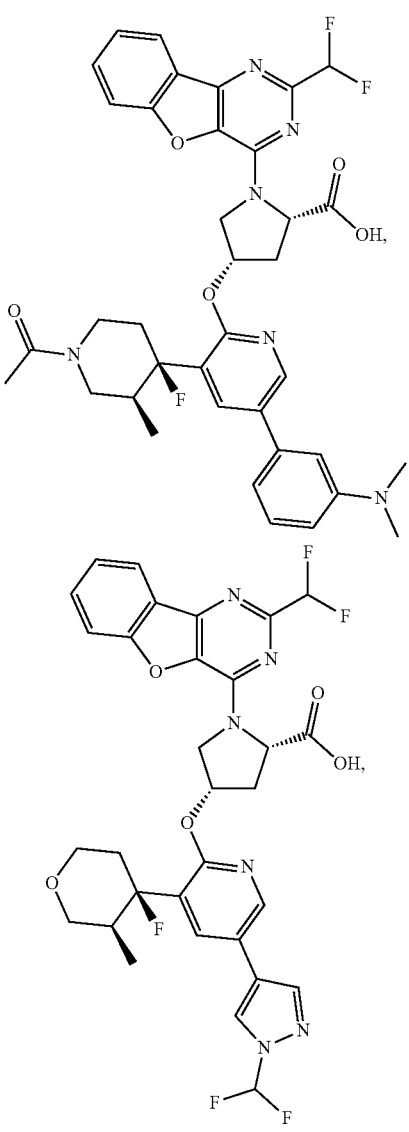
256
-continued
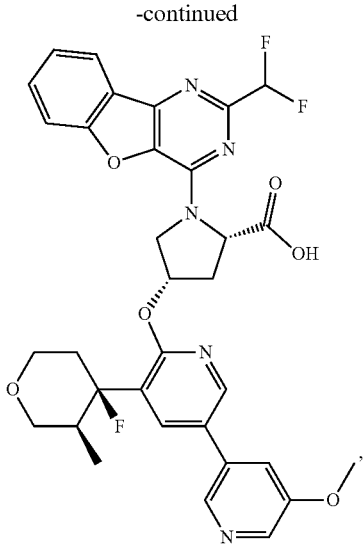
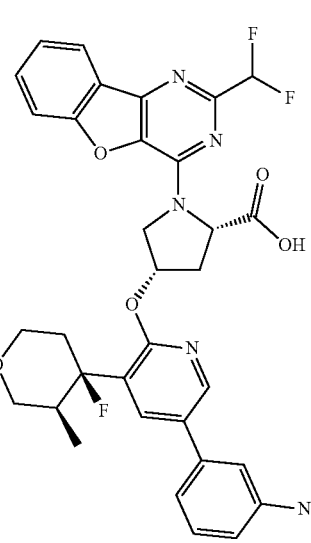
and
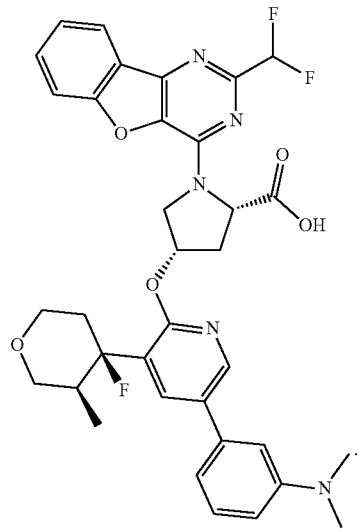 [SMILES: C[C@H]1COCC[C@]1(F)c1cc(-c2cccc(N(C)C)c2)cnc1O[C@H]1C[C@@H](C(=O)O)N(c2nc(C(F)F)nc3c2oc2ccccc23)C1]

46. A compound of formula:
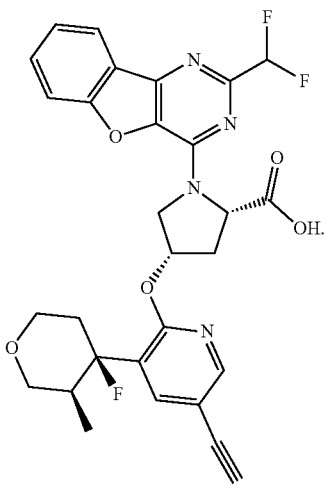 [SMILES: C#Cc1cnc(O[C@H]2C[C@@H](C(=O)O)N(c3nc(C(F)F)nc4c3oc3ccccc34)C2)c([C@@]2(F)CCOC[C@@H]2C)c1]
47. A compound of formula:
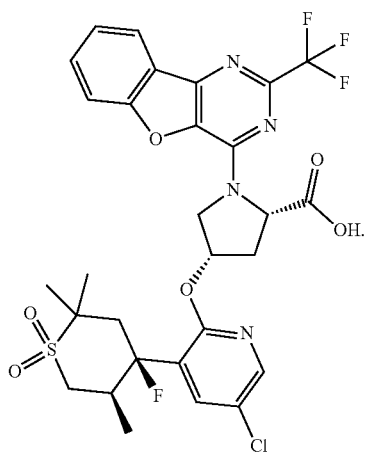 [SMILES: C[C@H]1CS(=O)(=O)C(C)(C)C[C@]1(F)c1cc(Cl)cnc1O[C@H]1C[C@@H](C(=O)O)N(c2nc(C(F)(F)F)nc3c2oc2ccccc23)C1]
48. A compound of formula:
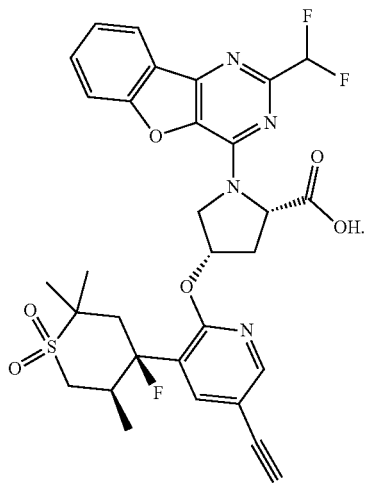 [SMILES: C#Cc1cnc(O[C@H]2C[C@@H](C(=O)O)N(c3nc(C(F)F)nc4c3oc3ccccc34)C2)c([C@@]2(F)CC(C)(C)S(=O)(=O)C[C@@H]2C)c1]
49. A compound of formula:
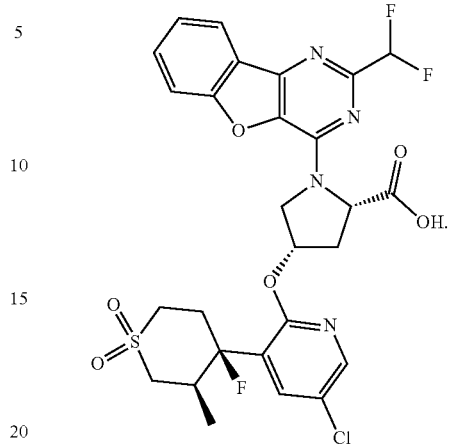
50. A compound of formula:
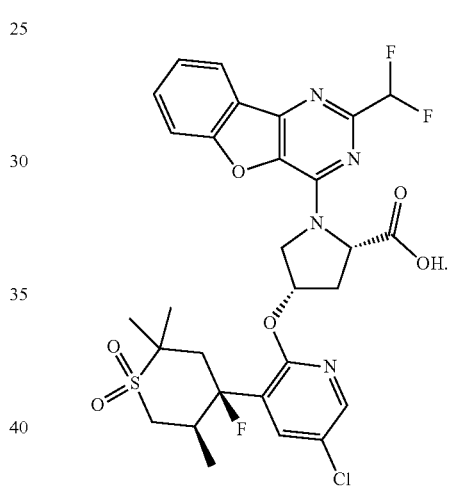
51. A compound of formula:
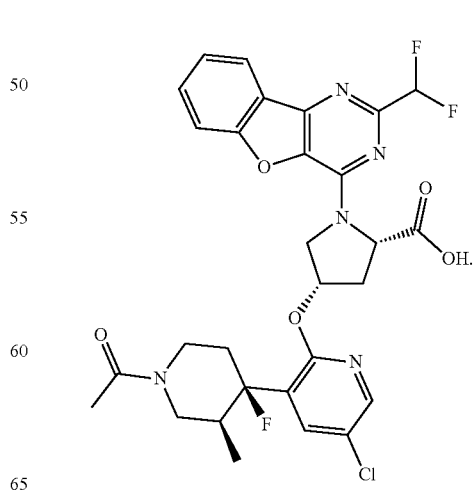

52. A compound of formula:
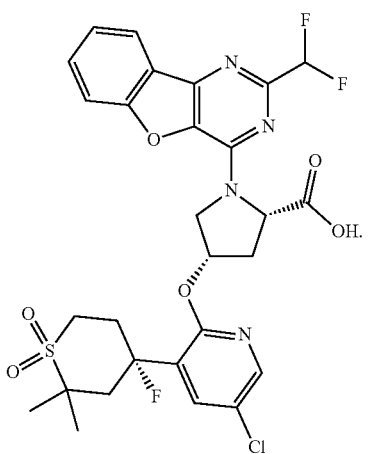 [SMILES: CC1(C)C[C@](F)(c2cc(Cl)cnc2O[C@H]2C[C@@H](C(=O)O)N(c3nc(C(F)F)nc4c3oc3ccccc34)C2)CCS1(=O)=O]
53. A compound of formula:
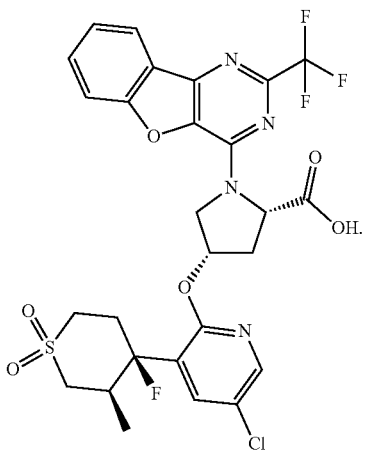 [SMILES: C[C@H]1CS(=O)(=O)CC[C@]1(F)c1cc(Cl)cnc1O[C@H]1C[C@@H](C(=O)O)N(c2nc(C(F)(F)F)nc3c2oc2ccccc23)C1]
54. A compound of formula:
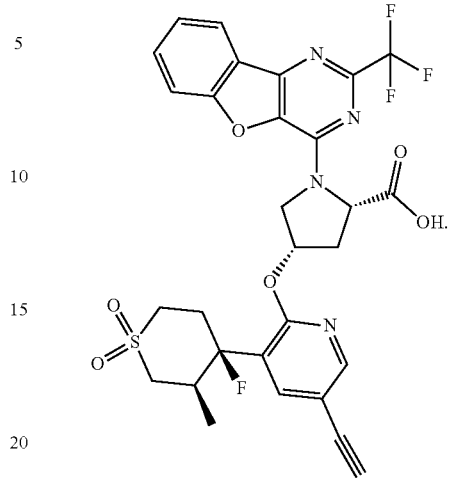
55. A compound of formula:
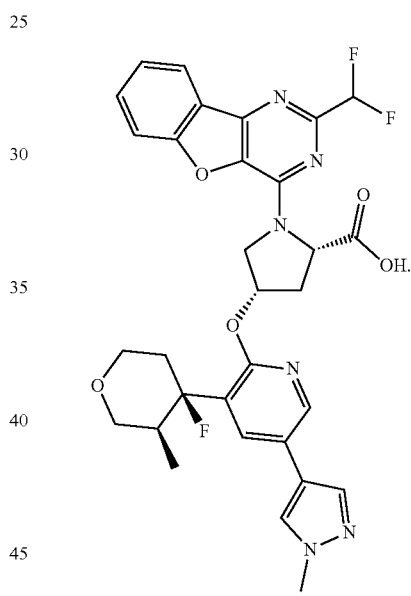
* * * * *